US006902743B1

(12) United States Patent
Setterstrom et al.

(10) Patent No.: US 6,902,743 B1
(45) Date of Patent: *Jun. 7, 2005

(54) THERAPEUTIC TREATMENT AND PREVENTION OF INFECTIONS WITH A BIOACTIVE MATERIAL(S) ENCAPUSLATED WITHIN A BIODEGRADABLE-BIO-COMPATABLE POLYMERIC MATRIX

(75) Inventors: Jean A. Setterstrom, Alpharetta, GA (US); Thomas R. Tice, Birmingham, AL (US); Elliot Jacob, Silver Spring, MD (US); Robert H. Reid, Kensington, MD (US); John van Hamont, West Point, NY (US); Edgar C. Boedecker, Crownsville, MD (US); Ramassubbu Jeyanthi, Columbia, MD (US); Phil Friden, Bedford, MA (US); F. Donald Roberts, Dover, MA (US); Charles E. McQueen, Olney, MD (US); Apurba Bhattacharjee, Kensington, MD (US); Alan Cross, Chevy Chase, MD (US); Jerald Sadoff, Washington, DC (US); Wendell Zollinger, Silver Spring, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/055,505

(22) Filed: Apr. 6, 1998
(Under 37 CFR 1.47)

Related U.S. Application Data

(63) Continuation-in-part of application No. 08/920,326, filed on Aug. 21, 1997, now Pat. No. 6,447,796, which is a continuation-in-part of application No. 08/896,197, filed on Jul. 17, 1997, now abandoned, and a continuation-in-part of application No. 08/788,734, filed on Jan. 23, 1997, now Pat. No. 5,892,337, which is a continuation-in-part of application No. 08/698,896, filed on Aug. 16, 1996, now Pat. No. 5,705,197, which is a continuation-in-part of application No. 08/675, 895, filed on Jul. 5, 1996, now Pat. No. 6,217,911, which is a continuation-in-part of application No. 08/598,874, filed on Feb. 9, 1996, now Pat. No. 5,762,965, which is a continuation-in-part of application No. 08/590,973, filed on Jan. 24, 1996, now abandoned, which is a continuation of application No. 08/446,149, filed on May 22, 1995, now abandoned, which is a continuation-in-part of application No. 08/446,148, filed on May 22, 1995, now Pat. No. 6,410,056.

(51) Int. Cl.$^7$ .......................... A61K 9/14; A61K 39/40; A61K 9/48; A61K 9/26; A61K 9/16

(52) U.S. Cl. ...................... 424/489; 424/177; 424/179; 424/451; 424/470; 424/482; 424/490

(58) Field of Search .............................. 424/489, 451, 424/455, 463, 468, 469, 470, 477, 482, 453, 490

(56) References Cited

U.S. PATENT DOCUMENTS

| 3,540,444 A | 11/1970 | Moreland ................... 128/173 |
| 3,788,315 A | 1/1974 | Laurens ................... 128/173 H |
| 4,166,800 A | 9/1979 | Fong ......................... 252/316 |
| 4,384,975 A | 5/1983 | Fong ..................... 427/213.36 |
| 4,530,840 A | 7/1985 | Tice et al. .................. 514/179 |

(Continued)

FOREIGN PATENT DOCUMENTS

EP               0052510 B2      10/1994

OTHER PUBLICATIONS

Gilding, Biodegradable polymers for use in surgery–polyglycolic/poly (ac c acid) homo– and copolymers: 1, Polymer, vol. 20, Dec. 1979, pp1459–1464.

Biotechnology News, Aug. 22, 1997, vol. 17, No. 20, Topical DNA vaccine elicits immune response.

Hall, et al., Purification and Analysis of Colonization Factor Antigen I, *Coli* Surface Antigen 1, and *Coli* Surface Antigen 3 Fimbriae from Enterotoxigenic *Escherichia Coli*, Journal of Bacteriology, Nov. 1989, p6372–6374, vol. 171, No. 11.

Evans, et al. Purification and Characterization of the CFR/I Antigen of Enterotoxigenic *Escherichia coli*, Infection and Immunity, Aug. 1979, p 738–748, vol. 25.

Karjalainen, et al., Molecular Cloning and Nucleotide Sequence of the Colonization Factor Antigen I Gene of *Escherichia coli*, Infection and Immunity, Apr. 1989, p1126–1130, vol. 57.

Jeyanthi, et al., Novel, Burst Free Programmable Biodegradable Microspheres For Controlled Release of Polypeptides, Proceedings Int. Symp. control Release Bioact. Mater. (1996) p351–3521.

Yeh, A novel emulsification–solvent extraction technique for production of potein loaded biodegradable microparticles for vaccine and drug delivery, Journal of Controlled Release, 33 (1005) 437–445. (1990).

Yan, Characterization and morphological analysis of protein–loaded poly(lactide–co–glycolide) microparticles prepared by watewr–in–oil–in–water emulsion technique, Journal of Controlled Release, 32 (1994) 231–241.

(Continued)

*Primary Examiner*—Theodore J. Criares
(74) *Attorney, Agent, or Firm*—Elizabeth Arwine; John Francis Moran; Charles H. Harris

(57) ABSTRACT

Novel burst-free, sustained release biocompatible and biodegrable microcapsules which can be programmed to release their active core for variable durations ranging from 1–100 days in an aqueous physiological environment. The microcapsules are comprised of a core of polypeptide or other biologically active agent encapsulated in a matrix of poly (lactide/glycolide) copolymer having a molar composition of lactide/glycolide from 90/10 to 40/60, which may contain a pharmaceutically-acceptable adjuvant, as a blend of uncapped free carboxyl end group and end-capped forms ranging to ratios from 100/0 to 1/99.

154 Claims, 86 Drawing Sheets

U.S. PATENT DOCUMENTS

| | | | |
|---|---|---|---|
| 4,542,025 A | 9/1985 | Tice et al. | 424/78 |
| 4,585,482 A | 4/1986 | Tice et al. | 106/15.05 |
| 4,622,244 A | 11/1986 | Lapka et al. | 427/213.32 |
| 4,637,905 A | 1/1987 | Gardner | 264/4.3 |
| 4,675,189 A | 6/1987 | Kent et al. | 424/490 |
| 4,798,786 A | 1/1989 | Tice et al. | 435/177 |
| 4,835,139 A | 5/1989 | Tice et al. | 514/15 |
| 4,863,735 A | 9/1989 | Kohn et al. | 524/422 |
| 4,897,268 A | 1/1990 | Tice et al. | 424/422 |
| 4,938,763 A | 7/1990 | Dunn et al. | 604/891.1 |
| 4,941,880 A | 7/1990 | Burns | 604/143 |
| 5,000,886 A | 3/1991 | Lawter et al. | 264/4.3 |
| 5,019,096 A | 5/1991 | Fox, Jr. et al. | 623/1 |
| 5,059,187 A | 10/1991 | Sperry et al. | 604/290 |
| 5,064,413 A | 11/1991 | McKinnon et al. | 604/70 |
| 5,075,109 A | 12/1991 | Tice et al. | 424/88 |
| 5,102,872 A | 4/1992 | Singh et al. | 514/21 |
| 5,129,825 A | 7/1992 | Discko, Jr. | 433/90 |
| 5,133,701 A | 7/1992 | Han | 604/289 |
| 5,236,355 A | 8/1993 | Brizzolara et al. | 433/80 |
| 5,278,202 A | 1/1994 | Dunn et al. | 523/113 |
| 5,290,494 A | 3/1994 | Coombes et al. | 264/41 |
| 5,360,610 A | 11/1994 | Tice et al. | 424/426 |
| 5,384,133 A | 1/1995 | Boyes et al. | 424/501 |
| 5,407,609 A | 4/1995 | Tice et al. | 264/46 |
| 5,417,986 A | 5/1995 | Reid et al. | 424/499 |
| 5,429,822 A * | 7/1995 | Gresser et al. | 424/426 |
| 5,500,228 A | 3/1996 | Lawter et al. | 424/486 |
| 5,538,739 A | 7/1996 | Bodmer et al. | 424/501 |
| 5,639,480 A | 6/1997 | Bodmer et al. | 424/501 |
| 5,643,605 A | 7/1997 | Cleland et al. | 424/489 |
| 5,648,096 A * | 7/1997 | Gander et al. | 424/489 |
| 5,650,173 A * | 7/1997 | Ramstack et al. | 424/489 |
| 5,688,530 A | 11/1997 | Bodmer et al. | 424/501 |
| 5,693,343 A | 12/1997 | Reid et al. | 424/491 |
| 5,762,965 A | 6/1998 | Burnett et al. | 424/499 |
| 5,811,128 A | 9/1998 | Tice et al. | 424/501 |
| 5,814,344 A | 9/1998 | Tice et al. | 424/501 |
| 5,820,883 A | 10/1998 | Tice et al. | 424/501 |
| 5,853,763 A | 12/1998 | Tice et al. | 424/489 |
| 6,447,796 B1 * | 9/2002 | Vook et al. | 424/422 |

OTHER PUBLICATIONS

Wang, et al., Influence of formulation methods on the in vitro controlled release of protien from poly (ester) microspheres Journal of Controlled Release, 17 (1991) 23–32.

Brown, Wonder Drugs' Losing Healing Aura, The Washing Post, Jun. 26, 1995, A section.

Setterstrom, Controlled Release of Antibiotics From biodegradable Microcapsules For Wound infection Control, Chemical Abstracts, 1983, pp215–226.

Perez–Casal, et al., Gene Encoding the Major Subunit of CS1 Pili of Human Enterotoxigenic *Escherichia Coli*, Infection and Immunity, Nov., 1990, p 3594–3600, vol. 58, No. 11.

Jordi, et al., Analysis of the first two genes of the CS1 fimbrial operon in human enterotoxigenic *Escherichia coli* of serotype 0139: H28, FEMS Microbiology Letters 80, (1991) p265–270.

Tan, et al., Mapping the Antigenic Epitopes of Human Dihydrofolate Reductase by Systematic Synthesis of Peptides on soid Supports, The Journal of Biological Chemistry, vol. 265, No. 14, Issue of May 15, pp. 8022–8026 (1990).

McConnel, et al., Antigenic homology within human enterotoxigenic *Esherichia coli* fimbrial colonization factor antigens: CFA/I, coli–surface–associated antigens (CS)1, CS2, CS4 and CS17, FEMS Microbiology Letters 61 (1989) 105–108.

Van der Zee, Efficient mapping and characterization of a T cell epitope by the simultaneous synthesis of multiple peptides, Eur. J. Immunol. 1989, 19: 43–47.

Cassels, et al., Analysis of *Escherichia coli* Colonization Factor AntigenI Linear B–Cell Epitopes, as Determined by Primate Responses, following Protein Sequence Verification, Infection and Immunity, Jun. 1992, p. 2174–2181, vol. 60, No. 6.

Romagnoli, et al. Peptide–MHC Interaction: A Rational Approach to Vaccine Design, Inter, RE. Immunol. 6, 1990, 004 61–73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70–85 (1992).

Brown, A hypothetical model of the foreign antigen biinding site of Class II histocompatibility molecules, Nature, vol. 332, Apr. 28, 1988, p845–850.

* cited by examiner

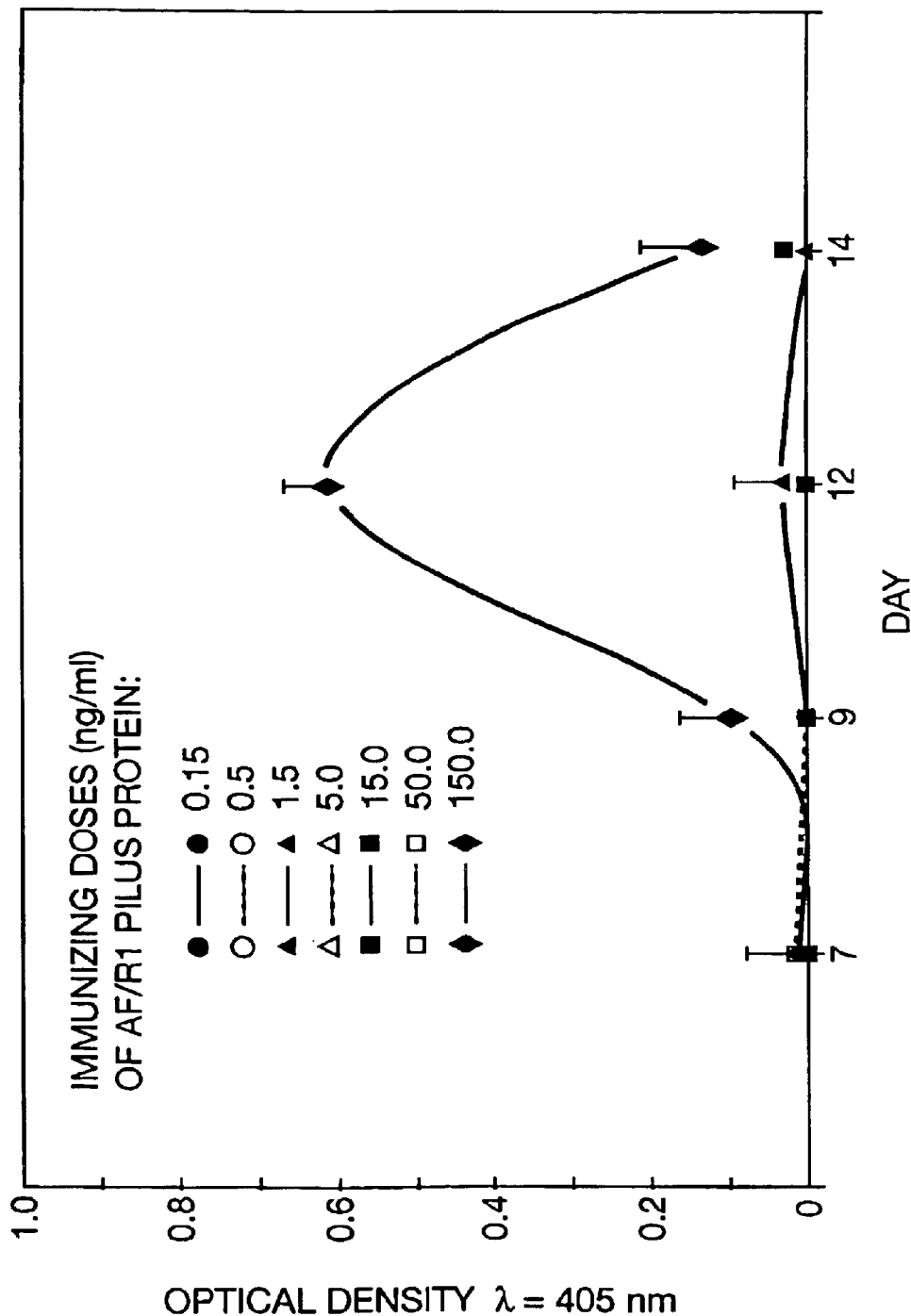

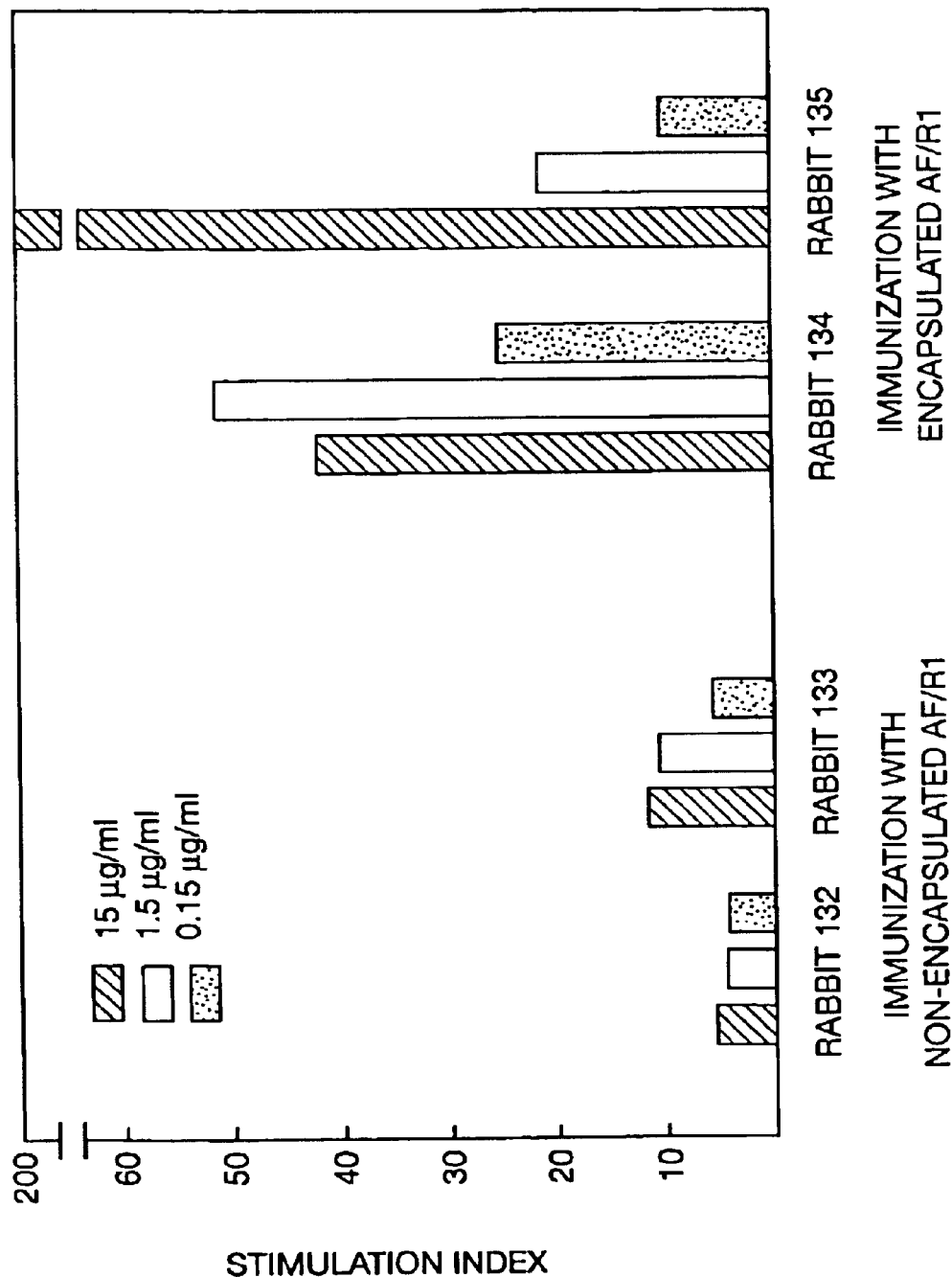

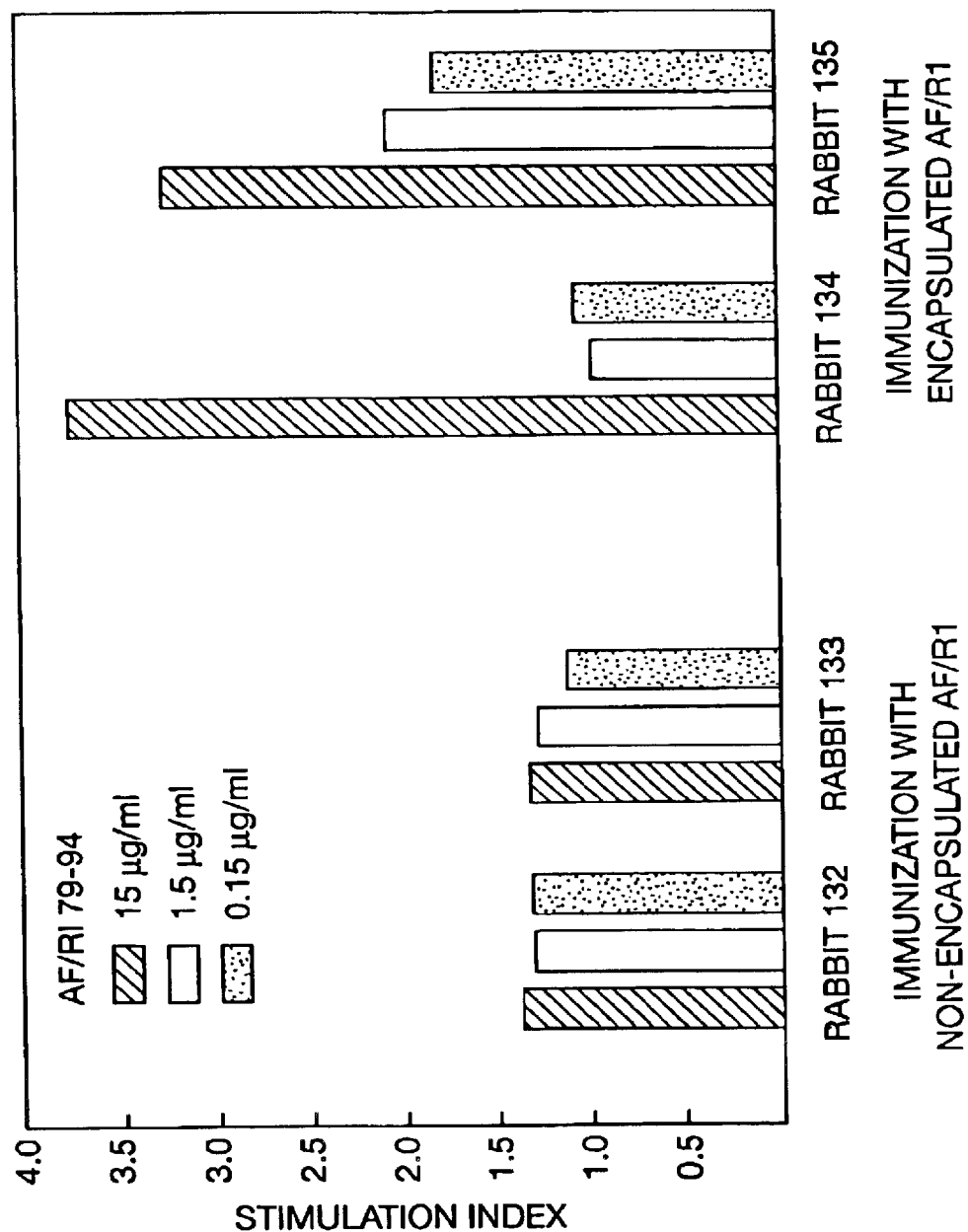

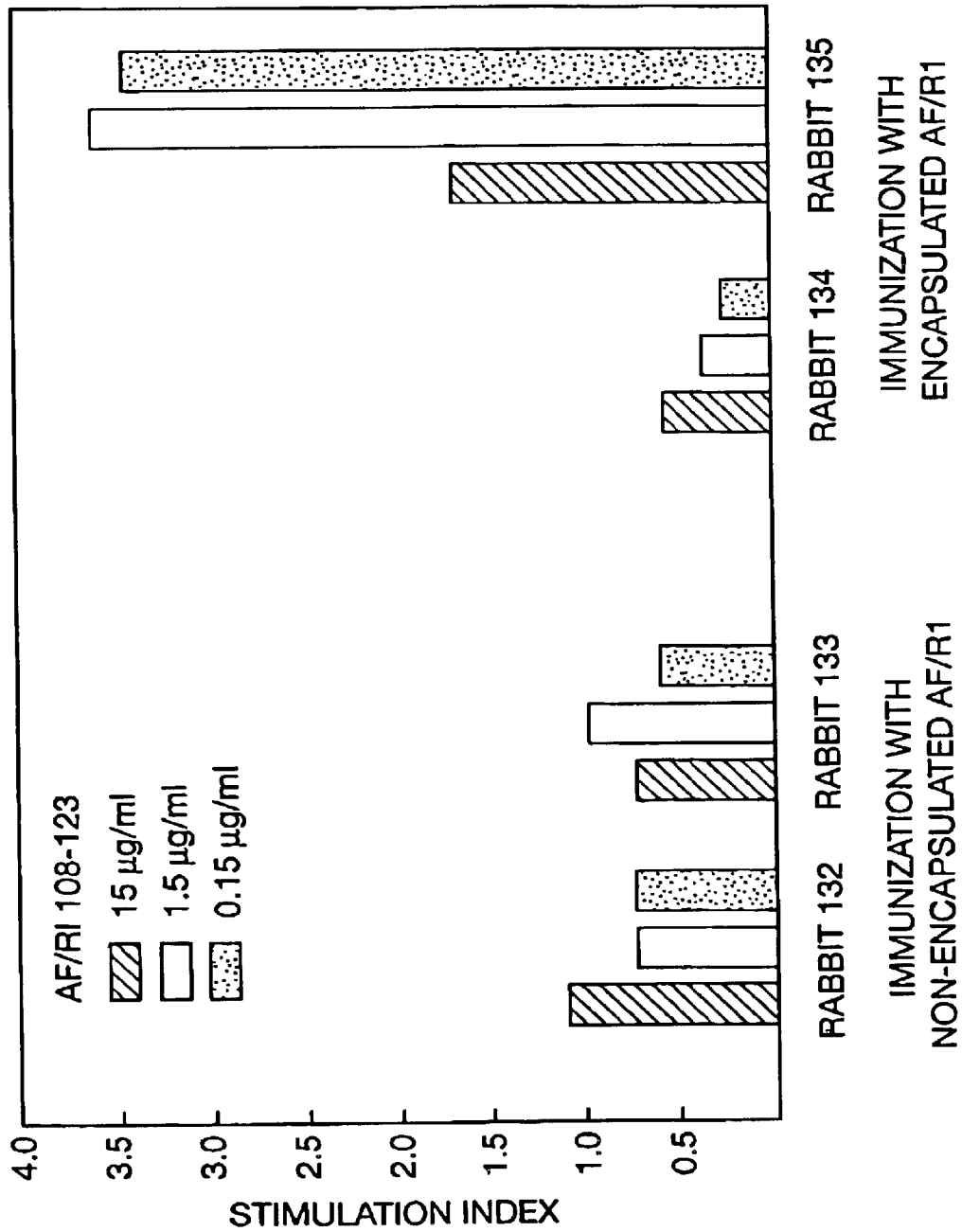

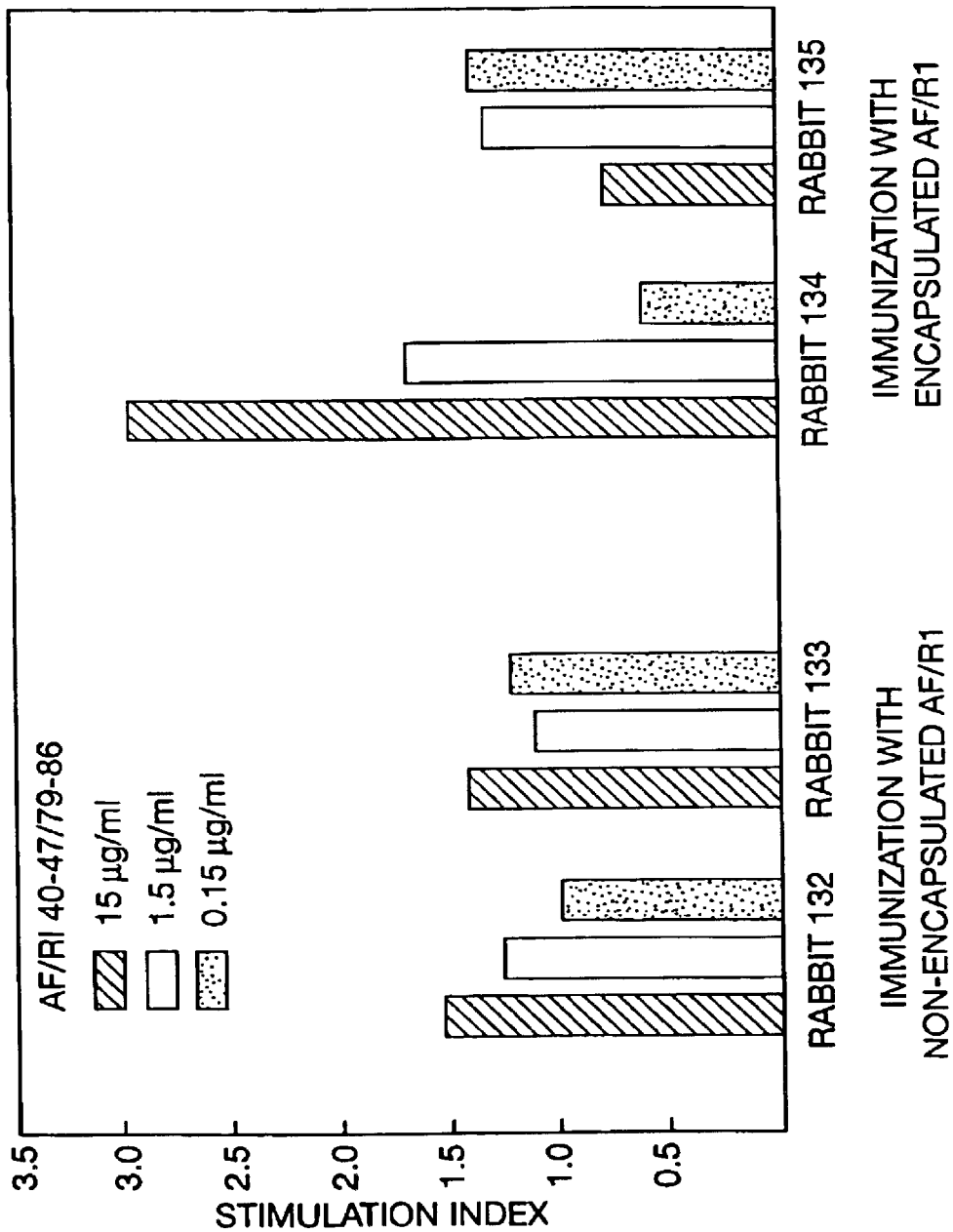

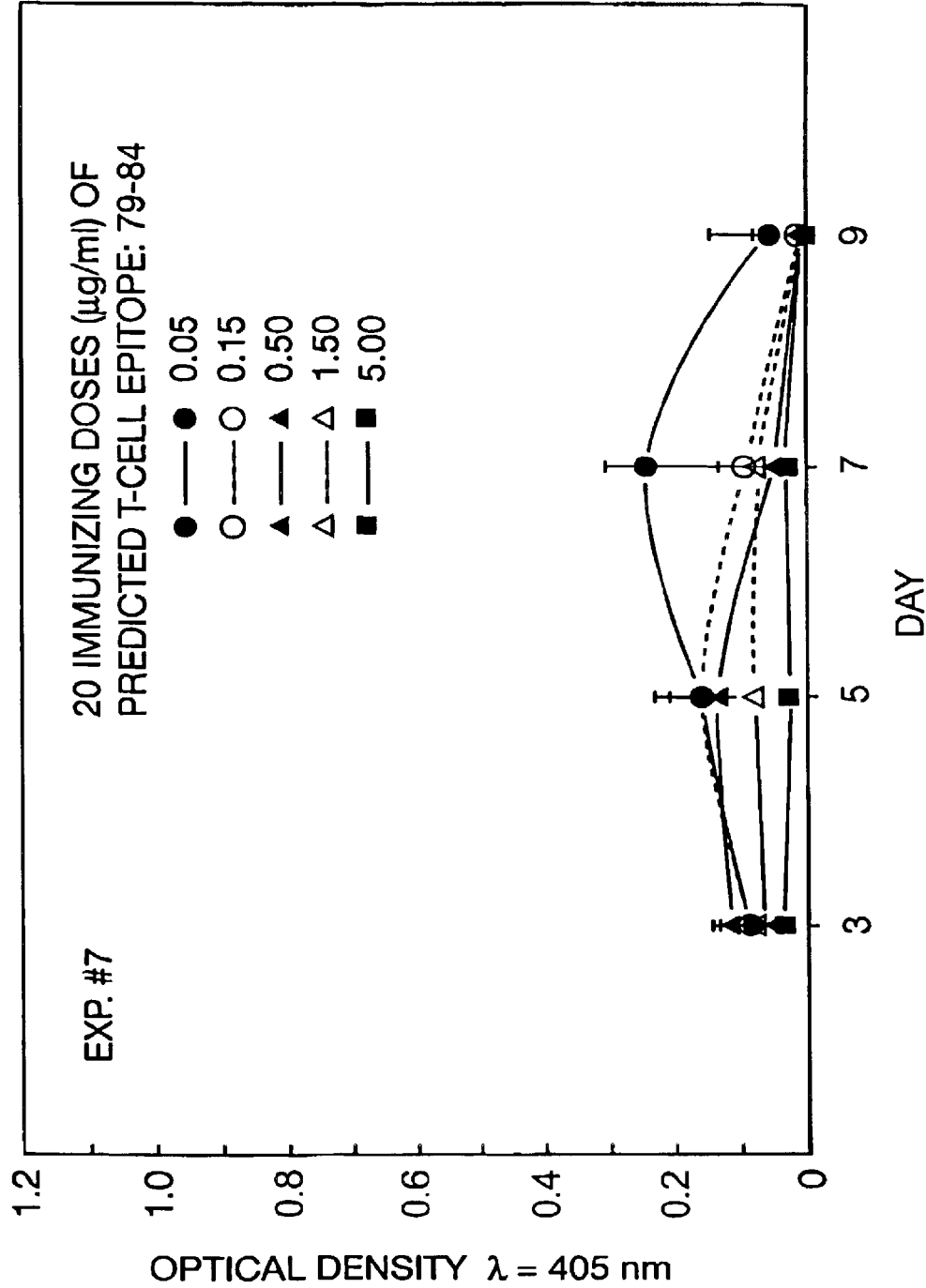

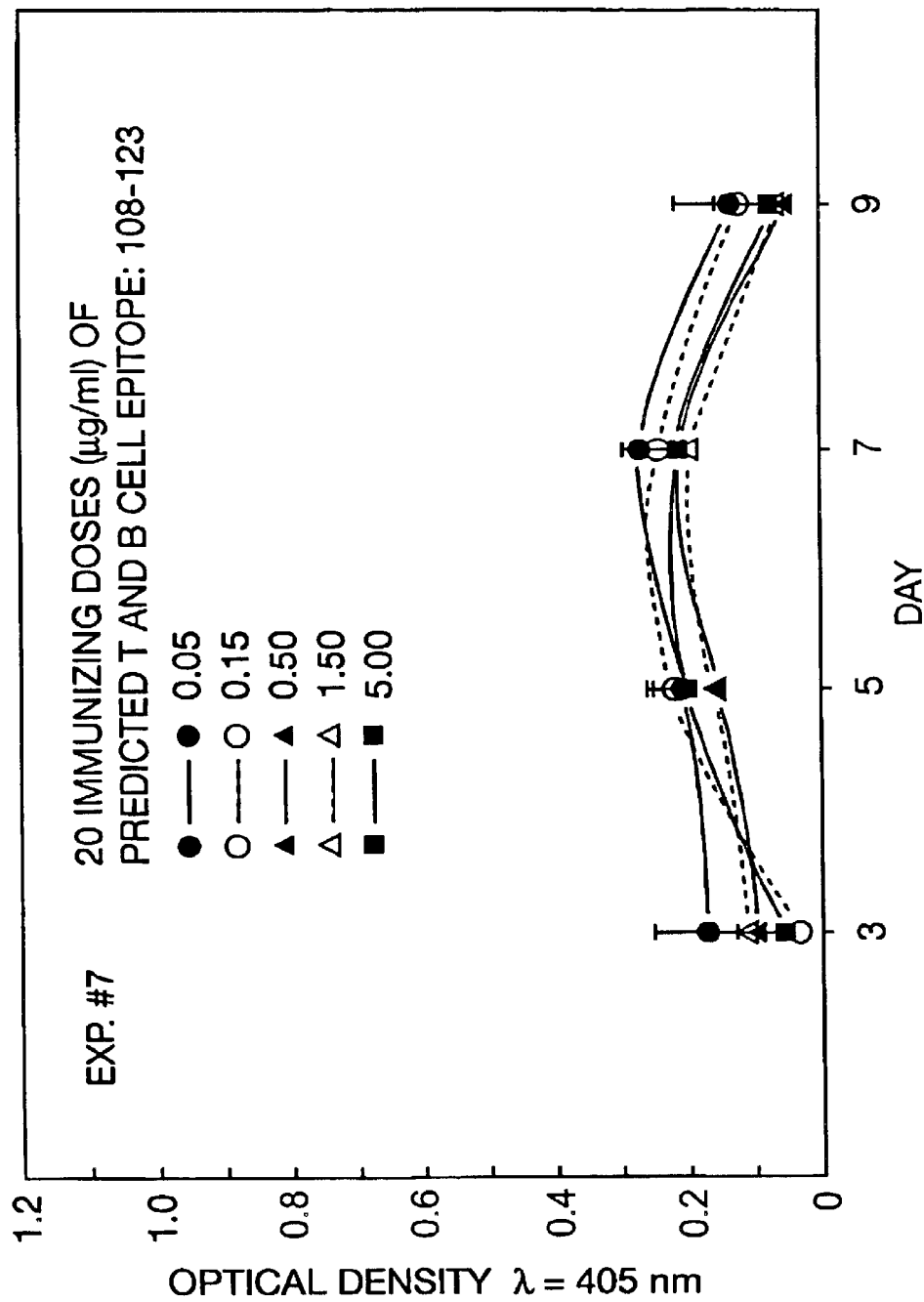

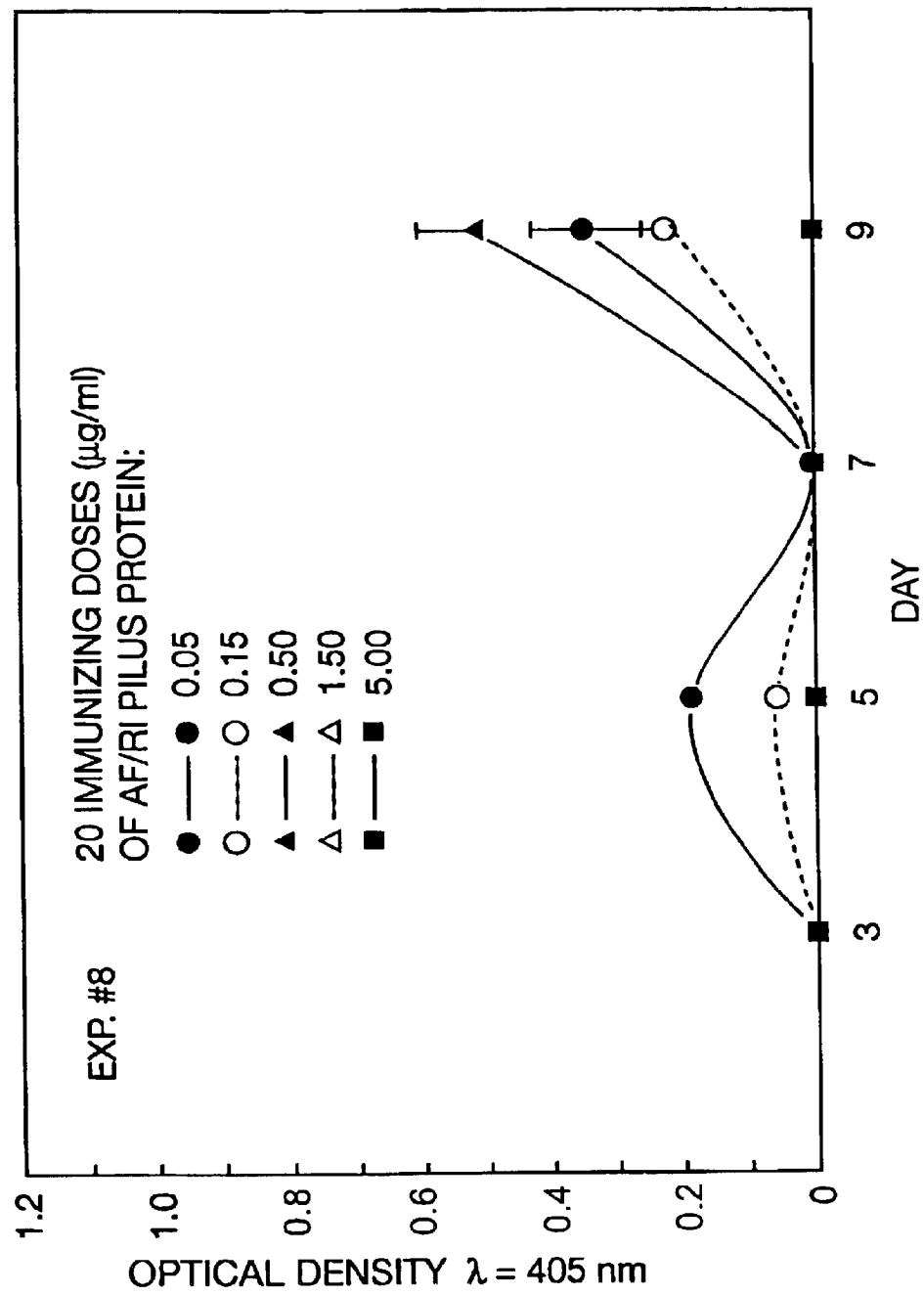

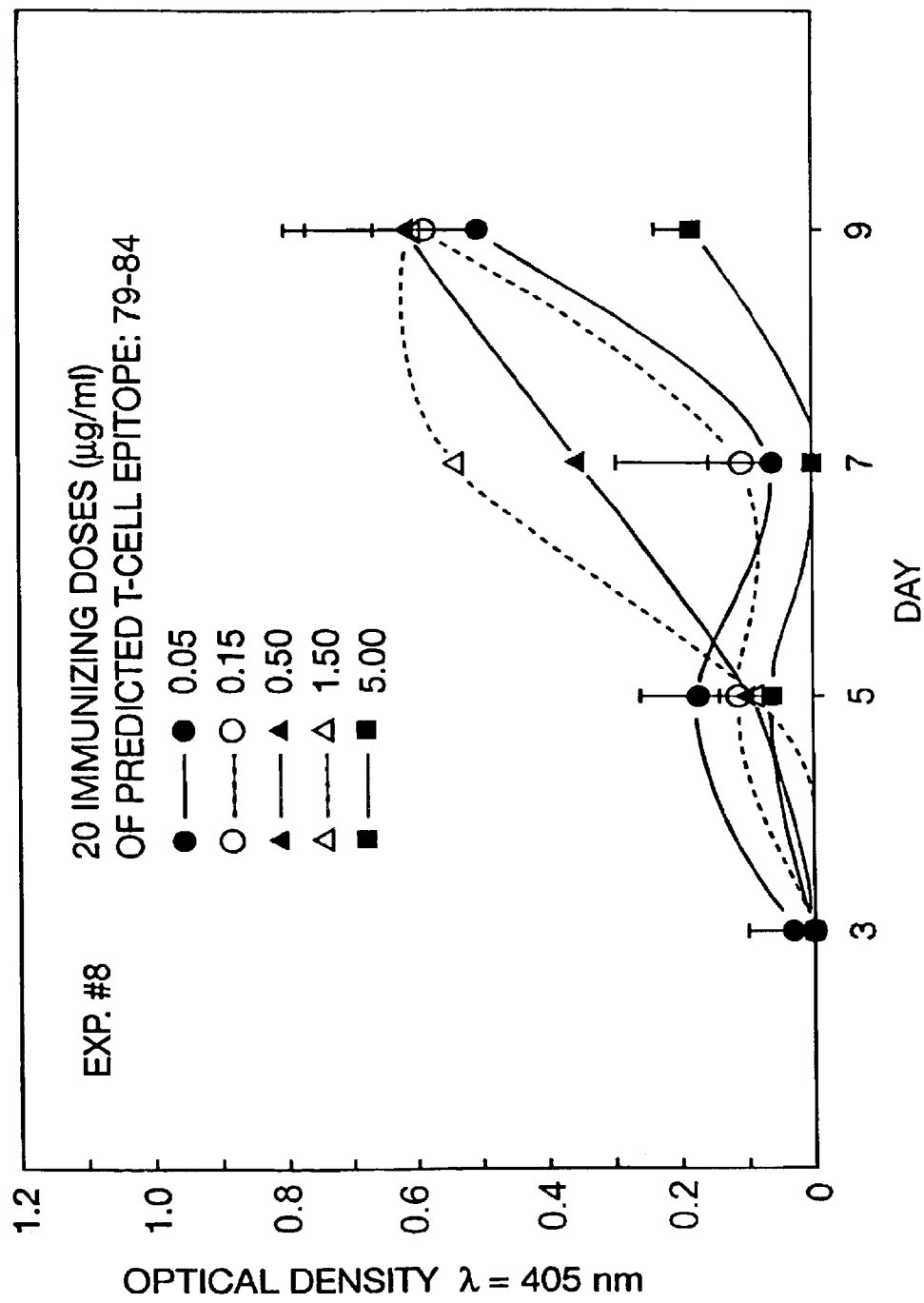

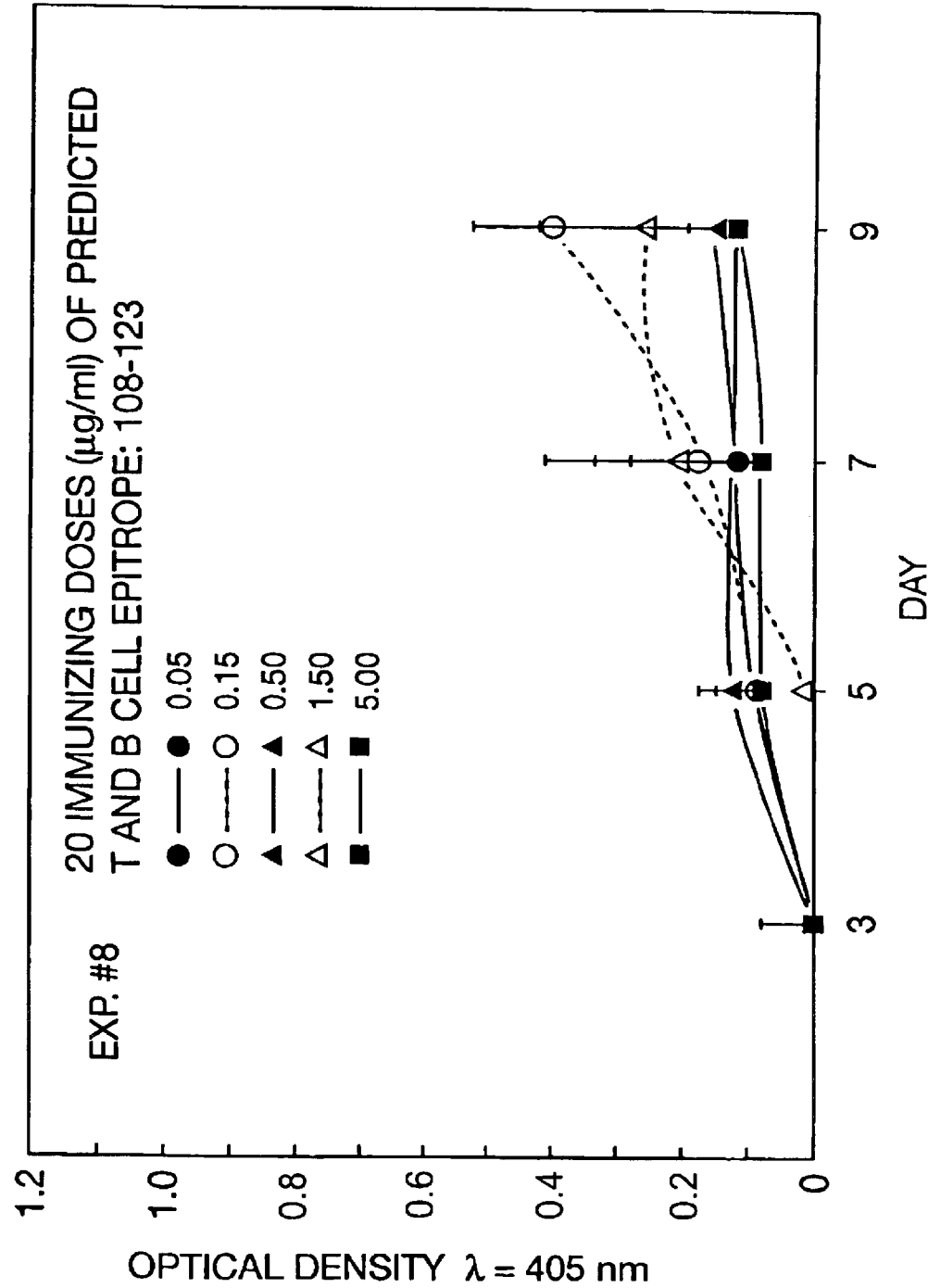

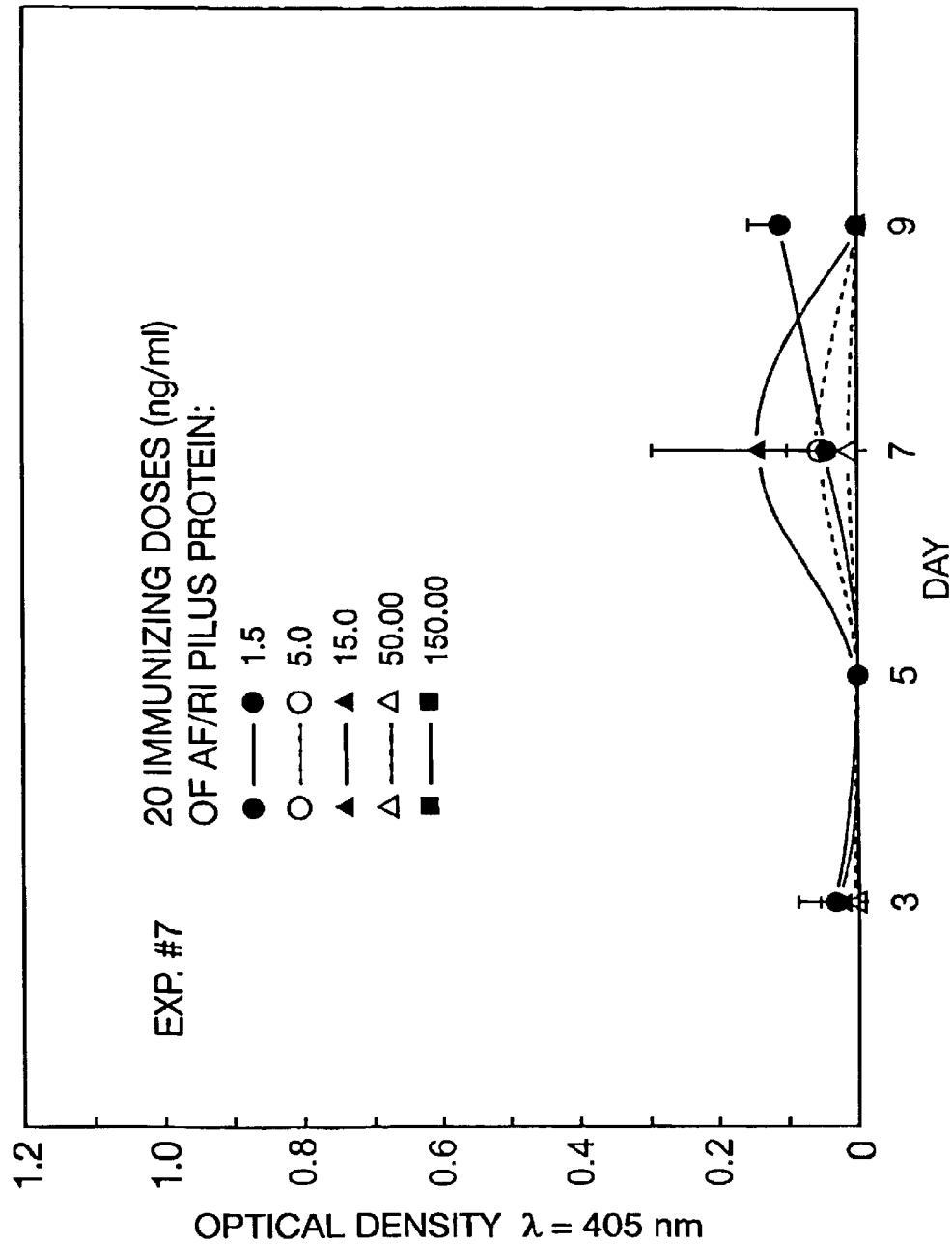

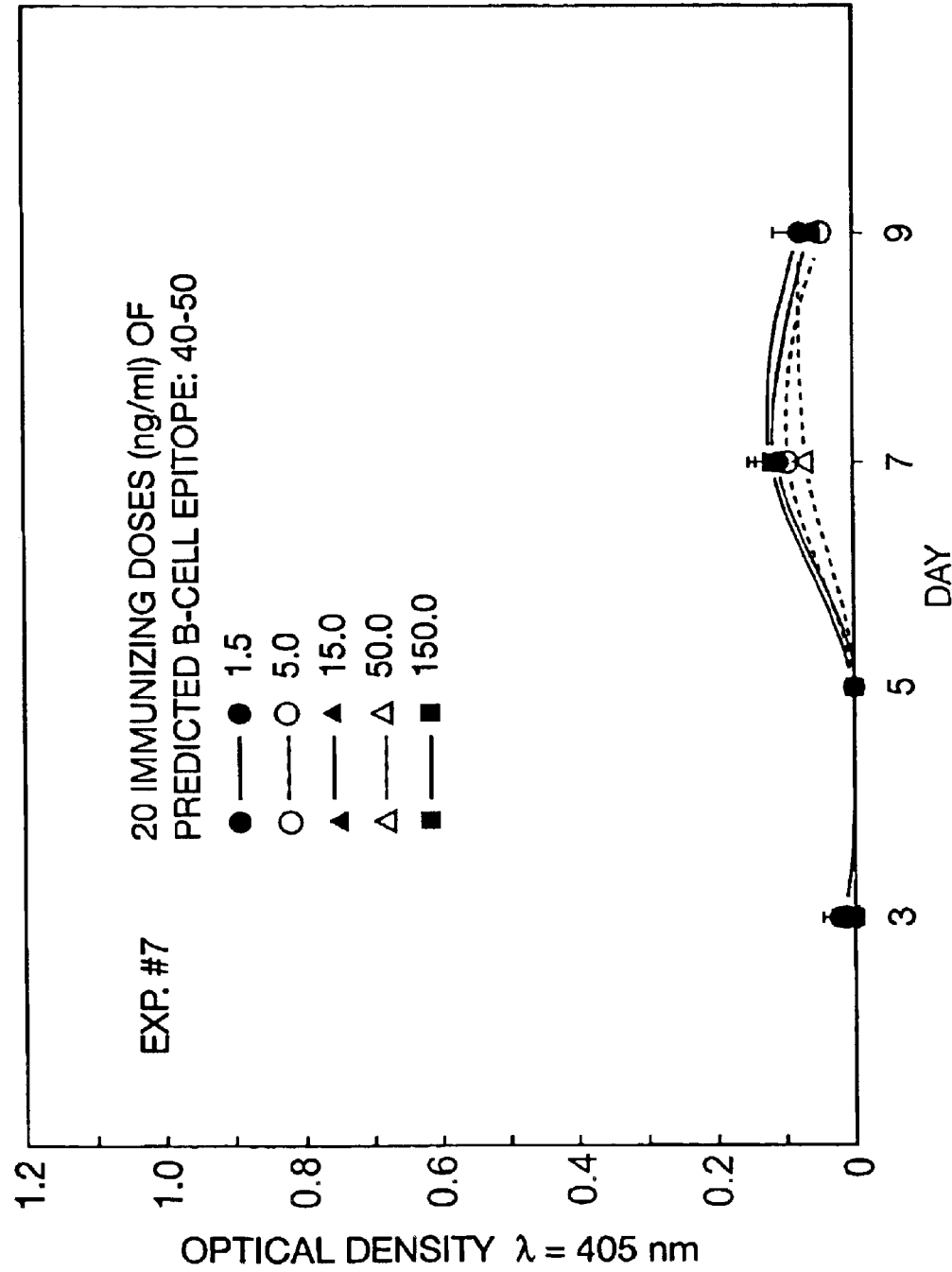

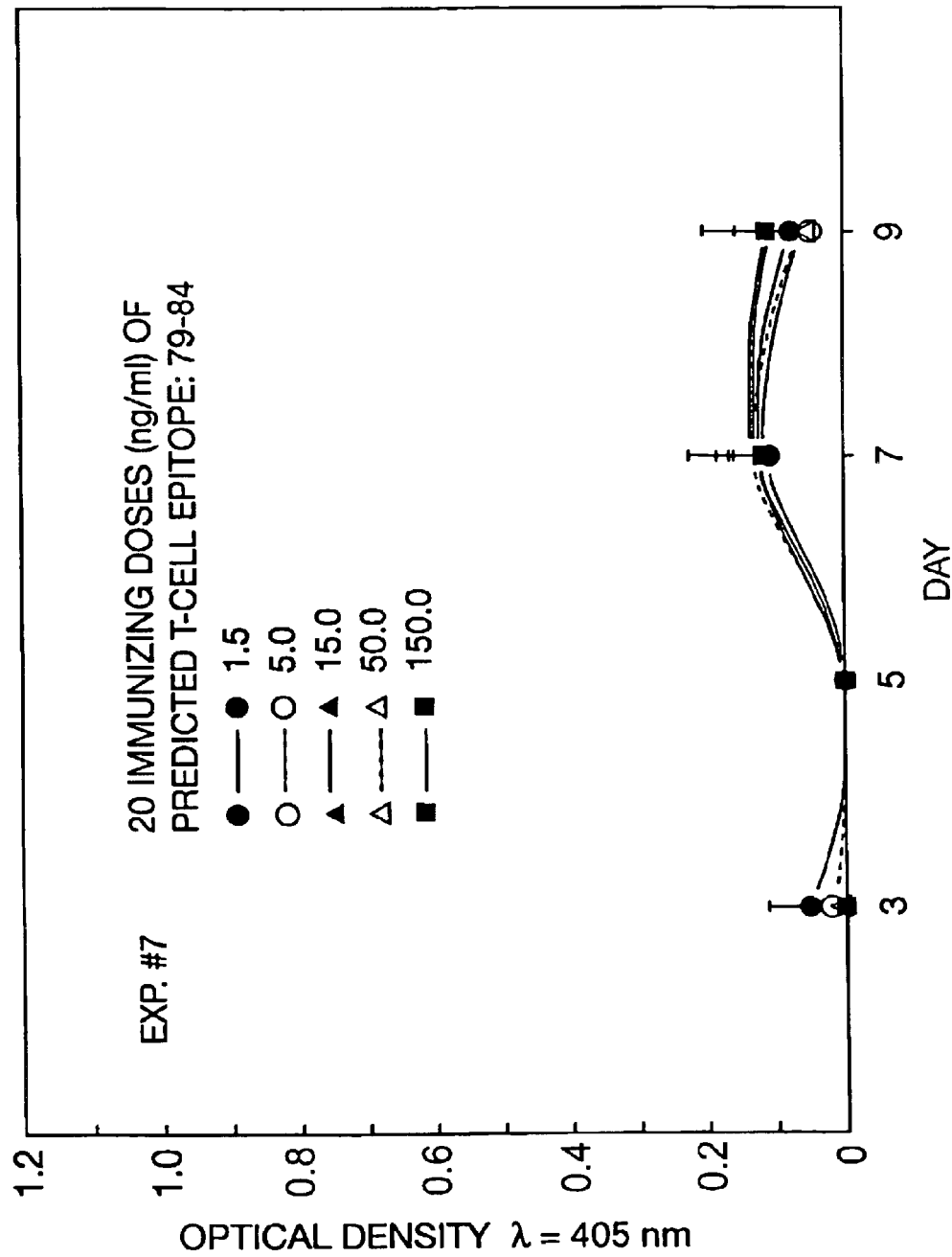

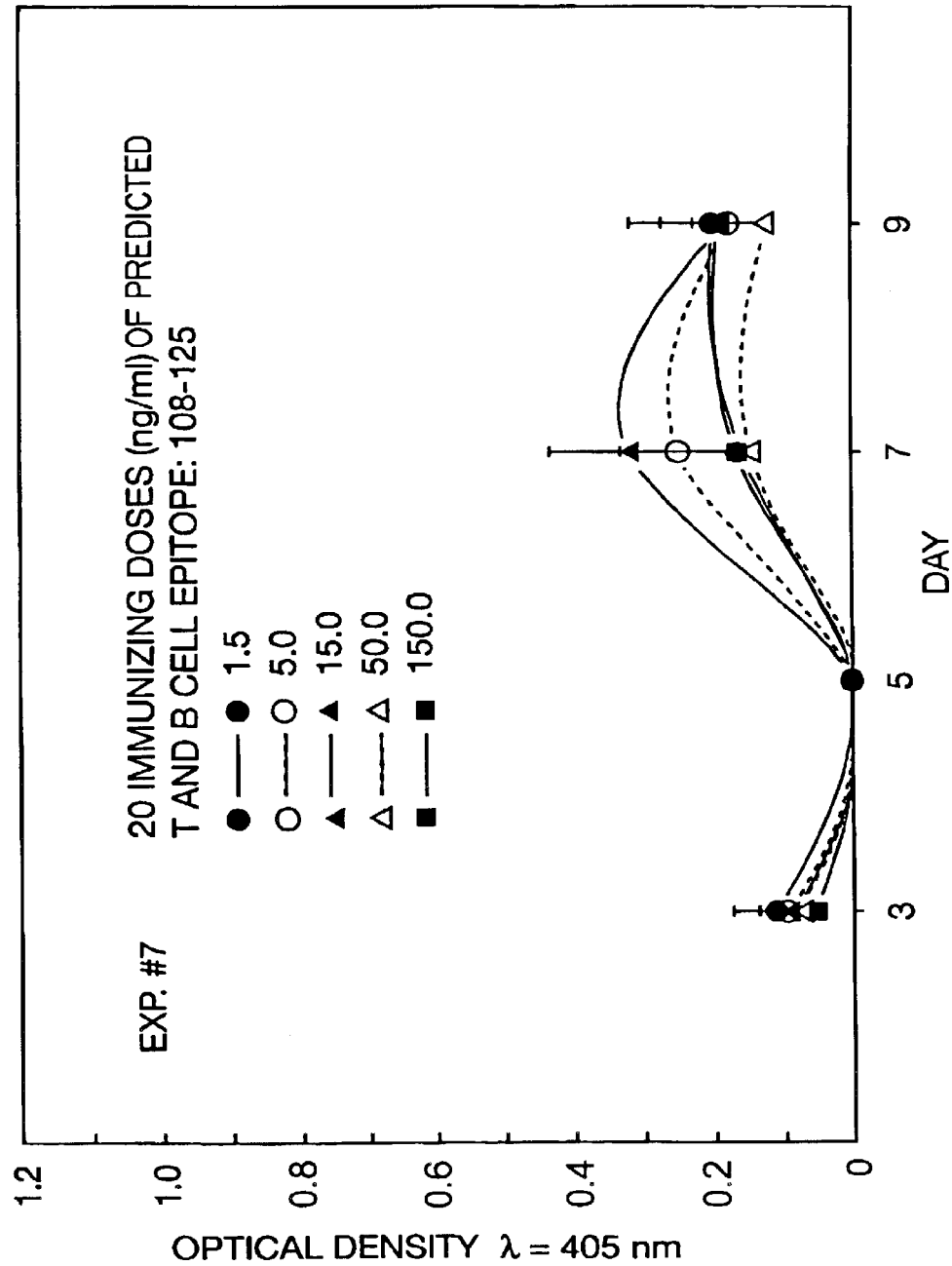

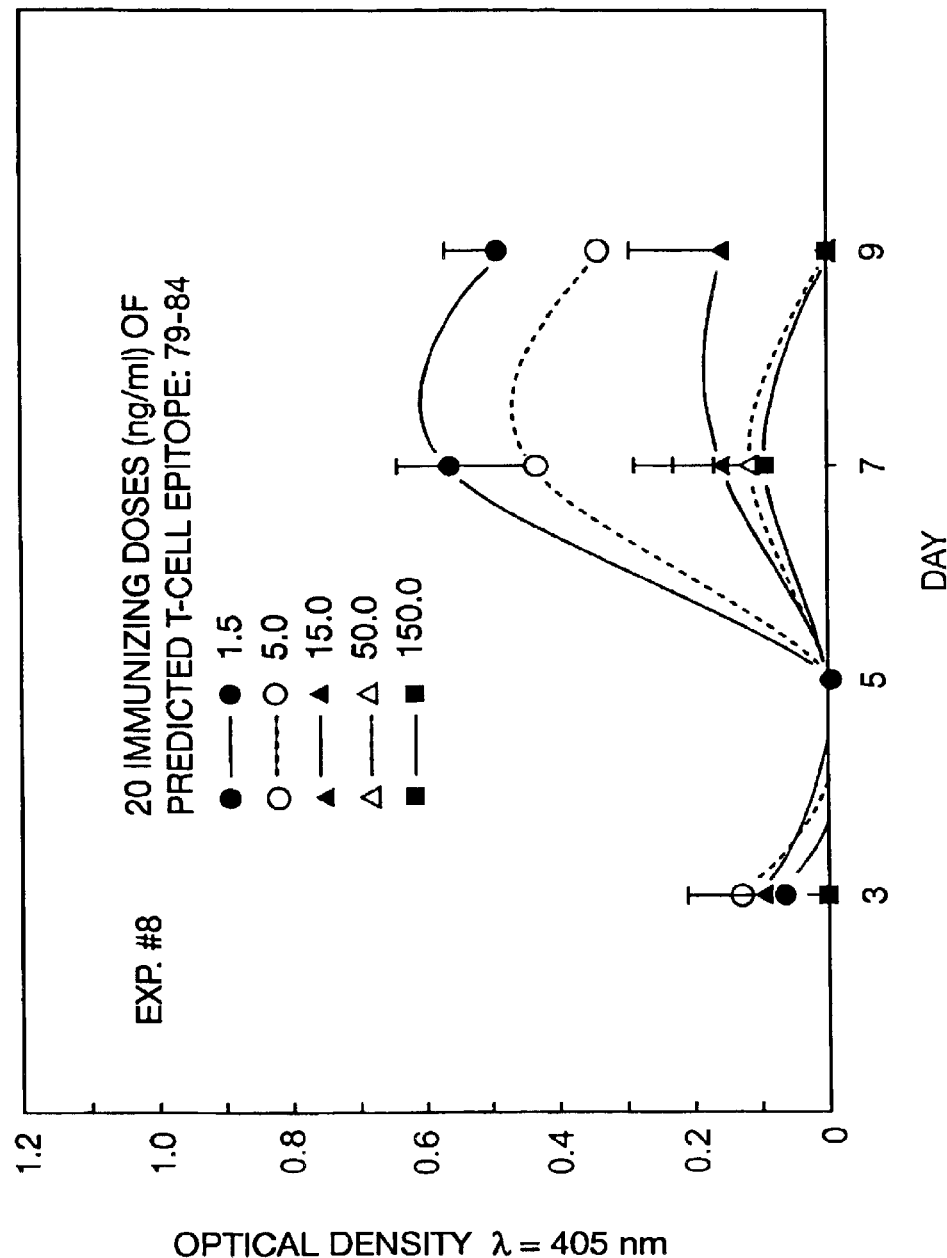

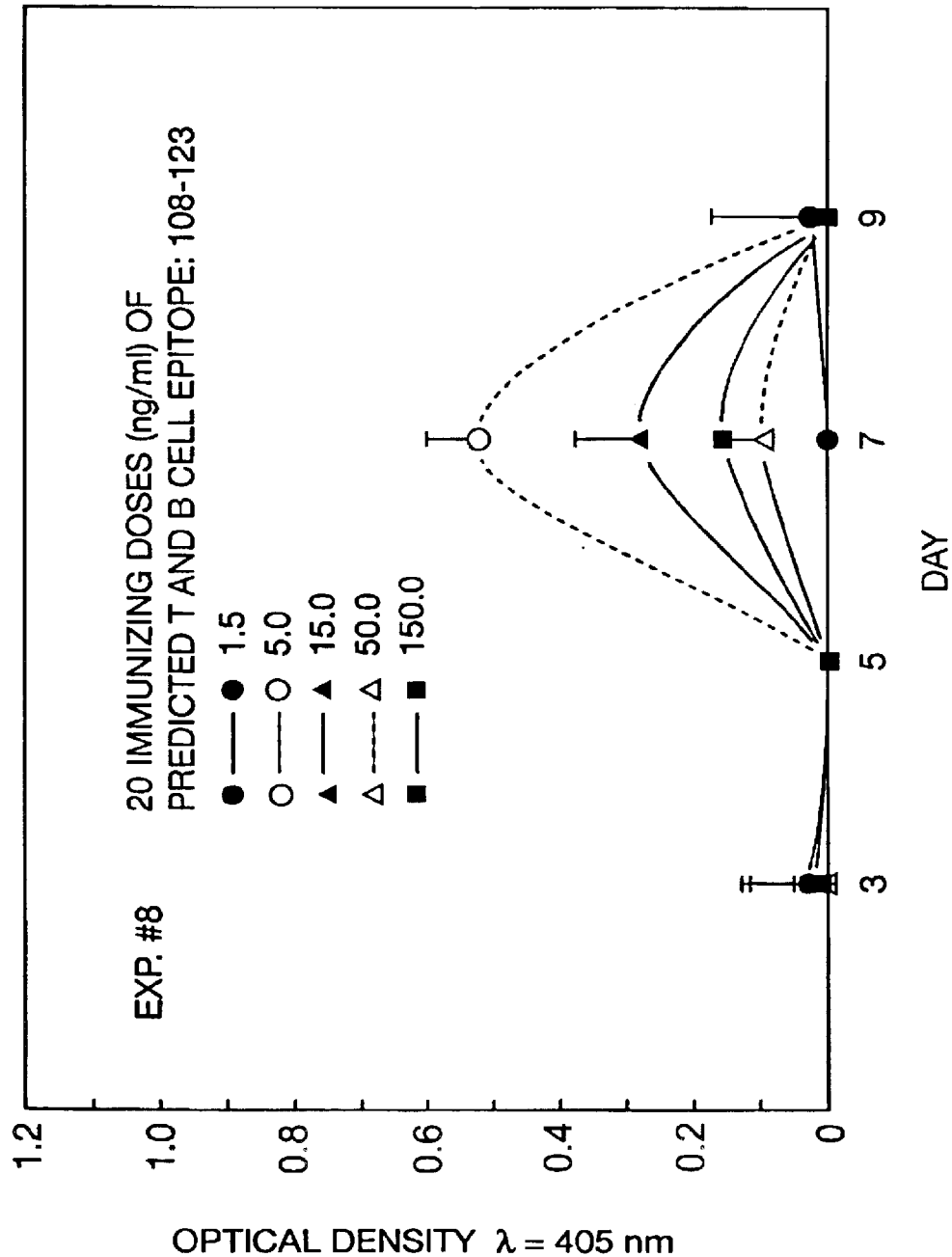

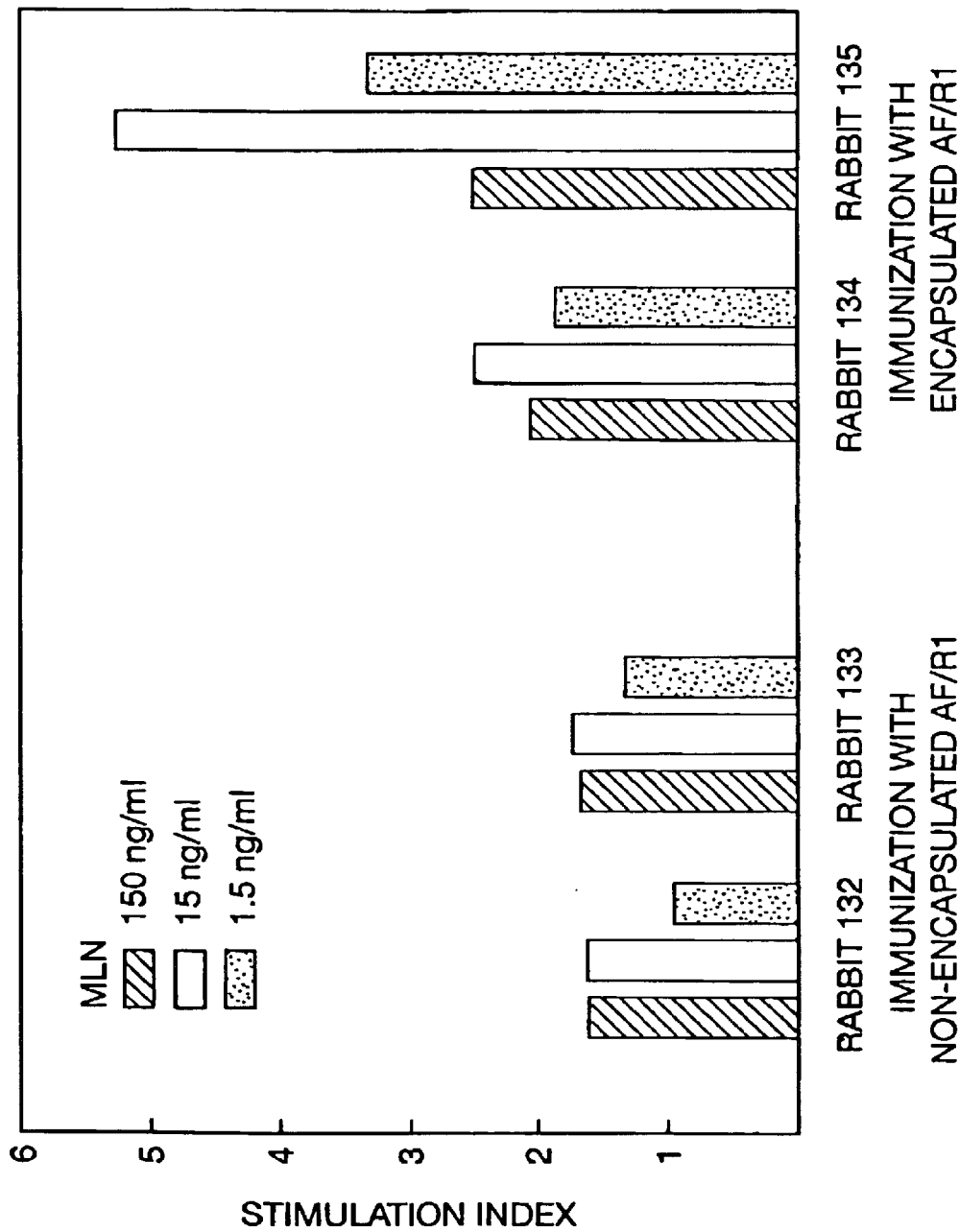

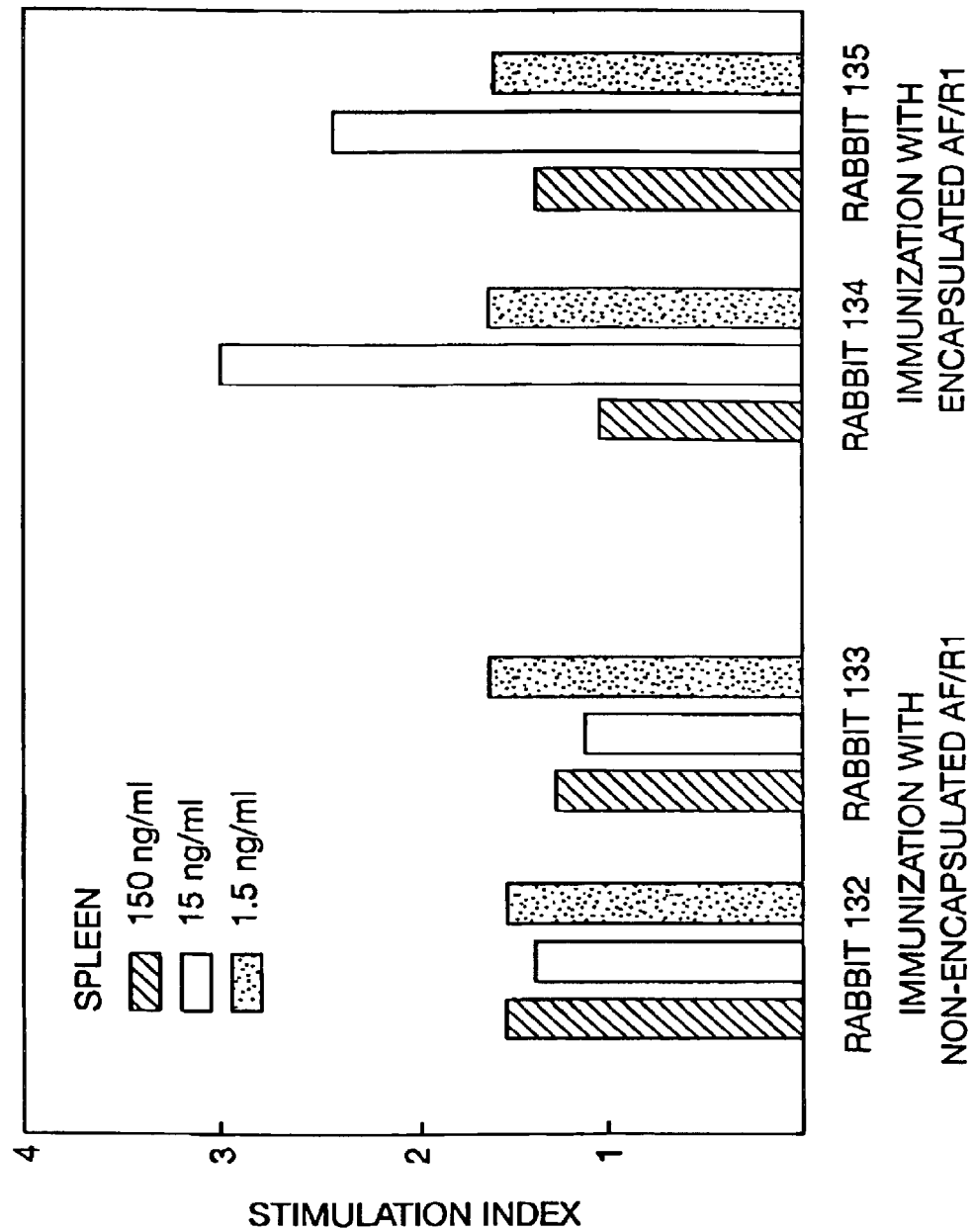

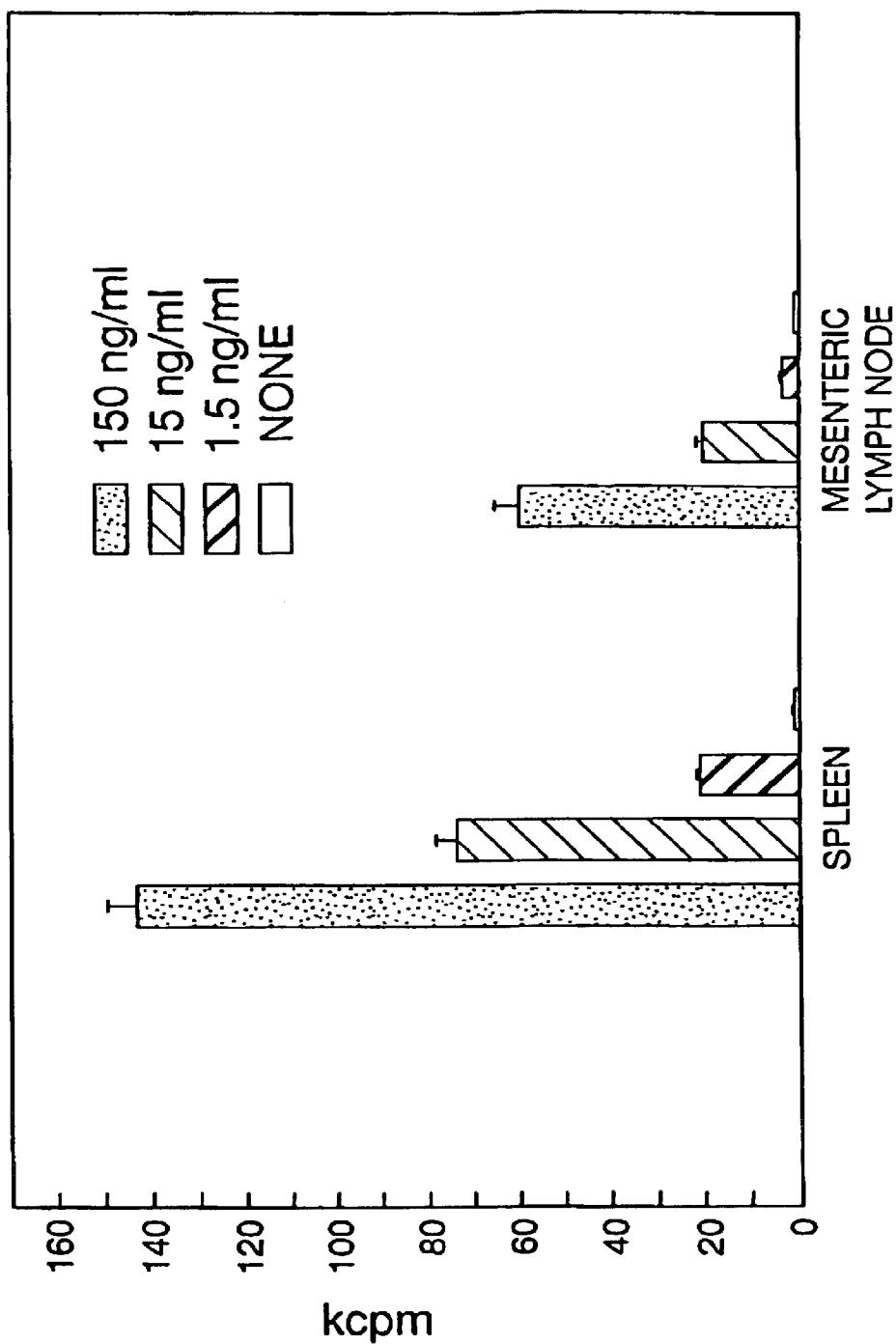

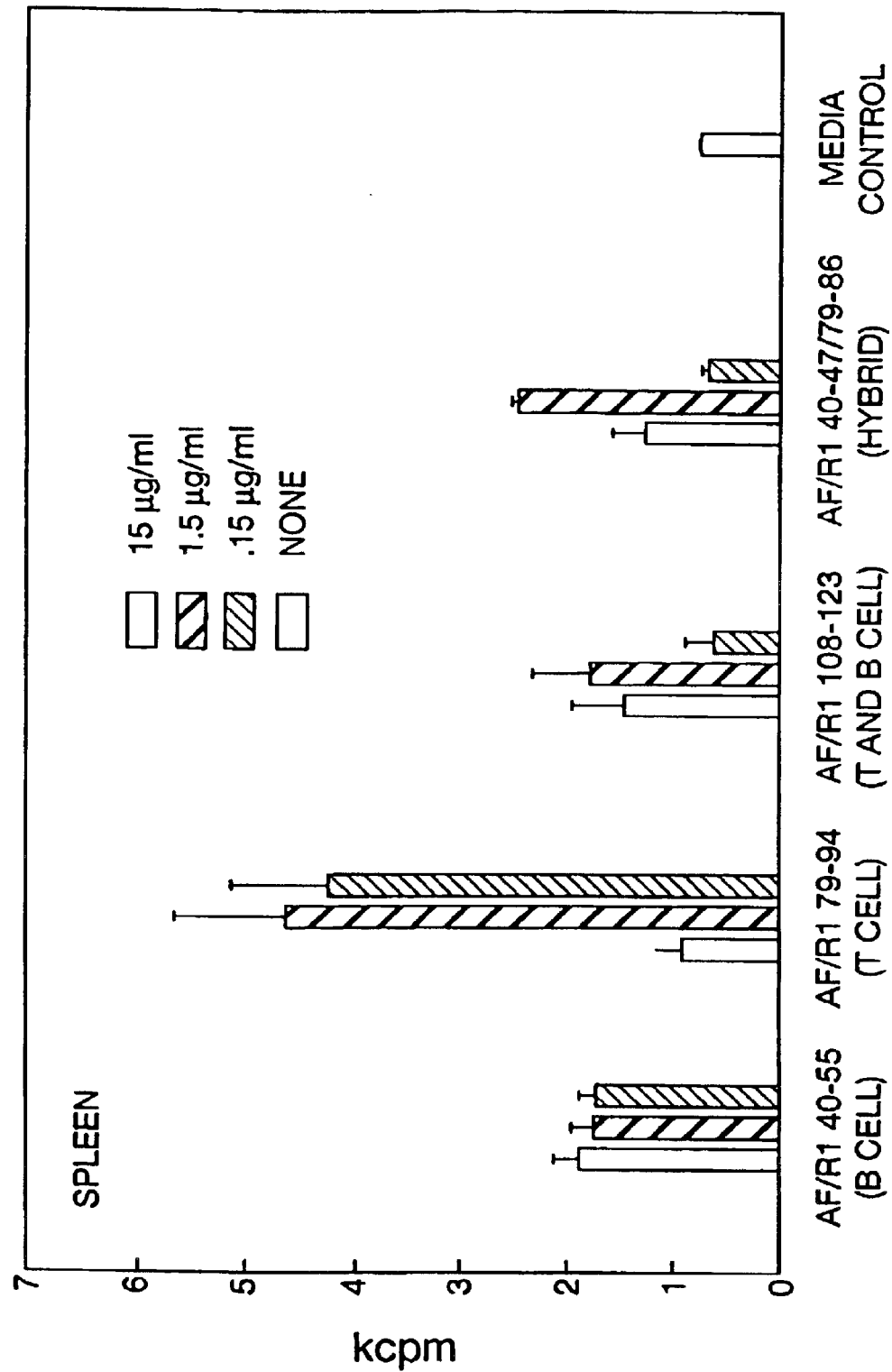

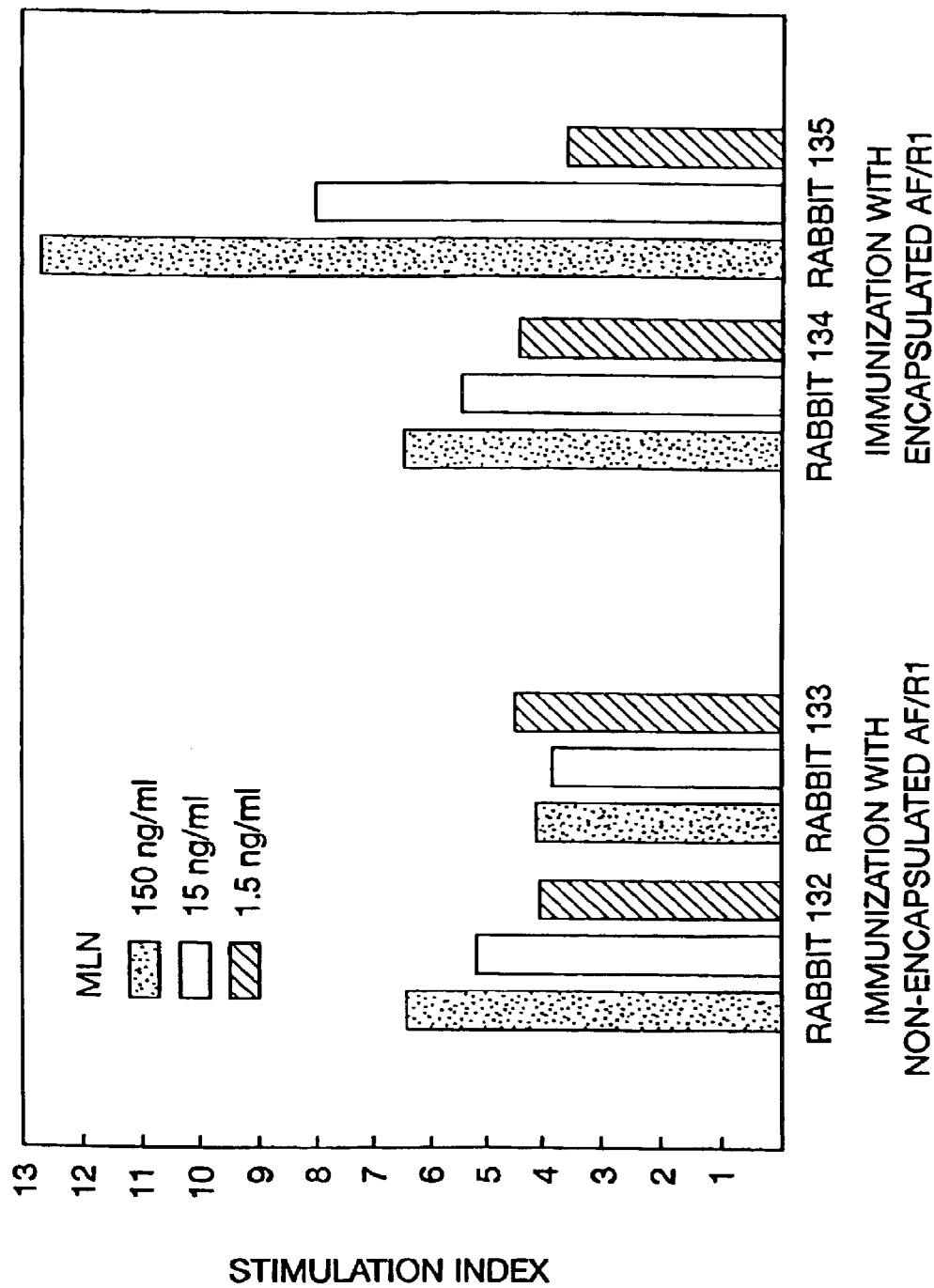

Lane 2  LADTPQLTDVLNSTVQMP    SEQ. ID. NO.: 49 (62-79)
Lane 3  SYRVMTQVHTNDATKKVIV   SEQ. ID. NO.: 50 (42-60)

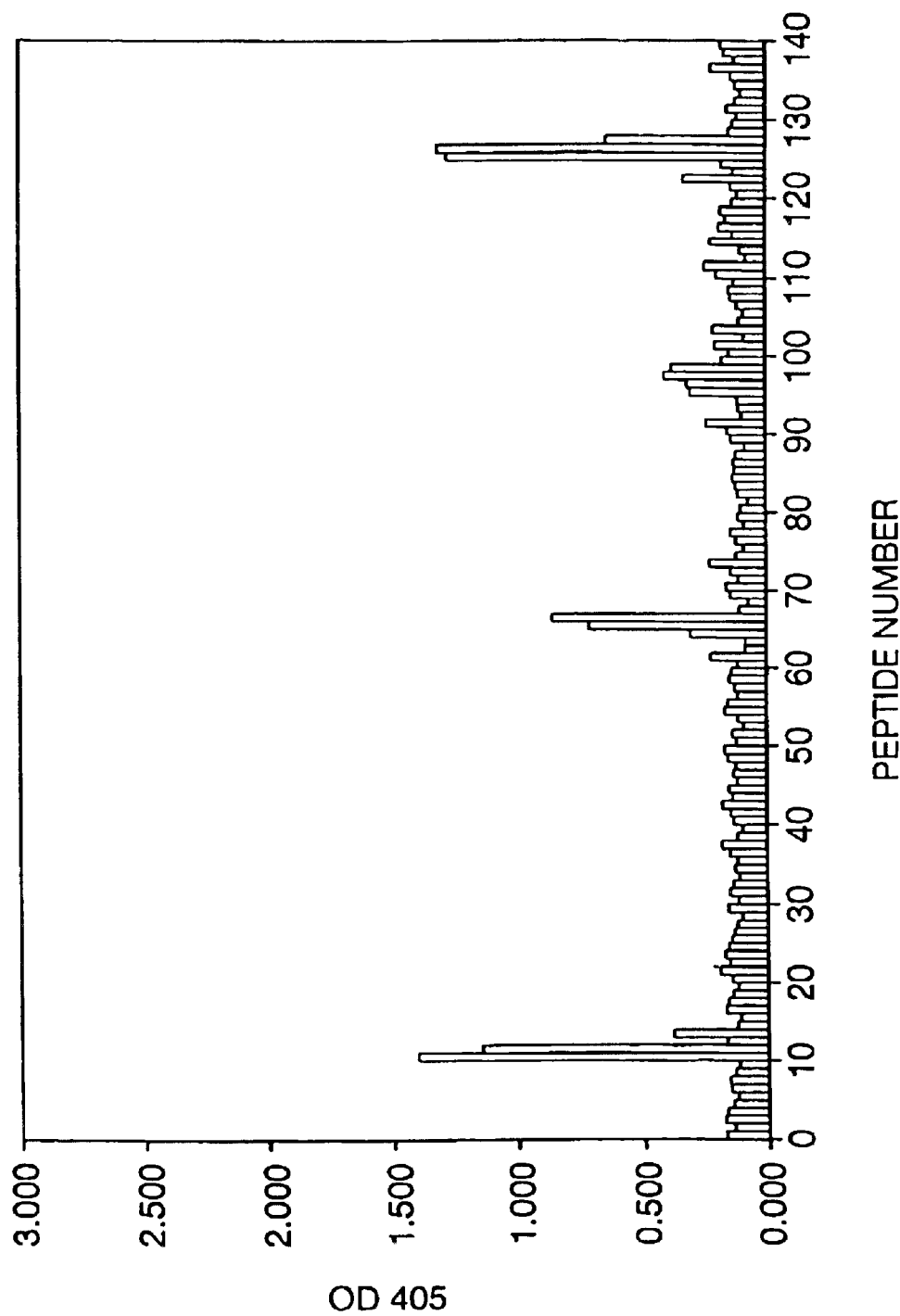

FIG. 26

```
              10              20              30              40              50
2%62   VEKNITVTASVDPVIDLLQADGNALPSAVKLAYSPASKTFESYRVMTQVH
184D   VEKNITVTASVDPVIDLLQADGNALPSAVKLAYSPASKTFESYRVMTQVH
34     VEKNITVTASVDPVIDLLQADGNALPSAVKLAYSPASKTFESYRVMTQVH 60              70              80              90             100
2%62   TNDATKKVIVKLADTPQLTDVNSTVQMPISVSWGGQVLSTTAKEFEAAA
184D   TNDATKKVIVKLADTPQLTDVNSTVQMPISVSWGGQVLSTTAKEFEAAA
34     TNDATKKVIVKLADTPQLTDVNSTVQMPISVSWGGQVLSTTAKEFEAAA 110             120             130             140      147
2%62   LGYSASGVNGVSSQELVISAAPKTAGTAPTAGNYSGVVSLVMTLGS   SEQ.ID.NO.:51
184D   LGYSASGVNGVSSQELVISAAPKTAGTAPTAGNYSGVVSLVMTLGS   SEQ.ID.NO.:52
34     LGYSASGVNGVSSQELVISAAPKTAGTAPTAGNYSGVVSLVMTLGS   SEQ.ID.NO.:53
```

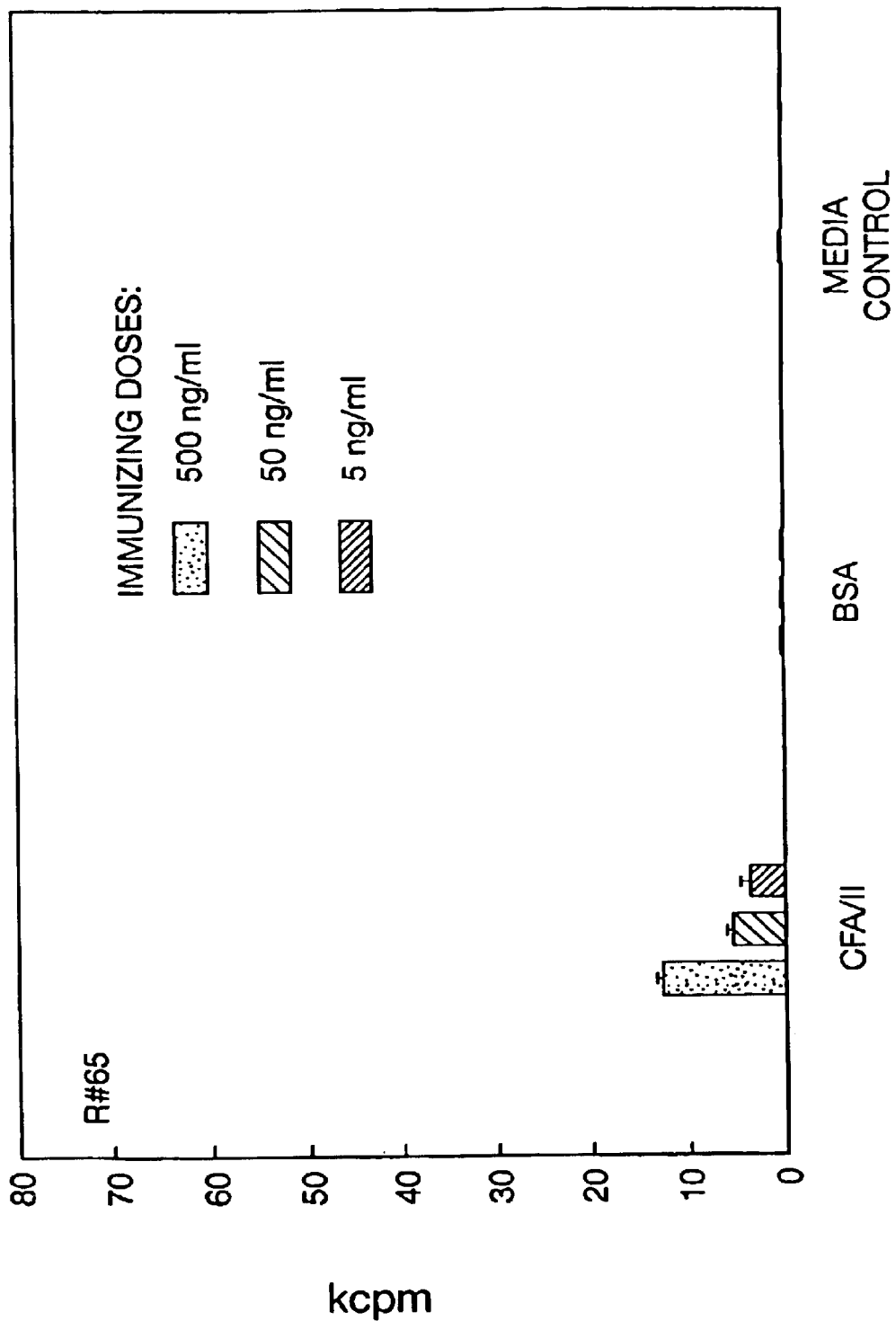

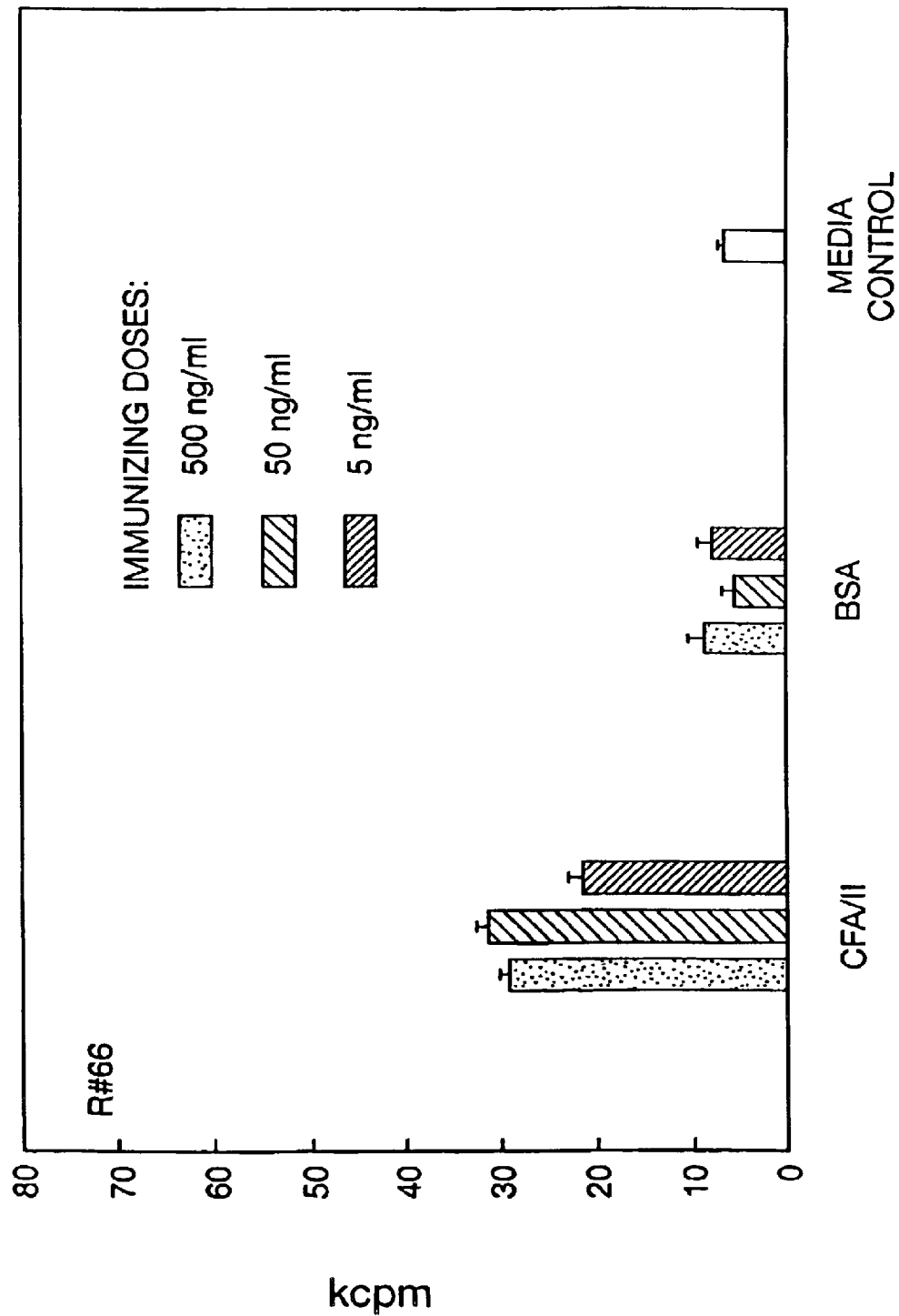

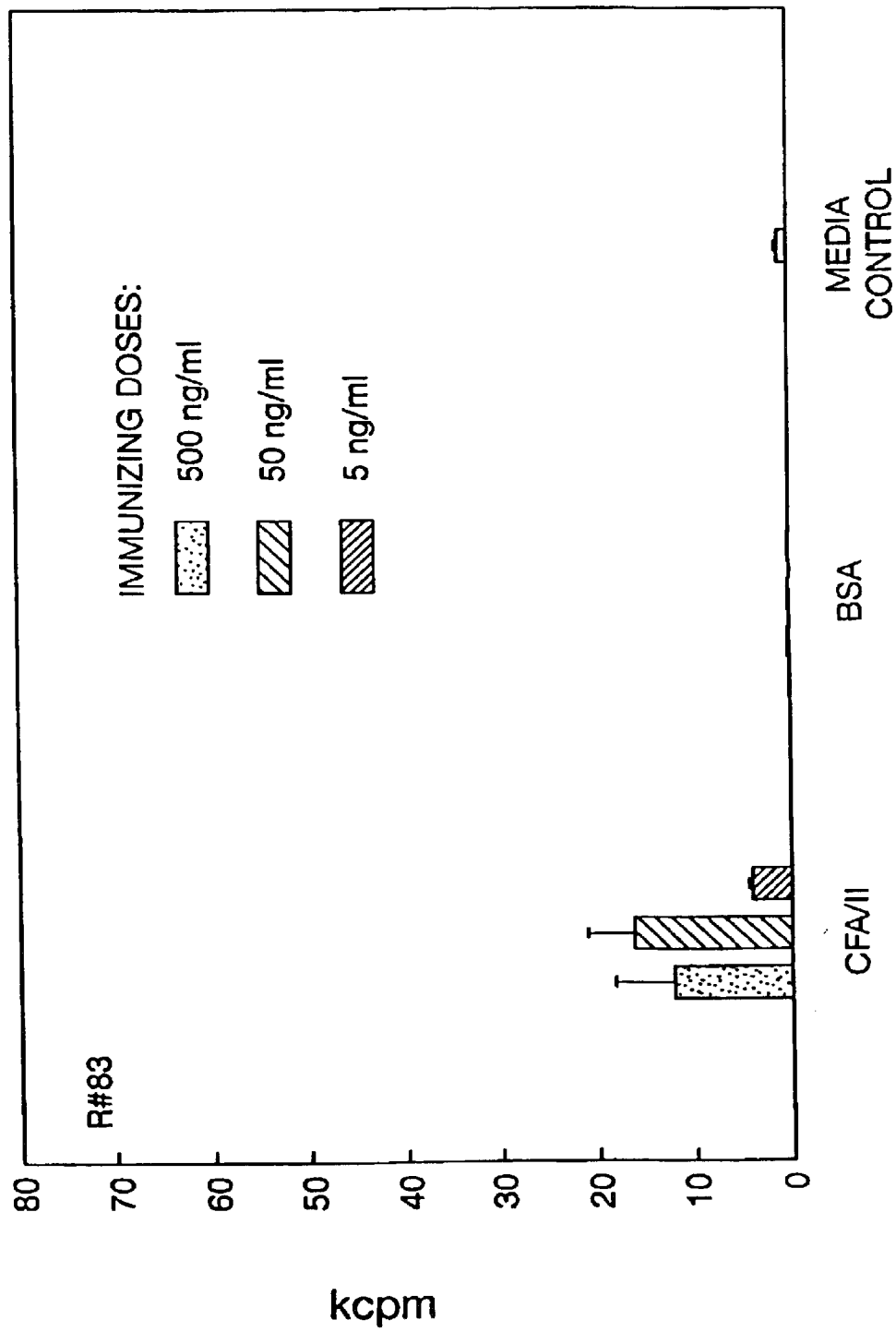

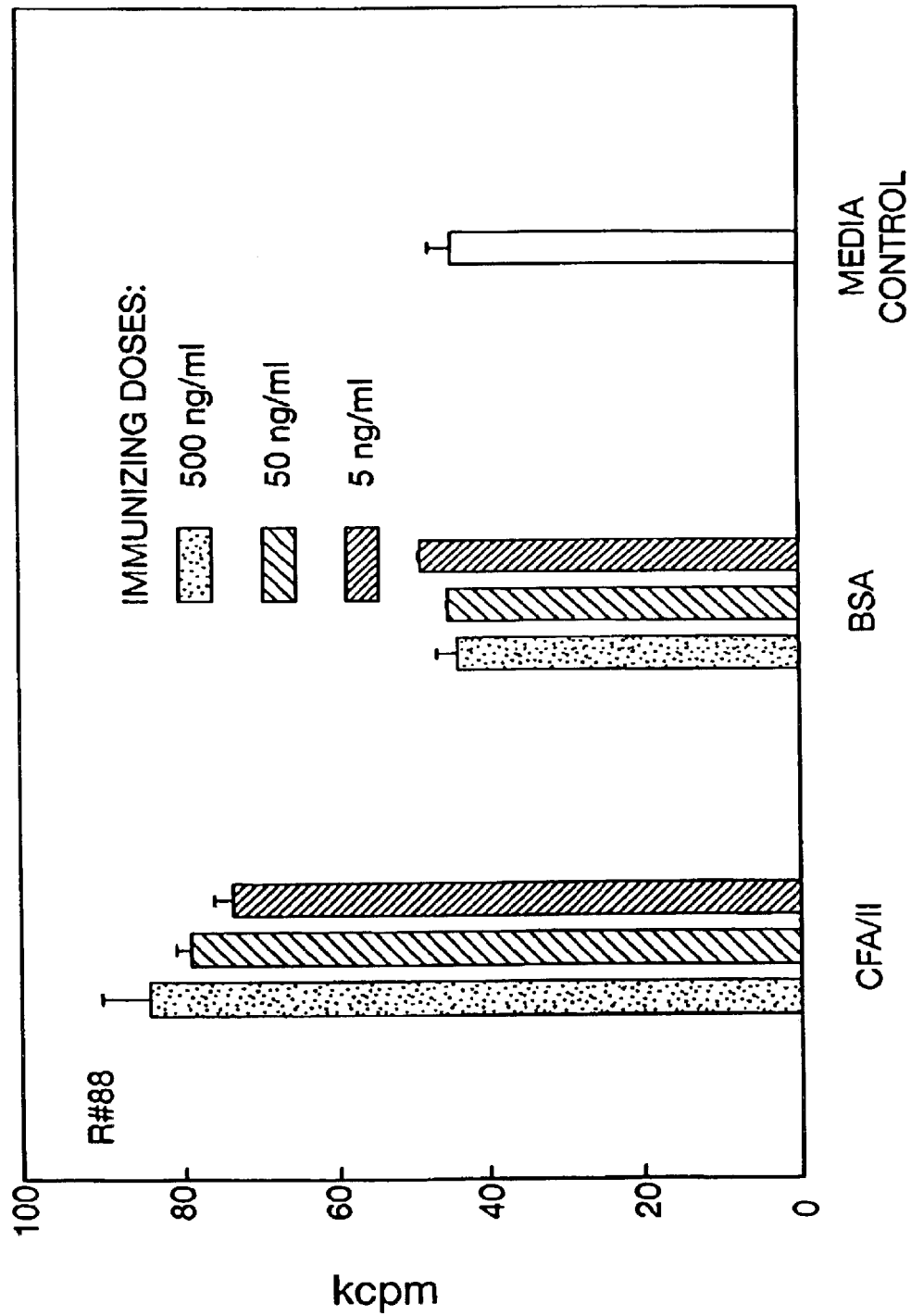

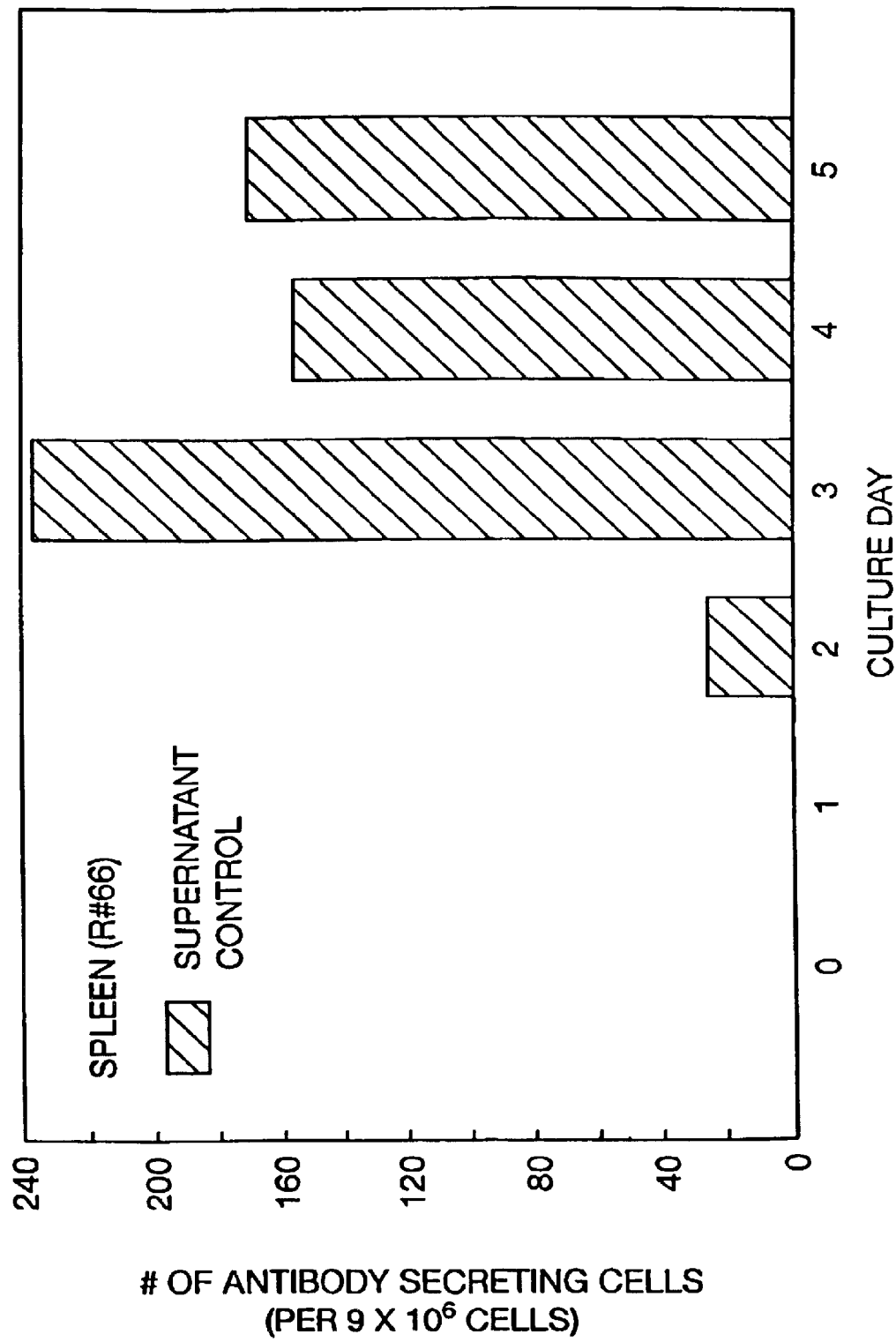

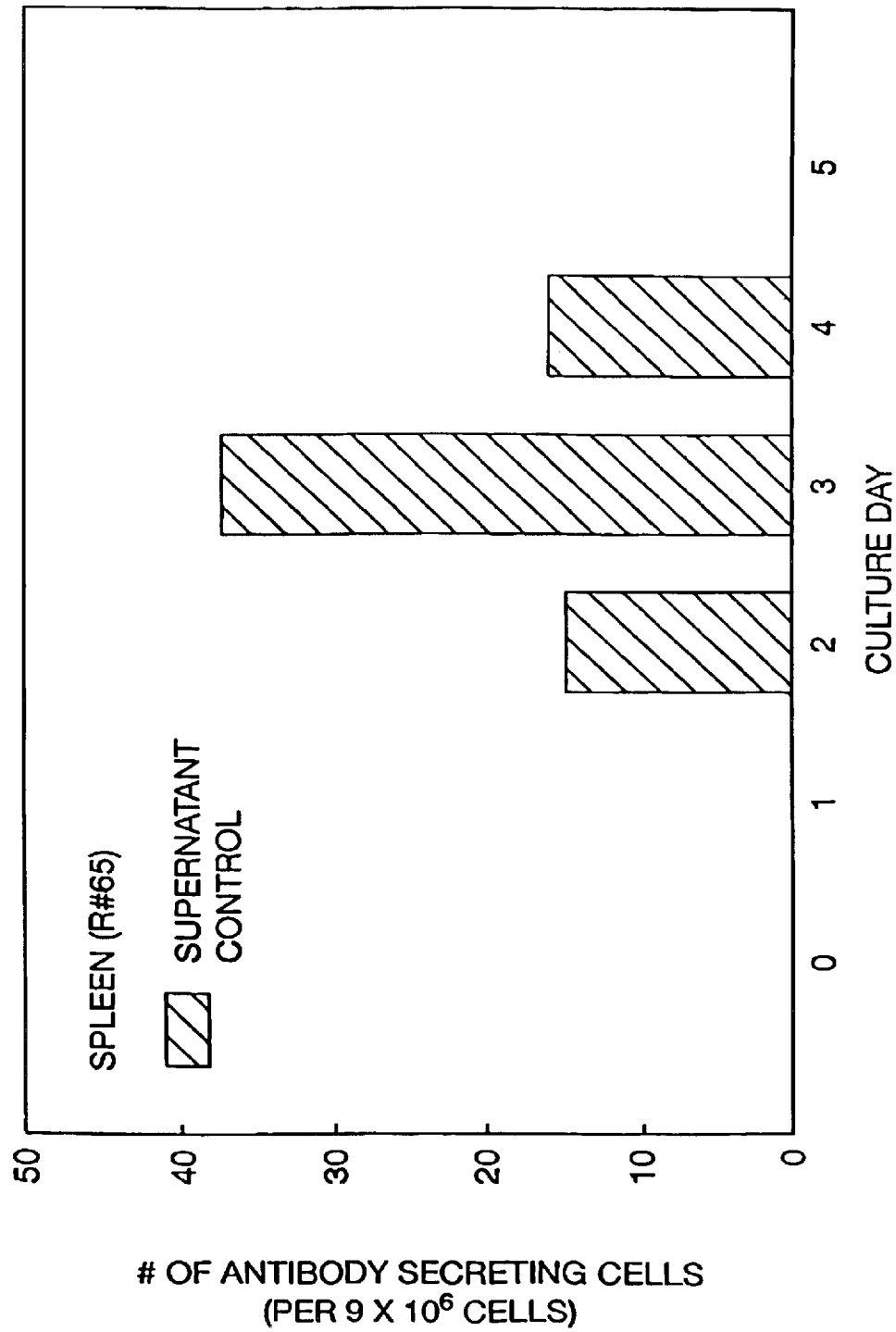

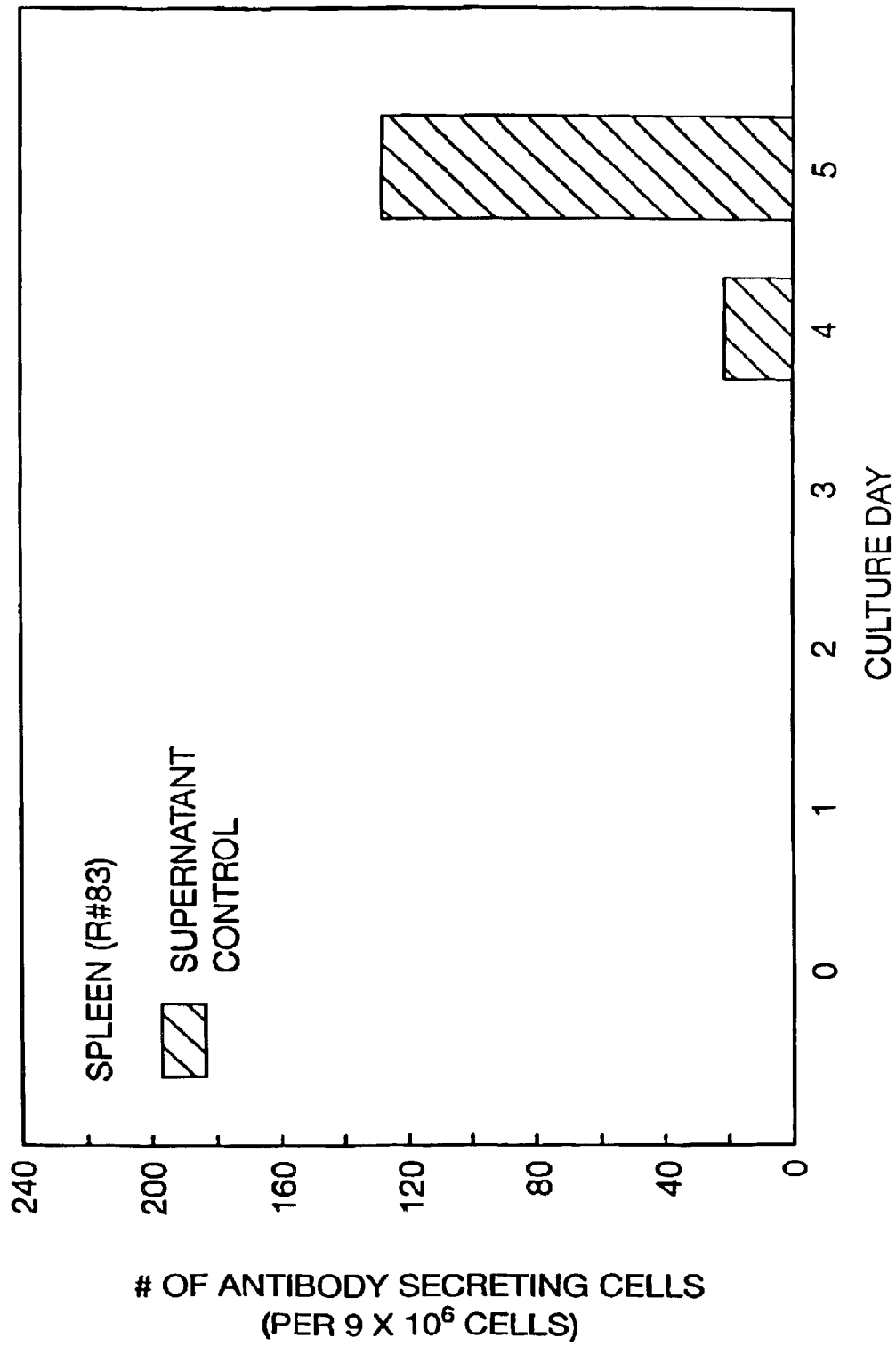

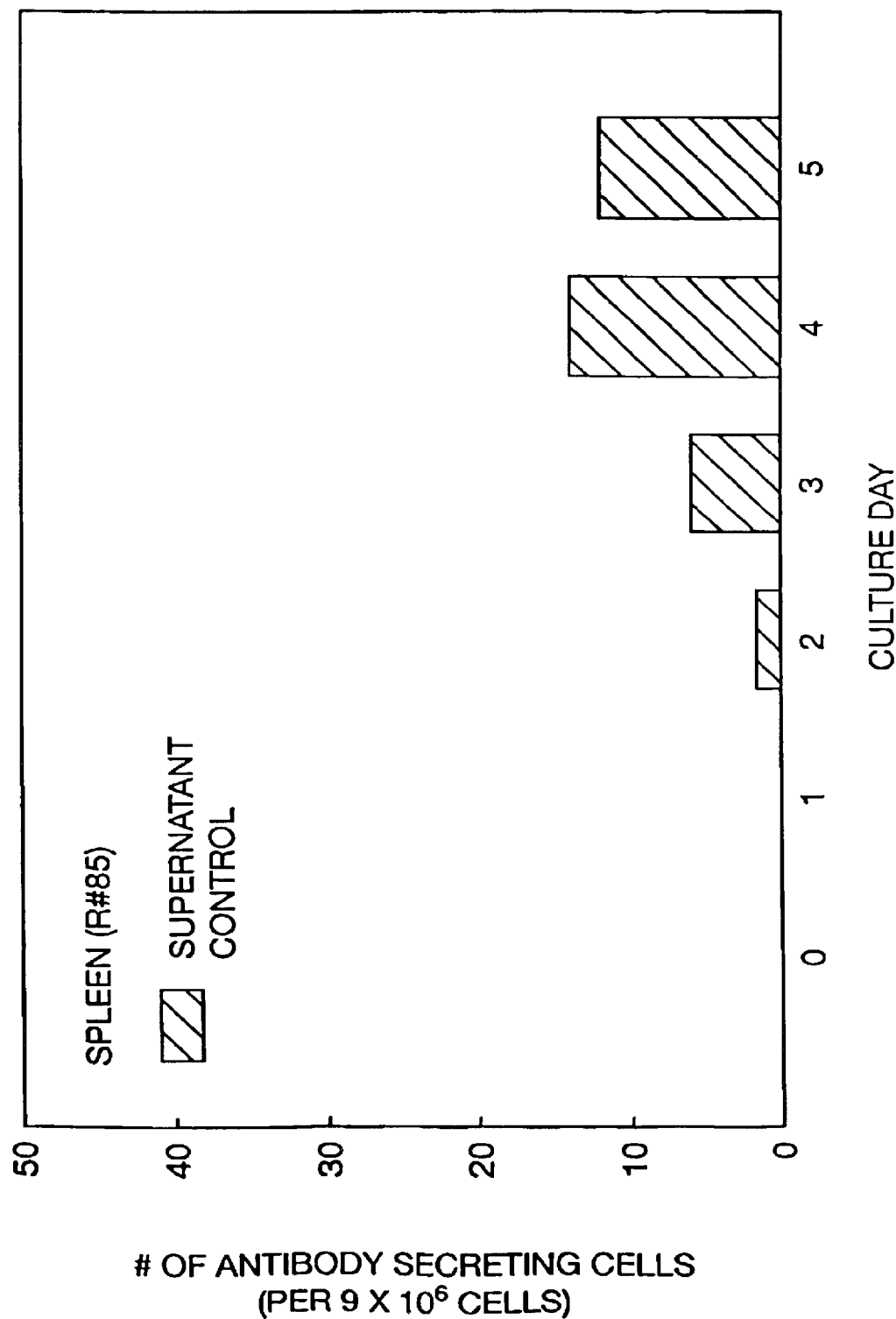

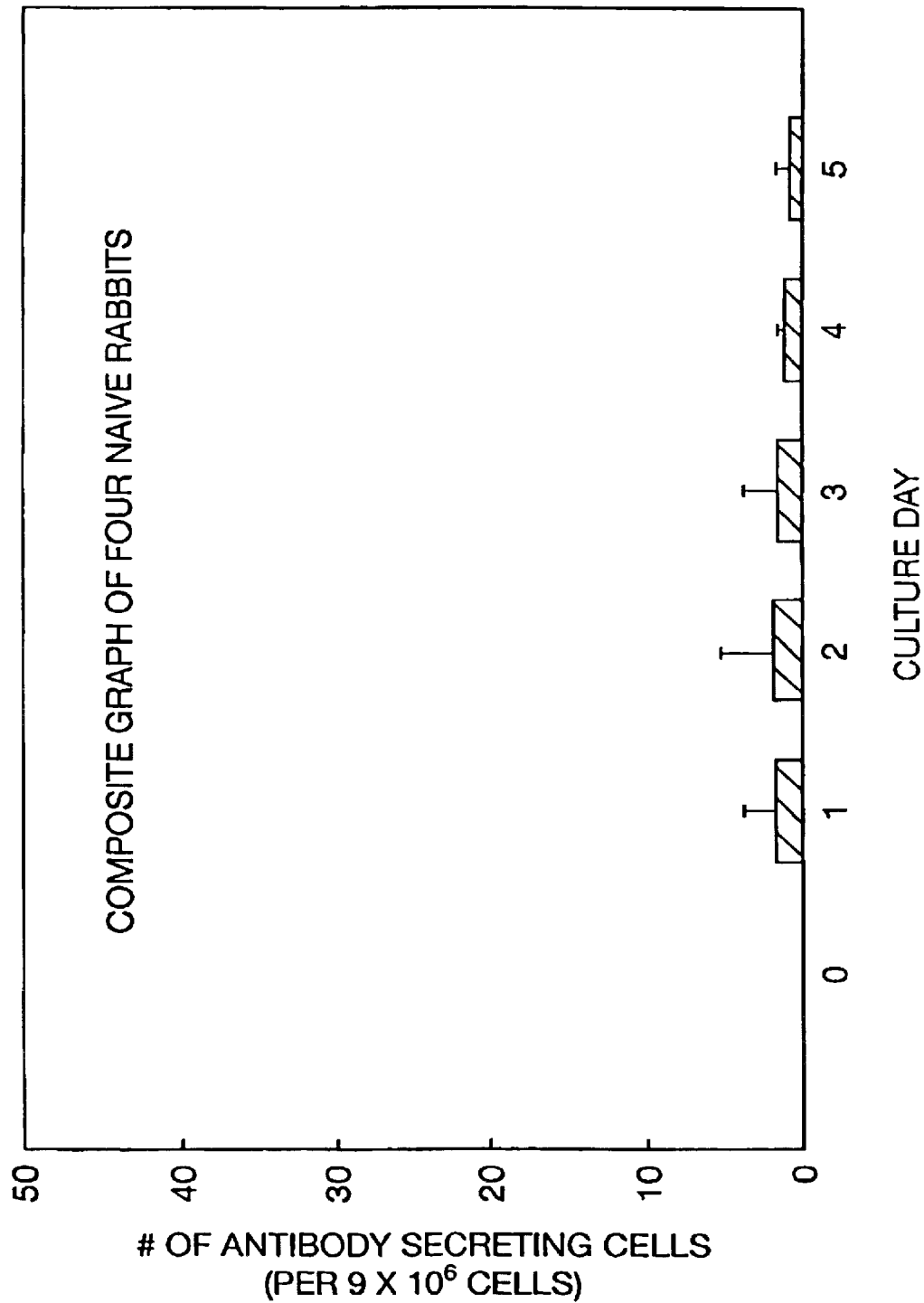

SEQUENCE LISTING

<160> NUMBER OF SEQ ID NOS: 56

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Ser His Ala Lys Arg His His Gly Tyr Lys Arg Lys Phe His Glu
1               5                   10                  15

Lys His His Ser His Arg Gly Tyr
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 2

Lys Arg His His Gly Tyr Lys Arg Lys Phe His Glu Lys His His Ser
 1               5                  10                  15

His Arg Gly Tyr Arg
            20

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Arg His His Gly Tyr Lys Arg Lys Phe His Glu Lys His His Ser
 1               5                  10                  15

Arg

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Lys Phe His Glu Lys His His Ser His Arg Gly Tyr Arg
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Lys Arg His His Gly Tyr Lys Arg Lys Phe His
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Arg His His Gly Tyr Lys Arg Lys Phe
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu His Trp Ser Tyr Gly Leu Arg Pro Gly
 1               5                  10
```

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ile Thr Val Thr Ala Ser Val Asp Pro
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ala Ser Val Asp Pro Val Ile Asp Leu
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Pro Val Ile Asp Leu Leu Gln Ala Asp
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Asp Leu Leu Gln Ala Asp Gly Asn Ala
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Asp Gly Asn Ala Leu Pro Ser Ala Val
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 13

Pro Ser Ala Val Lys Leu Ala Tyr Ser Pro
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Asn Ser Thr Val Gln Met Pro Ile Ser
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Pro Ile Ser Val Ser Trp Gly Gly Gln
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Val Leu Ser Thr Thr Ala Lys Glu Phe
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Gly Thr Ala Pro Thr Ala Gly Asn Tyr
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asn Tyr Ser Gly Val Val Ser Leu Val
 1               5                  10

<210> SEQ ID NO 19
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Asp Ile Thr Val Thr Ala Ser Val
  1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Asp Pro Val Ile Asp Leu Leu Gln Ala Asp
  1               5                  10

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Tyr Ser Pro Ala Ser Lys Thr Phe Lys Thr Phe Glu Ser Tyr Arg
  1               5                  10                  15

Val

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Tyr Ser Pro Ala Ser Lys Thr Phe
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Thr Phe Glu Ser Tyr Arg Val
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Pro Gln Leu Thr Asp Val Leu Asn Ser
  1               5
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ala Lys Glu Phe Glu Ala Ala Ala
  1               5
```

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Lys Thr Ala Gly Thr Ala Pro Thr
  1               5
```

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gly Thr Ala Pro Thr Ala Gly Asn Tyr Ser
  1               5                  10
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Lys Thr Ala Gly Thr Ala Pro Thr Ala Gly Asn Tyr Ser
  1               5                  10
```

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Lys Asn Ile Thr Val Thr Ala Ser Val Asp Pro
  1               5                  10
```

<210> SEQ ID NO 30
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 30

Thr Ala Ser Val Asp Pro Val Ile Asp Leu Leu Gln Ala Asp
 1               5                  10

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Asn Ala Leu Pro Ser Ala Val
 1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Asp Pro Val Ile Asp Leu Leu Gln Ala Asp
 1               5                  10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Lys Asn Gly Thr Val Thr Tyr Ala His Glu Thr Asn Asn Ser Ala
 1               5                  10                  15

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Asn Ile Thr Val Thr Ala Ser Val Asp Pro
 1               5                  10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ala Ser Val Asp Pro Val Ile Asp Leu Leu Gln Ala Asp
 1               5                  10
```

```
<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Asp Pro Val Ile Asp Leu Leu Gln Ala Asp
 1               5                  10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Ser Val Asp Pro Val Ile Asp Leu Leu Gln Ala Asp
 1               5                  10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Asn Ala Gly Thr Asp Ile Gly Ala Asn Lys Ser Phe Thr Leu Lys
 1               5                  10                  15

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Asp Pro Val Ile Asp Leu Leu Gln
 1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Glu Phe Glu Ala Ala Ala
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Gly Pro Ala Pro Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Gln Leu Thr Asp Val Leu Asn
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Asn Ala Leu Pro Ser Ala Val
1               5

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Glu Ser Tyr Arg Val Met Thr Gln Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Tyr Ser Gly Val Val Ser Leu Val Met
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Asp Pro Val Ile Asp Leu Leu Gln Ala Asp
1               5                   10

<210> SEQ ID NO 47
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 47

Thr Ala Ser Val Asp Pro Val Ile Asp Leu Leu Gln Ala Asp
 1               5                  10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Asp Pro Val Ile Asp Leu Leu Gln Ala Asp
 1               5                  10

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Ala Asp Thr Pro Gln Leu Thr Asp Val Leu Asn Ser Thr Val Gln
 1               5                  10                  15

Met Pro

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Tyr Arg Val Met Thr Gln Val His Thr Asn Asp Ala Thr Lys Lys
 1               5                  10                  15

Val Ile Val

<210> SEQ ID NO 51
<211> LENGTH: 147
<212> TYPE: PRT
<213> ORGANISM: Escherichia coli

<400> SEQUENCE: 51

Val Glu Lys Asn Ile Thr Val Thr Ala Ser Val Asp Pro Val Ile Asp
 1               5                  10                  15

Leu Leu Gln Ala Asp Gly Asn Ala Leu Pro Ser Ala Val Lys Leu Ala
                20                  25                  30

Tyr Ser Pro Ala Ser Lys Thr Phe Glu Ser Tyr Arg Val Met Thr Gln
            35                  40                  45

Val His Thr Asn Asp Ala Thr Lys Lys Val Ile Val Lys Leu Ala Asp
        50                  55                  60

Thr Pro Gln Leu Thr Asp Val Leu Asn Ser Thr Val Gln Met Pro Ile
 65                  70                  75                  80
```

```
Ser Val Ser Trp Gly Gly Gln Val Leu Ser Thr Thr Ala Lys Glu Phe
            85                  90                  95

Glu Ala Ala Ala Leu Gly Tyr Ser Ala Ser Gly Val Asn Gly Val Ser
                100                 105                 110

Ser Ser Gln Glu Leu Val Ile Ser Ala Ala Pro Lys Thr Ala Gly Thr
            115                 120                 125

Ala Pro Thr Ala Gly Asn Tyr Ser Gly Val Val Ser Leu Val Met Thr
            130                 135                 140

Leu Gly Ser
145

<210> SEQ ID NO 52
<211> LENGTH: 147
<212> TYPE: PRT
<213> ORGANISM: Escherichia coli

<400> SEQUENCE: 52

Val Glu Lys Asn Ile Thr Val Thr Ala Ser Val Asp Pro Val Ile Asp
  1               5                  10                  15

Leu Leu Gln Ala Asp Gly Asn Ala Leu Pro Ser Ala Val Lys Leu Ala
                 20                  25                  30

Tyr Ser Pro Ala Ser Lys Thr Phe Glu Ser Tyr Arg Val Met Thr Gln
             35                  40                  45

Val His Thr Asn Asp Ala Thr Lys Lys Val Ile Val Lys Leu Ala Asp
         50                  55                  60

Thr Pro Gln Leu Thr Asp Val Leu Asn Ser Thr Val Gln Met Pro Ile
 65                  70                  75                  80

Ser Val Ser Trp Gly Gly Gln Val Leu Ser Thr Thr Ala Lys Glu Phe
                 85                  90                  95

Glu Ala Ala Ala Leu Gly Tyr Ser Ala Ser Gly Val Asn Gly Val Ser
                100                 105                 110

Ser Ser Gln Glu Leu Val Ile Ser Ala Ala Pro Lys Thr Ala Gly Thr
            115                 120                 125

Ala Pro Thr Ala Gly Asn Tyr Ser Gly Val Val Ser Leu Val Met Thr
            130                 135                 140

Leu Gly Ser
145

<210> SEQ ID NO 53
<211> LENGTH: 147
<212> TYPE: PRT
<213> ORGANISM: Escherichia coli

<400> SEQUENCE: 53

Val Glu Lys Asn Ile Thr Val Thr Ala Ser Val Asp Pro Val Ile Asp
  1               5                  10                  15

Leu Leu Gln Ala Asp Gly Asn Ala Leu Pro Ser Ala Val Lys Leu Ala
                 20                  25                  30

Tyr Ser Pro Ala Ser Lys Thr Phe Glu Ser Tyr Arg Val Met Thr Gln
             35                  40                  45

Val His Thr Asn Asp Ala Thr Lys Lys Val Ile Val Lys Leu Ala Asp
         50                  55                  60

Thr Pro Gln Leu Thr Asp Val Leu Asn Ser Thr Val Gln Met Pro Ile
 65                  70                  75                  80

Ser Val Ser Trp Gly Gly Gln Val Leu Ser Thr Thr Ala Lys Glu Phe
                 85                  90                  95
```

```
-continued

Glu Ala Ala Ala Leu Gly Tyr Ser Ala Ser Gly Val Asn Gly Val Ser
            100                 105                 110

Ser Ser Gln Glu Leu Val Ile Ser Ala Ala Pro Lys Thr Ala Gly Thr
        115                 120                 125

Ala Pro Thr Ala Gly Asn Tyr Ser Gly Val Val Ser Leu Val Met Thr
    130                 135                 140

Leu Gly Ser
145

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Gly Thr Ala Pro Thr Ala Gly Asn Thr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gly Thr Ala Pro Thr Ala Gly Asn Tyr Ser
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Thr Ala Gly Thr Ala Pro Thr Ala Gly Asn Thr Ser
1               5                   10
```

THERAPEUTIC TREATMENT AND PREVENTION OF INFECTIONS WITH A BIOACTIVE MATERIAL(S) ENCAPUSLATED WITHIN A BIODEGRADABLE-BIO-COMPATABLE POLYMERIC MATRIX

II. CROSS REFERENCE

This application is a continuation-in-part of U.S. patent application Ser. No. 08/920,326 filed Aug. 21, 1997, now U.S. Pat. No. 6,447,796 which in turn is a continuation in part of 08/896,197 filed Jul. 17, 1997, now abandoned which in turn is a continuation of U.S. patent application Ser. No. 08/446,149 filed May 22, 1995, now abandoned and a continuation in part of U.S. patent application Ser. No. 08/788,734 filed Jan. 23, 1997, now U.S. Pat. No. 5,892,337 which in turn is a continuation in part of Ser. No. 08/675,895 filed Jul. 5, 1996, now U.S. Pat. No. 6,217,911 which in turn is a continuation in part of U.S. patent application Ser. No. 08/598,874 filed Feb. 9, 1996, now U.S. Pat. No. 5,762,965 which in turn is a continuation in part of U.S. patent application Ser. No. 08/698,896, filed Aug. 16, 1996, now U.S. Pat. No. 5,705,197 which in turn is a continuation-in-part of U.S. patent application Ser. No. 08/590,973 filed Jan. 24, 1996, now abandoned which in turn is a continuation in part of U.S. patent application Ser. No. 08/446,148 filed May 22, 1995, now U.S. Pat. No. 6,410,056.

I. GOVERNMENT INTEREST

The invention described herein may be manufactured, used and licensed by or for the Government for Governmental purposes without the payment to use of any royalties thereon.

This invention relates to compositions comprising active core materials(s) such as biologically active agent(s), drug(s) or substance(s) encapsulated within an end-capped or a blend of uncapped and end-capped biodegradable-biocompatible poly(lactide/glycolide) polymeric matrix useful for the effective prevention or treatment of bacterial, viral, fungal, or parasitic infections, and combinations thereof. In the areas of general and orthopedic surgery, and the treatment of patients with infectious or chronic disease conditions, this invention will be especially useful to physicians, dentists and veternarians.

IV. BACKGROUND OF THE INVENTION

Wounds characterized by the presence of infection, devitalized tissue, and foreign-body contaminants have high infection rates and are difficult to treat.

To prevent infection, in bone and soft tissues systemic antibiotics must be administered within 4 hours after wounding when circulation is optimal. This has been discussed by J. F. Burke in the article entitled "The Effective Period of Preventive Antibiotic Action in Experimental Incisions and Dermal Lesions", Surgery, Vol. 50, Page 161 (1961). If treatment of bacterial infections is delayed, a milieu for bacterial growth develops which results in complications associated with established infections. (G. Rodeheaver et al., "Proteolytic Enzymes as Adjucts to Antibiotic Prophylaxis of Surgical Wounds", American Journal of Surgery, Vol. 127, Page. 564 (1974)). Once infections are established it becomes difficult to systemically administer certain antibiotics for extended periods of time at levels that are safe and effective at the wound site. Unless administered locally, drugs are distributed throughout the body, and the amount of drug hitting its target is only a small part of the total dose. This ineffective use of the drug is compounded in the trauma patient by hypoglycemic shock, which results in a decreased vascular flow to tissues. (L. E. Gelin et al., "Trauma Workshop Report: Shockrheology and Oxygen Transport", Journal Trauma. Bol. 10, Page 1078 (1970)).

Additionally, infections caused by multiple-antibiotic resistant bacterial are on the up-swing and we are on the verge of a potential world-wide medical disaster. According to the Centers for Disease Control, 13,300 patients died in U.S. hospitals in 1992 from infections caused by antibiotic-resistant bacterial. Methicillin-resistant *S. aureus* (MRSA) is rapidly emerging as the "pathogen of the 90's".

a. Some major teaching hospitals in the U.S. report that up to 40% of strains of *S. aureus* isolated from patients are resistant to methicillin. Many of these MRSA strains are susceptible only to a single antibiotic (vancomycin).

b. Should MRSA also develop resistance to vancomycin, the mortality rate among patients who develop MRSA infections could approach 80%, thereby increasing the threat of this infectious killer.

Moreover, Vancomycin resistance is on the up-swing:

a. 20% of Enterococci are now resistant to vancomycin b. In 1989, only one hospital in New York City reported vancomycin-resistant Enterococci. By 1991, the number of hospitals reporting vancomycin resistance rose to 38.

c. transfer of vancomycin-resistant gene (via plasmid) has been shown experimentally between Enterococcus and *S. aureus*.

Many major pharmaceutical companies around the world have either completely eliminated or significantly reduced their research and development programs in the area of antibiotic research. According to a 1994 report by the Rockefeller University Workshop in Multiple Antibiotic Resistant Bacteria, we are on the verge of a "medical disaster that would return physicians back to the pre-penicillin days when even small infections could turn lethal due to the lack of effective drugs."

Despite recent advances in antimicrobial therapy and improved surgical techniques, osteomyelitis (hard tissue or bone infection) is still a source of morbidity often necessitating lengthy hospitalization. The failure of patients with chronic osteomyelitis to response uniformly to conventional treatment has prompted the search for more effective treatment modalities. Local antibiotic therapy with gentamicin-impregnated poly(methylmethacrylate) (PMMA) bead chains (SEPTOPAL™, E. Merck, West Germany) has been utilized in Germany for the treatment of osteomyelitis for the past decade and has been reported to be efficacious inseveral clinical studies. The beads are implanted into the bone at the time of surgical intervention where they provide significantly higher concentrations of gentamicin than could otherwise be achieved via systemic administration. Serum gentamicin levels, on the other hand, remain extremely low thereby significantly reducing the potential for nephro- and ototoxicity that occurs in some patients receiving gentamicin systemically.

Since SEPTOPAL™ is not currently approved by the Food and Drug Administration for use in the United States, some orthopedic surgeons in this country are fabricating their own "physician-made beads" for the treatment of chronic osteomyelitis. A major disadvantage of the beads, however, is that because the PMMA is not biodegradable it represents a foreign body and should be removed at about 2-weeks postimplantation thereby necessitating in some cases an additional surgical procedure. A biodegradable-biocompatable, antibiotic carrier, on the other hand, would eliminate the need for this additional surgical procedure and may potentially reduce both the duration as well as the cost of hospitalization.

The concept of local, sustained release of antibiotics into infected bone is described in recent literature wherein antibiotic-impregnated PMMA macrobeads are used to treat chronic osteomyelitis. The technique as currently used involves mixing gentamicin with poly(methylmethacrylate) bone cement and molding the mixture into beads that are 7 mm in diameter. These beads are then locally implanted in the infected site at the time of surgical debridement to serve as treatment. There are, however, significant problems with this method. These include: 1) initially, large amounts of antibiotics diffuse from the cement but with time the amount of antibiotic leaving the cement gradually decreases to subtherapeutic levels; 2) the bioactivity of the antibiotic gradually decreases; 3) poly(methylmethacrylate) has been shown to decrease the ability of polymorphonuclear leukocytes to phagocytize and kill bacteria; 4) the beads do not biodegrade and usually must be surgically removed; and 5) the exothermic reaction that occurs during curing of poly(methymethacrylate) limits the method to the incorporation of only thermostable antibiotics (primarly aminoglycosides). Nevertheless, preliminary clinical trials using these beads indicate that they are equivalent in efficacy to longer term (4–6 weeks) administration of systemic antibiotics.

In many instances, infectious agents have their first contact with the host at a mucosal surface; therefore, mucosal protective immune mechanisms are of primary importance in preventing these agents from colonizing or penetrating the mucosal surface. Numerous studies have demonstrated that a protective mucosal immune response can best be initiated by introduction of the antigen at the mucosal surface, and parenteral immunization is not an effective method to induce mucosal immunity. Antigen taken up by the gut-associated lymphoid tissue (GALT), primarily by the Peyer's patches in mice, stimulates T helper cell (Th) to assist in IgA B cell responses or stimulates T suppressor cells (Ts) to mediate the unresponsiveness of oral tolerance. Particulate antigen appears to shift the response towards the (Th) whereas soluble antigens favor a response by the (Ts). Although studies have demonstrated that oral immunization does induce an intestinal mucosal immune response, large doses of antigen are usually required to achieve sufficient local concentrations in the Peyer's patches. Unprotected protein antigens may be degraded or may complex with secretory IgA in the intestinal lumen.

In the process of vaccination, medical science uses the body's innate ability to protect itself against invading agents by immunizing the body with antigens that will not cause the disease but will stimulate the formation of antibodies that will protect against the disease. For example, dead organisms are injected to protect against bacterial diseases such as typhoid fever and whooping cough, toxins are injected to protect against viral diseases such as poliomyelitis and measles.

It is not always possible, however, to stimulate antibody formation merely by injecting the foreign agent. The vaccine preparation must be immunogenic that is, it must be able to induce an immune response. Certain agents such as tetanus toxoid are innately immunogenic, and may be administered in vaccines without modification. Other importantagents are not immunogenic, however, and must be converted into immunogenic molecules before they can induce an immune response.

The immune response is a complex series of reactions that can generally be described as follows:
1. the antigen enters the body and encounters antigen-presenting cells which process the antigen and retain fragments of the antigen on their surfaces;
2. the antigen fragment retained on the antigen presenting cells are recognized by T cells that provide help to B cells; and
3. the B cells are stimulated to proliferate and divide into antibody forming cells that secrete antibody against the antigen.

Most antigens only elicit antibiodies with assistance from the T cells and, hence, are known as T-dependent (TD). These antigens, such as proteins, can be processed by antigen presenting cells and thus activate T cells in the process described above. Examples of such T-dependent antigens are tetanus and diphtheria toxoids.

Some antigens, such as polysaccharides, cannot be properly processed by antigen presenting cells and are not recognized by T cells. These antigens do not require T cell assistance to elicit antibody formation but can activate B cells directly and, hence, are known as T-independent antigens (TI). Such T-independent antigens include $H\ influenzae$ type by polyribosyl-ribitol-phosphate and pneumococcal capsular polysaccharides.

T-dependent antigens differ from T-independent antigens in a number of ways. Most notably, the antigens differ in their need to be administered in conjunction with an adjuvant (a compound that will nonspecifically enhance the immune response). The vast majority of soluble T-dependent antigens elicit only low level antibody responses unless they are administered with an adjuvant. It is for this reason that the standard DPT vaccine (diptheria, pertussis, tetanus) is administered with the adjuvant alum. Insolubilization of TD antigens into an aggregated form can also enhance their immunogenicity, even in the absence of an adjuvant. Golub E S and W O Weigle, J. Immunol. 102:389, 1969). In contrast, T-independent antigens can stimulate antibody responses when administered in the absence of an adjuvant, but the response is generally of lower magnitude and shorter duration.

Four other differences between T-independent and T-dependent antigens are:
  a) T-dependent antigens can prime an immune response so that a memory response can be elicited upon secondary challenge with the same antigen. Memory or secondary responses are stimulated very rapidly and attain significantly higher titers of antibody that are seen in primary responses. T-independent antigens are unable to prime the immune system for secondary responsiveness.
  b) The affinity of the antibody for antigen increases with time after immunization with T-dependent but not T-independent antigens.
  c) T-dependent antigens stimulate an immature or neonatal immune system more effectively than T-independent antigens.
  d) T-dependent antigens usually stimulate IgM, IgG1, IgG2a, and IgE antibodies, while T-independent antigens stimulate IgM, IgG1, IgG2b, and IgG3 antibodies.

These characteristics of T-dependent vs. T-independent antigens provide both distinct advantages and disadvantages in their use as effective vaccines. T-dependent antigens can stimulate primary and secondary responses which are long-lived in both adult and in neonatal immune systems, but must frequently be administered with adjuvants. Thus, vaccines have been prepared using only an antigen, such as diptheria or tetanus toxoid, but such vaccines may require the use of adjuvants, such as alum for stimulating optimal responses. Adjuvants are often associated with toxicity and have been shown to nonspecifically stimulate the immune system, thus inducing antibodies of specificities that may be undesirable.

Another disadvantage associated with T-dependent antigens is that very small proteins such as peptides, are rarely immunogenic, even when administered with adjuvants. This is especially unfortunate because many synthetic peptides are available today that have been carefully synthesized to represent the primary antigenic determinants of various pathogens, and would otherwise make very specific and highly effective vaccines.

In contrast, T-independent antigens, such as polysaccharides, are able to stimulate immune responses in the absence of adjuvants. Unfortunately, however, such T-independent antigens cannot stimulate high level or prolonged antibody responses. An even greater disadvantage is their inability to stimulate an immature or B cell defective immune system (Mond J. J., Immunological Reviews 64:99, 1982) Mosier D E, et al., J. Immunol. 119:1874, 1977). Thus, the immune response to both T-independent and T-dependent antigens is not satisfactory for many applications.

With respect to T-independent antigens, it is critical to provide protective immunity against such antigens to children, especially against polysaccharides such as *H. influenzae* and *S. pneumoniae*. With respect to T-dependent antigens, it is critical to develop vaccines based on synthetic peptides that represent the primary antigenic determinants of various pathogens.

One approach to enhance the immune response to T-independent antigens involves conjugating polysaccharides such *H. influenzae* PRP (Cruse J. M., Lewis R. E. Jr. ed., Conjugate vaccines in Contributions to Microbiology and Immunology, vol. 10, 1989) or oligosaccharide antigens (Anderson P W, et al., J. Immunol. 142:2464, 1989) to a single T-dependent antigen such as tetanus or diptheria toxoid. Recruitment of T cell help in this way has been shown to provide enhanced immunity to many infants that have been immunized. Unfortunately, only low level antibody titers are elicited, and only some infants response to initial immunizations. Thus, several immunizations are required and protective immunity is often delayed for months. Moreover, multiple visits to receive immunization may also be difficult for families that live distant from medical facilities (especially in underdeveloped countries). Finally, babies less than 2 months of age may mount little or no antibody response even after repeated immunization.

One possible approach to overcoming these problems is to homogeneously disperse the antigen of interest within the polymeric matrix of appropriately sized biodegradable-biocompatable microspheres that are specifically taken up by GALT. Eldridge et al. have used a murine model to show that orally-administered 1–10 micrometer microspheres consisting of polymerized lactide and glycolide, (the same materials used in resorable sutures), were readily taken up into Peyer's patches, and the 1–5 micrometer size were rapidly phagocytized by macrophages. Microspheres that were 5–10 micrometers (microns) remained in the Peyer's patch for up to 35 days, where as those less than 5 micrometers disseminated to the mesenteric lymph node (MLN) and spleen within migrating MAC-1+ cells. Moreover, the levels of specific serum and secretory antibody to staphyloccal enterotoxin B toxoid and inactivated influenza A virus were enhanced and remained elevated longer in animals which were immunized orally with microencapsulated antigen as compared to animals which received equal doses of non-encapsulated antigen. These data indicate that microencapsulation of an antigen given orally may enhance the mucosal immune response against enteric pathogens. AF/R1 pili mediate the species-specific binding of *E. coli* RDEC-1 with mucosal glycoproteins in the small intestine of rabbits and are therefore an important virulence factor. Although AF/R1 pili are not essential for *E. coli* RDEC-1 to produce enteropathogenic disease, expression of AF/R1 to produce enteropathogenic disease, expression of AF/R1 promotes a more severe disease. Anti-AF/R1 antibodies have been shown to inhibit the attachment of RDEC-1 to the intestinal mucosa and prevent RDEC-1 disease in rabbits. The amino acid sequence of the AF/R1 pilin subunit has recently been determined, but specific antigenic determinants within AF/R1 have not been identified.

In the current study we have used these theoretical criteria to predict probable T or B cell epitopes from the amino acid sequence of AF/R1. Four different 16 amino acid peptides that include the predicted epitopes have been synthesized: AF/R1 40–55 as a B cell epitope, 79–94 as a T cell epitope, 108–123 as a T and B cell epitope, and AF/R1 40–47/79–86 as a hybrid of the first eight amino acids from the predicted B cell epitope and the T cell epitope. We have used these peptides as well as the native protein to stimulate the in vitro proliferation of lymphocytes taken from the Peyer's patch, MLN, and spleen of rabbits which have received introduodenal priming with microencapsulated or non-encapsulated AF/R1. Our results demonstrate the microencapsulation of AF/R1 potentiates the cellular immune response at the level of the Peyer's patch, thus enhancing in vitro lymphocyte proliferation to both the native protein and its linear peptide antigens. CFA/I pili, rigid thread-like structures which are composed of repeating pilin subunits of 147 amino acid found on serogroups 015, 025, 078, and 0128 of enterotoxigenic *E. coli* (ETEC) (1–4, 18). CFA/I promotes mannose resistant attachment to human brush borders (5); therefore, a vaccine that established immunity against this protein may prevent the attachment to host tissues and subsequent disease. In addition, because the CFA/I subunit shares N-terminal amino acid sequence homology with CS1, CFA/II(CS2) and CFA/IV(CS4(4), a subunit vaccine which contained epitopes from this area of the molecule may protect against infection with various ETEC.

Until recently, experiments to identify these epitopes were time consuming and costly; however, technology is now available which allows one to simultaneously identify all the T cell and B cell epitopes in the protein of interest. Multiple Peptide synthesis (Pepscan) is a technique for the simultaneous synthesis of hundreds of peptides on polyethylene rods (6). We have used this method to synthesize all the 140 possible overlapping octapeptides of the CFA/I protein. The peptides, still on the rods, can be used directly in ELISA assays to map B call epitopes (6. 12–14). We have also synthesized all 138 possible overlapping decapeptides of the CFA/I protein. For analysis of T cell Epitopes, these peptides can be cleaved from the rods and used in proliferation assays (15). Thus this technology allows efficient mapping and localization of both B cell and T cell epitopes to a resolution of a single amino acid (16). These studies were designed to identify antigenic epitopes of ETEC which may be employed in the construction of an effective subunit vaccine.

CFA/II pili consist of repeating pilin protein subunits found on several serogroups of enterotoxigenic *E coli* (ETEC) which promote attachment to human intestinal mucosa. We wished to identify areas within the CFA/I molecule that contain immunodominant T cell epitopes that are capable of stimulating the cell-mediated portion of the immune response in primates as well as immunodominant B cell epitopes. To do this, we (a) resolved the discrepancy in the literature on the complete amino acid sequence of CFA/I, (b) immunized three Rhesus monkeys with multiple i.m. injections of purified CFA/P subunit in Freund's adjuvant, (c) synthesized 138 overlapping decapeptides which represented the entire CFA/I protein using the Pepscan technique (Cambridge Research Biochemicals), (d) tested each of the peptides for their ability to stimulate the spleen cells from the immunized monkeys in a proliferative assay (e) synthesized 140 overlapping octapeptides which represented the entire CFA/I protein, and (f) tested serum from each monkey for its ability to recognize the octapeptides in a modified ELISA assay. A total of 39 different CFA/I decapeptides supported a significant proliferative response with the majority of the responses occurring within distinct regions of the protein (peptides beginning with residues 8–40, 70–80, and 126–137). Nineteen of the responsive peptides contained a serine residue at positions 2, 3, or 4 in the peptide, and a nine contained a serine specifically at position 3. Most were predicted to be configured as an alpha helix and have a high amphipathic index. Eight B cell epitopes were identified as positions 3–11, 11–21, 22–29, 32–40, 38–45, 66–74, 93–101, and 124–136. The epitope at position 11–21 was strongly recognized by all three individual monkeys, while the epitopes at 93–101, 124–136, 66–74, and 22–29 were recognized by two of the three monkeys.

Recent advances in the understanding of B cell and T cell epitopes have improved the ability to select probably linear epitopes from the amino acid sequence using theoretical criteria. B cell epitopes are often composed of a string of hydrophilic amino acids with a high flexibility index and a high probability of turns within the peptide structure. Prediction of T cell epitopes are based on the Rothbard method which identifies common sequence patterns that are common to known T cell epitopes or the method of Berzofsky and others which uses a correlation between algorithms predicting amphipathic helices and T cell epitopes.

V. SUMMARY OF THE INVENTION

This invention relates to active core materials such as biologically active agent(s), drug(s), or substance(s) encapsulated within a biodegradable-biocompatible polymeric matrix. In view of the enomorus scope of this invention it will be presented herein as Phases I, II, and III. Phase I illustrates the encapsulation of antibiotics within a biodegradble-biocompatable polymeric matrix for the prevention and treatment of wound infections. Phase II illustrates the encapsulation of antigens (including oral-intestinal vaccine antigens) within a biodegradable-biocompatable polymeric matrix against diseases such as those caused by enteropathogenic organism. Phase III illustrates the use of a biodegradable-biocompatible polymeric matrix, as the delivery system, for burst-free programmable sustained release of biologically active agents, inclusive of peptides, over a period of up to 100 days in an aqueous physiological environment.

Controlled drug delivery from a biodegradable-biocompatible matrix offers profound advantages over conventional drug/antigen dosing. Drugs/antigens can be used more effectively and efficiently, less drug/antigen is required for optimal therapeutic effect and, in the case of drugs, toxic side effects can be significantly, reduced or essentially eliminated through drug targeting. The stability of some drugs/antigens can be improved allowing for a longer shelf-life, and drugs/antigens with a short half-life can be protected within the matrix from destruction, thereby ensuring sustained release of active agent over time. The benefit of a continuous sustained release of drug/antigen is beneficial because drug levels can be maintained within a constant therapeutic range and antigen can be presented either continuously or in a pulsatile mode as required to stimulate the optimal immune response. All of this can be accomplished with a single dose of encapsulated drug/antigen.

This invention contemplates, but is not limited to, medically acceptable methods for the effective local delivery of biologically active agents that, of themselves, are directly (e.g. drugs, such as antibiotics) or indirectly (e.g. vaccine antigens) therapeutic or prophylactic. It also includes drugs/agents that elicit/modulate natural biological activity.

Wounds characterized by the presence of infection, devitalized tissue, and foreign-body contaminants have high infection rates and are difficult to treat. This invention describes antibiotic formulation encapsulated within microspheres of a biodegradble-biocompatable polymer that, when applied locally to contaminated or infected wounds, provides immediate, direct, and sustained (over a period up to 100 days), high concentrations of antibiotic in the wound site (soft tissue and bone). By encapsulating antibiotics and applying them directly, one can achieve a significant reduction in nonspecific binding of the drug to body proteins, a phenomena commonly observed following conventional systemic administration of free drugs.

Thus, less drug is required, higher concentrations are maintained at the site of need, and efficacy is enhanced. This approach provides superior treatment over conventional systemic administration of antibiotics for wound infections because higher bacteriocidal concentrations can be achieved and maintained in the wound environment. Higher concentrations kill more bacteria. Applicants' invention for this application is described in Phase I. Furthermore, applicants reasoned that a protective mucosal immune response might be best initiated by introduction of an antigen at the mucosal surface, because unprotected protein antigens delivered in a free form may be degraded or may complex with secretory IgA in the intestinal lumen precluding entry and subsequent processing in local immune cells. The formulation of microspheres containing antigen small enough in size to be phagocytized locally in the gut was envisioned as being able to induce an elevated localized immune response. Applicants' invention for this application is described in Phase II. In summary, applicants propose using several methods for the local application of drugs including: 1) the direct application of the encapsulated drug to a surgical/traumatized area, 2) oral delivery that provides either local deposition of microencapsulated antigen/drugs at mucosal membranes or transport across these membranes to provide local adherence of microencapsulated drugs/antigen to mucosal membranes to provide sustained release of drug/antigen into such tissue or a body cavity, and/or 3) sustained intercellular or extracellular drug/antigen release following subcutaneous injection.

In those instances where antibiotics are administered locally, applicants have found that the controlled release of the antibiotic from within a biodegradable-biocompatible polymeric matrix within 14 days to about 4 weeks without significant drug trailing is especially useful. However, if desired, the release of a biologically active agent from a polymeric matrix comprised of an active agent and a blend of uncapped and end-capped biodegradable poly DL(lactide-co-glycolide), can be controlled over a period of 1 to about 100 days without significant drug dumping or trailing. Such novel biocompatable-biodegradable microspheres developed with a burst-free programmable sustained release of biologically active agents, inclusive of polypeptides, are described in applicants' U.S. patent application Ser. No. 08/590,973 filed Jan. 24, 1996.

When antibiotics are administered systemically in the conventional manner, or locally as contemplated by the applicants, the immune response to the antibiotic and the potential for hypersensitivity and/or anaphylactoid response (especially to beta-lactam antibiotics such as penicillins/ampicillin) is a clinical concern. In early studies the inventors observed a specific IgG response to ampicillin as it was released from the microencapsulated formulation (illustrated in the histogram, FIGS. 1 and 2). The response is reminiscent of antibody elicited by vaccine antigens in conventional vaccines. The response to vaccine antigens is known to be accentuated by the use of an adjuvant such as alum. Alum is a crude, less adaptable delivery vehicle than its counterpart, the biodegradble-biocompatable poly DL(lactide-co-glycolide), of this invention—the polymeric matrix. This knowledge stimulated additional studies relevant to the effects of sustain release of agents on the immune response.

There are, in general, two forms of localized delivery which can be achieved with PLGA microspheres-delivery which is localized to individual cell's of the body (intracellular delivery); and delivery which is localized to tissues within a specific region of the body (localized extracellular delivery).

Applicants have prepared antibiotic and hepatitis vaccine formulations which functioned by delivering localized extracellular doses of their active agents. This was achieved by using relatively large microspheres which served as a depot for the drug or antigen. Their large size 40–100 microns in diameter precluded their being phagocytized or diffusing throughout the intercellular fluid compartments of the body. Their drug agent loads were thus released within their immediate vicinity which resulted in the generation of very high local concentrations of antibiotic or the release of sufficiently high concentrations of free antigen to induce an immune response.

The large-diameter antibiotic bearing microspheres were originally developed by applicants primarily for topical application on exposed debrided tissues of combat wounds. However, an inherent property exhibited by the antibiotics when topically applied to a wound site is the generation of measurable levels of immune response. This concept of local delivery by topical application of microspheres to tissue to achieve localized concentrations of therapeutic agents was subsequently applied to the development of an oral vaccine for protection against traveler's dierrhea caused by *E. coli*. Vaccine antigen was encapsulated into microspheres whose diameters were predominantly in the 5–10 micron size range based on an understanding that microspheres of this size would not readily be either phagocytized or transported across the gut wall into the body. Ingestion of these microspheres thus constituted a localized delivery achieved by topical application of the spheres to the wall tissue of the gut. This topical application resulted in the localized trapping of a small percentage of these sphere into the Peyer's patches where the spheres proceeded to release their antigen in a localized fashion to immune cells located within the intestinal Patches.

The concept of localized sustained local delivery has been further extended to the delivery of analgesics and anesthetics to exposed dental pulp to control pain and inflammatory responses. Again, the PLGA microsphere used for this type of delivery are relatively large (40–100 um in diameter) and serve as a topical depot for localized extracellular release of the drug.

Consistent with their understanding of the inherent immunogenic properties exhibited by active core materials in vivo, applicants have moved on to other non-topical application methods of using their microsphere delivery system. Some of these center on the use of small diameter microspheres ranging from sub micron to under 5 microns in diameter. These spheres allow intracellular targeting of drug or antigen. They also allow for transmucosal delivery of drugs or antigens. The concept of localized delivery in these instances refers to the localized delivery of drug or agent within individual target cells of the body regardless of their location or distribution within the body. This approach is useful in development of antitubercular, antimalarial, antiviral, and antichlamydial formulations against intracellular parasites. It is also useful for the development of vaccines against intracellular parasites and for direct delivery of agents to presenting cells of the immune system.

Another nontopical application method of using PLGA microspheres resides in their usefulness as injectable depots for drugs intended for either localized or systemic delivery. Typically larger diameter microspheres are used for depots as these are less likely to diffuse away. The local or systemic nature of these delivery systems is, in part a function of the release rate of the drug from the depot and the diffusional and solubility characteristics of the drug being released. Cancer chemotherapeutics, systemic antibiotics, delivery of antibiotics to infected bonare are potential application of this system. Additional this non-topical systemic depot application can be extended to the intravenous iv injection of cancer-agent laden microspheres to embolize and destroy a malignant tumor. Additionally, the PLGA microspheres can be used as a carrier to deliver substances useful for the in modification of cells or genes in bioengineering or genetic procedures.

Interest in the concept that antigens encapsulated within a biodegradable-biocompatable polymeric matrix could be formulated as a vaccine with superior efficacy over conventional vaccines, originated from the inventors' own observations that the drug, ampicillin, when sustain released from poly DL(lactide-co-glycolide) elicited antibody production. In these studies, the applicants were able to measure specific IgG antibodies to free ampicillin and to ampicillin released from microencapsulated ampicillin formulations in the sera of mice previously "treated" with the ampicillin formulations using ELISA. Numerous other studies also document the ability of beta-lactam antibiotic to elicit antibody. Selected, more recent studies whose findings are consistent with earlier discoveries made by applicants when conducting experiments with ampicillin include those by Klein et al. (1993) whose detected specific IgG antibodies (IgG and IgG3 subclasses) to the B-lactam ring in patients receiving penicillin therapy, work by Nagakura, et al. (1990) which detected specific antibodies to cephalexin, a B-lactam antibiotic in the sera of guinea pigs, and Auci et al. (1993) who detected benzyl penicilloyl specific IgM, IgG IgE, and IgA antibody forming cells in lumphoid cells of mice given benzyl penicilloyl-Keyhole Limpet Hemocyanin. Pharmaceutical compositions of antigens encapsulated with poly DL(lactide-co-glycolide) are described in Phase II. The microspheres of the invention allow for introduction of vaccine antigens to mucosal surfaces in particles that can be subsequently taken up locally by phagocytic cells. Such an approach for both drugs and antigens provides significant advantages in potency and efficacy over conventional systemically administered drugs or vaccines. A partial list of biologically active agents or drugs that will potentially derive significant medical benefits from this delivery system includes: antibacterial agents; peptides; polypeptides; antibacterial peptides; antimycobacterial agents; antimycotic agents; antiviral agents; antiparastic agents; antifungal; antiyeast agents; hormonal peptides; cardiovascular agents; hormonal peptides; cardiovascular agents; narcotic antagonists; analgesics; anesthetics; insulins; steroids including HIV therapeutic drugs (including protease inhibitors) and AZT; estrogens; progestins; gastrointestinal therapeutic agents; non-steroidal anti-inflammatory agents; parasympathoimetic agents; psychotherapeutic agents; tranquilizers; decongestants; sedative-hypnotics; non-estrogenic and non-progestional steroids; sympathomimetic agents; vaccines; vitamins; nutrients; and-migrain drugs; electrolyte replacements; ergot alkaloids; and anti-inflammary agents; prostaglandins; cytoxic drugs; antigens; antibodies; enzymes; growth factors; immumodulators; pheromones; prodrugs; prohormones; psychotropic drugs; nicotine; antiblood clotting drugs; appetite suppressants/stimulants and combinations thereof; contraceptive agents include estrogens such as diethyl silbestrol; 17-beta-estradiol; estrone; ethinyl estradiol; mestranol; progestins such as norethindrone; norgestryl; ethynodiol diacetate; lynestrenol; medroxyprogesterone acetate; dimethisterone; megestrol acetate; chlormadinone acetate; norgestimate; norethisterone; ethisterone; melentate; norgestimate; norethisterone; ethisterone; melengestrol; and spermicidal compounds such as nonyphenoxypolyoxyethylene glycol; benzethonium chloride; chlorindanol; include gastrointestinal therapeutic agents-such as aluminum hydroxide; calcium carbonate; magnesium carbonate; sodium carbonate and the like; non-steroidal. antifertility agents; parasympathomimetic agents; psychotherapeutic agents; major tranquilizers such as chloropromaquine HCl; clozapine; mesoridazine; metiapine; reserpine; thioridazine; minor tranquilizers such as chlordiazepoxide; diazpam; meprobamate; temazepan and the like; rhinological decongestants; sedative-hypnotics such as codeine; phenobarbital; sodium pentobarbital; sodium secobarbital; other steroids such as testosterone and testosterone propionate; sulfonmides; sympathomimetic agents; vaccines; vitamins and nutrient such as the essential amino acids; essential fats; anti-HIV agents; including AZT; antimalarials such as 4-aminoquinolines; 8 aminoquinolines; pyrimethamine; anti-migraine agents such as mazindol; phentermine; anti-Parkinson agents such as L-dopa; antispasmodics such as atropine; methscopolamine bromide; antispasmodics and anticholingeric agents such as bile therapy; digestants; enzymes and the like; antitussives such as dextromethorphan and noscapine; bronchodialtors; cardiovascular agents such as anti-hypertensive compounds; Rauwolfia alkaloids; coronary vasodilators; nitroglycerin; organic nitrites; pentaerythriotetranitrate; electrolyte replacements such as potassium chloride; ergotalkalodis such as ergotamine with and without caffein; hydrogenated ergot alkaloids; dihydroergocristine methanesulfate; dihydroergocornine methanesulfonate; dihydroergokroyptine methaneusulfate and combinations thereof; alkaloids such as stropine sulfate; Belladonna; hyoscine hydrobromide; analgesics; narcotics such as codeine; dihydrocodienone; meperidine; morphine; non-narcotics such as salicylates; aspirin; caffeine; nicotine; acetaminophen; and d-propoxyphene; antibiotics such as the cephalosporins including ceflacor and cefuroxime; chloranphenical; gentamicin; Kanamycin A. Kanamycin B; the penicillins; ampicillin; amoxicillin; streptomycin A; antimycin A; chloropamtheniol; metromidazole; oxytetracyline penicillin G; the tetracyclines; including minocycline; fluoro-quinolones including ciprofloxacin; ofoxacin; macrolides including clarithromycin; frythromycin; aminoglycosides including gentamicin; amikacin; tobramycin and kanamycin; beta-lactams including ampicillin; polymyxin-B; amphotercin-B; aztrofonam; chloramphenicol; fusidans; lincosamides; metronidazaole; nitro-furantion; imipenem/cilastin; quinolones; systemic antibodies including rifampin; polygenes; sulfonamides; trimethoprim; glycopeptides including vancomycin; teicoplanin and imidazoles; anti-cancer agents; including anti-kaposi's sarcoma; agents and taxol anti-convulsants such as mephenytoin; phenobarbital; trimethadione; anti-emetics such as triethylperazine; antihistamines such as chlorophinazine; dimenhydrinate; diphenhydramine; perphenazine; tripelennamine and the like; anti-inflammatory agents such as hormonal agents; hydrocortisone; prednisolone; prednisone; non-hormonal agents; allopurinol; water-soluble hormone drugs; antibiotics; antiumor agents; anti inflammatory agents; antipyretics; analgesics; such as acetaminophen, acetylsalicylic acid, and the like; anesthetics such as lidocaine, xylocaine, and the like; anorexics such as dexedrine, phendimetrazinetartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erytromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapione, and the like; antihistamines such as diphenhydramine HCl, chlorpheniramine maleate, and the like; hormones such as insulin, progestins, estrogens, corticoids, glucocorticoids, androgens, and the like; tranquilizers such thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamins A, B12, C, D and E, and the like; cardiovascular agents such as prazosin HCl, nitroglycerin, propranolol HCl, nydralazine HCl, verapamil HCl, and the like; enzymes such as lactase, pancrelipase, succinic acid dehydrogenase, and the like; peptides and proteins such as LHRH, somatostatin, calcitonin, growth hormone, growth releasing factor, angiotensin, FSH, EGF, vasopressin, ACTH, human serum albumin, gamma globulin, and the like; prostaglandins; nucleic acids; carbohydrates; fats; narcotics such as morphine, codein, and the like; psychoterapeitucs; anti-malarials; L-dopa, diuretics such as furosemide, spironolactone, and the like; antiulcer drugs such as ranitidine HCl, cimetidine HCl and the like, antitussives; expectorants; sedatives; muscle relaxants; antiepileptic agents; antidepressants; antiallergic drugs; cardiotonics; antiarrhythmic drugs; vasodilators; antihypertensives; diuretics; anticoagulants; and antinaroctics; in the molecular weight range of 100–100,000 daltons; indomethacin; phenylbutazone; prostaglandins; cytotoxic drugs such as thiotepa; chloramucil; cyclosphosphamide; melphala; nitrogen mustard; methotrexate; antigens such as proteins; glycoproteins; synthetic peptides; carbohydrates; synthetic polysaccharides; lipids; glycolipids; lipopolysaccharides (LPS); synthetic lipopolysaccharides and with or without attached adjuvants such as synthetic muramyl dipeptide and with or without attached adjuvants such as synthetic muramyl dipeptide derivatives; antigens of such microorganisms as *Neisseria gonorrhea; Mycobacterium tuberculosis, Picarinii Pnfumonia*; Herpes virus (humonis types 1 and 2); Herpes zoster; *Candidia albicans; Candida tropicals; Trichomonas vaginalis; Haemophilus vaginalis*; Group B *streptoccoccus ecoli; Microplasma hominis; Hemophilus ducreyi; Granuloma inguimale; Lymphopathia venerum; Treponema palidum; Brucela aborus Brucela meitensis Brucela suis; Brucella canis Campylobacter fetus; Campylobacer fetus intesinalis; Leptospira pomona. Listeria monocytogens; Brucella ovis*; Equine herpes virus 1; Equine arteritis virus; IBR-IBP virus; *Chlamydia psittaci; Trichomonas foetus; Taxoplasma gondii; Escherichia coli; Actinobacillus equuli; Salmonella abortus ovis. Salmonella abortus eui; Pseudomonas aeruginosa; Corynebacterium equi; Corynebacterium pyogenes; Actinobaccilus seminis; Mycoplasma bovigenitalium, Aspergil us fumigatus; Absidia ramosa; Trypanosoma equiperdum; Babesia cabali; Clostridium tetani*; antibodies which counteract the above microorganisms; and enzymes such as ribonuclease; neuramidinase; trypsin; glycogen phosphorylase; sperm lactic dehydrogenase; sperm hyaluronidase; adenossinetriphosphase; alkaline phosphatase; alkaline phospha esterase; amino peptides; typsin chymotrypsin amylase; muramidase; acrosomal proteinase; dieterase; glutamic acid dehydrogense; succunic and dehydrogenase; beta-glycophosphatase lipase; ATP-ase alpha-peptate gamma-glutamyiotranspeptidase; sterold-beta-ol-dehydrogenase; DPN-di-aprorase; and combinations thereof.

Immunological agents that can be encapsulated by this method include, interleukins, interferon, colony stimulating factor, tumor necrosis factor, and the like; allergens such as cat dander, burch pollen, house dust mite, grass pollen, and the like; antigens of such bacterial organisms as *Streptoccus poneumoniae, Haemophilus influenzae, Staphylococcus aureus, Streptococcus pyogenes, Corynebacterium diphtheriae, Listeria monocytogenes, bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, vibrio cholerae, legionella pheumophila, Mycobacterium tubercolosis, Mycobacterium leprae, Treponema pallidum, Leptspriosis interrogans, borrelia burgdorferi, Campylobacer jejuni*; and the like; antigens of such viruses as smallpox, influenza A and B, respiratory syncytial, parainfluenza, measles, HIV, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroides, Rickettsia ricketsil, Rickettsia typhi, Mycoplasma pneumoniae, Chlamydial psittaci, chlamydial trachomatis, plasmodium falciparum, Trypanosoma brucei, Entamoeba histolytica, Toxaplasma gondii, Trichomonas vaginalis, Schistosoma mansoni*, and the like. These antigens may be in the form of whole killed organisms, peptides, proteins, glycoproteins, carbohydrates, or combinations thereof. Having generally described the invention; a further understanding can be obtained by reference to certain specific examples which are provided herein for purpose of illustration only and are not intended to be limiting unless otherwise specified. Moreover; the polymeric matrix of this invention may be used for the in situ production and controlled release of products that are produced by the controlled release of encapsulated reactants. Additionally; effective testing or monitoring devices for chemical agents or bioactive agents can be made by encapsulating reagents which react as they are released from the polymeric matrix, with agents sought to be detected. The novel delivery system of this invention is applicable to all categories of active substances capable of being used for the prevention and/or treatment of human, animal and plant diseases. This delivery system is also applicable to the design of novel diagnostic tests. Additionally, it can be useful for the delivery to a subject of a polyfunctional mixture or cocktail formulation of encapsulated active (i.e. biologically) substances for the prevention and/or treatment of diseases of the same or different origin. The encapsulated formulation ingredients would be comprised of multiple drugs, multipe vaccines or a combination thereof.

Applicants contemplate that the invention will be useful in the formulation of disease specific compositions for the prevention and/or treatment of diseases and/or ailments which include: viral infections; bacterial infections; fungal infections; yest infections; parastic infections and more specific diseases and/or ailments; such as, aids; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; cutaneous & metastatic; cachexia in AIDS; campylobacter infection; cancer; pnemonia; sexually transmitted diseases (STDs); cancer; viral diseases; candida albicians in AIDS and cancer; candidiasis in HIV infection; pain in cancer; pancreatic cancer; parkinson's disease; peritumoral brain edema; postoperative adhesions (prevent); proliferative diseases; prostate cancer; ragweed allergy; renal disease; restenosis; rheumatoid arthritis; rheumatoid arthritis; allergies; rotavirus infection; scalp psoriasis; septic shock; small-cell lung cancer; solid tumors; stroke; thrombosis; type I diabetes; type I diabetes w/kidney transplants; type II diabetes; viseral leishmaniasis; malaria; periodontal or gum disease; cardiac rthythm disorders; central nervous system diseases; central nervous system disorders; cervical dystonia (spasmodic torticollis); choridal neovascularization; chronic hepatitis A, B and C; colitis associated with antibiotics; colorectal cancer; coronary artery thrombosis; cryptosporidiosis in AIDS; cryptosporidium parvum diarrhea in AIDS; cystic fibrosis; cytomegalovirus disease; depression; social phobias; panic disorder; diabetic complications; diabetic eye disease; diarrhea associated with antibiotics; erectile dysfunction; genital herpes; graft-vs host disease in transplant patients; growth hormone deficiency; head and neck cancer; head trauma; stroke; heparin neutralization after cardiac bypass; hepatocellular carcinoma; HIV; HIV infection; huntington's disease; CNS diseases; hypercholesterolemia; hypertension; inflammation; inflammation and angiogensis; inflammation in cardiopulmonary bypass; influenza; migrain head ache; interstitial cystitis; kaposi's sarcoma; kaposi's sarcoma in AIDS; lung cancer; melanoma; molluscum contagiosum in AIDS; multiple sclerosis; neoplastic meningitis from solid tumors; non-small cell lung cancer; organ transplant rejection; osteoarthritis; rheumatoid arthritis; osteoporosis; drug addiction; shock; ovarian cancer; and pain.

Also contemplated here are those diseases or health conditions capable being benefitted by the list of biologically active agents or drugs previously listed in the Summary of the Invention.

Effects of Microencapsulated Antibiotics on the Immune Responce

Preclinical studies evaluating microencapsualted antibiotics in animals have demonstrated that targeted local release of antibiotics directly into infected soft tissue and bone via sustained release of the drug from poly DL(lactide-co-glycolide) will greatly enhance antibiotic efficacy for both prophylaxis and treatment. Antibiotic hypersensitivity was, from the beginning, the most obvious untoward clinical concern of this novel approach to antibiotic delivery. What effect would sustained antibiotic release have on the hypersensitive patient?Prior to the filing of applicants' parent application Ser. No. 590,308 on Mar. 16, 1984, which disclosed the local application of encapsulated antibiotics to treat wound infection, it was commonly known that an inherent property of free antibiotics such as ampicillin, is that they elicit an immune response in man and induce the production of antibodies. Thus, interest in the immune response elicited from the sustained release of immunogens intensified in order to capture the beneficial aspects of this immunogenic event in a manner which would advance the frontiers of medical science. This led to additional studies with sustain released antibiotics and led the inventors to postulate that antigens encapsulated in lactide/glycolide could potentially provide a more effective method of active immunization than free antigen alone. The recent report in "Vaccination onto Bare Skin", by De-chu Tang, et al., Nature, vol. 388, August 1977, of the success with gene-based vaccines by topical application to the skin continues to support position that an inherent property of topically applied antibiotics is that they elicit an immune response in man and induce the production of antibiodies. In follow on experiments, vaccine antigens were encapsulated and studies were performed to explore this hypothesis as illustrated in Phase II, herein.

VI. BRIEF DESCRIPTION OF THE DRAWINGS

FIG. 1 shows the effect of microencapsulated ampicillin (MEAA) on the immune response when mice are treated with free ampicillin, ampicillin encapsulated within biodegradble-biocompatible microspheres and placebo poly (lactide/glycolide) microspheres, by measuring the specific IgG antibodies to free ampicillin and MEAA in sera of treated mice by ELSIA.

FIG. 2 shows that guinea pigs sensitized with free or microencapsualted ampicillin developed specific IgG antibodies to ampicillin as measured by ELISA.

FIG. 3 shows the in vitro release of ($^{14}$C)-ampicillin anhydrate from sterilized microcapsulses/spheres (45 to 106 micrometers in diameter) into 0.1 molar potassium phosphate receiving fluid (pH 7.4) maintained at 37° C. The microcapsules consisted of about 10 weight percent ampicillin anhydrate and about 65 weight percent 53:47 DL-PLG polymer.

FIG. 4 shows the in vitro release of ($^{14}$C)-ampicillin anhydrate from sterilized microcapsules (10 to 100 micrometers consisting of about 35 weight percent ampicillin and about 65 weight percent of 53:47 DL-PLG polymer.

FIG. 5 shows the mean daily excretion of ($^{14}$C) from rats receiving subcutane ous injections of sterilized microencapsulated and unencapsulated ($^{14}$C)-ampicillin anhydrate.

FIG. 6 illustrates that encapsulated as well as the ampicillin anhydrate showed a fast releaseof drug during Day 1. By Day 4, the amount of ampicillin found in the serum of animals dosed with the unencapsulated drug was below the level of detection of the assay, whereas serum levels of ampicillin were dectable in animals receiving encapsulated ampicillin for up to 11 days.

FIG. 7 shows mean serum levels of ampicillin at 1-hour following implantation of either microencapsulated ampicillin or unencapsulated ampicillin into the medullary canal of the rabbit tibia with experimental osteomyelitis.

Serum Cefazolin Levels. FIG. 8 shows the mean serum concentrations of cefazolin that were measured at 1 hour and 24 hours following local antibiotic therapy with either CZ microspheres (Group A) or free CZ powder (Group B) in the rabbit fracture-fixation model. At 1 hour, the mean serum cefazolin levels were approximately 32 times higher for the Group B animals who had received local antibiotic therapy with free CZ powder (18.7±5.1 ug/ml) as compared to the Group A animals who were treated with CZ microspheres) 0.57±0.27 ug/ml). This difference in the mean serum cefazolin levels between the two groups was statistically significant (p=0.0023) by Student's t test. At 24 hours following local treatment, no cefazolin was detected in the sera of the rabbits who had received free CZ powder (Group B), however, low cefazolin concentrations were detected in the sera of Group A animals who were treted with the CZ microspheres. It is evident from the data that the free antibiotic diffuses rapidly from the wound and is absorbed into the systemic circulation, whereas, the-microspheres remain localized and continue to release low but measurable levels of antibiotic for an extended time interval.

FIG. 9 shows the size destribution of microspheres wherein the particle size distribution (%)is (a) By number 1–5 (91) and 6–10 (9) and (b) By weight 1–5 (28) and 6–10 (72).

FIG. 10 shows a scanning electron micrograph of microspheres.

FIGS. 11(a) and (b) show the in vitro immunization of spleen cells and demonstrates that AF/RI pilus protein remains immunogenic to rabbit spleen cells immunized in vitro after microencapsulation AF/R1 pilus protein has been found to be immunogenic for rabbit spleen mononuclear cells in vitro producing a primary IgM antibody response specific to AF/R1. Immunization with antigen encapsulated in biodegradable, biocompatable microspheres consisting of lactide/glycolide copolymers has been shown to endow substantially enhance immunity over immunization with the free antigen. To determine if microencapsulated AF/R1 maintains the immunogenicity of the free pilus protein, a primary in vitro immunization assay was conducted. Rabbit spleen monoculear cells at a concentration of $3\times10^5$ cells/well. Triplicate wells of cells were immunized with free AF/Fl in a dose range from 15 to 150 ng/ml or with equivalent doses of AF/R1 contained in microspheres. Supernatants were harvested on days 7, 9, 12, and 14 of culture and were assayed for free AF/R1 pilus protein specific IgM antibody by the ELISA. Supernatant control values were subtracted from those of the immunized cells. Cells immunized with free pilus protein showed a significant positive IgM response on all four days of harvest, with the antibody response increasing on day 9, decreasing on day 12, and increasing again on day 14. Cells immunized with microencapsulated pilus protein showed a comparble positive IgM antibody response as cells immunized with free pilus protein. In conclusion, AF/R1 maintains immunogenicity to rabbit spleen cells immunized in vitro after microencapsulation.

FIGS. 12(a) and (b) show in vitro immunization of Peyer's patch cells. Here the AF/R1 pilus protein remains immunogenic to rabbit Peyer's patch cells immunized in vitro after microencapsulation. AF/R1 pilus protein has been found to be immunogenic for rabbit Peyer's patch mononuclear cells in vitro producing a primary IgM antibody response specific to AF/R1. Immunization with antigen encapsulated in biodegradble, biocompatible microspheres consisting of lactide/glycolide copolymers has been shown to endow substantially enhanced immunity over immunization with the free antigen. To determine if microencapsulated AF/R1 maintains the immunogencity of the free pilus protein, a primary in vitro immunization assay was conducted. Rabbit Peyer's patch mononuclear cells at a concentration of $3 \times 10^4$ cells/ml were cultured in 96-well, round bottom microculture plates at a final concentration of $6 \times 10^5$ cells/well. Triplicate wells of cells were immunized with free AF/R1 in a dose range from 15 to 150 ng/ml or with equivalent dose of AF/R1 contained in microspheres. Supermatants were harvested on days 7, 9, 12, and 14 of culture and were assayed for free AF/R1 pilus protein specific IgM antibody by the ELISA. Supernatant control values were subtracted from those of the immunized cells. Cells immunized with free pilus protein showed a significant positive IgM response on all four days of harvest, with the highest antibody response on day 12 with the highest antigen dose. Cells immunized with encapsulated pilus protein showed a positive response on day 12 with all three antigen doses. In conclusion, AF/R1 pilus protein maintains immunogenicity to rabbit Peyer's patch cells immunized in vitro after microencapsulation.

FIG. 13 shows proliferative responses to AF/R1 by rabbit Peyer's patch cells. Naive rabbits were primed twice with 50 mirograms of either non-encapsulated (rabbits 132 and 133) or microencapsulated (rabbits 134 and 135) AF/R1 pili by endoscopic intraduodenal inoculation seven days apart. Seven days following the sedond priming. Peyer's patch cells were cultured with AF/R1 in 96 well plates for four days followed by a terminal six hour pulse with ($^3$H) thymidine. Data shown is the SI calculated from the mean cpm of quadruplicate cultures. Responses were significant for all rabbits: 132 (p=0.013), 133 (p=0.0006), 134 (p=0.0016), and 135 (p=0.0026). Responses were significantly different between the two groups. Comparison of the best responder in the nonencapsualted antigen group (rabbit 133) with the lowest responder in the microencapsulated antigen group (rabbit 134) demonstrated an enhanced response when the immunizing antigen was microencapsulated (p=0.0034).

Additionally, FIG. 13 relates to the in vitro lymphocyte proliferation after senitization of rabbit lumphoid tissues with encapsulated or non-encapsulated AF/R1 pilus adhesion of E. coli strain REDEC-1. The AF/R1 adherence factor is a plasmid encoded pilus protein that allows RDEC-1 to attach to rabbit intestinal brush borders. We investigate the immunopotentiating effect of encapsulating purified AF/R1 into biodegradble non-reactive microspheres composed of polymerized lactide and glycolide, materials used in resorable sutures. The microspheres had a size range of 5–10 microns, a size selected for Peyer's Patch localization, and contained 0.62% protein by weight. NZW rabbits were immunized twice with 50 micrograms of either encapsulated or non-encapsulated AF/R1 by intraduodenal later of non-encapsulated AF/R1 by intraduodenal inoculation seven days apart. Lymphocyte proliferation in response to purified AR/R1 was conducted in vitro at seven days and showed that encapsulating the antigen into microspheres enhanced the cellular immune response in the Peyer's Patch; however, no significant increase was observed in spleen or mesenteric lumph node. These data suggest that encapsulation of AF/R1 may potentiate the mucosal cellular immune response.

FIGS. 14a–d show proliferative responses to AF/R1 synthetic peptides by rabbid Peyer's patch cells. Naive rabbits were primed twice with 50 micrograms of either non-encapsulated (rabbits 132 and 133) or microencapsulated (rabbits 134 and 135) AF/R1 pili by endoscopic intraduodenal inoculation seven days apart. Seven days following the second priming, Peyer's patch cells from each rabbit were cultured with AF/R1 40–55 (FIG. 14a), AF/R1 79–94 (FIG. 14b), AF/R1 108–123 (FIG. 14c) or AF/R1 40–47/79–86 (FIG. 16d) in 96-well plates for four days followed by a terminal six hour pulse with ($^3$) thymidine. Data shown is the SI calculated from the mean cpm of quadruplicate cultures. The responses of rabbits 132 and 133 were not significant to any of the peptides tested. Rabbit 134 had a significant response to (a) AF/R1 40–55 (p=0.0001), (b) AF/R1 79–94 (p=0.0280), and (d) AF/R1 40–57/79–86 (p=0.025), but not to (c) AF/R1 108–123. Rabbit 135 had a significant response to (a) AF/R1 40–55 (p=0.034), (b) AF/R1 79–94 (p=0.040), and (c) AF/R1 108–123 (p<0.0001), but not to (d) AF/R1 40–47/79–86. This demonstrates enhanced proliferative response to peptide antigens following mucosal priming with microencapsulated pili. AF/R1 pili promotes RDEC-1 attachment to rabbit intestinal brush borders. Three 16 amino acid peptides were selected by theoretical criteria from the AF/R1 sequence as probably T or B cell epitopes and were synthesized: Af/R1 40–55 as a B cell epitope, 79–94 as a T cell epitope, and 108–123 as a T and B cell epitope. We used these peptides to investigate a possible immunopotentiating effect of encapsulating purified AF/R1 pili into biodegradable, biocompatible microspheres composed of polymerized lactide and glycolide at a size range that promotes localization in the Peyer's Patch (5–10 micrometers) NZW rabbits were primed twice with 50 micrograms AF/R1 by endoscopic intraduadenal inoculation and their Peyer's Patch cells were cultured in vitro with the AF/R1 peptides. In two rabbits which had received encapsulated AF/R1, lumphocyte proliferation was observed to Af/R1 40–55 and 79–94 in both rabbits and to 108–123 in one of two rabbits. No responses to any of the peptides were observed in rabbits which received non-encapsulated AF/R1. These data'suggest that encapsulation of AF/R1 may enhance the cellular response to peptide antigens.

FIGS. 15a–d show B-cell responses of Peyer's patch cells to Af/R1 and peptides.

FIGS. 16a–d show B-cell responses of Peyer's Patch cells to AF/R1 and peptides.

FIGS. 17a–d show B-cell responses of spleen cells to AF/R1 and peptides.

FIGS. 18a–d show B cell responses of spleen cells to AF/R1 and peptides.

FIGS. 15 through 18 illustrate enhanced lymphocyte antibody response by mucosal immunization, of rabbits with microencapsulated AF/R1 pilus protein. The AF/R1 pilusprotein has been found to be immunogenic for rabbit spleen and Peyer's patch cells in vitro producing a primary Ig Mantibody response. The purpose of this study was to determine if AR/R1 pilus protein immune response is enhanced by microencapsualtion. The AF/R1 was incorporated into biodegradable, biocompatible microspheres composed of lactide-glycolide copolymers, had a size range of 5–10 micrometer and containing 0.62% pilus protein by weight. Initially, NZW rabbits were immunized twice with 50 micrograms of either encapsulated of non-encapsulated AF/R1 via intraduodenal route seven days apart. For in vitro challenge, 6×10⁵ rabbit lymphocytes, were set in microculture at final volume of 0.2 ml. Cells were challenged with AR/R1 or three different synthetic 16 amino acid peptides representing, either predicted T, B or T and B cell epitopes in a dose range of 15 to 150 ng/ml for splenic cells or 0.05 to 5.0 micrograms/ml for Peyer's patch mononuclear cells (in triplicate). Supernatants were collected on culture days 3, 5, 7, and 9 assayed by ELISA for anti-AF/R1 antibody response as compared to cell supernatant control. Significant antibody responses were seen only from spleen and Peyer's patch cells from rabbits immunized with microencapsulated AF/R1. The antibody response tended to peak between days 5 and 9 was mainly an IgM response. The results for the predicted epitopes were similar to those obtained with purified AF/R1. In conclusion, intestinal immunization with AF/R1 pilus protein contained within microspheres greatly enhances both the spleen and Peyer's patch B-cell responses to predicted T & B-cell epitopes.

FIG. 19 shows proliferative responses to AF/R1 40–55 by rabbit MLN cells. Naive rabbits were primed twice with 50 micrograms of either nonencapsulated (rabbits 132 and 133) or microencapsulated (rabbits 134 and 135) AF/R1 pili by endoscopic intraduodenal inoculation seven days apart. Seven days following the second priming, MLN cells were cultured with AF/R1 40–55 for four days in 24-well plates. Cultures were transferred into 96-well plates for a terminal ($^3$H)thymidine pulse. Data shown is the SI calculated from the mean cpm of quadruplicate cultures. Responses of rabbits 132 and 133 were not statistically significant. Responses were significant for rabbits 134 (p=0.0051) and 135 (p=0.0055).

FIG. 20 shows proliferative responses to AF/R1 40–55 by rabbit spleen cells. Naive rabbits were primed twice with 50 micrograms of either nonencapsulated (rabbits 132 and 133) or microencapsulated. (rabbits 134 and 135) AF/RI pili by endoscopic intraduodenal inoculation seven days apart. Seven days following the second priming, spleen cells were cultured with AF/RI 40–55 for four days in 24-well plates. Cultures were transferred into 96 well plates for a terminal [$^3$H]thymidine pulse. Data shown is the SI calculated from the mean cpm of quadruplicate cultures. Responses of rabbits 132 and 133 were not statistically significant. Responses were significant for rabbits 134 (p=0.0.0005) and 135 (p=0.0066).

FIG. 21 shows kcpm levels for rabbit spleen cells and mesenteric lymph node in response to encapsulated AF/R1.

FIG. 22 shows kcpm levels for rabbit spleen cells and mesenteric lymph node in response to encapsulated AF/R1.

FIG. 23 shows stimulation index responses of rabbit to immunization with non-encapsulated AF/R1 and encapsulated AF/R1.

FIG. 24 shows A. SDS-PAGE of intact CFA/I (lane 1), trypsin treated CFA/I (lane 2), and *S. aureus* V8 protease treated CFA/I. Molecular masses of individual bands were estimated from molecular weight standards (on left). Multiple lanes of both trypsin and Vi treated CFA/I were transferred to PVDF membranes where bands corresponding to the approximate molecular masses of 3500 (trypsin digest, see arrow lane 2) and 6000 (V8 digest, see arrow lane 3) were excised and subjected to Edman degradation 24 and B. The resulting sequence of protein fragments from each lane of A (position of sequenced portion of fragment in the intact protein. Underlined, italicized residues are amino acids under dispute in literature.

FIG. 25 shows the ELISA assay results testing hyperimmune sera of monkeys[25](A) 2Z2 (monkey 3), [25](B) 184 (D) (monkey 1) and [25](C) 34 (monkey 2) to CFA/I primary structure immobilized on polyethylene pins. Monkey sera diluted 1:1000. Peptide number refers first amino acid in sequence of octapeptide on pin from CFA/I primary structure OD 405 refers to optical density wavelength at which ELISA plates were read (405 nm)

FIG. 26 shows the complete sequence of CFA/I (147 amino acids) with B cell recognition site (boxed areas) as defined by each individual monkey response (2Z2, 184D, and 34). Derived from data in FIG. 25.

FIGS. 27–29 shows lymphocyte proliferation to synthetic decapeptides of CFA/I. Each monkey was immunized with three i.m. injections of CFA/I subunits in adjuvant, and its spleen cells were cultured with synthetic decapeptides which had been constructed using the Pepscan technique. The decapeptides represented the entire CFA/I protein. Concentrations of synthetic peptide used included 6.0, 0.6, and 0.06 micrograms/ml. Values shown represent the maximum proliferative response produced by any of the three concentrations of antigen used ± the standard deviation. The cpm of the control peptide for each of the three monkeys was 1,518±50, 931±28, and 1,553±33 respectively. The cpm of the media control for each of the three monkeys was 1,319±60, 325±13, and 1,951±245 respectively.

FIGS. 30–32 show lymphocyte proliferation to 6.0, 0.6, and 0.06 micrograms/ml synthetic decapeptides of CFA/I in one monkey. The monkey (2Z2) was immunized with three i.m. injections of CFA/I subunits in adjuvant, and its spleen cells were cultured with synthetic decapeptides which had been constructed using the Pepscan technique. The decapeptides represented the entire CFA/I protein. Values shown represent the proliferative response which occurred to 6.0 micrograms/ml (FIG. 30), 0.6 micrograms/ml (FIG. 31), or 0.06 micrograms/ml (FIG. 32) of antigen ± the standard deviation. The cpm of the control peptide was 1,553±33 and the cpm of the media control was 1,951±245.

FIG. 33 shows that rabbits numbers 21 and 22 received intraduodual administration of AF/RI microspheres at doses of AF/RI of 200 micrograms (ug) on day 0 and 100 ug on day 7, 14, and 21 then sacrificed on day 31. The spleen, Peyer's patch and ileal lamina propria cells at $6\times10^5$ in 0.2 ml in quadriplate were challenged with AF/RI and AF/RI 1–13, 40–55, 79–94, 108–123, and 40–47, 79–85 synthetic peptides at 15, 1.5 and 0.15 ug/ml for 4 days. The supernatants were tested for IL-4 using the IL-p-4/IL-2 dependent cell line cells CT4R at 50,000/well with 0.1 ml of 6.25% supernatant for 3 days then pulsed with tritiated thymidine for 4 hrs, cells harvested and the tritiated thymidine incorporation determined, averaged and expressed with one standard deviation thousand counts per minute (kcpm).

FIG. 34 shows that RDEC-1 colonization (log CFU/gm) in cecal fluids was similar in both groups (mean 6.3 vs 7.3; p=0.09)

FIG. 35 shows that rabbits given AF/RI-MS remained well and 4/6 gained weight after challenge, whereas 9/9 unvaccinated rabbits lost weight after challenge (mean weight change +10 vs −270 grams p<0.001).

FIG. 36 shows that the mean score of RDEC-1 attachment to the cecal epithelium was zero in vaccinated, and 2+ in unvaccinated animals.

FIG. 37 shows that the particle size distribution of CFA/II microsphere vaccine Lot L74F2 values are percent frequency of number of volume verses distribution. Particle size (diameter) in microns. 63% by volume are between 5–10 um and 88% by volume are less then 10 um.

FIG. 38 shows a s canning electron photomicrograph of CFA/II microsphere vaccine Lot L7472 standard bar represents 5 um distance.

FIG. 39 shows a twenty-two hour CFA/II release study of CFA/II microsphere vaccine Lot L7472. Percent cumulative release of CFA/II from three sample: A, 33.12 mgm; B, 29.50 mgm, 24.20 mgm at 1, 3, 6, 8, 12 and 22 hour intervals. Average represents the mean±ISD.

FIG. 40 shows a serum IgG antibody response to CFA/II microsphere vaccine Lot L7472 following 2 25 ug protein IM immunization on day 0 in 2 rabbits. Antibody determines on serial dilution of sera by ELISA and expressed as mean titer versus day 0, 7 and 14.

FIG. 41 shows a serum IgG antibody response to CFA/II microsphere vaccine Lot L7F2 following 2 25 ug protein IM immunizations on day 0 if rabbit 107 & 109. Antibody determined on serial dilution (in duplicate) of sera by ELISA and expressed as mean titer versus day 0, 7 and 14.

FIG. 42 shows a lymphocyte proliferative responses for Peyer's patch cells of rabbits 65 (FIG. 42(a)), 66 (FIG. 42(b)), 83 (FIG. 42(c)), 86 (FIG. 42(d)), and 87 (FIG. 42(e)) immunized intraduodenally with 50 mgm protein of CFA/II microsphere vaccine 4 and 7 days earlier. The cells are challenged in vitro with CFA/II or BSA at 500, 50 and 5 ug/ml or media in triplicate. The uptake of tritiated thymidine in Kcp is expressed as mean±ISD. Using the paired student t-test, the p values of 500 ug/ml dose of CFA/II compared to media control are: 65, p=0.0002; 66, p=0.0002; 83, p=0.0002; and 86, p=0.0002.

FIG. 43 shows a lymphocyte proliferative responses from Peyer's patch cells of rabbits 77 (FIG. 43(a)), 78 (FIG. 43(b)), 80 (FIG. 43 (c)), 88 (FIG. 43(d)), and 91 (FIG. 43(e)) immunized introduodenally with 50 mgm protein of CFA/II microspheres vaccine 14 and 7 days earlier. The cells are challenged in vitro with CFA with CFA/II or BSA at 500, 50 and 5 ug/ml or media in triplicate the uptake of triciplate. The uptake of tritiated thymidine in Kcp is expressed as mean±ISD. Using the paired student t-test, the protein of 500 ug/ml dose of CFA/II compared to media control are: 77, p=0.0001; 78; ==0.0015; 80, p=insignificant; 88, p=0.0093; and 91 p=0.0001.

FIG. 44 shows an ELISPOT assay of spleen cells from rabbits 65 (FIG. 44(a)), 66 (FIG. 44(b)), 83 (FIG. 44(c)), 86 (FIG. 44(d)), and 87 (FIG. 44(e)) immunized intraduodenally with 50 mgm protein of CFA/II microsphere vaccine 14 and 7 days earlier. These were cells placed into microculture and tested on day 0, 1, 2, 3, 4 and 5 by ELISPOT for cells secreting antibodies specific for CFA/II antigen. The tesults are expressed as number per $9 \times 10^6$ spleen cells versus culture day tested.

FIG. 45 shows an ELISPOT assay of spleen cells from normal control rabbits, 67, 69, 72 and 89. The cells were placed into microculture and tested on days 0, 1, 2, 3, 4 and 5 by ELISPOT for cells secreting antibodies specific for CFA/II antigen. The results are expressed as number per $9 \times 10^6$ spleen cells versus culture day tested.

FIG. 46 shows a curve for determining vaccination dosages for regimen b.

FIG. 47 shows a hepatitis B surface antigen release from 50:50 poly(DL-lactide-co-glycolide).

FIGS. 19 and 20 serve to illustrate that inclusion of Escherichia coli pilus antigen in microspheres enhances cellular immunogenicity.

FIG. 48 shows a comparison of drug release from a conventional system versus a controlled release system. Peak and valley levels from conventional administrations are shown, in contrast to the steady therapeutic levels from the controlled release administration.

FIG. 49 shows a scanning electron micrograph of PLGA microspheres prepared by the process described in the invention using 50/50 uncapped polymer of Mw 8–12 k dalton and shows superior sphere morphology, sphere integrity, and narrow size distribution.

FIG. 49a shows a scanning electron micrograph of PLGA microspheres prepared by conventional solvent evaporation method using a 05/50 uncapped polymer of Mw 8–12 k dalton.

FIG. 50 shows cumulative Histatin release from PLGA microspheres, wherein release profiles from several batches are prepared using 50/50, uncapped polymer (of Mw 8–12 k dalton) and wherein the process parameters are varied to modulate release between 10 and 100 days.

FIG. 51 shows a scanning electron micrograph of solid, smooth spherical surfaces of PLGA microspheres prepared by the method of in the invention using 50/50, end-capped polymer (of Mw 30–40 k dalton).

FIG. 52 shows cumulative Histatin release from PLGA microspheres, wherein the release profiles are from several batches prepared using 50/50, uncapped and end-capped polymer of Mw 30–40 k daltons, and wherein the process parameters are varied to modulate release between 28 to 60 days.

FIG. 53 shows cumulative Histatin release from PLGA microspheres, wherein combined release profiles from several batches have been prepared using 50/50, uncapped and end-capped polymer of Mw 8–40 k daltons, while varying the process parameters to modulate release between 1 and 60 days.

FIG. 54 shows a cumulative percent release of LHRH from PLGA microspheres prepared using uncapped polymer of Mw 8–12 daltons.

FIG. 55 shows survival data from the neutropenic rat model of sepsis, wherein the rat is treated with IgG isolated from the post-immune serum of a rabbit immunized with J5 LPS-GBOMP non-covalent complex vaccine (R #62, post-immune serum IgG, +---+); IgG isolated from the serum of rabbit #42374 that was immunized against J5 DLPS-GBOMP (Δ--Δ); Preimmune rabbit serum IgG (-o-); PBS control (+--+).

VII. DETAILED DESCRIPTION OF THE INVENTION

This invention relates to the encapsulation of active core materials, especially those which are medically beneficial to the mammalian animal kingdom, such as biologically active agent(s), drug(s), or substance(s) within a biodegradable-biocompatable polymeric matrix.

More precisely, applicants have discovered a medicinally beneficial composition and process with the following itemized features:

1. A composition for the burst-free, sustained, programmable release of active material(s) over a period from 1–100 days, which comprises: (1) An active material and (2) A carrier which may contain pharmaceutically-acceptable adjuvant, comprised of a blend of uncapped and end-capped biodegradable-biocompatable copolymer.

2. The composition of Item 1 wherein the polymeric substance is poly(lactide/glycolide).

3. The composition of Item 2, wherein the poly(lactide/glycolide) is a blend of uncapped and end-capped forms, in ratios ranging from 100/0 to 1/99.
4. The composition of Item 3 wherein the copolymer (lactide to glycolide L/G) ratio for uncapped and end-capped polymer is 90/10 to 40/60.
5. The composition of Item 4 wherein the copolymer (lactide to glycolide L/G) ratio for uncapped and end-capped polymer is 48/52 to 52/48.
6. The composition of Item 2 wherein the molecular weight of the copolymer is between 2,000–60,000 daltons.
7. The composition of Item 3 wherein the active material is biologically active agent.
8. The composition of Item 7 wherein the agent is selected from the group consisting essentially of antibacterial agents; peptides; polypeptides; antibacterial peptides; antimycobacterial agents; antimycotic agents; antiviral agents; antiparasitic agents; antifungal agents; hormonal peptides; cardiovascular agents; narcotic antagonists; analgesics; anesthetics; insulins; steroids including HIV therapeutic drugs (including protease inhibitors) and AZT; estrogens; progestins; gastrointestinal therapeutic agents; non-steroidal anti-inflammatory agents; parasympathomimetic agents; psychotherapeutic agents; tranquilizers; decongestants; sedative-hypnotics; non-estrogenic and non-progestional steroids; sympathomimetic agents; vaccines; vitamins; nutrients; anti-migraine drugs; electrolyte replacements; ergot alkaloids; anti-inflammary agents; prostaglandins; cytotoxic drugs; antigens; antibodies; enzymes; growth factors; immunomodulators; pheromones; prodrugs; psychotropic drugs; nicotine; anti-blood clotting drugs; appetite suppressants; stimulants and combinations thereof; contraceptive agents include estrogens such as diethyl silbestrol; 17-beta-estradiol; estrone; ethinyl estradiol; mestranol; progestins such as norethindrone; norgestryl; ethynodiol diacetate; lynestrenol; medroxyprogesterone acetate; dimethisterone; megestrol acetate; chlormadinone acetate; norgestimate; norethisterone; ethisterone; melentate; norgestimate; norethisterone; ethisterone; melengestrol; norethynodrel; and spermicidal compounds such as nonyphenoxypolyoxethylene glycol; benzethonium chloride; chlorindanol; include gastrointestinal therapeutic agents such as aluminum hydroxide; calcium carbonate; magnesium carbonate; sodium carbonate and the like; non-steroidal antifertility agents; parasympathomimetic agents; psychotherapeutic agents; major tranquilizers such as chloropromaquine HCl; clozapine; mesoridazine; metiapine; reserpine; thioridazine; minor tranquilizers such as chlordiazepoxide; diazepam; meprobamate; temazepam and the like rhinological decongestants; sedative-hypnotics such as codeine; phenobarbital; sodium pentobarbital; sodium secobarbital; other steroids such as testosterone and testosterone proprionate; sulfonamides; sympathomimetic agents; vaccines; vitamins and nutrients such as the essential amino acids; essential fats; anti-HIV agents; including AZT; antimalarials such as 4-aminoquinolines; 8 aminoquinolines; pyrimethamine; anti-migraine agents such as mazindol; phentermine; anti-Parkinson agents such as L-dopa; antispasmodics such as atropine; methscopolamine bromide; antispasmodics and anticholingeric agents such as bile therapy; digestants; enzymes and the like; antitussives such as dextromethorphan and noscapine; bronchodilators; cardiovascular agents such as anti-hypertensive compounds; Rauwolfia alkaloids; coronary vasodilators; nitroglycerin; organic nitrites; pentaerythriotetranitrate; electrolyte replacements such as potassium chloride; ergotalkaloids such as ergotamine with and without caffeine; hydrogenated ergot alkaloids; dihydroergocristine methanesulfate; dihydroergocornine methanesulfonate; dihydroergokrouyptine methanesulfate and combinations thereof; alkaloids such as atropine sulfate; Belladonna; hyoscine hydrobromide; analgesics; narcotics such as codeine; dihydrocodienone; meperidine; morphine; non-narcotics such as salicylates; aspirin; acetaminophen; and d-propoxyphene; antibiotics such as the cephalosporins including ceflacor and cefuroxime; chloranphenical; gentamicin; Kanamycin A. Kanamycin B; the penicillins; ampicillin; amoxicillin; streptomycin A; antimycin A; chloropamtheniol; metrbnidazole; oxytetracycline penicillin G; the tetracyclines; including minocycline; fluoroquinolones including ciprofloxacin; ofoxacin; macrolides including clarithromycin; frythromycin; aminioglycosides including gentamicin; amikacin; tobramycinand kanamycin; beta-lactams including ampicillin; polymyxin-B; amphotericin-B; aztrofonam; chloramphenicol; fusidans; lincosamides metronidazole; nitro-furantion; imipenem/cilastin; quinolones; systemic antibodies including rifampin; polygenes; sulfonamides; trimethoprim; glycopeptides including vancomycin; teicoplanin and imidazoles; anti-cancer agents, including anti-kaposi's sarcoma; anticonvulsants such as mephenytoini; phenobarbital; trimethadione; antiemetics such as triethylperazine; antihistamines such as chlorophinazine; dimenhydrinate; diphenhydramine; perphenazine; tripelennamine and the like; anti-inflammatory agents such as hormonal agents; hydrocortisone; prednisolone; prednisone; non-hormonal agents; allopurinol; for claims water-soluble hormone drugs; antibiotics; anti-tumor agents; anti inflammatory agents; antipyretics; analgesics; antitussives; expectorants; sedatives; muscle relaxants; antiepileptics; anticulcer agents; antidepressants; antiallergic drugs; cardiotonics; antiarrhythmic drugs; vasodilators; antihypertensives; diuretics; anticoagulants; and antinarcotics; in the molecular weight range of 100–100,000 daltons; indomethacin; phenylbutazone; prostaglandins; cytotoxic drugs such thiotepa; chloramucil; cyclophosphamide; melphala; nitrogen mustard; methotrexate; antigens such as proteins; glycoproteins; synthetic peptides; carbohydrates; synthetic polysaccharides; lipids; glycolipids; lipopolysaccharides(LPS); synthetic lipopolysaccharides and with or with attached adjuvants such as synthetic muramyl dipeptide derivatives; antigens of such microorganisms as *Neisseria gonorrhea; Mycobacterium tuberculosis; Picarinii Phfumonia*; Herpes virus (humonis types1 and 2); Herpes zoster; *Candidia albicans; Candida tropicalis; Trichomonas vaginalis; Haemophilus vaginalis;* Group B *streptococcus ecoli; Microplasma hominis; Hemophilus ducreyi; Granuloma inguimale; Lymphopathia venerum;Treponema palidum; Brucela aborus Brucela meitensis Brucela suis; Brucella canis Campylobacter fetus; Campylobacter fetus intesinalis; Leptospira pomona; Listeria monocytogenes; Brucella ovis*; Equine herpes virus 1, equine arteritis virus; IBR-IBP virus; *Chlamydia psittaci; Trichomonas foetus; Taxoplasma gondii; Escherichia coli; Actinobacillus equili; Salmonella abortus ovis; Salmonella abortus eui; Pseudomonas aeruginosa; corynebacterium equi;, Corynebacterium pyogenes; Actinobacillus seminis; mycoplasma bovigenitalum; aspergilus fumigatus; absidia ramosa; Trypanosoma equiperdum; Babesia cabil; Clostridium tetani*; antibodies which counteract the above microorganisms; and enzymes including ribonuclease; neuramidinase; trypsin; glycogen phosphorylase;

sperm lactic dehydrogenase; sperm hyaluronidase; adenossinetriphosphase; alkaline phosphatase; alkaline acrosomal proteinase; diesterase; glutamic acid dehydrogenase; succunic and dehydrogenase; beta-glycophosphatase lipase; ATP-ase alpha-peptate gamma-glutamyiotranspeptidase; sterid-beta-ol-dehydrogenase; DPN-di-aprorase; and combinations thereof.

9. The composition of Item 8 wherein the agent is selected from the group consisting essentially of antibacterial agents; antibacterial peptides; antimycobacterial agents; antimycotic agents; antiviral agents; antiparasitic agents; antifungal; hormonal peptides; cardiovascular agents; narcotic antagonist; analgesics; anesthetics; vaccines; insulins; HIV therapeutic. drugs (protease inhibitors), estrogens; progestins; gastrointestinal therapeutic agents; non-steroidal anti-inflammatory agents; parasympathomimetic agents; psychotherapeutic agents; tranquilizers; decongestants; sedative-hypnotics; non-estrogenic and non-progestional steroids; sympathomimetic agents; vaccines;vitamins; nutrients; anti-malarial compounds; anti-migraine drugs; electrolyte replacements; ergot alkaloids; analgetic; non-narcotics; anti-cancer agents; anticonvulsants; anti-emetics; antihistamines; anti-inflammary agents; prostaglandins; cytotoxic drugs; antigen; antibodies; enzymes; growth factors; immunomedulators; pheromones; prodrugs; psychotropic drugs; appetite suppressants/stimulants; and combinations thereof.

10. The composition of Item 8 wherein the agent is a peptide or polypeptide.

11. The composition of Item 10 wherein the agent is a poly peptide.

12. The composition of Item 11 wherein the molecular weight of the polypeptide is between 1,000 and 250,000 daltons.

13. The composition of Item 12 wherein the polypeptide is histatin consisting of 12 amino acids and having a molecular weight of 1563.

14. The composition of Item 1 characterized by the capacity to completely release histatin in an aqueous physiological environment within from 1 to 40 days with a 100/0 blend of uncapped and end-capped poly(lactide/glycolide) having a L/G ratio of 48/52 to 52/48, and a molecular weight less than 15,000.

15. The composition of Item 14 wherein the histatin can be completely released within 18 to 40 days and the molecular weight o the poly(lactide/glycolide) is within the range of 28,000 to 40,000.

16. The composition of Item 2 characterized by the capacity to release up to 90% of the histatin in an aqueous physiological environment from 28–70 days with a 1/99 blend of uncapped and end-capped poly(lactide/glycolide) having a L/G ratio of 48/52 to 52/48 and a molecular weight range of 10,000–40,000 daltons.

17. The composition of Item 2 characterized by the capacity to release up to 80% of histatin in an aqueous physiological environment from 56–100 days with a 1/99 blend of uncapped and end-capped poly(lactide/glycolide) having a L/G ration of 75/25 and a molecular weight of less than 15,000 daltons.

18. The composition of Item 13 having analogs of histatin with chain lengths of from 11–24 amino acids of molecular weights from 1,500–3,000 daltons and characterized by the following structures:
1. DSHAKRHHGYKRKFHEKHHSHRGY, SEQ. ID. NO: 1
2. KRHHGYKRKFHEKHHSHRGYR, SEQ. ID. NO: 2
3. KRHHGYKRKFHEKHHSHR, SEQ. ID. NO: 3
4. RKFHEKHHSHRGYR, SEQ. ID. NO: 4
5. AKRHHGYKRKFH, SEQ. ID. NO: 5
6. *AKRHHGYKRKFH, SEQ. ID. NO: 5
7. KRHHGYKRKF, SEQ. ID. NO: 6

* D-amino acid

19. The composition of Item 10 wherein the biologically active agent is a polypeptide Luteinizing hormone releasing hormone (LHRH) that is a decapeptide of molecular weight 1182 in its acetate form, and having the structure: p-EHWSYGLRPG SEQ. ID. NO: 7.

20. The composition of Item 13 having a molecular weight of from 1,000 to 250,000 daltons.

21. The composition of Item 2 wherein release profiles of variable rates and durations are achieved by blending uncapped and capped microspheres as a cocktail in variable amounts.

22. The composition of Item 2 wherein release of profiles of variable rates and duration are achieved by blending uncapped and capped polymer in different ratios within the same microspheres.

23. The composition of Item 12 wherein the entrapped polypeptide is any of the vaccine agents against enterotoxigenic E. coli (ETEC) selected from the group consisting of CFA/I, CFA/II, CS1, CS3, CS6 and CS17, ETEC-related enterotoxins, and combinations thereof.

24. The composition of Item 23 wherein the entrapped polypeptide consists of peptide antigens of molecular weight range of 800–5000 daltons for immunization against enterotoxigenic E. coli (ETEC).

25. The composition of Item 24 wherein the entrapped polypeptide is selected from the group consisting essentially of an antigenic synthetic peptide containing CFA/I pilus protein T-cell epitopes; B-cell epitopes, or mixtures thereof.

26. The composition of Item 24 wherein the poly(lactide/glycolide) is a blend of uncapped and end-capped forms, in ratios ranging from 48/52 to 52/48.

27. The composition of Item 7 wherein said agent are selected from the group consisting of water-soluble hormone drugs, antibiotics, antitumor agents, anti inflammatory agents, antipyretics, analgesics antitussives, expectorants, sedatives, muscle relaxants, antiepileptics, antiulcer agents, antidepressants, antiallergic drugs, cardiotonics, antiarrhythmic drugs, vasodilators, antihypertensives, diuretics, anticoagulants, antinarcotics, in the molecular weight range of 100–100,000 daltons.

28. The composition of Item 1 wherein said biodegradable poly(lactide/glycolide) is in an oil phase, and is present in about 1–50% (w/w).

29. The composition of Item 28 wherein concentration of the active agent is in the range of 0.1 to about 60% (w/w).

30. The composition of Item 29 wherein a ration of the inner aqueous to oil phases is about 1/4 to 1/40 (v/v).

31. The composition of Item 11 wherein the entrapped polypeptide is active at a low pH, such as LHRH, adrenocorticotropic hormone, epidermal growth factor, calcitonin released polypeptide is bioactive.

32. The composition of Item 11 when entrapped polypeptide such as histatin is inactive at a low pH, a pH-stabilizing agent of inorganic salts are added to the inner aqueous phase to maintain-biological activity of the released peptide.

33. The composition of Item 11 wherein when entrapped polypeptide such as histatin is inactive at a low pH, a non-ionic surfactant such as polyoxyethylene sorbitan fatty acid esters (Tween 80, Tween 60 and Tween 20) and polyoxyethylene—polyoxypropylene block copolymers (Pluronics) is added to the inner aqueous phase to maintain biological activity of the released polypeptide.

34. The composition of Item 32 wherein placebo spheres loaded with the pH-stabilizing agents are coadministered with polypeptide-loaded spheres to activity of the released peptide in instances where the addition of pH-stabilizing agents in the inner aqueous phase is undesirable for the successful encapsulation of the acid pH sensitive polypeptide.

35. The composition of Item 33 wherein placebo spheres loaded with non-ionic surfactant are coadministered with polypeptide-loaded spheres to maintain biological activity of the released peptide where the addition of non-ionic surfactants in the inner aqueous phase is undesirable for successful encapsulation of the acid pH sensitive polypeptide.

36. The composition of Item 1 comprising a blend of uncapped and capped polymer, wherein complete solubilization of the copolymer leaves no residual polymer at the site of administration and occurs concurrently with the complete release of the entrapped agent.

37. A process of using composition of Item 1 for human administration via parenteral routes, such as intramuscular and subcutaneous.

38. A process of using the composition of Item 1 for human administration via topical route.

39. A process of using the composition of Item 1 for human administration via oral routes.

40. A process of using the composition of Item 1 for human administration via nasal, transdermal, rectal, and vaginal routes.

41. A process of using the composition of Item 1 for human administration in the form of an oral or nasal inhalant for the respiratory tract.

42. A process for preparing controlled release compositions characterized by burst-free, sustained, programmable release of biologically active agents, comprising: Dissolving biodegradable poly(lactide/glycolide), in uncapped form in methylene chloride, and dissolving a biologically active agent or active core in water; adding the aqueous layer to the polymer solution and w/o emulsion in a solvent-saturated aqueous phase containing a oil-in-water (o/w) emulsifier; adding said w/o emulsion to an external aqueous layer containing oil-in-water emulsifier to form a ternary emulsion; and stirring the resulting water-in-oil-in-water (w/o/w) emulsion for sufficient time to remove said solvent, and rinsing hardened microcapsules with water and lyophilizing said hardened microcapsules.

43. The process of Item 42 wherein a solvent-saturated external aqueous phase is added to emulsify the inner w/o emulsion prior to addition of the external aqueous layer, to provide microcapsules of narrow size distribution range between 0.05–500 um.

44. The process of Item 42 wherein a low temperature of about 0–4 degree C. is provided during preparation of the inner w/o emulsion, and a low temperature of about 4–20 degree C. is provided during preparation of the w/o/w emulsion to provide a stable emulsion and high encapsulation efficiency.

45. A process for preparing controlled release compositions characterized by burst-free, sustained compositions characterized by burst-free, sustained, programmable release of biologically active agents, comprising:
dissolving biodegradable poly(lactide/glycolide) in end-capped form in methylene chloride, and dissolving a biologically active agent or active core in water; adding the aqueous layer to the polymer solution and emulsifying to provide an inner water-in-oil emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring a resulting water-in-oil-water (w/o/w) emulsion for sufficient time to remove said solvent; and rinsing heardened microcapsules with water; and lyophilizing said hardened microcapsules.

46. The process of Item 42 wherein a 100/0 blend of uncapped and end-capped polymer is used to provide release of the active core in a continuous and sustained manner without a lag phase.

47. The process of Item 45 wherein a solvent-saturated external aqueous phase is added to emulsify the inner w/o emulsion prior to addition of the external aqueous layer, to provide microcapsules of narrow size distribution range between 0.05–500 um.

48. The process of Item 45 wherein a low temperature of about 0–4 degree C. is provided during preparation of the inner w/o emulsion, and a low temperature of about 4–20 degree C. is provided during preparation of the w/o/w emulsion to provide a stable emulsion and high encapsulation efficiency.

49. A method for the protection against infection of a mammal by pathogenic organisms comprising administering orally to said mammal an immunogenic amount of an immunostimulating composition consisting essentially of an antigenic synthetic peptide encapsulated within a poly(lactide/glycolide) matrix.

50. The method of Item 49 wherein the poly(lactide/glycolide) is a blend of uncapped and end-capped forms, in ratios ranging from 100/0 to 1/99.

51. The method of Item 49 wherein the poly(lactide/glycolide) is a blend of uncapped and end-capped forms in ratios ranging from 90/10 to 40/60.

52. The method of Item 49 wherein the infection is bacterial infection.

53. The method of Item 49 where the synthetic peptide contains an epitope selected from the group consisting of CFA/I pilus protein T-cell epitopes, B-cell epitopes or mixtures thereof.

54. The method of Item 49 wherein the infection is a viral infection.

55. The method of Item 49 wherein the infection is parasitic infection.

56. The method of Item 49 wherein the infection is a fungal infection.

57. The method of Item 52 wherein the bacterial infection is caused by a bacteria selected from the group consisting essentially of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Legionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.
58. The method in accordance with Item 49 comprising administering orally to said mammal an immunogenic amount of a pharmaceutical composition consisting essentially of an antigenic synthetic peptide in the amount of 0.1 to 1%.
59. A vaccine for the immunization of a mammal against infection caused by pathogenic organisms prepared from the composition of Item 1.
60. The vaccine according to Item 59 wherein the polymeric substance is poly(DL-lactide-co-glycolide).
61. The vaccine according to Item 59 wherein the relative ratio between the uncapped and end-capped forms of the lactide and glycolide (L/G) component is within the range of 40/60 to 0/100.
62. The vaccine according to Item 61 wherein the relative ratio between the amount of the uncapped and end-capped forms is within the range of 90/10 to 40/60.
63. A vaccine according to Item 62 wherein the pathogenic organisms are bacterial.
64. A vaccine according to Item 62 wherein the pathogenic organisms are viral.
65. A vaccine according to Item 62 wherein the pathogenic organisms are fungal.
66. A vaccine according to Item 62 wherein the pathogenic organisms are parasitic.
67. The vaccine according to Item 63 wherein the antigenic synthetic peptide is selectedfrom the group consisting essentially of Synthetic Peptides Containing CFA/Pilus Protein T-cell epitopes (Starting Sequence # given)

4(Asn-Ile-Thr-Val-Thr-Ala-Ser-Val-Asp-Pro), SEQ ID NO: 8

8(Thr-Ala-Ser-Val-Asp-Pro-Val-Ile-Asp-Leu), SEQ ID NO: 9

12(Asp-Pro-Val-Ile-Asp-Leu-Leu-Gln-Ala-Asp), SEQ ID NO: 10

15(Ile-Asp-Leu-Leu-Gln-Ala-Asp-Gly-Asn-Ala), SEQ ID NO: 11

20(Ala-Asp-Gly-Asn-Ala-Leu-Pro-Ser-Ala-Val), SEQ ID NO: 12

26(Pro-Ser-Ala-Val-Lys-Leu-Ala-Tyr-Ser-Pro) SEQ ID NO: 13

72(Leu-Asn-Ser-Thr-Val-Gln-Met-Pro-Ile-Ser), SEQ ID NO: 14

78(Met-Pro-Ile-Ser-Val-Ser-Trp-Gly-Gly-Gln), SEQ ID NO: 15

87(Gln-Val-Leu-Ser-Thr-Thr-Ala-Lys-Glu-Phe), SEQ ID NO: 16

126(Ala-Gly-Thr-Ala-Pro-Thr-Ala-Gly-Asn-Tyr), SEQ ID NO: 17 and

133(Gly-Asn-Tyr-Ser-Gly-Val-Val-Ser-Leu-Val), SEQ ID NO: 18, and mixtures thereof.

Synthetic Peptides Containing CFA/I Pilus Protein B-Cell (antibody) Epitopes (Starting Sequence # given)

3(Lys-Asp-Ile-Thr-Val-Thr-Ala-Ser-Val), SEQ ID NO: 19

11(Val-Asp-Pro-Val-Ile-Asp-Leu-Leu-Gln-Ala-Asp), SEQ ID NO: 20

32(Ala-Tyr-Ser-Pro-Ala-Ser-Lys-Thr-Phe-Lys-Thr-Phe-Glu-Ser-Tyr-Arg-Val), SEQ ID NO: 21

32(Ala-Tyr-Ser-Pro-Ala-Ser-Lys-Thr-Phe) SEQ ID NO: 22

38(Lys-Thr-Phe-Glu-Ser-Tyr-Arg-Val), SEQ ID NO: 23

66(Pro-Gln-Leu-Thr-Asp-Val-Leu-Asn-Ser), SEQ ID NO: 24

93(Ala-Lys-Glu-Phe-Glu-Ala-Ala-Ala), SEQ ID NO: 25

124(Lys-Thr-Ala-Gly-Thr-Ala-Pro-Thr), SEQ ID NO: 26

127(Gly-Thr-Ala-Pro-Thr-Ala-Gly-Asn-Tyr-Ser), SEQ ID NO: 27 and

124(Lys-Thr-Ala-Gly-Thr-Ala-Pro-Thr-Ala-Gly-Asn-Tyr-Ser), SEQ ID NO: 28 and mixtures thereof.

Synthetic peptides containing CFA/I Pilus Protein T-cell and B-cell (antibody) Epitopes (Starting Sequence # given)

3(Lys-Asn-Ile-Thr-Val-Thr-Ala-Ser-Val-Asp-Pro), SEQ ID NO: 29

8(Thr-Ala-Ser-Val-Asp-Pro-Val-Ile-Asp-Leu-Leu-Gln-Ala-Asp), SEQID NO: 30

11(Val-Asp-Pro-Val-Ile-Asp-Leu-Leu-Gln-Ala-Asp), SEQ ID NO: 20

20(Ala-Asp-Gly-Asn-Ala-Leu-Pro-Ser-Ala-Val), SEQ ID NO: 12

124(Lys-Thr-Ala-Gly-Thr-Ala-Pro-Thr-Ala-Gly-Asn-Tyr-Ser), SEQ ID NO: 28 and

126(Ala-Gly-Thr-Ala-Pro-Thr-Ala-Gly-Asn-Tyr-Ser), SEQ ID NO: 55, and mixtures thereof.

68. The vaccine according to Item 67 wherein the bacteria is selected from the group consisting essentially of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Legionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

69. The vaccine according to Item 67 wherein the antigenic synthetic peptide is selected from the group consisting essentially of 4(Asn-Ile-Thr-Val-Thr-Ala-Ser-Val-Asp-Pro), SEQ ID NO: 8

8(Thr-Ala-Ser-Val-Asp-Pro-Val-Ile-Asp-Leu), SEQ ID NO: 9

12(Asp-Pro-Val-Ile-Asp-Leu-Leu-Gln-Ala-Asp), SEQ ID NO: 10

15(Ile-Asp-Leu-Leu-Gln-Ala-Asp-Gly-Asn-Ala), SEQ ID NO: 11

20(Ala-Asp-Gly-Asn-Ala-Leu-Pro-Ser-Ala-Val), SEQ ID NO: 12

26(Pro-Ser-Ala-Val-Lys-Leu-Ala-Tyr-Ser-Pro) SEQ ID NO: 13

72(Leu-Asn-Ser-Thr-Val-Gln-Met-Pro-Ile-Ser), SEQ ID NO: 14

78(Met-Pro-Ile-Ser-Val-Ser-Trp-Gly-Gly-Gln), SEQ ID NO: 15

87(Gln-Val-Leu-Ser-Thr-Thr-Ala-Lys-Glu-Phe), SEQ ID NO: 16

126(Ala-Gly-Thr-Ala-Pro-Thr-Ala-Gly-Asn-Tyr), SEQ ID NO: 17 and

133(Gly-Asn-Tyr-Ser-Gly-Val-Val-Ser-Leu-Val), SEQ ID NO: 18, and mixtures thereof.

70. The vaccine according to Item 69 wherein the antigenic synthetic peptide is 4(Asn-Ile-Thr-Val-Thr-Ala-Ser-Val-Asp-Pro), SEQ ID NO: 8.

71. The vaccine according to Item 69 wherein the antigenic synthetic peptide is 8(Thr-Ala-Ser-Val-Asp-Pro-Val-Ile-Asp-Leu), SEQ ID NO: 9.

72. The vaccine according to Item 69 wherein the antigenic synthetic peptide is 12(Asp-Pro-Val-Ile-Asp-Leu-Leu-Gln-Ala-Asp) SEQ ID NO: 10.

73. The vaccine according to Item 69 wherein the antigenic synthetic peptide is 15(Ile-Asp-Leu-Leu-Gln-Ala-Asp-Gly-Asn-Ala) SEQ ID NO: 11.

74. The vaccine according to Item 69 wherein the antigenic synthetic peptide is 20(Ala-Asp-Gly-Asn-Ala-Leu-Pro-Ser-Ala-Val) SEQ ID NO: 12.

75. The vaccine according to Item 69 wherein the antigenic synthetic peptide is 26(Pro-Ser-Ala-Val-Lys-Leu-Ala-Tyr-Ser-Pro) SEQ ID NO: 13.

76. The vaccine according to Item 69 wherein the antigenic synthetic peptide is 72(Leu-Asn-Ser-Thr-Val-Gln-Met-Pro-Ile-Ser) SEQ ID NO: 14.

77. The vaccine according to Item 69 wherein the antigenic synthetic peptide is 78(Met-Pro-Ile-Ser-Val-Ser-Trp-Gly-Gly-Gln) SEQ ID NO: 15.

78. The vaccine according to Item 69 wherein the antigenic synthetic peptide is 87(Gln-Val-Leu-Ser-Thr-Thr-Ala-Lys-Glu-Phe) SEQ ID NO: 16.

79. The vaccine according to Item 69 wherein the antigenic synthetic peptide is 126(Ala-Gly-Thr-Ala-Pro-Thr-Ala-Gly-Asn-Thr) SEQ. ID. NO. 54.

80. The vaccine according to Item 69 wherein the antigenic synthetic peptide is 133(Gly-Asn-Tyr-Ser-Gly-Val-Val-Ser-Leu-Val) SEQ ID NO: 18.

81. The vaccine according to Item 67 wherein the antigenic synthetic peptide is selected from the group consisting essentially of 3(Lys-Asp-Ile-Thr-Val-Thr-Ala-Ser-Val), SEQ ID NO: 19

11(Val-Asp-Pro-Val-Ile-Asp-Leu-Leu-Gln-Ala-Asp), SEQ ID NO: 20

22(Gly-Asn-Ala-Leu-Pro-Ser-Ala-Val), SEQ. ID. NO: 31

32(Ala-Tyr-Ser-Pro-Ala-Ser-Lys-Thr-Phe-Lys-Thr-Phe-Glu-Ser-Tyr-Arg-Val), SEQ ID NO: 21

32(Ala-Tyr-Ser-Pro-Ala-Ser-Lys-Thr-Phe) SEQ ID NO: 22

38(Lys-Thr-Phe-Glu-Ser-Tyr-Arg-Val), SEQ ID NO: 23

66(Pro-Gln-Leu-Thr-Asp-Val-Leu-Asn-Ser), SEQ ID NO: 24

93(Ala-Lys-Glu-Phe-Glu-Ala-Ala-Ala), SEQ ID NO: 25

124(Lys-Thr-Ala-Gly-Thr-Ala-Pro-Thr), SEQ ID NO: 26

127(Gly-Thr-Ala-Pro-Thr-Ala-Gly-Asn-Tyr-Ser), SEQ ID NO: 27 and

124(Lys-Thr-Ala-Gly-Thr-Ala-Pro-Thr-Ala-Gly-Asn-Tyr-Ser), SEQ ID NO: 28 and mixtures thereof.

82. The vaccine according to Item 81 wherein the antigenic synthetic peptide is 3(Lys-Asp-Ile-Thr-Val-Thr-Ala-Ser-Val) SEQ ID NO: 19.

83. The vaccine according to Item 81 wherein the antigenic synthetic peptide is 11(Val-Asp-Pro-Val-Ile-Asp-Leu-Leu-Gln-Ala-Asp) SEQ ID NO: 20.

84. The vaccine according to Item 81 wherein the antigenic synthetic peptide is 22(Gly-Asn-Ala-Leu-Pro-Ser-Ala-Val) SEQ. ID. NO: 31.

85. The vaccine according to Item 81 wherein the antigenic synthetic peptide is 32(Ala-Tyr-Ser-Pro-Ala-Ser-Lys-Thr-Phe-Lys-Thr-Phe-Glu-Ser-Tyr-Arg-Val) SEQ ID NO: 21.

86. The vaccine according to Item 81 wherein the antigenic synthetic peptide is 32(Ala-Tyr-Ser-Pro-Ala-Ser-Lys-Thr-Phe) SEQ ID NO: 22.

87. The vaccine according to Item 81 wherein the antigenic synthetic peptide is 38(Lys-Thr-Phe-Glu-Ser-Tyr-Arg-Val) SEQ ID NO: 23.

88. The vaccine according to Item 81 wherein the antigenic synthetic peptide is 66(Pro-Gln-Leu-Thr-Asp-Val-Leu-Asn-Ser) SEQ ID NO: 24.

89. The vaccine according to Item 81 wherein the antigenic synthetic peptide is 93(Ala-Lys-Glu-Phe-Glu-Ala-Ala-Ala) SEQ ID NO: 25.

90. The vaccine according to Item 81 wherein the antigenic synthetic peptide is 124(Lys-Thr-Ala-Gly-Thr-Ala-Pro-Thr) SEQ ID NO: 26.

91. The vaccine according to Item 82 wherein the antigenic synthetic peptide is 127(Gly-Thr-Ala-Pro-Thr-Ala-Gly-Asn-Tyr-Ser) SEQ ID NO: 27.

92. The vaccine according to Item 82 wherein the antigenic synthetic peptide is 124(Lys-Thr-Ala-Gly-Thr-Ala-Pro-Thr-Ala-Gly-Asn-Tyr-Ser) SEQ ID NO: 28.

93. The vaccine according to Item 67 wherein the antigenic synthetic peptide is selected from the group consisting essentially of 3(Lys-Asn-Ile-Thr-Val-Thr-Ala-Ser-Val-Asp-Pro) SEQ. ID. NO: 29, 8(Thr-Ala-Ser-Val-Asp-Pro-Val-Ile-Asp-Leu-Leu-Gln-Ala-Asp) SEQ ID NO: 30, 11(Val-Asp-Pro-Val-Ile-Asp-Leu-Leu-Gln-Ala-Asp) SEQ ID NO: 20, 20(Ala-Asp-Gly-Asn-Ala-Leu-Pro-Ser-Ala-Val) SEQ ID NO: 12, 124(Lys-Thr-Ala-Gly-Thr-Ala-Pro-Thr-Ala-Gly-Asn-Tyr-Ser) SEQ ID NO: 28, and 126(Ala-Gly-Thr-Ala-Pro-Thr-Ala-Gly-Asn-Tyr-Ser), SEQ ID NO: 55, and mixtures thereof.

94. The vaccine according to Item 92 wherein the antigenic synthetic peptide is 3(Lys-Asn-Ile-Thr-Val-Thr-Ala-Ser-Val-Asp-Pro) SEQ ID NO: 29.

95. The vaccine according to Item 93 wherein the antigenic synthetic peptide is 8(Thr-Ala-Ser-Val-Asp-Pro-Val-Ile-Asp-Leu-Leu-Gln-Ala-Asp) SEQ ID NO: 30.

96. The vaccine according to Item 93 wherein the antigenic synthetic peptide is 1(Val-Asp-Pro-Val-Ile-Asp-Leu-Leu-Gln-Ala-Asp) SEQ. ID. NO: 32.

97. The vaccine according to Item 93 wherein the antigenic synthetic peptide is 20(Ala-Asp-Gly-Asn-Ala-Leu-Pro-Ser-Ala-Val) SEQ ID NO: 12.

98. The vaccine according to Item 93 wherein the antigenic synthetic peptide is 124(Lys-Thr-Ala-Gly-Thr-Ala-Pro-Thr-Ala-Gly-Asn-Tyr-Ser) SEQ. ID. NO: 56.

99. The vaccine according to Item 93 wherein the antigenic synthetic peptide is 126(Ala-Gly-Thr-Ala-Pro-Thr-Ala-Gly-Asn-Tyr-Ser), SEQ. ID. NO: 55.

100. The method of Item 54, wherein the viral infection is caused by a virus selected from the group consisting essentially of hepatitis A, hepatitis B, hepatitis C, Varicella-Zoster virus, Epstein-Barr virus, Rotaviruses, polio virus, human immunodeficiency virus (HIV), herpes simplex virus type 1, human retroviruses, herpes simplex virus type 2, Ebola virus, cytomegalo viruses, Herpes Simplex viruses, Human cytomegalovirus, Varicella-Zoster Virus, Epstein-Barr virus, Poxvirus, Influenza viruses, Parainfluenza viruses, Respiratory Syncytial virus, Rhinoviruses, Coronaviruses, Adenoviruses, Measles virus, Mumps virus, Robella Virus, Human Parvoviruses, Arboviruses, Rabies virus, Enteroviruses, reoviruses, Viruses Causing gastroenteritis Hepatitis Viruses, Filoviruses, Arenaaviruses, Papillomaviruses, Polyomaviruses, Human Immunodeficiency viruses, Human Retroviruses, and Spbngiform Encephalopathies.

101. The method in accordance with Item 49 comprising administering orally to said mammal an immunogenic amount of a pharmaceutical composition consisting essentially of an antigen in the amount of 0.1 to 1%.

102. A vaccine for the immunization of a mammal against infection by pathogenic organisms consisting essentially of an antigen in the amount of 0.1 to 1% encapsulated within a biodegradable-biocompatible polymeric poly (DL-lactide-co-glycolide) matrix wherein the polymer is end-capped or a blend of uncapped and end-capped polymers.

103. The vaccine according to Item 100 wherein the polymer is a blend of end-capped and uncapped polymers.

104. The vaccine according to Item 103 wherein the relative ratio between the lactide and glycolide component is within the range of 90/10 to 40/60.

105. The vaccine according to Item 103 wherein the relative ratio between the amount of lactide and glycolide component is within the range of 48/52 to 52/48.

106. The vaccine according to Item 102 wherein the antigen is a bacteria or derivatives thereof.

107. The vaccine according to Item 103 wherein the antigen is a virus or derivatives thereof.

108. The vaccine according to Item 103 wherein the antigens is parasite or derivative thereof.

109. The vaccine according to Item 103 wherein the antigen is a fungus or derivative thereof.

110. The vaccine according to Item 106 wherein the bacteria is selected from the group coconsisting essentially of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Legionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

111. The vaccine of Item 107 wherein the virus is selected from the group consisting essentially of hepatitis A, hepatitis B, hepatitis C, Varicella-Zoster virus, Epstein-Barr virus, Rotaviruses, polio virus, human immunodeficiency virus (HIV), herpes simplex virus type 1, human retroviruses, herpes simplex virus type 2, Ebola virus, cytomegalo viruses, Herpes Simplex. viruses, Human cytomegalovirus, Varicella-Zoster Virus, Epstein-Barr virus, Poxvirus, Influenza viruses, Parainfluenza viruses, Respiratory Syncytial virus, Rhinoviruses, Coronaviruses, Adenoviruses, Measles virus, Mumps virus, Robella Virus, Human Parvoviruses, Arboviruses, Rabies virus, Enteroviruses, reoviruses, Viruses Causing gastroenteritis Hepatitis Viruses, Filoviruses, Arenaaviruses, Papillomaviruses, Polyomaviruses, Human Immunodeficiency viruses, Human Retroviruses, and Spongiform Encephalopathies.

112. An immunostimulating composition comprising encapsulating-microspheres, which may contain a pharmaceutically-acceptable adjuvant, wherein said microspheres having a diameter between 1 nanogram (ng) to 10 microns (um) are comprised of (a) a biodegradable-biocompatible poly(DL-lactide-co-glycolide) as the bulk matrix, wherein the copolymer (lactide to glycolide L/G) ratio for uncapped and end-capped polymer is 0/100 to 1/99 and (b) an immunogenic substance comprising a bacteria, virus, fungus, parasite, or derivative thereof, that serves to elicit the production of antibodies in animal subjects.

113. An immunostimulating composition according to Item 112 wherein the amount of said immunogenic substance is within the range of 0.1 to 1.5% based on the volume of said bulk matrix.

114. An immunostimulating composition according to Item 110 wherein the immunogenic substance comprises Colony Factor Antigen (CFA/II), hepatitis B surface antigen (HBsAg), a mixture thereof physiologically similar antigen.

115. An immunostimulating composition according to Item 113 where the relative ratio between the lactide and glycolide component is within the range of 48/52 to 52/48.

116. An immunostimulating composition according to Item 113 wherein the size of more than 50% of said microspheres is between 5 to 10 um in diameter by volume.

117. An immunostimulating composition according to Item 113 wherein the immmunogenic substance is the synthetic peptide representing the peptide fragment beginning with the amino acid residue 63 through 78 of Pilus Protein CS3, said d residue having the amino acid sequence, 63(Ser-Lys-Asn-Gly-Thr-Val-Thr-Thr-Ala-His-Glu-Thr-Asn-Asn-Ser-Ala). SEQ. ID. NO: 33.

118. A vaccine comprising an immunostimulating composition of Item 113 and a sterile, pharmaceutically-acceptable carrier thereof.

119. A vaccine comprising an immunostimulating composition of Item 118 wherein said immunogenic substance is Colony Factor Antigen (CFA/II).

120. A vaccine comprising an immunostimulating composition of Item 119 wherein said immunogenic substance is hepatitis B surface antigen (HBsAg).

121. A method for the vaccination against bacterial infection comprising administering to a human, an antibactericidally effective amount of a composition of Item 118.

122. A method according to Item 121 wherein the bacterial infection is caused by a bacteria selected from the group consisting essentially of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Legionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

123. A method for the vaccination against viral infection comprising administering to a human an antivirally effective amount of a composition of Item 108.

124. A diagnostic assay for bacterial infections comprising a composition of Item 7.

125. A method of preparing an immunotherapeutic agent against infections caused by a bacteria comprising the steps of (1) immunizing a plasma donor with a vaccine according to Item 52 such that a hyperimmune globulin is produced which contains antibodies directed against the bacteria; (2) separating the hyperimmune globulin and (3) purifying the hyperimmune globulin.

126. A method preparing an immunotherapeutic agent against infections caused by a vires comprising the step of immunizing a plasma donor with a vaccine according to Item 54 such that hyperimmune globulin is produced which contains antibodies directed against the hepatitus B virus.

127. An immunotherapy method comprising the step of administering to a subject an immunostimulatory amount of hyperimmune globulin prepared according to item 125.

128. An immunotherapy method comprising the step of administering to a subject an immunostimulatory amount of hyperimmune globulin prepared according to Item 125.

129. A method for the protection against infection of a subject by enteropathogenic organisms of hepatitis b virus comprising administering to said subject an immunogenic amount of an immunostimulating composition of Item 114.

130. A method according to Item 127 wherein the immunostimulating composition is administered orally.

131. A method according to Item 127 wherein the immunostimulating composition is administered parenterally.

132. A method according to Item 127 wherein the immunostimulating composition is administered in four separate doses on day 0, day 7, day 14, and day 28.

133. A method according to Item 114 wherein the immunogenic substance is the synthetic peptide representing the peptide fragment beginning with the amino acid residue 63 through 78 of Pilus Protein CS3 said residue having the amino acid sequence 63(Ser-Lys-Asn-Gly-Thr-Val-Thr-Thr-Ala-His-Glu-Thr-Asn-Asn-Ser-Ala). SEQ. ID. NO: 33.

134. A method for the protection against or therapeutic treatment of bacterial infection in the soft tissue or bone of a mammal comprising administering locally to said mammal a bactericidally-effective amount of a composition of Item 2, wherein the active material is an antibiotic which is controlled release within a period of about 1 to 10 days.

135. The method according to Item 134 wherein the biodegradable poly(DL-lactide-co-glycolide) is a blend of uncapped and end-capped forms having a relative ratio between the amount of lactide and glycolide component within the range of 100/0 to 1/99.

136. A method according to Item 135 wherein the bacterial infection is (1) a subcutaneous infection secondary to contaminated abdominal surgery, (2) an infection surrounding prosthetic devices and vascular grafts, (3) ocular infections, (4) topical skin infections, (5) orthopedic infections, including osteomyelitis, and (6) oral infections.

137. The method according to Item 136 wherein the oral infections are pericoronitis or periodontal disease.

138. The method according to Item 135 wherein the administration is effected prior to infection.

139. The method according to Item 135 wherein the administration is effected subsequent to infection.

140. The method according to Item 135 wherein said animal is a human.

141. The method according to Item 135 wherein said animal is a nonhuman.

142. The method in accordance with Item 135 comprising applying to the soft tissue or bone tissue of said animal a bactericidally-effective amount of a pharmaceutical composition consisting essentially of an antibiotic in the ant, selected from the group consisting of a beta-lactam, aminoglycolide, polymyxin-b, Amphotericin B, Aztreonam, cephalosporins, chloramphenicol, fusidans, lincosamides, macrolides, methronidazole, nitro-furation, Imipenem/cilastin, quinolones, refampin, polyenes, tetracycline, sulfonamides, trimethoprim, vancomycin, teicoplanin, imidazoles, and erythromycin, encapsulated within a biodegradable poly(DL-lactide-co-glycolide) polymeric matrix, wherein the amount of the lactide and glycolide (L/G) component is within the range of 48/52 to 52/48 based on the weight of said polymeric matrix which is present in the amount of from 40 to 95 percent, resulting in the controlled release of a bacteriacidal amount of the said antibiotic over a period of from 1 to 100 days.

143. The method of Item 142 wherein the polymeric matrix consists essentially of a poly(DL-lactide-co-glycolide) wherein the relative ratio between the amount of lactide and glycolide (L/G) component is within the range of 48/52 to 52/48.

144. The method of Item 142 wherein the bacterial infection is caused by a resistant or non-resistant bacteria selected from the group consisting essentially of Enterobacteriaceae; Klebsiella spp.; Bacteroides sp. Enterococci; Proteus sp.; Streptococcus sp.; Staphylococcus sp.; Pseudomonas sp.; Neisseria sp.; Pedptostreptococcus sp.; fusobacterium sp.; Actinomyces sp.; Mycobacterium sp.; Listeria sp.; Corynebacterium sp.; Proprionibacterium sp.; Actinobacillus sp.; Aerobacter sp.; Borrelia sp.; Campylobacter sp.; cytophaga sp.; Pasteurella sp.; Clostridium sp.; *Enterobacter aerogenes*, Peptococcus sp.; *Proteus vulgaris, Proteus morganii, Staphylococcus aureus, Streptococcus pyogenes*, Actinomyces sp., *Campylobacter fetus*, and *Legionella pneumophila*, ampillin-resistant strain of *S. aureus*, and methicillin-resistant strain of *S. aureus*.

145. The method of Item 142 wherein the antibiotic is selected from the group consisting essentially of a beta-lactam, aminoglycolide, polymyxin-b, Amphotericin B, Aztreonam, cephalosporins, chloramphenicol, fusidans, lincosamides, macrolides, methronidazole, nitro-furation, Imipenem/cilastin, quinolones, refampin, polyenes, tetracycline, sulfonamides, trimethoprim, vancomycin, teicoplanin, imidazoles, and erythromycin.

146. The method of Item 145 wherein the beta-lactam is cephalosporin.

147. The method of Item 145 wherein the beta-lactam is penicillin.

148. The method of Item 145 wherein the aminoglucolide is gentamicin.

149. The method of Item 145 wherein the aminoglycolide is amikacin.

150. The method of Item 145 wherein the aminoglycolide is tobramycin.

151. The method of Item 145 wherein the aminoglycolide is kanamycin.

152. The method of Item 145 wherein the beta-lactam is an ampicillin.

153. The method of Item 152 wherein the polymeric matrix consists essentially of a poly(DL-lactide-co-glycolide)

wherein the relative ratio between the amount of lactide and glycolide (L/G) component is within the range of 48/52 to 58/42.

154. The method of Item 152 wherein the ampicillin is present in an amount of from 5 to 60 percent and the amount of polymeric matrix is from 40 to 95 percent.

155. The process of using the composition of Item 1 to treat humans in need, thereof, suffering from diseases and/or ailments from the group consisting of: viral infections; bacterial infections; fungal infections; parasitic infections and more specific diseases and/or ailments; such as aids; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; cervical cancer; cutaneous & metastatic; cachexia in AIDS; campylpbacter infection; cancer; pneumonia; sexually transmitted diseases (STDs); cancer; viral diseases; *candida albicans* in AIDS and cancer; candidiasis in HIV infection; pain in cancer; pancreatic cancer; parkinson's disease; peritumoral brain edema; postoperative adhesions (prevent); proliferative diseases; prostate cancer; ragweed allergy; renal disease; restenosis; rheumatoid arthritis; rheumatoid arthritis; allergies; rotavirus infection; scalp psoriasis; septic shock; small-cell lung cancer; solid tumors; stroke; thrombosis; type I diabetes; type I diabetes w/kidney transplants; type II diabetes; viseral leishmania sis; malaria; peridontal or gum disease; cardiac rhythm disorders; central nervous system diseases; central nervous system disorders; cervical dystonia (spasmodic torticollis); choridal neovascularization; chronic hepatitis A, B and C; colitis associated with antibotics; colorectal cancer; coronary artery thrombosis; cryptosporidiosis in AIDS; cryptosporidium *parvum* diarrhea in AIDS; cystic fibrosis; cytomegalovirus disease; depression; social phobias; panic disorder; diabetic complications; disabetic eye disease; diarrhea associated with antibiotics; erectile dysfunction; genital herpes; graft-vs host disease in trapsplant patients; growth hormone deficiency; head and neck cancer; head trauma; stroke; heparin neutralization after cardiac bypass; hepatocellular carcinoma; HIV; HIV infection; huntington's disease; CNS diseases; hypercholesterolemia; hypertension; inflammation; inflammation and angiogensis; inflammation in cardiopulmonary bypass; influenza; migrain head ache; interstitial cystitis; kaposi's sarcoma; kaposi's sarcoma in AIDS; lung cancer; melanoma; molluscum contaiosum in AIDS; multiple sclerosis; neoplastic meningitis from solid tumors; non-small cell lung cancer; organ transplant rejection; osteoarthritis; rheumatoid arthritis; osteoporosis; drug addition; shock; ovarian cancer; Amebiasis; Babesiasis; Chagas' disease (*Trypanosoma cruzi*); Cryptosporidiosis; Cysticercosis; Fascioliasis; Filariasis; Echinococcosis; Giardiasis; Leishmaniasis; Malaria; Paragonimiasis; Pneumocystosis; Schistosomiasis; Strongylodiasis; Toxocariasis; Toxoplasmosis; Trichinellosis; Trichomoniasdis; yeast infection; and pain.

156. A vaccine for prepared from the composition of Item 1 to prevent the occurrence in humans of diseases and/or ailments comprising viral infections; bacterial infections; fungal infections; parasitic infections and more specific diseases and/or ailments; such as aids; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; cervical cancer; cutaneous & metastatic; cachexia in AIDS; campylobacter infection; cancer; pneumonia; sexually transmitted diseases (STDs); cancer; viral diseases; candida albicians in AIDS and cancer; candidiasis in HIV infection; pain in cancer; pancreatic cancer; parkinson's disease; peritumoral brain edema; postoperative adhesions (prevent); proliferative diseases; prostate cancer; ragweed allergy; renal disease; restenosis; rheumatoid arthritis; rheumatoid arthritis; allergies; rotavirus infection; scalp psoriasis; septic shock; small-cell lung cancer; solid tumors; stroke; thrombosis; type I diabetes; type I diabetes w/kidney transplants; type rhythm disorders; central nervous system diseases; central nervous system disorders; cervical dystonia (spasmodic torticollis); choridal neovascularization; chronic hepatitis A, B and C; colitis associated with antibotics; colorectal cancer; coronary artery thrombosis; cryptosporidiosis in AIDS; cryptosporidium parvum diarrhea in AIDS; cystic fibrosis; cytomegalovirus disease; depression; social phobias; panic disorder; diabetic complications; disabetic eye disease; diarrhea associated with antibiotics; erectile dysfunction; genital herpes; graft-vs host disease in trapsplant patients; growth hormone deficiency; head and neck cancer; head trauma; stroke; heparin neutralization after cardiac bypass; hepatocellular carcinoma; HIV; HIV infection; huntington's disease; CNS diseases; hypercholesterolemia; hypertension; inflammation; inflammation and angiogensis; inflammation in cardiopulmonary bypass; influenza; migrain head ache; interstitial cystitis; kaposi's sarcoma; kaposi's sarcoma in AIDS; lung cancer; melanoma; molluscum contagiosum in AIDS; multiple sclerosis; neoplastic meningitis from solid tumors; non-small cell lung cancer; organ transplant rejection; osteoarthritis; rheumatoid arthritis; osteoporosis; drug addiction; shock; ovarian cancer; Amebiasis, Babesiasis; Chagas' disease (*Trypanosoma cruzi*); Cryptosporidiosis; Cysticerosis; Fascioliasis; Filariasis; Echinococcosis; Giardiasis; Leishmaniasis; Malaria; Paragonimiasis; Pneumocystosis; Schistosomiasis; Strongylodiastis; Toxocariasis; Toxoplasmosis; Trichinellosis; Trichomoniasis; yeast infection; and pain.

157. Animmunostimulating composition of Item 112 wherein the immunogenic substance is derived from bacteria.

158. A composition of Item 157 wherein the immunogenic substance is comprised of (i) a non-covalent complex between purified, detoxified LPS endotoxin derived form *E. coli* and (ii) purified outer membrane protein derived from *N. meningitis*.

159. A composition of Item 158, wherein said *E. coli* is strain J5 (Rc chemotype).

160. A composition of Item 158, wherein said *N. meningitis* is group B strain.

161. A composition of Item 158, wherein said purified LPS endotoxin of said non-covalent complex is also detoxified.

162. A composition of Item 158, wherein said purified outer membrane protein to said purified LPS endotoxin in said non-covalent complex is between 1 and 2.

163. An immunostimulating composition according to Item 157 wherein the amount of said immunogenic substance is within the range of 0.1 to 1.5% based on the volume of said bulk matrix.

164. A vaccine according to Item 106, effective in actively immunizing a subject against infection by Gram-negative bacteria or against lipopolysaccharide (LPS) endotoxin-mediated pathology, comprising a non-covalent complex between purified LPS endotoxin derived from *E. coli* and purified outer membrane protein derived from *N. meningitis*.

165. A vaccine of Item 164, wherein said *E. coli* is strain J5 (Rc chemotype).
166. A vaccine of Item 164, wherein said *N. meningitis* is group B strain.
167. A vaccine of item 164, wherein said purified LPS endotoxin of said non-covalent complex is also detoxified.
168. A vaccine of Item 164, wherein the weight ratio of said purified outer membrane protein to said purified LPS endotoxin in said non-covalent complex is between 1 and 2.
169. A method of actively immunizing a subject against infection by Gram-negative bacteria and LPS-induced pathology, comprising administering to said subject an effective amount of a vaccine of Item 164.
170. A method of Item 169, wherein said *E. coli* is strain J5 (Rc chemotype).
171. A method of Item 169, wherein said *N. meningitis* is group B strain.
172. A method of Item 169, wherein said purified LPS endotoxin is detoxified.
173. A method of Item 169, wherein said Gram-negative bacterial infection is a meningococcal infection.
174. A method of passively conferring upon a second subject protection against infection by Gram-negative bacteria or LPS-mediated pathology, comprising the steps of:
    a) actively immunizing a first subject with a vaccine of Item 164 comprising a non-covalent complex between purified LPS endotoxin derived from *E. coli* and purified outer membrane protein derived from *N. meningitis*;
    b) collecting gram said first subject a postimmune serum or plasma, or IgG isolated therefrom; and,
    c) administering to said second subject an amount off said serum or plasma or IgG isolated therefrom that is effective in conferring passive protection against a infection by Gram-negative bacteria and LPS-mediated pathology.
175. A method of Item 174, wherein said *E. coli* is strain J5 (Rc chemotype).
176. A method of Item 174, wherein said *N. meningitis* is group B strain.
177. A method of Item 174, wherein said purified LPS endotoxin is detoxified.
178. Serum, plasma or specific polyclonal antibody obtained from a subject immunized with a vaccine according to Item 164.

As noted in the Summary of the Invention Section herein, a discussion of this invention will be presented as Phase I, II and III.

Phase I

This illustrative phase of the invention presents the novel pharmaceutical composition, a micro- or macrocapsule/sphere formulation, which comprises an antibiotic encapsulated within a biodegradable polymeric matrix such as poly (DL-lactide-co-glycolide) (DL-PLG) and its use in the effective pretreatment of animals to prevent bacterial infections and the posttreatment of animals (including humans) with bacterial infections. Microcapsules and microspheres are usually powders consisting of spherical particles of 2 millimeter or less in diameter, usually 500 micrometer or less in diameter. If the particles are less than 1 micron, they are often referred to as nanocapsules or nanospheres. For the most part, the difference between microcapsules and nanocapsules is their size; their internal structure is about the same. Similarly, the difference between microspheres and nanospheres is their size; their internal structure is about the same.

A microcapsule (or nanocapsule) has its encapsulated material, herein after referred to as agent, centrally located within a unique membrane, usually a polymeric membrane. This membrane may be termed a wall-forming material, and is usually a polymeric material. Because of their internal structure, permeable microcapsules designed for controlled-release applications release their agent at a constant rate (zero-order rate of release). Also, impermeable microcapsules can be used for repture-release application. Hereinafter, the term microcapsule will include nanocapsules, and particles in general that comprise a central core surrounded by a unique outer membrane.

A microsphere has its agent dispersed throughout the particle; that is, the internal structure is a matrix of the agent and excipient, usually a polymer excipient. Usually controlled-release microspheres release their agent at a declining rate (first-order). But microspheres can be designed to release agents at a near zero-order rate. Microspheres tend to be more difficult to rupture as compared to microcapsules because their internal structure is stronger. Hereinafter, the term microspheres will include nanospheres, microparticles, nanoparticles, microsponges (porous microspheres) and particles in general, with an internal structure comprising a matrix of agent and excipient.

One can use other terms to describe larger microcapsules or microspheres, that is, particles greater than 500 micrometer to 7 millimeter or larger. These terms are macrocapsules, macrospheres, macrobeads and beads.

Macrocapsules, macrospheres, macrobeads and beads will be used interchangably herein.

More particularly, the applicants have discovered efficacious pharmaceutical compositions wherein the relative amounts of antibiotic to the polymer matrix are within the ranges of 5 to 60 preferred that relative ratio between the lactide and glycolide component of the poly(DL-lactide-co-glycolide) is within the range of 40:60 to 100:0, most preferably. Applicants' most preferred composition consists essentially of 30 to 40(core loading) and 60 to 70 poly(DL-lactide-co-glycolide) (DL-PLG). However, it is understood that effective core loads for other antibiotics will be influenced by the nature of the drug, the microbialetiology and type of infection being prevented and/or treated. From a biological perspective, the DL-PLG excipient is well suited for in vivo drug release because it elicits a minimal inflammatory response, is biologically compatible, and degrades under physiologic conditions to products that are nontoxic and readily metabolized. Similar polymeric compositions which afford in vitro release kinetics, as discussed below for DL-PLG, are considered by applicants to be within the scope of this invention. Applicants have discovered that antibiotic encapsulated microcapsules/spheres or macrocapsules/spheres (beads) having a diameter within the range of about 40 microns to about 7 millimeters to be especially useful in the practice of this invention.

Surprisingly, applicants have discovered an extremely effective method of treating bacterial infections of soft-tissue or (bone osteomyelitis) and preventing these type infections with antibiotics such as beta-lactams, aminoglycosides, polymyxin-B, amphotericin B, aztreonam, cephalosporins, chloramphenicol, fusidans, lincosamides, macrolides, metronidazole, nitro-furantion, Imipenem/cilastin, quinolones, rifampin, polyenes, tetracycline, sulfonamides, trimethoprim, vancomycin, teicoplanin, imidazoles, and erythromycin 1) micro- and macroencapsulated or 2) micro- and macrospheres formulated within a polymeric matrix such as a poly(DL-lactide-co-glycolide), which has been formulated to release the antibiotic at a controlled, programmed rate over a desirable extended period of time. The microcapsules/spheres have been found to be effective when applied locally, including topically, to open contaminated wounds thereby facilitating the release of the antibiotic from multiple sites within the tissue in a manner which concentrates the antibiotic in the area of need. Similarly, the encapsulated antibiotics of this invention both in the microcapsule/sphere and macrocapsule/sphere (bead) form are effective for the prevention and treatment of orthopedic infections that include osteomyelitis, contaminated open fractures, and exchange revision arthroplasty. The macrocapsules/sphere form offers the same advantages as the microcapsule/sphere, but offers in addition the option to the surgeon of using the subject invention as a packing material for dead space. The subject invention offers an optimal treatment for orthopaedic infections because release of the antibiotic from the micro- or macrocapsule/sphere is completely controllable over time; antibiotic can be encapsulated into the sphere; the sphere can be made of any size; and unlike the methylmethracrylate beads, the subject invention biodegrades over time to nontoxic products and does not have to be surgically removed from the treated site. Since virtually any antibiotic can be encapsulated into the polymer the instant invention can be used to sustain release all known antibiotics.

Applicants have discovered and/or contemplate that local application of microencapsulated or macroencapsulated antibiotic provides immediate, direct, and sustained dosing which targets the antibiotic to the pre- or post infected soft-tissue or bone site, and minimizes problems inherent in systemic drug administration. It appears to applicants that there is a significant reduction of nonspecific binding of antibiotic to body proteins, as compared to systemic administered antibiotics, while in route to targeted sites. Additionally, antibiotics with short half-lives can be used more efficiently, undesirable side-effects can be minimized, and multiple dosing can be eliminated. These attributes satisfy a long-felt need to improve the effectiveness and predictability of drug delivery to accomplish the desired clinical result in patients.

The ability to concentrate the antibiotic within the wound site ensures an extended period of direct contact between an effective antibiotic level and the infecting microorganisms. Many drugs have a therapeutic range below which they are ineffective and above which they are toxic. Oscillating drug levels, commonly observed following systemic administration, may cause alternating periods of ineffectiveness and toxicity. A single dose of applicants' controlled-release preparation can maintain the antibiotic in the desired therapeutic range. Applicants have discovered that microencapsulated or macroencapsulated heavy concentrated doses of antibiotics are effective for the treatment and prevention of infections caused by antibiotic-resistant bacteria.

Topical application of the antibiotic microcapsule/sphere formulation to infected wounds allows local application of the antibiotic in a single dose, whereby an initial burst of antibiotic for immediate soft- or hard-tissue perfusion, followed by a prolonged, effective level of antibiotic is achieved in the tissue at the wound site. Applicants contemplate herein antibiotic microcapsules/spheres and macrocapsules/spheres consisting of an antibiotic and DL-PLG and the summarized results of illustrative experiments that evaluated the prototype microcapsules in vitro and in vivo.

The subject invention is successful in preventing and treating (1) soft-tissue infections, (2) osteomyelitis, and (3) infections surrounding internally fixed fractures. These results were confirmed using the microcapsule/sphere form of the encapsulated antibiotics. The microcapsule/sphere and macrocapsule/sphere are also of value in numerous other applications including soft-tissue infections that involve, but are not limited to the prevention and treatment of (1) subcutaneous infections secondary to-contaminated abdominal surgery, (2) infections surrounding prosthetic devices and vascular grafts, (3) ocular infections, (4) topical skin infections, and (5) in oral infections such as pericoronitis and periodontal disease.

The biodegradation rate of the excipient is controllable because it is related to the mole ratio of the constituent monomers, the exhipient molecular weight and the surface area of the microcapsules produced.

Microcapsules/spheres with diameters of 250 micrometers or less are amendable to direct administration to a wound by a shaker-type dispenser or aerosol spray. The macrocapsules/spheres are manually placed in the tissue on bone by the surgeon at the time of surgical debridement. Due to the unique pharmacokinetic advantages realized with the continuous delivery of antibiotic into tissue from a controlled-release vehicle, applicants have found that a small total dose is required to obtain an optimal therapeutic effect.

VII. EXAMPLES

The herein offered examples provide methods for illustrating, without any implied limitation, the practice of this invention in the treatment of bacterial wound infections.

The profile of the representative experiments have been chosen to illustrate the antibacterial activity of antibiotic-polymeric matrix composites.

All temperatures not otherwise indicated are in degrees Celcius (C. deg) and parts or percentages are given by weight.

Materials and Methods

A. Microcapsules/spheres. The ampicillin anhydrate microspheres used in these studies (Composite Batch D 856-038-1) consisted of 30.7 wt in a copolymer of 52:48 poly (DL-lactideco-glycolide). The size of the microspheres ranged from 45 to 150 microns and they were sterilized with 2.0 Mrad of gamma irradiation.

Animals. New Zealand white rabbits (Dutchland Laboratories, Denver, Pa.), weighing 2.0 to 2.5 kg each, were used. The animals were housed in individual cages and were fed a standard laboratory diet. The experiments described herein were conducted in accordance with the principles set forth in the Guide for the Care and Use of Laboratory Animals.

Example 1

Osteomyelitis Model. The technique used to produce osteomyelitis was a modification of the procedure described previously by Norden. Briefly, New Zealand white rabbits (2.0–2.5 kg, each) were anesthetized with ketamine hydrochloride and xylazine and access to the medullary canal was gained by inserting an 18-guage Osgood needle (Becton Dickinson Corp., Rutherford, N.J.) into the right proximal tibial metaphysis. Through this needle was injected 0.1 ml of 5 Pharmaceuticals, Tenafly, N.J.) followed by injection of approximately $5 \times 10^6$ CFU of *S. aureus* ATCC 6538P. The hole in the bone was sealed with bone wax and each animal received a single subcutaneous injection of 3-ml TOR-BUTROL™ (A. J. Buck, Hunt Valley, Md.) for postoperative pain control. Antibiotic therapy was then initiated either immediately or was delayed for 7-days as described in detail below.

Example 2

Immediate Antibiotic Therapy. The initial experiment was designed to evaluate the efficacy of local therapy with microencapsulated ampicillin for the prevention of experimental osteomyelitis. A total of 31 rabbits were infected in the right proximal tibia with sodium morrhuate and *S. aureus* and treatment was initiated immediately as follows:

Group A (n=6) received three daily subcutaneous injections (75 mg/kg/day) of aqueous sodium ampicillin (Polycillin-N™, Bristol Laboratories, Syracuse, N.Y.) at 8-hour intervals for 14 consecutive days;]

Group B (n=7) received a single intramedullary injection of 100 mg of microencapsulated ampicillin containing an equivalent of 30.7 mg of ampicillin anhydrate. The microcapsules/spheres were suspended in 0.2-ml of the injection vehicle) and were then injected into the medullary canal through the same needle that was used to inject the sclerosing agent and bacteria;

Group C (n=4) received a single intramedullary injection of 0.12 ml (30.7 mg) of aqueous sodium ampicillin (representing the unencapsulated free drug); and Groups D, E, and F (n=14) served as controls and received either an intramedullary injection of placebo microcapsules (100 mg) without antibiotic; injection vehicle (0.2 ml) without antibiotic; or no treatment.

The animals were observed for a total of 8-weeks during which time roentgenograms were obtained to evaluate the progression of the disease. All surviving animals were euthanized intraveneously at two months postinfection with T-61 euthanasia solution (1 mg/kg/iv) and the tibiae were harvested for bacteriological analysis as described below.

Example 3

Delayed Antibiotic Therapy Without Debridement. In the second experiment, a total of 30 rabbits were injected in the right proximal tibia with sodium morrhuate and *S. aureus* and the infection was allowed to become established for 7-days. On Day 7, the animals were reanesthetized and an incision was made over the patellar tendon to expose the tibial tuberosity. A 5-mm drill hole was made in the tibial tuberosity and a trocar, measuring approximately 15 centimeters in length, was inserted into the medullary canal to obtain a marrow specimen for culture. The animals were then randomly assigned to the following treatment groups:

Group A (n=8) received three daily subcutaneous injections of aqueous sodium ampicillin (75 mg/kg/day) at 8-hour intervals for 14-days;

Group B (n =8) received an intramedullary application of 150 mg of microencapsulated ampicillin containing an equivalent of 45 mg of ampicillin anhydrate. The microcapsules were initially suspended in 0.2 ml of the injection vehicle and then aspirated into a sterile trocar. The trocar was then inserted into the medullary canal through the drill hole in the tibial tuberosity;

Group C (n=8) received an intramedullary application of 0.18 ml (45 mg) of aqueous sodium ampicillin which was also delivered into the canal with a trocar; and Group D (n=6) served as controls and received no treatment.

Following the implantation of the antibiotics into the medullary canal, the hole in the tibial tuberosity was sealed with bone wax and the incision site was closed with 3-0 Dexon sutures. All of the surviving animals were euthanized 8 weeks following the initiation of treatment and the tibiae were harvested for bacteriological analysis.

Example 4

Delayed Antibiotic Therapy With Debridement. Because standard treatment of chronic osteomyelitis requires the surgical removal of devitalized osseous tissue, the objective of this experiment was to evaluate the efficacy of local antibiotic therapy with microencapsulated ampicillin anhydrate when used in conjunction with debridement. A total of 30 rabbits were injected in the right proximal tibia with sodium morrhuate and *S. aureus* and the infection was allowed to establish for 7 days. On Day 7 each animal underwent a standardized surgical debridement of the infected tibia. The animals were anesthetized and an incision was made to expose the medial aspect of the tibia. A Hall drill was used to decorticate approximately one-third of the bone thereby creating a channel that extended the length of the bone. The canal was thoroughly debrided with a curette and then irrigated with 20 ml of sterile saline. Cultures of the marrow were obtained at this time for bacteriological analysis. Immediately following completion of the debridement procedure, the animals were randomly assigned to the following treatment groups:

Group A (n=10) received 150 mg of microencapsulated ampicillin containing an equivalent of 45 mg of ampicillin anhydrate. The microcapsules were suspended in 0.2-ml of injection vehicle and were then implanted into the debrided canal with a sterile trocar;

Group B (n=10) received 45 mg of unencapsulated sodium ampicillin in powder form which was applied uniformly into the debrided canal; and Group C (n=5) and Group D (n=5) served as controls and received either an intramedullary application of placebo microcapsules (150 mg) without antibiotic or (2) an injection vehicle (0.2 ml) without antibiotic, respectively.

Immediately following the implantation of the materials into the medullary canal, the incision site was closed with 3-0 Dexon sutures and each animal received 3-ml of Tor-butrol™ for 3 consecutive days for postoperative pain. The animals were euthanized at 8 weeks following the initiation of treatment and the tibiae were harvested for bacteriological evaluation.

Example 5

Roentgenographic Evaluation. Radiographs of the infected tibiae were obtained at various time intervals and were evaluated by a board certified skeletal radiologist (LMM) using a grading system that was originally developed by Norden et al. Four radiographic parameters (sequestrum formation, periosteal reaction, bone destruction, and extent of disease) were evaluated for each animal and a numerical value was assigned for each variable. The scores were then totaled to arrive at an overall radiographic severity score. The highest total score possible with this grading scheme was +7 and reflected the maximum degree of radiographic severity.

Example 6

Cultures of Bone. For bacteriological evaluation, the tibiae were dissected free of adherent soft-tissue and the surface of the bone was cleaned with alcohol pads. The bone was then weighed and crushed to small pieces with a sterile mortar and pestle. The crushed bone was suspended in 5 ml of sterile saline and serial 10-fold dilutions were prepared in 0.1. Each dilution (0.1 ml) was then streaked onto both sheep blood agar and mannitol salt agar plates which were incubated aerobically at 37° C. for 24 hours. The recovery of any *S. aureus* colonies from the bones was evidence of a persistent osseous infection and was considered as a treatment failure.

Example 7

Measurement of Serum Ampicilin Levels. In the experiment where local antibiotic therapy was used in conjunction with debridement, serum levels of ampicillin were measured for all of the animals treated with either an intramedullary application of microencapsulated ampicillin anhydrate (Group A) or unencapsulated free drug (Group B). Serum was obtained from all animals at 1 hour, 1 day, and 7 days following the implantation of the antibiotics into the tibiae and serum ampicillin levels were measured using the agar-well diffusion assay described previously in detail by Bennett et al. A standard curve was constructed relating the size of the zones of inhibition obtained with a series of ampicillin standards tested against *Sarcina lutea* ATCC 9341 as the reference organism. Ampicillin concentrations in the test sera were then calculated from this standard curve.

Results of Examples 1 Through 7

Immediate Antibiotic Therapy. The results of the initial experiment showing the effect of immediate parenteral versus local ampicillin therapy for the prevention of experimental osteomyelitis are presented in Table 1. Radiographic changes were initially detected in the control animals (Groups D, E, and F) at 2 weeks postinfection and consisted predominantly of periosteal reaction. By 7 weeks, however, the majority of the control animals (75 scores ranging from +5.25 to +7.00 indicating extensive osseous involvement. Radiographic evidence of osteomyelitis was absent in animals that received either a 14 day course of parenteral ampicillin therapy (Group A) or those that received an intramedullary injection of unencapsulated ampicillin (Group C). Only a minimal periosteal reaction was noted at day 42 for Group B animals that received an intramedullary injection of microencapsulated ampicillin, however, all other radiographic parameters were found to be within normal limits. Cultures of the tibiae at 8 weeks following the initiation of treatment showed that all of the animals treated with either a 14 day

TABLE 1

Effect of Immediate Antibiotic Therapy for prevention of Experimental Osteomyelitis in a Rabbit Tibia Model

| Group | Treatment | Radiographic Severity[a] | Positive Bone Cultures | Bacterial Counts[b] |
|---|---|---|---|---|
| A | Parenteral therapy for 14 days | 0 | 0/6 | 0 |
| B | Microencapsulated ampicillin[c] | 0.43 ± 1.13 | 0/7 | 0 |
| C | Unencapsulated ampicillin[c] | 0 | 1/4 | 1.2(±2.3) × 10² |
| D | Placebo microcapsules[c] | 7.00 ± 0.0 | 4/4 | 4.9(±8.3) × 10⁶ |
| E | Injection vehicle[c] | 6.67 ± 0.58 | 4/4 | 1.3(±0.7) × 10⁶ |
| F | No treatment | 5.25 ± 2.06 | 5/5 | 2.0(±4.5) × 10⁷ |

[a]Mean radiographic severity score at 7-weeks post treatment.
[b]Mean (± standard deviation) CFU of *S. aureus* recovered per gram of bone.
[c]Intramedullary injection.

course of parenteral ampicillin therapy or a single intramedullary injection of microencapsulated ampicillin had sterile bone cultures. Free unencapsulated ampicillin, injected locally into the bone, was also effective and sterilized the tibiae of 3 of 4 (75 In contract, all 13 surviving control animals in Groups D, E, and F developed culture-positive osteomyelitis with *S. aureus* counts ranging from $1.3 \times 10^6$ to $2.0 \times 10^7$ CFU recovered per gram of bone.

Delayed Antibiotic Therapy Without Debridement. Table 2 shows the results of the experiment when antibiotic therapy was delayed for 7 days postinfection and was then initiated without debridement. Of the 8 animals in Group A that received a 14 day course of parenteral ampicillin therapy, 6 (75 *aureus* bone cultures. Only 2 of these animals survived the entire length of the experimental protocol; six animals died within 1–2 weeks of completing their antibiotic therapy after developing profuse diarrhea. Of the 7 surviving rabbits in Group C that received an intramedullary application of 45 mg of unencapsulated ampicillin, 5 (71 with a single intramedullary application of microencapsulated ampicillin anhydrate (Group B) sterilized the tibiae of 4 of 8 (50 of *S. aureus* recovered from the tibiae of the other animals in this group as compared with the controls (Group D). All of the control animals developed osteomyelitis with an average of $2.8 \times 10^5$ CFU of *S. aureus* recovered per gram of bone. A Chi square analysis of the proportion of animals in each treatment group with positive bone cultures showed no statistically significant differences among the groups (p=0.23).

TABLE 2

Effect of Delayed Therapy without Debridement for Treatment of Experimental Osteomyelitis in a Rabbit Tibia Model

| Group | Treatment | Positive Bone Cultures | Bacterial Counts[b] |
|---|---|---|---|
| A | Parenteral therapy for 14 days | 6/8 | 5.9(±16.7) × 10⁶ |
| B | Microencapsulated ampicillin[c] | 4/8 | 1.2(±2.2) × 10³ |
| C | Unencapsulated ampicillin[c] | 5/7 | 2.6(±7.0) × 10⁵ |
| D | No treatment | 6/6 | 2.8(±2.9) × 10⁵ |

[a]No statistically significant differences between groups by Chi square analysis (p = 0.23)
[b]Mean (± standard deviation) CFU of *S. aureus* recovered per gram of bone.
[c]Intramedullary injection.

Delayed Antibiotic Therapy With Debridement. In this experiment we evaluated the effect of local antibiotic therapy when used in conjunction with debridement for the treatment of a 7-day established osseous infection. Bacteriological cultures of the tibiae at the time of debridement (before antibiotic therapy was initiated) yielded S. aureus in 29 of 30 (97 shown in Table 3, all 10 of the animals in Group A that were treated with debridement plus microencapsulated ampicillin anhydrate had sterile bone cultures. In contrast, of the 10 animals in Group B that were treated with debridement plus unencapsulated ampicillin only 3 had sterile bone cultures whereas 7 developed culture-positive osteomyelitis. A Chi squire analysis showed a statistically significant difference (p<0.01) in the proportion of animals with sterile bone cultures in the microencapsulated ampicillin treated group as compared with the group that was treated with the unencapsulated form of the antibiotic. Debridement alone, without local antibiotic therapy, was not effective for the treatment of this established osseous infection with all 10 control animals (Groups C and D) developing culture positive osteomyelitis.

Serum Ampicillin Levels. In the experiment where local antibiotic therapy was initiated in conjunction with debridement, serum concentrations of ampicillin were measured for all animals that received either an intramedullary application of

TABLE 3

Effect of Delayed Therapy with Debridement for Treatment of Experimental Osteomyelitis in a Rabbit Tibia Model

| Group | Treatment[a] | Positive Bone Cultures | Bacterial Counts[b] |
|---|---|---|---|
| A | Microencapsulated ampicillin | 0/10[c] | 0 |
| B | Unencapsulated ampicillin | 7/10 | $3.3(\pm4.8) \times 10^2$ |
| C | Placebo microcapsules | 5/5 | $9.1(\pm10.9) \times 10^4$ |
| D | Injection vehicle | 5/5 | $3.7(\pm4.9) \times 10^5$ |

[a]All substances were implanted locally into the medullary canal at the time of debridement.
[b]Mean (± standard deviation) CFU of S. aureus recovered per gram of bone.
[c]Significantly different (p < 0.01) from all other groups by Chi square analysis.

microencapsulated ampicillin anhydrate or an equivalent dose of unencapsulated free ampicillin. The data is presented in FIG. 1. Serum levels of ampicillin were only detected at 1-hour after the implantation of the antibiotics into the tibiae. At this time interval, the mean serum concentration of ampicillin in the Group B animals that received 45 mg of unencapsulated ampicillin (0.79±0.24 micrograms/ml) was approximately 7-fold higher than the mean serum ampicillin concentration of the Group A animals that received an equivalent dose of the microencapsulated form of the antibiotic (0.11±0.08 micrograms/ml).

Discussion Related to Examples 1 Through 7

Previous attempts to develop a biodegradable antibiotic delivery system for the local treatment of bone infections have met with only limited success. Zilch and Lambiris reported on the treatment of 46 patients with chronic osteomyelitis using a biodegradable fibrin-cefotaxim compound that was implanted into the bone at the time of surgical intervention and reported healing in only 67 limitation of this system was the rapid diffusion of the antibiotic from the fibrin carrier. High concentrations of cefotaxim could only be maintained locally in the would exudate for up to 72 hours. In a separate study, Dahners and Funderburk implanted gentamicin-loaded plaster of paris into the tibiae of rabbits with established staphylococcal osteomyelitis. Although they observed clinical and roentgenographic improvements as compared with nontreated controls, nevertheless, Boanimals treated with the gentamicin-loaded plaster of paris developed culture-positive osteomyelitis. Recently Gerhart et al. evaluated poly(propylenefumarate-co-methylmethacrylate) (PPF-MMA), as a potential biodegradable carrier for antibiotics. Following the subcutaneous implantation of gentamicin- or vancomycin-loaded cylinders of PPF-MMA in rats, high concentrations of each antibiotic were detected locally in the wound exudate while serum antibiotic levels remained low. Although the PPF-MMA appears promising as a potential biodegradable antibiotic carrier, the efficacy of this system remains to be demonstrated in an experimental animal model of osteomyelitis.

In the present application we evaluated biodegradable microspheres of poly(DL-lactide-co-glycolide), containing 30.7 weight percent ampicillin anhydrate, in an experimental osteomyelitis model of the rabbit tibia. In the initial experiment where treatment was initiated immediately following the injection of S. aureus into the medullary canal, a single intramedullary injection of 100 mg of microencapsulated ampicillin effectively prevented the establishment of osteomyelitis in 100 of the animals tested (Table 1). Although a 14 day course of parenteral ampicillin therapy also prevented osteomyelitis in all animals, the total dose of antibiotic administered to these animals (1,050 mg) was 34 times higher than the dose administered to the animals treated locally with the ampicillin-loaded microcapsules (30.7 mg).

In the second experiment, where antibiotic therapy was delayed for 7 days and was instituted without debridement, a 14 day course of parenteral ampicillin therapy resulted in a 75 treatment failure rate (Table 2). Free unencapsulated ampicillin, implanted locally into the bone, was also ineffective with 71 these animals developing culture-proven osteomyelitis. A single intramedullary application of microencapsulated ampicillin, on the other hand, sterilized the tibiae of 50 significantly reduced the mean number of S. aureus colonies recovered from the tibiae of the other animals in this group. It is noteworthy that al 1 animals treated locally with microencapsulated ampicillin anhydrate survived the duration of the experimental protocol without developing adverse side-effects. In contrast, 6 of 8 (75 parenteral ampicillin died within 1 to 2 weeks of completing their antibiotic therapy. The cause of death in these animals was most likely antibiotic-induced diarrhea resulting from colonization of the normal intestinal flora by *Clostridium difficile*, a phenomenon that has been previously noted with rabbits receiving parenteral ampicillin therapy.

In the final experiment, where local antibiotic therapy was delayed for 7 days and was instituted in conjunction with debridement, a 100 animals treated with debridement plus microencapsulated ampicillin (Table 3). In contrast, of the 10 animals treated with debridement plus an equivalent dose of unencapsulated ampicillin powder, 70 seen in FIG. 4, at 1 hour after implantation of the antibiotics into the medullary canal, the mean serum concentration of ampicillin in the animals receiving unencapsulated ampicillin was approximately 7 times higher (0.79±0.024 micrograms/ml) than in the group that was treated with microencapsulated ampicillin anhydrate (0.11±0.08 micrograms/ml). This finding suggests that the free unencapsulated drug diffuses rapidly from the site of administration and does not remain localized for a sufficient time interval to eradicate the infection. The fact that 70 animals treated with the unencapsulated form of the drug developed osteomyelitis substantiates this conclusion. The ampicillin-loaded microcapsules/spheres, on the other hand, remain localized at the site of administration thereby continuing to release high concentrations of the antibiotic over time resulting in the elimination of the infecting organisms.

Applicants' experimental studies have demonstrated that a controlled-release and biodegradable antibiotic delivery system was successful for the eradication of a susceptible organism from an osteomyelitic focus when used in conjunction with adequate debridement.

TABLE 4

Survival of *E. coli* and *S. aureus* in rat soft-tissue at 28 days following local or systemic treatment with cefazolin.

| Treatment Group (N) | Dose | Mean (±sd) Log CFU/g tissue | | Contamination Rate |
|---|---|---|---|---|
| | | *E. coli* | *S. aureus* | |
| A: CZ microspheres (6) | 50 mg | 1.01 ± 1.59 | 0.50 ± 1.21 | 2/6 (33%) |
| B: CZ microspheres (6) | 250 mg | 0.91 ± 1.41 | 0.42 ± 1.04 | 2/6 (33%) |
| C: CZ microspheres (6) | 500 mg | 0 | 0 | 0/6 (0%) |
| D: Free CZ powder (6) | 110 mg | 0.57 ± 1.40 | 0.53 ± 1.29 | 1/6 (17%) |
| E: Systemic CZ (6) | 30 mg/kg | 4.14 ± 0.91 | 0.83 ± 2.03 | 6/6 (100%) |
| F: No treatment (3) | 0 | 4.26 ± 0.34 | 2.12 ± 1.83 | 3/3 (100%) |

Rat wound infection model. Table 4 shows the effect of local versus systemic cefazolin therapy on the contamination rate in rat soft-tissue wounds at 28 days postinfection. Local antibiotic therapy with CZ microspheres, in doses ranging from 50 to 500 mg per wound, was highly effective for eliminating both organisms from the wounds. The maximum effect was achieved in the Group C animals who received the highest dose of CZ microspheres (500 mg) where both *E. coli* and *S. aureus* were eliminated from 100% of the wounds. Even at the lowest dose used (50 mg/wound), 4 of 6 wounds were rendered Completely sterile. Local antibiotic therapy with free CZ powder sterilized the wounds in 5 of 6(83%) Animals. In contrast, systemic administration of cefazolin (30 mg/kg) failed to sterilize the wounds in any of the 6 Group E animals tested. Chi-square analysis revealed that there was a statistically difference in the frequency of recovery of either *E. coli* and/or *S. aureus* (contamination rate) between all groups receiving local antibiotic therapy with CZ microspheres (groups A, B, and C) or free CZ powder (group D) versus the group E animals who received systemic cefazolin therapy ($p<0.05$). Comparisons of the mean log *E. coli* counts by analysis of variance showed a statistically significant reduction ($p<0.01$) for all groups treated by local depot administration of cefazolin (groups A thru D) versus group E sytemic CZ therapy). There were no significant differences, however, in the mean log *S. aureus* counts Among any of the treatment groups ($p>0.05$).

Preparation of Ampicillin Anhydrate Microcapsules

Example 8

About 500 g of a 10 wt alcohol) (PVA) was added to a 1-L (liter) resin kettle and cooled to 5° C. while being stirred at 650 rpm with a 2.5-in. Teflon turbine impeller driven by a motor and a control unit. A solution consisting of 5 g of 68:32 poly(DL-lactide-co-glycolide) in a mixture of 40 g of dichloromethane and 20 g of acetone was prepared in a separate container and stirred magnetically while in an ice bath. In still another container, 5 g of ampicillin anhydrate was dispersed in 15 g acetone. This mixture was stirred magnetically and then sonicated to achieve uniform dispersion of single ampicillin anhydrate crystals. After sonication, the container was placed in an ice bath, magnetic stirring was continued, and additional acetone was added to give a total of 30 g of acetone. After complete dissolution of the copolymer, the ampicillin-acetone dispersion was added to the copolymer solution. The resulting mixture was stirred magnetically in an ice bath for about 30 minutes or until homogeneous, and it was then added to the reaction-flask containing the aqueous PVA solution. The stir rate was reduced from 650 to 500 rpm after the addition was complete. After 15 minutes, the pressure was reduced to 550 torr to begin slow evaporation of the organic solvent (dichloromethane and acetone). The pressure was further reduced to 250 torr. This pressure was maintained for another 18 to 24 hours. The flask was then opened, the suspension was removed, and the microcapsules were separated from the PVA solution by centrifugation. The microcapsules were then washed twice with water, centrifuged, and washed once more with water and recovered by filtration. The microcapsules were then dried in vacuo and separated into various size fractions by sieving. A free-flowing powder of spherical particles was obtained.

Example 9

Dissolve 1.2 g of 50:50 poly(DL-lactide-co-glycolide) in 102 g of methylene chloride. Ampicillin anhydrate (0.8 g) is next added to the stirring copolymer solution. This mixture (dispersion of drug in the copolymer solution) is then placed in a 200-mL resin kettle equipped with a true bore stirrer having a 1.5-inch Teflon turbine impeller driven by a motor. While the mixture is stirring at 700 to 800 rpm, 48 mL of 100 centastoke (cSt) silicone oil is pumped into the resin kettle to cause the poly(DL-lactide-co-glycolide) to coacervate and coat the dispersed ampicillin anhydrate particles. After the silicone oil is added to the resin kettle, the contents of the kettle are poured into heptane to harden the microcapsules/ spheres. After stirring in the heptane for 2 hours, the microcapsules/spheres are collected on a funnel an dried. A free-flowing powder of spherical different sized particles is obtained.

In Vitro Characterization of Microcapsules/spheres

The core loadings of microcapsules/spheres comprising [$^{14}$C]-ampicillin anhydrate and DL-PLG were measured by liquid scintillation counting. The core loading of microcapsules/spheres consisting of unlabeled ampicillin anhydrate and some radiolabeled ampicillin anhydrate and DL-PLG was measured by using a microbial assay. In the former instance, microcapsules/spheres (about 15 mg) were solubilized in 1 mL of 0.5 N dimethyl dialkyl quarternary ammonium hydroxide in toluene (Soluene-350) at 55° C. for 2 to 4 hours. Then, 14 ml of scintillation cocktail (1,4-bis [2-(5-phenyloxazolyl]benzene (PPO/POPOP) in toluene) was added, and the radioactivity was measured with a liquid scintillation spectrometer. In the latter instance, microcapsules/spheres (about 15 mg) were placed in 5 mL of methylene chloride. Following dissolution of the DL-PLG excipient, the insoluble ampicillin anhydrate was extracted from the methylene chloride with four-volumes of sterile 0.1 M potassium phosphate buffer (pH 8.0). These aqueous extracts were then assayed for the antibiotic using *Sarcina lutea* ATCC 9341 (American Tye Culture Collection, Rockville, Md.) and the agar-diffusion microbial assay previously described in the literature by Kavanagh, F. (ed.) Antibiotic Substances in Analytical Microbiology, Vol. II, 1972.

The in vitro release kinetics of [$^{14}$C]-ampicillin anhydrate microcapsules/spheres was determined following the placement of 30 mg of microcapsules in an 8-ounce bottle. The release study was initiated by the addition of 50 mL of receiving fluid consisting of 0.1 m potassium phosphate buffer (pH 7.4). The bottle was then sealed and placed in an oscillating (125 cycles/minutes) shaker bath maintained at 37° C. Periodically, a 3-ml aliquot of the receiving fluid was removed for assay and replaced with a fresh 3-ml aliquot of receiving fluid to maintain a constant volume of receiving fluid throughout the study. The 3-ml aliquots were assayed for drug by liquid scintillation counting using 12 ml Scinti Verse-I (Fisher Scientific Co., Pittsburgh, Pa.). The cumulative amount of the drug released into the receiving fluid was calculated.

The in vitro release kinetics of unlabeled ampicillin anhydrate microcapsules/spheres was determined in the following manner:

A known amount of ampicillin anhydrate microcapsules/spheres (about 4 mg of microencapsulated ampicillin anhydrate) and 5.0 ml of sterile receiving fluid (0.1 M potassium phosphate buffer, pH 7.4) were added into dialysis tubing. The ends of the tubing were sealed with plastic clamps. The clamped dialysis tubing containing the microcapsules/spheres were placed into a sterile 8-ounce bottle containing 100 ml of sterile receiving fluid (0.1 M potassium phosphate buffer, pH 7.4). The bottle was placed in a shaker bath maintained at 37° C. and shaked at 120 cycles per second with about 3-cm stroke. The receiving fluid was previously sterilized in an autoclave for 20 minutes at 121° C. Several dialysis tubing assemblies were prepared for one release study. At Days 1, 2, 4, 7, 10, 13, 15, 18, and 25, one assembly was removed from its receiving fluid and air dried.

After drying the assembly, all particles remaining inside the dialysis tubing were quantitatively transferred to a sterile, glass test tube (16 by 125 mm), 5 ml of methylene chloride were added to dissolve the microcapsules, and the drug was extracted with three 5-ml portions of sterile 0.1 M potassium phosphate buffer (pH 8.1). The extraction and preparation of the sample (along with controls) was performed using the procedures for core-loading analysis as discussed above in the extracted samples and controls using the microbiological assay. Knowing the amount of microencapsulated drug initially placed in the dialysis tubing and the amount of drug remaining in the dialysis tubing after incubation with receiving fluid, the amount of drug released was determined by calculating the difference between them.

In Vivo Release Profiles of Ampicillin from Microcapsules/spheres

The rate and duration of release of ampicillin anhydrate from the microcapsules/spheres were determined in vivo in rats. In one experiment, about 50- to 80-mg doses of microencapsulated and unencapsulated ampicillin anhydrate were sterilized in disposable syringes with a 2.0- or 2.5-Mrad dose of gamma radiation at dry-ice temperature. The sterile microcapsules/spheres and unencapsulated [$^{14}$C]-ampicillin anhydrate were then suspended in about 2.0 mL of an injection vehicle comprising 2 wt percent of commercially available carboxymethyl cellulose (Type 7LF, Hercules Inc., Wilmington, Del.) and 1 wt percent Tween 20 (ICI Americas Inc., Wilmington, Del.) in sterile water and autoclaved at 121° C. for 15 minutes. The microcapsules/spheres were administered subcutaneously into the midback region of lightly anesthestized (ether), male Sprague-Dawley rats. The rats were fed standard laboratory food and water ad libidum and were housed in individual stainless steel cages fitted with metabolism funnels and screens that separated and collected the feces and urine. The urine from each rat was collected, weighed, and analyzed for [$^{14}$C]-content by liquid scintillation counting. The actual doses of microcapsules/spheres or unencapsulated drug administered to each rat was determined after injection by measuring the amount of drug residue in each syringe by liquid scintillation counting. The amount of radioactivity excreted daily by each rat was normalized by the dose of microencapsulated or unencapsulated ampicillin anhydrate that each rat actually received. This result was then plotted as a function of time.

In a second experiment, unlabelled ampicillin anhydrate microcapsules/spheres were tested in rats. The rats were administered the microcapsules/spheres in the same manner as that described in the first experiment. The microbiological assay described above was used to determine the amount of ampicillin in the serum of these rats.

In Vivo Efficacy Evaluation of Microcapsules/spheres

Experiments to evaluate the efficacy of prototype microcapsules/spheres in vivo were performed in 250- to 300-g male, Walter Reed strain, albino rats that were anesthetized with sodium pentobarbital. The right hind leg was razor-shaved, scrubbed with Betadine (The Purdue Frederick Co., Norwalk, Conn.), and swabbed. An experimental wound 1 cm deep was made in the thigh muscle and contaminated with 0.2 g of sterile dirt. The muscles were traumatized by uniformly pinching them with tissue forceps, and then the wounds were inoculated with known quantities of *Staphylococcus aureus* ATCC 6538P and *Streptococcus pyogenes* ATCC 19615. All rats were inoculated on the same day of the experiment with the same quantitated bacterial suspension to insure uniform inoculum in all wounds. The artificially contaminated wounds were treated within 1 hour by layering sterile, pre-weighed amounts of microencapsulated antibiotic directly on the wounds. Control groups consisted of animals with wounds that either received no therapy, were overlaid with placebo (unloaded) microcapsules/spheres, or were treated with locally applied, powdered unencapsulated ampicillin anhydrate. Following treatment, all wounds were sutured closed with 3-0 black silk.

Three groups of 20 rats each were used in an efficacy experiment to evaluate microcapsules/spheres A382-140-1 formulated from 70:30 DL-PLG. In this experiment, a group of animals with wounds overlaid with 0.5 g of unloaded microcapsules/spheres was substituted for the untreated (no therapy) group evaluated in each succeeding dose-response experiment. In addition, a group of 20 rats treated with 0.5 g of ampicillin anhydrate microcapsules/spheres per wound, and a group of 20 rats treated with 120 mg of locally applied uncapsulated ampicillin anhydrate powder per wound were evaluated. Five animals from each group were sacrificed at 2, 6, 8, and 14 days and evaluated for the presence of ampicillin in the serum and tissue and for the presence of infection.

Two dose-response experiments were performed in which Microcapsules/spheres A681-31-1, formulated from 70:30

DL-PLG, and Microcapsules/spheres B213-66-1S, formulated from 53:47 DL-PLG were evaluated. Seven groups of 15 rats each were treated with the doses of microcapsules shown in Table 5. Each experiment included an additional group of 15 rats which remained untreated.

TABLE 5

Ampicillin Anhydrate Microcapsules Evaluated in Rats

| In Vivo Experiment | Microcapsule Batch | Antibiotic Core Loading, Wt percent | Microcapsule Dose/Wound, g (Antibiotic Equivalent, mg) |
|---|---|---|---|
| Efficacy | A382-140-1 | 18.5 | 0.50 (92.50) |
| Dose-Response I | A681-31-1 | 18.1 | 0.50 (90.50) |
| | | | 0.25 (45.25) |
| | | | 0.10 (18.40) |
| | | | 0.05 (9.05) |
| Dose-Response II | B213-66-1S | 11.4 | 0.25 (28.50) |
| | | | 0.15 (17.10) |
| | | | 0.05 (5.70) |

In dose-response Experiment I, five animals from each group were sacrificed at 2, 7, and 14 days and evaluated for ampicillin levels and number of bacteria present per gram of tissue at each wound site. Serum ampicillin levels were assayed at 2, 4, 7, and 14 days. In dose-response Experiment II, five animals from each group were sacrificed at 7, 14, and 21 days and evaluated for ampicillin levels and number of bacteria present per gram of tissue. Serum ampicillin levels were determined at 2, 7, 14, and 21 days.

Microcapsules/spheres in a 45 to 106 micron size range made by the phase-separation process were evaluated in these experiments. The ampicillin anhydrate content of the microcapsules/spheres (core loading), batch number, and ampicillin anhydrate equivalent for each dose of microcapsules/spheres are shown in Table 5.

In all experiments, bacterial counts were performed on homogenized, preweighed tissue that had been aseptically removed from the wound sites. Serial dilutions of the homogenized tissue specimens were plated on sheep blood agar. Colonies of *Staphylococcus aureus* could be easily differentiated from *Streptococcus pyogenes* on the basis of colonial morphology. Tissue from varying distances around the wound site and serum removed by cardiac puncture were assayed for antibiotic content. This was accomplished by placing discs saturated with known quantities of serum or tissue homogenates on the surface of Mueller-Hinton agar which had been previously seeded with standardized amounts of *Sarcina lutea* ATCC 9341. Following incubation at 37° C., inhibition zones were measured. Freshly diluted stock solutions containing known quantities of ampicillin anhydrate served as standards. Diameters of the inhibition zones were converted to antibiotic concentrations using standard curves generated by plotting the logarithm of the drug concentration against the zone diameters.

Test Results

Microcapsule/spheres In Vitro Evaluation

Ampicillin anhydrate was microencapsulated with DL-PLG excipient. DL-PLG is a biocompatible aliphatic polyester that undergoes random, nonenzymatic, hydrolytic scission of the ester linkages under physiological conditions to form lactic acid and glycolic acid. These hydrolysis products are readily metabolized. The purpose of the DL-PLG is to control the release of the ampicillin anhydrate from the antibiotic microcapsule/spheres formulation and to protect the reservoir of ampicillin anhydrate from degradation before it is released from the microcapsules/spheres. Two DL-PLG excipients were used in this study. One DL-PLG had a lactide-to-glycolide mole ratio of 70:30 and the other, 53:47. The 53:47 DL-PLG biodegrades faster than the 70:30 DL-PLG because of its higher glycolide content.

A phase-separation microencapsulation process afforded microcapsules/spheres in yields of better than 95. The microencapsulated ampicillin anhydrated product was a fine, free-flowing powder. The microcapsules/spheres are relatively spherical in shape, but have puckered regions. Although these puckered regions exist, the polymer coating was continuous, and there was no evidence of any fractures or pinholes on the surfaces of the microcapsules. Moreover, the photomicrograph obtained by scanning electron microscopy of ampicillin anhydrate microcapsules did not show any evidence of free unencapsulated ampicillin anhydrate crystals either among the microcapsules or protruding through the surface of the microcapsules.

The drug content (coreloading) of the ampicillin anhydrate microcapsule/sphere formations was measured to assess how much ampicillin anhydrate was incorporated in the microcapsules and to determine the bioactivity of the ampicillin anhydrate after it had been microencapsulated.

In general, the core loading of the 45-to 106 microns size fraction was similar to the theoretical core loading. The core loading of a few batches of [$^{14}$C]-ampicillin anhydrate microcapsules/spheres was determined by microbial assay as well as by radioassay. Within experimental error, both assays gave similar results. This indicates that the ampicillin anhydrate was not inactivated during the microencapsulation process. Also, the core loading of ampicillin anhydrate microcapsules/spheres was determined by the microbial assay to determine the effect of 2.5 Mrad of gamma radiation on the microencapsulated drug. The radiation did not inactivate the drug because the core loading remained the same. For instance, 19.3 spheres with 70:30 DL-PLG assayed as 19.0 irradiation and 11.0 DL-PLG assayed as 11.4 irradiated unencapsulated and microencapsulated drug were also checked by thin layer chromatography. Irradiated and non-irradiated samples chromatographed the same, again indicating that no degradation of the drug was caused by gamma radiation at a dose of 2.5 Mrad.

In vitro release measurements were used to identify an ampicillin anhydrate microcapsule/sphere formulation that would release all of its drug at a controlled rate over a period of two weeks. The formulation that displayed the desired in vitro release kinetics were microcapsules/spheres with diameters of 45 to 106 microns consisting of about 10 wt percent ampicillin anhydrate (Bristol Laboratories, Syracuse, N.Y.) and microcapsules/spheres with diameters of 10 to 100 microns consisting of about 35 wt percent ampicillin anhydrate (Wyeth Laboratories, West Chester, Pa.) and about 65 wt percent 53:47 DL-PLG. FIGS. 1 and 2 show the in vitro release profiles of two samples of these prototype microcapsules. The microcapsules released a desirable initial burst of drug, representing about 30 percent. The remaining drug was then released at a slower controlled rate.

The in vitro release profile of sterilized (2.5 Mrad), 17.6 compared with the release profiles of sterilized (2.0 Mrad), 9.6 and 7.8 DL-PLG (FIG. 2).

Microcapsule/sphere In Vivo Evaluation

Pharmacokinetic studies were performed with unencapsulated ampicillin anhydrate and the same samples of microcapsules that were tested in vitro, as previously described. As shown in FIGS. 2 and 3, the unencapsulated drug as well as the microcapsules/spheres showed a fast release of drug during Day 1. By Day 4, the amount of ampicillin found in the urine or serum of animals dosed with the unencapsulated drug was below the level of detection of the assay. On the other hand, the microcapsule/sphere formulations maintained an elevated level of drug in the urine or serum for extended periods. Both samples of microcapsules/spheres made with the 53:47 DL-PLG had similar release profiles and released drug for about two weeks. As illustrated in FIG. 4, the microcapsules/spheres prepared with 70:30 DL-PLG released drug for at least four weeks. The results of these pharmacokinetic studies corroborate results of the in vivo release studies described. The 53:47 microcapsules/spheres closely meet the desired target duration of release of two weeks.

The slow rate of ampicillin release from the 70:30 microcapsules/spheres, as shown in FIG. 4, may be undesirable because a low level of ampicillin anhydrate released over a long period may provide favorable conditions for the development of drug-resistant bacterial strains. This slower release of drug could be attributed to the slower biodegradation rate of the 70:30 DL-PLG, where the water-soluble ampicillin anhydrate remained trapped inside the hydrophobic DL-PLG excipient until the excipient biodegraded completely. More specifically, for microcapsules/spheres prepared with either the 70:30 or 53:47 DL-PLG, one could speculate that the release of drug is due to diffusion of the drug through water-filled pores, pores that enlarge as more and more drug is released and as the DL-PLG bioerodes.

However, all ampicillin anydrate microcapsules/spheres formulated effectively reduced bacterial counts in contaminated wounds. The most dramatic observation was the rapid elimination of *Streptococcus pyogenes*. *Streptococcus pyogenes* was present in 90 from microcapsule/sphere-treated wounds within 48 hours. All three of the microcapsule/sphere batches evaluated were equally successful in eliminating this organism within two days. At 7 days *Staphylococcus aureus* remained in all treated wounds; however, compared to untreated controls, the bacterial count per gram of tissue decreased by at least 2 $\log_{10}$ between Days 2 and 7. This reduction was not observed in untreated controls. In the efficacy evaluation of microcapsules/spheres A382-140-1, wounds treated with unloaded DL-PLG microcapsules, as well as those treated with topical unencapsulated ampicillin anhydrate, remained infected at 14 days with >$10^5$ organisms per gram of tissue; whereas, 60 ampicillin anhydrate were sterile. The wounds of the remaining $4010^3$ organisms per gram of tissue. By 14 days, regardless of the dose administered (0.5–0.05 g), all wounds treated with microcapsule/sphere sample A681-31-1 were sterile; whereas, all untreated wounds remained infected with >$10^5$ organisms per gram of tissue. At 14 days, all wounds treated with 0.15 g of microcapsules/spheres B213-66-1S were sterile, however, $5.7 \times 10^2$ *Staphylococcus aureus* per gram of tissue were counted in the wounds of one animal treated with a 0.25-g dose of encapsulated ampicillin anhydrate. This failure was attributed to an abscess around a suture on the wound surface. All wounds treated with 0.15 g of microcapsules/spheres (B213-66-1S) were sterile; however, in the group treated with a 0.05-g dose of microcapsules/spheres, one wound remained contaminated with $3.6 \times 10^4$ *Staphylococcus aureus* per gram of tissue. The untreated control animals, evaluated in parallel with the microcapsule/sphere-treated groups, averaged $1.4 \times 10^5$ *Staphylococcus aureus* per gram of tissue.

Serum levels of drug were dependent upon the ampicillin anhydrate reservoir present inside the microcapsules/spheres (core loading), the dose, and the ampicillin release characteristics. Administration of 0.25 g of Microcapsules/spheres A681-31-1, which contained a 45.25 mg ampicillin reservoir per wound, maintained a serum ampicillin level of 8.0±7.3 microgram/milliliter for up to 4 days post-treatment. A dose twice that amount (90.50 mg ampicillin equivalent) maintained detectable serum ampicillin for up to 7 days post-treatment at a serum ampicillin concentration of 15.95±5.0 microgram/milliliter for the first 4 days. Serum ampicillin was not detected in animals whose wounds were treated with microcapsule/sphere doses containing an ampicillin equivalent of 28.50 mg or less. Even though serum ampicillin was not detected in any animal at 14 days, the tissue levels at this time were above the minimal inhibitory concentrations required to kill both infecting organisms in all animals treated with microencapsulated ampicillin anhydrate. This was true with microcapsule/sphere doses as low as 0.05 gram per wound. Even though serum ampicillin was not detected, microbial bioassay for ampicillin in tissue removed from wounds treated with 0.05 gram of microcapsules/spheres (A681-31-1) contained a mean (n=5) ampicillin level of 54, 70, and 21 micrograms/gram of tissue at 2, 7, and 14 days, respectively. Because the minimal inhibitory concentrations of ampicillin required to kill 95 of *Staphylococcus aureus* and 97 *pyogenes* is 0.5 and 0.05 micrograms/milliliter, respectively, it is a reasonable assumption that a more than adequate therapeutic amount of drug was present at the wound site throughout the two-week treatment period.

In vitro release studies performed on microcapsules/spheres formulated with 70:30 DL-PLG (A382-140-1 and A681-31-1) showed drug release at an efficacious rate over two weeks, but also at a slower rate for an additional 50 days. The continued release of low amounts of antibiotic in wounds after two to three weeks is undesirable because of the potential to provide favorable conditions for the emergence of ampicillin resistant organisms in wounds which might harbor small numbers or bacteria. Therefore, to reduce or eliminate drug trailing microcapsules/spheres were reformulated by encapsulating ampicillin anhydrate within the faster biodegrading polymer 53:47, DL-PLG (sample B213-66-1S), in vitro release profiles showed a release of 85 to 92 within two weeks. On the seventh day following treatment of wounds with 0.15 gram of Microcapsules/spheres B213-66-1S, a mean (n=5) of 162.5 g of ampicillin per gram of tissue was quantitated. In vitro release studies suggest that this amount drops rapidly in the second week so that by 14 days marginal killing concentrations are present. In vivo analysis of tissue removed from wounds treated 15 days previously with 0.25 gram of these microcapsules/spheres contained <1.9 micrograms/gram of ampicillin per gram. Although <0.22 micrograms/gram of ampicillin was detected in wounds treated with 0.15 gram, it was unusual to detect any ampicillin at 14 days in tissue from wounds treated with 0.05 gram per wound. At 21 days post-treatment, ampicillin was not detected in any of the wounds.

No serum levels of ampicillin were detected in any of the rats treated with Microcapsules/spheres B213-66-1S. This was expected because lower doses (ampicillin equivalent) were administered. (Table 5).

B. Cefazolin (CZ) microspheres. The CZ microspheres used in these studies were produced by Southern Research Institute, Birmingham, Ala. The microspheres consisted of 77.8 weight % copolymer (50:50 molar ratio of lactide to glycolide) with a core leading dose of 22.2 weight % cefazolin. The size of the microspheres ranged from 90 to 355 um in diameter and they were sterilized with 2.7 Mrad of gamma radiation. In vitro release kinetic studies showed that approximately 20% of the cefazolin was released from the microspheres within 6 hours, with the remainder of antibiotic release extending over a period of 15 days.

Rat wound infection model. Experimental wounds were surgically created in the paraspinous muscles of Sprague-Dawley rats following induction of anesthesia with ketamine and xylazine. Sterile sand (100 mg) was implanted into the wound site to simulate a foreign body and the wounds were inoculated with $5 \times 10^6$ CFU each of *Staphylococcus aureus* ATCC 27660 and *Escherichia coli* ATCC 25922. The minimum inhibitory concentration (MIC) of cefazolin for each of these organisms was 4 ug/ml and 2 ug/ml, respectively. The animals were then randomly distributed in 6 groups. Groups A, B, and C (6 rats per group) received local antibiotic therapy with 50 mg, 250 mg, or 500 mg of CZ microspheres, respectively. The microspheres were applied directly to the wounds and care was taken to achieve a relatively uniform distribution of the drug throughout the wound site. Group D (6 rats) received local antibiotic therapy with 110 mg of CZ powder. This dose was equivalent to the core-loading dose of cefazolin contained in 500 mg of CZ microspheres used to treat the Group C animals. Group E (6 rats) received systemic antibiotic therapy with cefazolin (30 mg/kg) which was administered as a single intramuscular bolus immediately after bacterial contamination of the wounds. Group F (3 rats) served as controls and received no antibiotic therapy. The wounds were then closed with surgical staples and the animals were returned to their cages. On postoperative day #28, the rats were euthanized and tissue was obtained from each wound for quantitation of surviving bacteria. The tissue was weighed, homogenized, and serial 10-fold dilutions were prepared and plated on blood agar. The number of bacteria recovered from each wound was quantitated and expressed as CFFU/g tissue.

Rabbit fracture-fixation model. This study was conducted in two stages (I and II) and was designed to evaluate the effect of early as well as delayed local antibiotic therapy for the prevention of infection in experimental fractures.

In stage I, open fractures were created in the right tibiae of New Zealand White rabbits after induction of anesthesia with ketamine and xylazine. The fractures were then inoculated with 0.5 ml of *S. aureus* ATCC 27660 ($2.0 \times 10^7$ CFU/ml). Within 30 minutes following bacterial contamination, the animals were randomly distributed in 5 groups. Group A (8 rabbits) received local antibiotic therapy with 300 mg of cefazolin microspheres which was applied directly to the fracture site and the deep musculature. Group B (8 rabbits) received local antibiotic therapy with an equivalent dose of CZ powder. Group C (8 rabbits) received systemic antibiotic therapy with cefazolin (25 mg/kg/day) for 7 days. Groups D and E (4 rabbits per group) served as controls and received either local application of placebo microspheres (without cefazolin) or no treatment, respectively. The fractures were then reduced and plated with a 4-hole dynamic compression plate. Immediately prior to wound closure, animals in Groups A and B received an additional dose of either CZ microspheres (300 mg) or an equivalent dose of CZ powder, respectively, which was applied directly over the fixation plates and the periosteal tissue. The wounds were then repaired with sutures and the animals were returned to their cages. Blood was obtained within 1 hour and again at 24 hours after treatment from all Group A and B animals for quantitation of serum cefazolin levels which was measured by a microbial inhibition bioassay[9]. Eight weeks later, all surviving animals were euthanized and the tibiae were harvested for bacteriological analysis, the bones were crushed to small pieces with sterile mortar and pestle and saline was added to make a particulate suspension. Serial dilutions were then prepared and streaked on blood agar for bacterial isolation. The number of *S. aureus* colonies recovered from each specimen was quantitated and expressed as CFU/g of bone.

In stage II, fractures were created in the right tibia of 29 rabbits and contaminated with *S. aureus* as described above. After a 2 hour delay, the animals were randomly distributed in 3 groups. Group A (10 rabbits) received local antibiotic therapy with 600 mg of CZ microspheres. Group B (10 rabbits) received local antibiotic therapy with an equivalent dose of CZ powder. Group C (9 rabbits) served as controls and received no treatment. The fractures were then reduced, plated, and the wounds were closed with sutures. Eight weeks later, the surviving animals were euthanized and the tibiae were harvested and processed for isolation of bacteria as described above.

Results

Rat wound infection model. Table 4 shows the effect of local versus systemic cefazolin therapy on the contamination rate in rat soft-tissue wounds at 28 days postinfection. Local antibiotic therapy with CZ microspheres, in doses ranging from 50 to 500 mg per wound, was highly effective for eliminating both organisms from the wounds. The maximum effect was achieved in the Group C animals who received the highest dose of CZ microspheres (500 mg) where *E. coli* and *S. aureus* were eliminated from 100% of the wounds. Even at the lowest dose used (50 mg/wound), 4 of 6 wounds were rendered completely sterile. Local antibiotic therapy with free CZ powder sterilized the wounds in 5 of 6 (83%) animals. In contrast, systemic administration of cefazolin (30 mg/kg) failed to sterilize the wounds in any of the 6 Group E animals tested.

TABLE 6

Effect of early antibiotic therapy on infection in *S. aureus* contaminated rabbit tibial fractures stabilized with internal fixation.

| Treatment Group (N) | No. of Animals with: | | Mean (±SD) log bacteria (CFU/g) |
|---|---|---|---|
| | Deep Infection | Positive Bone Cultures | |
| A: CZ microspheres (7) | 0/7 | 1/7 | 0.3 ± 0.9 |
| B: CZ powder (6) | 0/6 | 1/6 | 0.2 ± 0.5 |
| C: Systemic CZ (5) | 3/5 | 4/5 | 3.0 ± 2.1 |
| D: Placebo microspheres (3) | 3/3 | 3/3 | 5.2 ± 0.2 |
| E: No treatment (4) | 2/4 | 4/4 | 4.2 ± 0.5 |

Rabbit fracture-fixation model. Table 6 shows the results of the clinical and bacteriological findings at 8 weeks in 25 surviving rabbits when local or systemic antibiotic therapy with cefazolin was initiated within 30 minutes following bacterial contamination of the fractures. Deep infection, defined as the presence of pus on the fixation plate or in the deep tissues, was noted in 6 of the 7 (86%) control animals in Group D (placebo microspheres) and group E (no treatment). Cultures of the tibiae from all 7 controls were positive for *S. aureus*. Of the 5 surviving Group animals who received a 1 week course of systemic cefazolin therapy, deep infection was noted in 3 cases and *S. aureus* was recovered from the bones of 4 of the 5 animals. In contrast, no clinical evidence of infection was detected in any of the 7 Group A animals who received an equivalent local dose of free CZ powder. Cultures of the tibiae were sterile in 6 of (86%) Group A and 5 of 6 (83%) Group B animals, respectively. There was a statistically significant difference in the mean log S. aureus counts of the Group A and Group B animals and all other groups by analysis of variance (p<0.05). The mean log S. aureus counts for Group C was also significantly different from all groups with the exception of Group E (no treatment).

Table 7 shows the results of the clinical and bacteriological findings at 8 weeks in 23 surviving rabbits when local antibiotic therapy was delayed for 2 hours following bacterial contamination of the fractures. Clinical evidence of infection was present in 5 of 7 (71% control animals in Group C and cultures of the tibiae yielded S. aureus in all cases. Of the 8 animals in Group B who received local antibiotic therapy with Cz powder, deep infection was noted in 4 animals and S. aureus was received in 6 of 8 (75%) cases. In contrast, none of the 8 animals in Group Aa (CZ microspheres) developed clinical infections and cultures of the tibiae were sterile in all cases. One way analysis of variance showed a statistically significant difference in the mean log S. aureus counts between Groups A and B (p=0.0014).; Groups A and C (p<0.0001); and Groups B and C (p=0.0269).

TABLE 7

Effect of delayed antibiotic therapy on infection rates in S. aureus contaminated rabbit tibial fractures.

| Treatment Group (N) | Deep Infection | Positive Bone Cultures | Mean (±SD) log bacteria (CFU/g) |
|---|---|---|---|
| A: CZ microspheres (8) | 0/8 | 0/8 | 0 |
| B. CZ powder (8) | 4/8 | 6/8 | 2.4 ± 1.8 |
| E. No treatment (7) | 5/7 | 7/7 | 4.3 ± 1.0 |

Table 7 shows the results of the clinical and bacteriological findings at 8 weeks in 23 surviving rabbits when local antibiotic therapy was delayed for 2 hours following bacterial contamination of the fractures. Clinical cadence of infection was present in 5 of 7 (71%) control animals in Group C and cultures of the tibiae yielded S aureus in all 7 cases. Of the 8 animals in Group B who received local antibiotic therapy with CZ powder, deep infection was noted in 4 animals and S aureus was recovered in 6 of 8 (75%) cases. In contrasts, none of the 8 animals in Group A (CZ microspheres) developed clinical infections and cultures of the tibiae were sterile in all cases. One way analysis of variance showed a statistically significant difference in the mean log S aureus counts between Groups A and B p=0.0014). Groups A and C (p<0.0001), and Groups B and C (p=0.0269).

References

1. E. Jacob and J. A. Setterstrom, Milit. Med. 154, 311 (1981).
2. E. Jacob, J. M. Erpelding, and K. P. Murphy, Milit. Med. 157, 552 (1992).
3. R. S. Klein, S. A. Berger, and P. Yekutiel, Ann. Surg. 182, 15 (1975).
4. R. D. Livingston, Milit. Med. 150, 72 (1985).
5. T. H. Witschi and G. E. Omer, J. Trauma 10, 105 (1970).
6. M. Seidenstein and A. Newman, Arch. Surg. 96, 176 (1968).
7. E. Simchen and T. Sachs, Ann. surg. 182, 754 (1975).
8. J. A. Setterstrom et al., in Recent Advances in Drug Delivery Systems, S. W. Kim, Ed., (Plenum, New York, 1984), pp. 185–198.
9. J. V. Bennett, J. L. Brodei, E. J. Benner, and W. N M. Kirby, Appl. Microbiol. 14, 170 (1966).
10. H. E. Noyes, N. H. Chi, and L. T. Link, Milit. Med. 132, 461 (1967).
11. C. Heisterkamp, J. Vernick, R. L. Simmons, and T. Matsumoto, Milit. Med. 134, 13 (1969).

Applicants have developed microencapsulated antibiotics for the local treatment of contaiminated surgical and traumatic wounds. Preliminary studies have shown that local application of biodegradable antibiotic microspheres to experimental wounds that were contaminated with resistant bacteria was extremely effective for prevention of wound infection. This success is attributed to the significantly higher local tissue antibiotic levels that can be achieved at the wound site with direct local application of microencapsulated antibiotics as compared to conventional systemic antibiotic dosing. The findings of the experimental studies are summarized below:

1. Ampicillin microspheres effectively prevented infection in 8/11 (73%) animals whose wounds were inoculated with an ampicillin-resistant strain of s. aureus (MIC=750 ug/ml). Systemic ampicillin failed in 9/9 (100%) cases.
2. Cefazolin microspheres effectively prevented infection in 5/6 (83%) animals whose wounds were inoculated with a methicillin-resistant strain of S. aureus which was also resistantto cefazolin (MIC=64 ug/ml). Systemic cefazolin failed in 5/6 (83%) cases.
3. It is preferred that a initial release (burst) of the encapsulated antibiotic occur within the first day and the remaining antibiotic be released over the next 2 to 3 weeks.

Experimental Design for Rat Soft-tissue Wound Infection Model

Experimental surgical wounds were created in the paraspinous muscle of anesthetized Sprague Dawley rats, each weighing between 450 to 550 grams. The wounds were then contaiminated with 100 mg of sterile sand as an infection-potentiating agent. The wounds were then inoculated with $5 \times 10^6$ CFU of S. aureus ATCC 33593. This is a methicillin-resistant strain of S. aureus which is also resistant to cefazolin (MIC=64 ug/ml). The animals were then assigned to the following treatment groups:

Group A (n=6): 500 mg of cefazolin (CZ) microspheres was applied directly to the wounds. This dose contained 110 mg of cefazolin equivalent.

Group B (n=6): 110 mg of free CZ powder was applied directly to the wounds.

Group C (n=6): This group received intramuscular injections of CZ (30 mg/kg/day) at 8 hour intervals for 7 consecutive days.

Group D (n=3): This group served as controls and did not receive any antibiotic therapy.

The wounds were then closed with surgical staples and the animals were returned to their cages for the next 5 weeks. At that time, the animals were humanely euthanized and tissue was removed from the wounds and cultured for the presence of bacteria. The bacteriological data are presented in Table 8.

VI. UTILITY

Successful controlled release of bioactive ampicillin anhydrate was achieved in vitro and in vivo. The prototype microcapsules/spheres effectively controlled or eliminated *Staphylococcus aureus* and *Steptococcus pyogenes* from infected wounds in rats. Additionally, the formulation would be effective in the treatment of all bacterial infections caused by organisms sensitive to the antibiotic encapsulated including but not Enterobacteriaceae; Klebsiella spp.; Bacteroides sp.; Enterococci; Proteus sp.; Streptococcus sp.; Staphylococcus sp.; Pseudomonas sp.; Neisseria sp.; Pedptostreptococcus sp.; Fusobacterium sp.; Actinomyces sp.; Mycobacterium sp.; Listeria sp.; Corynebacterium sp.; Proprionibacterium sp.; Actinobacillus sp.; Aerobacter sp.; Borrelia sp.; Campylobacter sp.; Cytophaga sp.; Pasteurella sp.; Clostridium sp.; *Enterobacter aerogenes*, Peptococcus sp.; *Proteus vulgaris, Proteus morganii, Staphylococcus aureus, Streptococcus pyogenes*, Actinomyces sp., *Campylobacter fetus*, and *Legionella pneumophila*. Results indicate that optimal microcapsules/spheres should exhibit a programmed release of an appropriate concentration of antibiotic over about a 14 day to about a 6 week time period after which time the microcapsule/sphere should biodegrade, leaving no trace of drug or excipient.

TABLE 8

Efficacy of Cefazolin Microspheres In Rat Soft Tissue Wounds Contaminated with a Cefazoll-Resistant Strain of *S. aureus* (MIC = 64 μg/ml)

| Treatment Group | Dose | Number of Animals | Number (%) Sterile Wounds |
| --- | --- | --- | --- |
| CZ microspheres | 500 mg[a] | 6 | 5/6 (83%) |
| Free CZ powder | 110 mg | 6 | 6/6 (100%) |
| Systemic CZ | 30 mg/kg × 7 days | 6 | 0/6 (0%) |
| Controls | No antibiotics | 3[b] | 2/2 (0%) |

[a]500 mg of CZ microspheres was applied to the wounds representing 110 mg of cefazolin equivalent
[b]One control animal died during the experiment and no cultures were performed.
LEGEND:
CZ microspheres = Cefazolin-loaded lactide-co-glycolide microspheres
Free CZ powder = Unencapsulated cefazolin powder
Systemic CZ = Intramuscular administration of cefazolin (30 mg/kg/day) given at 8 hour intervals for 7 consecutive days.
Controls = No antibiotic treatment.

*Campylobacter fetus*; and *Lepionella pneumophila*. Results indicate that optimal microcapsules/spheres should exhibit a programmed release of an appropriate concentration of antibiotic over about a 14 day to about a 6 week time period after which time the microcapsule/sphere should biodegrade, leaving no trace of drug or excipient.

Phase II

This illustrative phase of this invention relates to a novel pharmaceutical composition, a microcapsule/sphere formulation, may contain a pharmaceutically-acceptable adjuvant that comprises an antigen encapsulated within a biodegradable polymeric matrix—such as poly(DL-lactide-glycolide) (DL-PLG), herein the relative ratio between the lactide and glycolide component of the DL-PLG is within the range of 90:10 to 0:100, and its use, as a vaccine, in the effective pretreatment of animals (including humans) to prevent intestinal infections caused by a virus or bacteria. In the practice of this invention, applicants found that the AF/RI adherence factor is a plasmid encoded pilus composed of repeating pilin protein subunits that allows *E. coli* RDEC-1 to attach to rabbit intestinal brush borders. To identify an approach that enhances the immunogenicity of antigens that contact the intestinal mucosa, applicants investigated the effect of homogeneously dispersing AF/RI pili within biodegradable microspheres that included a size range selected for Peyer's Patch localization. New Zealand White rabbits were primed twice with 50 micrograms of either microencapsulated or nonencapsulated AF/RI by endoscopic intraduodenal inoculation. Lymphoid tissues were removed and cellular proliferative responses to AF/RI and synthetic AF/RI peptides were measured in vitro.

The synthetic peptides represented possible T and/or B cell epitopes which were selected from the AF/RI subunit sequence using theoretical criteria. In rabbits which had received nonencapsulated AF/R1, Peyer's Patch cells demonstrated slight but significant proliferation in vitro in response to AF/RI pili but not the AF/RI synthetic peptides. In rabbits which had received microencapsulated AF/RI, Peyer's Patch cells demonstrated a markedly enhanced response to AF/RI and the synthetic peptides. Cells from the spleen and mesenteric lymph nodes responded similarly to AF/RI pili in both groups of animals, while there was a greater response to the synthetic peptide.

AF/RI 40–55 in rabbits that had received microencapsulated AF/RI. These data demonstrate that microencapsulation of AF/RI potentiates the mucosal cellular immune response to both the native protein and its linear peptide antigens.

A primary mucosal immune response, characterized by antipilus IgA, follows infection of rabbits with *E.coli* RDEC-1. However, induction of an optimal primary mucosal response by enteral vaccination with pilus antigen depends on immunogenicity of pilus protein, as well as such factors as its ability to survive gastrointestinal tract (GI) transit and to target immunoresponsive tissue. We tested the effect of incorporating AF/RI pilus antigen into resorbable microspheres upon its ability to induce primary mucosal and systemic antibody responses after direct inoculation into the GI tract.

METHODS: rabbits were inoculated with 50 micrograms of AF/RI pilus antigen alone or incorporated into uniformaly sized (5–10 microns) resorbably microspheres (MIC) of poly(DL-lactide.coglycolide). Inoculation was by intraduodenal (ID) intubation via endoscopy or directly into the ileum near a Peyer's patch via the RLTARD procedure (with the cecum ligated to enhance recovery of gut secretions and a reversible ileal tie to slow antigen clerance).

ID rabbits were sacrificed at 2 weeks for collection of gut washes and serum.

RITARD rabbits were bled and purged weekly for 3 weeks with Co-lyte to obtain gut secretions. Anti-pilus IgA and IgG were measured by ELISA.

TABLE 9

| RESULTS: *pos/test | RITARD-PILI | RITARD-MIC | ID-PILI | ID-MIC |
|---|---|---|---|---|
| Anti-pilus IgA (fluid) | •7/8 | 4/B | 1/2 | 0/3 |
| And-pilus iGg (serum) | 0/8 | 3/8 | 0/2 | 0/3 |

Native pilus antigen led to a mucosal IgA response in 7/8 RITARD rabbits. MIC caused a similar response in only 4/8, but the groups were not statistically different. MIC (but not pili) induced some systemic IgG responses (highest in animals without mucosal responses). Results in rabbits inoculated ID were similar for pili, but no mucosal response to ID-MIC was noted.

SUMMARY: Inoculation with pilus antigen produces a primary mucosal IgA response. Microencapsulation does not enhance this response although the antigen remains immunogenic as shown by measurable mucosal and some strong serum responses. It must be determined whether priming with antigen in microspheres can enhance secondary responses.

B Cell Epitope Data

Materials and Methods

CFA/I PURIFICATION-INTACT CFA/1 pili were purified from H 10407 (078:H-)as described by Hall et al, (1989) [20]. Briefly, bacteria grown on colonization factor antigen agar were subjected to shearing, with the shearate subjected to differential centrifugation and isopycnic banding on cesium chloride in the presence of N-lauryl sarkosine. CFA/I were dissociated to free subunits in 6M guanididinium HCl, 0.2 M ammonium bicarbonate (2 hr, 25 deg), passed through an ultrafiltration membrane (Amicon XL 50 stirred cell, Danvers, Mass.), with concentration and buffer exchange to PBS on a YM 10 stirred cell (Amicon). Examination of dissociated pill by electron microscopy demonstrated a lack of pilus structure.

Protein Sequencing—The primary structure of CFA/I has been determined by protein sequencing techniques (Klemm, 1982) and through molecular cloning methods (Karjalainen, et al. 1989)(21). In these two studies there was agreement in all but two of the 147 amino acid residues (at positions 53 to 74). To resolve the apparent discrepancies, CFA/I was enzymatically digested in order to obtain internal amino acid sequence. Trypsin or S. aureus V8 protease (sequencing grade, Boehringer Mannheim) was incubated with CFA/I at a 1:50 w:w ratio (Tris 5.0 mM, 0.1% SDS, pH 8.5 for 16 h at 37 deg (trypsin) or 24 decC (V8)). Digested material was loaded onto precast 16% tricine SDS-PAGE gels (Schagger and von Jagow, 1987) (Novex, Encinitis, Calif.) and run following manufacturers instructions. Separated samples were electrophoretically transferred to PVDF membranes (Westrans, Schleicher and Schuell, Keene, N.H.) following Matsiduria (1987) using the Novex miniblot apparatus. Blotted proteins were stained with Rapid Coomassie stain (Diversifed Biotech, Newton Centre, Mass.). To obtain the desired fragment containing the residue of interest within a region accessible by automated gas phase sequencing techniques, molecular weights were estimated from standards of molecular weights 20,400 to 2,512 (trypsin inhibitor, myoglobin, and myoglobin cyanogen bromide gradments; Diversified Biotech) using the corrected molecular weights for the myoglobin fragments as given in Kratzin et al., (1989)(22). The estimated molecular weights for the unknown CFA/I fragments were compared to calculated molecular weights of fragments as predicted for CFA/I from the sequence of CFA/I as analyzed by the PEPTIDESORT program of a package developed by the University of Wisconsin Genetics Computer Group. Selected fragments were cut from the PVDF emebrane and subjected to gas phase sequencing (Applied Biosystem 470, Foster City, Calif.).

Monkey Immunization—Three rhesus monkeys (Macaca milatta) were injected intramuscularly with 250 ug of dissociated CFA/I in complete Freund's adjuvent and subsequently with two injections of 250 ug of antigen in incomplete Freund's adjuvent at weekly intervals. Blood was drawn three weeks after primary immunization.

Peptide Synthesis—Continuous overlapping octapeptides spanning the entire sequence CFA/I were synthesized onto polyethylene pins by the method of Ceysen Ct al. (16), also known as the PEPSCAN procedure. Derivitized pins and software were purchased from Cambridge Research Biochemicals (Valley Stream, N.Y.). Fmoc-amino acid pentafluorophenyl esters were purchased from Peninsular Laboratories (Belmont, Calif.), 1-hydroxybenzotriarole monohydrate (HYBT) was purchased from Aldrich, and reagent grade solvents from Fisher. Tospan the entire sequence of CPA/I with a single amino acid overlap of from one peptide to the next, 140 total pins were necessary, with a second complete set of 140 pins synthesized simultaneously.

ELISA procedure-Sera raised in monkeys to purified dissociated pili were incubated with the pins in the capture ELISA assay of Geysen et al. [16] with the preimmune sera of the same animal tested at the same dilution simultaneously with the duplicate set of pins bilution of sera used on the pins was chosen by initial titration of sera by standard ELISA assay and immunodot blot assay against the same antigen.

Results

It was essential to utilize the correct sequence of CFA/I in the synthesis of the pins for both T- and B-cell experiments to carry out the studies as planned. At issue were the amino acids at position 53 and 74; incorrect residues at those positions would effect 36 of 138 pins (26%) for T-11 epitope analysis and 30 of 140 pins (21) for B-cell analysis. To resolve the discrepancy in the literature, purified CFA/1 was proteolytically digested separately with trypsin and with S. aureus V8 protease (V8). These enzymes were chosen in order to give fragments with the residues of interest (53 and 74) relatively near to the N-terminus for automated Edman degradation (preferably 1–15 residues). These digests were separated on tricine SDS-PAGE gels (FIG. 24A) and molecular masses of fragments estimated. A fragment of 3459 calculated molecular mass is expected from the trypsin digest (corresponding to amino acids 62–94) and a fragment of 5889 calculated molecular mass is expected from the V8 digest (residues 42–95). These fragments were located within each digest (arrows in FIG. 24), and a companion gel with four lanes of each digest was run, electrophoreticaly transferred to PVDF, the bands excised and sequenced. N-terminal sequences of each fragment art given in FIG. 24B. The N-terminal eighteen residues from the trypsin fragment were determined that corresponded to positions 62–79 in CFA/I. Position 74, a serine residue was consistent with that determined by Karjalainen et al., (Karjalainen et al., 1989). Nineteen residues of the V8 fragment were determined, corresponding to residues 41–60 of the parent protein. The twelfth residue of the fragment contained an aspartic acid, also consistent with Karjalainen et al., (1989). All other residues sequenced were consistent with those published previously (including residues 1–29, not shown). For the following peptide synthesis were therefore utilized the complete amino acid sequence of CFA/I consistent with Karjalainen et al., (1989).

Sera from monkeys immunized with CFA/I subunits were tested in a modified ELISA assay, with the preimmunization sera tested simultaneously with duplicate pins. Assays results are displayed in FIG. 25. Monkey 272 (FIG. 2A) responded strongly to six regions of the CPA/I sequence. Peptide 14 (the octapeptide 14–21) gave the strongest response with four pins adjacent to it (11, 12, 13, and 15) also appearing to bind significant antibody. The other 222 epitopes are centered at peptides 3, 22, 33, 93, and 124. Monkey 184D (FIG. 17B) also responded strongly to peptide 14, although the maximum response was to peptide 13, with strong involvement of peptide 12 in the epitope. Additional epitopes recognized by 184d were centered at peptides 22, 33, 66, and 93. The third monkey serum tested, 34, responded to this region of the CFA/I primary structure, both at peptides 1, 12 and weakly at 14. Two other epitopes were identified by 34, centered at peptides 67 and 128. FIG. 26 illustrates the amino acids corresponding to the epitopes of CFA/I as defined by the response of these three monkeys aligned with the entire primary structure. The entire antigenic determinants are mapped and areas of overlap criteria published by Rothbard and Taylor [7]. The sequence numbers of the first amino acid of the predicted segments are shown in Table 10.

Lymphocyte proliferation of monkey spleen cells to CFA/I synthetic peptides. To determine which segments or the CFA/I protein are able to stimulate proliferation of CFA/I immune primate lymphocytes in vitro, three Rhesus monkeys were immunized with CFA/I subunits, and their splenic lymphocytes were cultured with synthetic overlapping decapeptides which represented the entire CF/I sequence. Concentrations of peptides used as antigen were 6.0, 0.6, and 0.6 ug/ml. Proliferative responses to the decapeptides were observed in each of the three monkeys (FIGS. 9–11). The majority of the responses occurred at the 0.6 and 0.06 ug/ml concentrations of antigen and within distinct regions of the protein (peptides beginning with residues 8–40, 70–80, and 27–137). A comparison of the responses at the 6.0, 0.6 and 0.06 ug/ml concentrations antigenic peptide for one monkey (2&2)are shown (FIGS. 12–14. Taking into account all concentrations of antigen tested, spleen cells from monkey 184D demonstrated a statistically significant response to decapeptides beginning with CEA/I amino acid residues 3, 4, 8, 12, 15, 21, 26, 28, 33, 88, 102, 10, 133, 134, and 136 (FIG. 27). Monkey 34 had a significant response to decapeptides beginning with residues 24, 31, 40, 48, 71, 72, 77, 78, 80, 87, and 102, 126 and 133 (FIG. 28): monkey 272 responded to decapeptides which began with residues 4, 9, 11, 12, 13, 14, 15, 16, 17, 20, 27, 35, 73, 79, 18, 127. 129, 132, and 133 (FIG. 27). Peptides beginning with amino acid residues 3 through 2 were synthesized with either a glutamic acid or an asparagine substituted for the aspartic acid residue at peptides twelve to prevent truncated peptides. The observed responses to peptides beginning with residue 8 (monkey 184d), and residues 9, 11, 12 (monkey 272) occurred in response to peptides that had the glutamic acid substitution. However, the observed responses to peptides beginning with residue 3, 4, and 12 (monkey 184D), a well as residue 4 (monkey 272) occurred in response to peptides that had the asparagine substitution. Monkey 34 did not respond to any of the peptides that had the substitution at position twelve. All other responses shown were to the natural amino acid sequence of the CFA/I protein. Statistical significance was determined by comparing the cpm of quadruplicate wells cultured with the CPA/I peptides to the cpm of wells cultured with the CFA/I peptides to the cpm of wells cultured with a control peptide.

Analysis of decapeptides that supported proliferation of lymphocytes from CFA/I immune animals. Of the 39 different peptides that supported proliferative responses, thirty contained a serine residue, 19 contained a serine at either position 2, 3, or 4, and nine had a serine specifically at position 3. Some of the most robust responses were to the peptides that contained a serine residue at the third position. The amino acid sequence of four such peptides is shown in Table 13.

Detailed Description of Phase II of The Invention

Applicants have discovered efficacious pharmaceutical compositions wherein the relative amounts of antigen to the polymeric matrix are within the range: of 0.1 to 1.5% antigen (core loading) and 99.9 to 98.5% polymer, respectively. It is preferred that the relative ratio between the lactide and glycolide component of the poly(DL-lactide-co-glycolide) (DL-PLG) is within the range of 90:10 to 0:100. However, it is understood that effective core loads for certain antigens will be influenced by its microscopic form (i.e. bacteria, protozoa, viruses or fungi) and type of infection being prevented. From a biological perspective, the DL-PLG or glycolide monomer excipient are well suited for in vitro drug (antigen) release because they elicit a minimal inflamatory response, are biologically compatible, and degrades under physiologic conditions to products that are nontoxic and readily metabolized.

Surprisingly, applicants have discovered an extremely effective method for the protection against bacterial or viral infections in the tissue or a mammal (human or nonhuman animal) caused by enteropathogenic organisms comprising administering orally to said animal an immunogenic amount of a pharmaceutical composition consisting essentially of an antigen encapsulated within a biodegradable polymeric matrix. When the polymeric matrix is DL-PLG, the most preferred relative ratio between the lactide and glycolide component is within the range of 48:52 to 52:48. The bacterial infection can be caused by bacteria (including any derivative thereof) which include *Salmonella typhi, Shigella sonnel, Shigella flexneria, Shigella dysenteriae, Shigella boydii, Escheria coli, Vibro cholera*, yersinia, staphyloccus, clostridium and campylobacter. Representative viruses contemplated within the scope of this invention, susceptible to treatment with the above-described pharmaceutical compositions, are quite extensive. For purposes of illustration, a partial listing of these viruses (including any derivative thereof) include hepatitis A, hepatitis B, hepatitis C, rotaviruses, polio virus human immunodeficiency viruses (HIV), Herpes Simplex virus type 1 (cold sores), Herpes Simplex virus type 2 qierpeseirus genitalis), Varicella-zoster virus. (chicken pox, shingles), Epstein-Barr virus (infectious mononucleosis; glandular fcvu; and Burkittis lymphorna), and cytomegalo viruses.

A further representation description of the instant invention is as follows:

A. (1) To homogeneously disperse antigens of enteropathic organisms within the polymeric matrix of biocompatible and biodegradable microspheres, 0.1 nanogram (ng) to 12 microns in diameter, utilizing equal molar parts of polymerized lactide and glycolide (50:50 DL-PLG, i.e. 48:52 to 52:48 DL-PLG) such that the core load is within the range of about 0.1 to 1.5% by volume. The microspheres containing the dispered antigen can then be used to immunize the intestine to produce a humoral immune response composed of secretory antibody, serum antibody and a cellular immune response consisting of specific T-cells and B-cells. The immune response is directed against the dispered antigen and will give protective immunity against the pathogenic organism from which the antigen was derived.

(2) AF/RI pilus protein is an adherence factor that allows *E-coli* RDEC-1 to attach to rabbit intestinal brush borders thus promoting colonization resulting in diarrhea. AF/R1 pilus protein was homogeneously dispered within a polymeric matrix of biocompatible and biodegradable microspheres, 1–12 microns in diameter (FIG. 9 and photograph 1) using equal molar parts of polymerized lactide and glycolide (50:50 DL-LG) such that the core load was 0.62% by weight.

(3) The microsphere were found to contain immunogenic AF/R1 by immunizing both rabbit spleen FIG. 10) and Peyer's patch (FIG. 3) B-cells in vitro. The resultant cell supernatants contained specific IgM antibody which recognized the AF/R1. The antibody response was comparable to immunizing with AF/R1 alone.

(4) Microspheres containing 50 micrograms of AF/R1 were used to intraintestinally (intraduodenally) immunize rabbits on two separate occasions I week apart. One week later, compared to rabbits receiving AF/RI alone, the intestinal lymphoid tissue, Peyer's patches, demonstrated an enhanced cellular immune response to AF/R1 and to three AF/R1 linear peptide fragments 40–55, 79–94 and 108–123 by both lymphocyte transformation T-cells) (FIGS. 12 and 13) and antibody producing B-cells (FIGS. 14 and 15. Similarly enhanced B-cell responses were also detected in the spleen (FIGS. 16 and 17). An enhanced T-cell response was also detected in the mesenteric lymph node and the spleen to one AF/R1 peptide fragment, 40–55 (FIGS. 18 and 19). The cellular immune response at two weeks was too early for either a serum or secretory antibody response (See Results in Table 1); but indicates that a secretory antibody response will develop such that the rabbits so immunized could be protected upon challenge with the *E. coli* RDEC-1.

B. Microspheres do not have to be made up just prior to use as with liposomes. Also liposomes have not been effective in rabbits for intestinal immunization of lipopolynocharide antigens.

C. (1) Only a small amount of antigen is required (ugs) when dispersed within microspheres compared to larger amounts (mgms) when antigen is used alone for intestinal immunization.

(2). Antigen dispersed within microspheres can be used orally for intestinal immunization whereas antigen alone used orally even with gastric acid neutralization requires a large amount of antigen and may not be effective for intestinal immunization.

(3) Synthetic peptides with and without attached synthetic adjuvants representing peptide fragments of protein antigens can also be dispersed within microspheres for oral-intestinal immunization. Free peptides destroyed by digestive processes at the level of the stomach and intestine. Any surviving peptide would probably not be taken up by the Intestine and therefore be ineffective for intestinal immunization.

(4) Microspheres containing antigen maybe placed into gelatin-like capsules for oral administration and intestinal release for improved intestinal immunization.

(5) Microspheres promote antigen uptake from the intestine and the development of cellular immune (T-cell and B-Cell) responses to antigen components such as linear peptide fragments of protein antigens.

(6) The development-at intestinal T-cell responses to antigens dispersed within microspheres indicate that T-cell immunological memory will be established leading to long-lived intestinal immunity. The long-lived intestinal immunity (T-cell) is very difficult to establish by previous means of intestinal immunintian. Failure to establish long-lived intestinal immunity is a fundamental difficulty for intestinal immunization with non-viable antigens. Utinal :miLLtLt ith˜LLvi˜le antigens. Without intestinal long-lived immunity only a short lived secretory antibody response is established lasting a few weeks after which no significant immunological protection may remain.

D. (I) Oral intestinal immunization of rabbits against *E coli* RDEC-I infection using either whole killed organisms, pilus protein preparations or lipopolysaccharide preparations.

(2) Microspheres containing adherence pilus protein AF/R1 or its antigen peptides for oral intestinal immunization of rabbits against RDEC-1 infection.

(3) Oral-intestinal immunintion of humans against enterotoxigenic *E. coli* infection using either whole killed organisms, pilus protein preparations or lipopolysaccharide preparations.

(4) Microspheres containing adherence pilus proteins CFA/1, II, III and IV or their antigen peptides for oral intestinal immunization of against human enterotoxigenic *E. coli* infections.

(5) Oral-intestinal immunization of humans against other enteric pathogens as salmonella, shigella, camphlobacter, hepatitis-A virus, rota virus and polio virus.

(6) Oral-intestinal immunization of animals and humans for mucosal immunological protection at distal mucosal sites as the bronchial tree in lungs, genito-urinary tract and breast tissue.

(5) Oral-intestinal immunizaiton of humans against other enteric pathogens as salmonella, shigella, camphlobacter, hepatitis-A virus, rota virus and polio virus.

(6) Oral-intestinal immunizaiton of animals and humans for mucosal immunological protection at distal mucosal sites as the bronchial tree in llyngs, genito-urinary tract and breast tissue.

E. (1) The biocompatable, biodegradable co-polymer has a long history of being safe for use in humans since it is the same one used in resorbable suture materials.

(2) By using the microspheres, we are now able to immunize the intestine of animals and man with antigens not normally immunogenic for the intestinal mucosa because they are either destroyed in the intestine, unable to be taken up by the intestinal mucosa or only weakly immunogenic if taken up.

(3) Establishing long-lived immunological memory in the intestine is now possible because T-cells are immunized using microspheres.

(4) Antigens that can be dispersed into microspheres for intestinal immunization include the following: proteins, glycoproteins, synthetic peptides, carbohydrates, synthetic polysaccharides, lipids, glycolipids, lipopolysaccharides (LPS), synthetic lipopolysaccharides and with and without attached adjuvants such as synthetic muramyl dipeptide derivatives.

(5) The subsequent immune response can be directed to either systemic (spleen and serum antibody) or local (intestine, Peyer's patch) by the size of the microspheres used for the intestinal immunization. Microspheres 5–10 microns in diameter remain within macrophage cells at the level of the Peyer's patch in the intestine and lead to a local intestinal immune response. Microspheres I ng–5 microns in diameter leave the Peyer's patch contained within macrophages and migrate to the mesenteric lymph node and to the spleen resulting in a systemic (serum antibody) immune response.

(6) Local or systemic antibody mediated adverse reactions because of preexisting antibody especially cytophyllic or IgE antibody my be minimized or eliminated by using microspheres because of their being phagocytized by macrophages and the antigen is only available as being attached to the cell surface and not free. Only the, free antigen could become attached to specific IgE antibody bound to the surface of mast cells resulting in mast cell release of bioactive amines necessary for either local or systemic anaphylaxis.

(7) Immunization with microspheres containing antigen leads to primarily IgA and IgG antibody responses rather than an IgE antibody response, thus preventing subsequent adverse IgE antibody reactions upon reexposure to the antigen.

In addition to the above, the encapsulation of the following synthetic peptides are contemplated and considered to be well within the scope of this invention:

(1) AF/R1 40–55;
(2) AF/R1 79–94;
(3) AF/R1 108–123;
(4) AF/R1 1–13;
(5) AF/R1 pepscan 16AA;
(6) CFA/I 1–13; and
(7) CFA/I pepscan 16AA.
(8) Synthetic Peptides Containing CFA/I Pilus Protein T-cell Epitopes (Starting Sequence I given)

4(Asn-Ile-Thr-Val-Thr-Ala-Ser-Val-Asp-Pro), SEQ ID NO: 8

8(Thr-Ala-Ser-Val-Asp-Pro-Val-Ile-Asp-Leu), SEQ ID NO: 9

12(Asp-Pro-Val-Ile-Asp-Leu-Leu-Gln-Ala-Asp), SEQ ID NO: 10

15(Ile-Asp-Leu-Leu-Gln-Ala-Asp-Gly-Asn-Ala), SEQ ID NO: 11

20(Ala-Asp-Gly-Asn-Ala-Leu-Pro-Ser-Ala-Val), SEQ ID NO: 12

26(Pro-Ser-Ala-Val-Lys-Leu-Ala-Tyr-Ser-Pro) SEQ ID NO: 13

72(Leu-Asn-Ser-Thr-Val-Gln-Met-Pro-Ile-Ser), SEQ ID NO: 14

78(Met-Pro-Ile-Ser-Val-Ser-Trp-Gly-Gly-Gln), SEQ ID NO: 15

87(Gln-Val-Leu-Ser-Thr-Thr-Ala-Lys-Glu-Phe), SEQ ID NO: 16

126(Ala-Gly-Thr-Ala-Pro-Thr-Ala-Gly-Asn-Tyr), SEQ ID NO: 17 and

133(Gly-Asn-Tyr-Ser-Gly-Val-Val-Ser-Leu-Val), SEQ ID NO: 18, and mixtures thereof.

(9) Synthetic Peptides Containing CFA/1 Pilus Protein B-Cell (an Epitopes (Starting Sequence # given)

3(Lys-Asp-Ile-Thr-Val-Thr-Ala-Ser-Val), SEQ ID NO: 19

11(Val-Asp-Pro-Val-Ile-Asp-Leu-Leu-Gln-Ala-Asp), SEQ ID NO: 20

22(Gly-Asn-Ala-Leu-Pro-Ser-Ala-Val), SEQ. ID. NO. 31

32(Ala-Tyr-Ser-Pro-Ala-Ser-Lys-Thr-Phe-Lys-Thr-Phe-Glu-Ser-Tyr-Arg-Val), SEQ ID NO: 21

32(Ala-Tyr-Ser-Pro-Ala-Ser-Lys-Thr-Phe) SEQ ID NO: 22

38(Lys-Thr-Phe-Glu-Ser-Tyr-Arg-Val), SEQ ID NO: 23

66(Pro-Gln-Leu-Thr-Asp-Val-Leu-Asn-Ser), SEQ ID NO: 24

93(Ala-Lys-Glu-Phe-Glu-Ala-Ala-Ala), SEQ ID NO: 25

124(Lys-Thr-Ala-Gly-Thr-Ala-Pro-Thr), SEQ ID NO: 26

127(Gly-Thr-Ala-Pro-Thr-Ala-Gly-Asn-Tyr-Ser), SEQ ID NO: 27 and

124(Lys-Thr-Ala-Gly-Thr-Ala-Pro-Thr-Ala-Gly-Asn-Tyr-Ser), SEQ ID NO: 28 and mixtures thereof.

(10) synthetic peptides containing CFA/I pilus protein T-cell and B-Cell (antibody) epitopes (Starting Sequence # given)

3(Lys-Asn-Ile-Thr-Val-Thr-Ala-Ser-Val-Asp-Pro), SEQ ID NO: 34

8(Thr-Ala-Ser-Val-Asp-Pro-Val-Ile-Asp-Leu-Leu-Gln-Ala-Asp), SEQ ID NO: 35

11(Val-Asp-Pro-Val-Ile-Asp-Leu-Leu-Gln-Ala-Asp), SEQ ID NO: 36

20(Ala-Asp-Gly-Asn-Ala-Leu-Pro-Ser-Ala-Val), SEQ ID NO: 12

124(Lys-Thr-Ala-Gly-Thr-Ala-Pro-Thr-Ala-Gly-Asn-Tyr-Ser), SEQ ID NO: 28 and

126(Ala-Gly-Thr-Ala-Pro-Thr-Ala-Gly-Asn-Tyr-Ser), SEQ ID NO: 55, and mixtures thereof.

(11) synthetic peptides containing CFA/I pilus protein T-cell and B-cell (antibody) epitopes (Starting Sequence # given CFA/I pilus protein T-cell epitopes 4(Asn-Ile-Thr-Val-Thr-Ala-Ser-Val-Asp-Pro), SEQ ID NO: 8

8(Thr-Ala-Ser-Val-Asp-Pro-Val-Ile-Asp-Leu), SEQ ID NO: 9

2(Asp-Pro-Val-Ile-Asp-Leu-Leu-Gln-Ala-Asp), SEQ ID NO: 10

15(Ile-Asp-Leu-Leu-Gln-Ala-Asp-Gly-Asn-Ala), SEQ ID NO: 11

20(Ala-Asp-Gly-Asn-Ala-Leu-Pro-Ser-Ala-Val), SEQ ID NO: 12

26(Pro-Ser-Ala-Val-Lys-Leu-Ala-Tyr-Ser-Pro) SEQ ID NO: 13

72(Leu-Asn-Ser-Thr-Val-Gln-Met-Pro-Ile-Ser), SEQ ID NO: 14

78(Met-Pro-Ile-Ser-Val-Ser-Trp-Gly-Gly-Gln), SEQ ID NO: 15

87(Gln-Val-Leu-Ser-Thr-Thr-Ala-Lys-Glu-Phe), SEQ ID NO: 16

126(Ala-Gly-Thr-Ala-Pro-Thr-Ala-Gly-Asn-Tyr), SEQ ID NO: 17 and

133(Gly-Asn-Tyr-Ser-Gly-Val-Val-Ser-Leu-Val), SEQ ID NO: 18, and synthetic peptides containing CFA/I Pilus protein B-cell (antibody) epitopes (Starting Sequence # given) CFA/I pilus protein B-cell epitopes 3(Lys-Asp-Ile-Thr-Val-Thr-Ala-Ser-Val), SEQ ID NO: 19

11(Val-Asp-Pro-Val-Ile-Asp-Leu-Leu-Gln-Ala-Asp), SEQ ID NO: 20

22(Gly-Asn-Ala-Leu-Pro-Ser-Ala-Val), SEQ. ID. NO. 31

32(Ala-Tyr-Ser-Pro-Ala-Ser-Lys-Thr-Phe-Lys-Thr-Phe-Glu-Ser-Tyr-Arg-Val), SEQ ID NO: 21

32(Ala-Tyr-Ser-Pro-Ala-Ser-Lys-Thr-Phe) SEQ ID NO: 22

38(Lys-Thr-Phe-Glu-Ser-Tyr-Arg-Val), SEQ ID NO: 23

66(Pro-Gln-Leu-Thr-Asp-Val-Leu-Asn-Ser), SEQ ID NO: 24

93(Ala-Lys-Glu-Phe-Glu-Ala-Ala-Ala), SEQ ID NO: 25

124(Lys-Thr-Ala-Gly-Thr-Ala-Pro-Thr), SEQ ID NO: 26

127(Gly-Thr-Ala-Pro-Thr-Ala-Gly-Asn-Tyr-Ser), SEQ ID NO: 27 and

124(Lys-Thr-Ala-Gly-Thr-Ala-Pro-Thr-Ala-Gly-Asn-Tyr-Ser), SEQ ID NO: 28 and mixtures thereof.

(12) synthetic peptides containing CFA/I pilus protein T-cell and B-cell (antibody) epitopes (Starting Sequence # given)

3(Lys-Asp-Ile-Thr-Val-Thr-Ala-Ser-Val), SEQ ID NO: 19

11(Val-Asp-Pro-Val-Ile-Asp-Leu-Leu-Gln-Ala-Asp), SEQ ID NO: 20

22(Gly-Asn-Ala-Leu-Pro-Ser-Ala-Val), SEQ. ID. NO: 31

32(Ala-Tyr-Ser-Pro-Ala-Ser-Lys-Thr-Phe-Lys-Thr-Phe-Glu-Ser-Tyr-Arg-Val), SEQ ID NO: 21

32(Ala-Tyr-Ser-Pro-Ala-Ser-Lys-Thr-Phe)
38(Lys-Thr-Phe-Glu-Ser-Tyr-Arg-Val), SEQ ID NO: 23
66(Pro-Gln-Leu-Thr-Asp-Val-Leu-Asn-Ser), SEQ ID NO: 24
93(Ala-Lys-Glu-Phe-Glu-Ala-Ala-Ala), SEQ ID NO: 25
124(Lys-Thr-Ala-Gly-Thr-Ala-Pro-Thr), SEQ ID NO: 26
127(Gly-Thr-Ala-Pro-Thr-Ala-Gly-Asn-Tyr-Ser), SEQ ID NO: 27 and
124(Lys-Thr-Ala-Gly-Thr-Ala-Pro-Thr-Ala-Gly-Asn-Tyr-Ser), SEQ ID NO: 28 synthetic peptides containing CFA/I pilus protein T-cell and B-cell (antibody) epitopes (Starting Sequence # given) CFA/I pilus protein B-cell epitopes
3(Lys-Asn-Ile-Thr-Val-Thr-Ala-Ser-Val-Asp-Pro) SEQ ID NO: 34,
8(Thr-Ala-Ser-Val-Asp-Pro-Val-Ile-Asp-Leu-Leu-Gln-Ala-Asp) SEQ ID NO: 37,
11(Val-Asp-Pro-Val-Ile-Asp-Leu-Leu-Gln-Ala-Asp) SEQ ID NO: 36,
20(Ala-Asp-Gly-Asn-Ala-Leu-Pro-Ser-Ala-Val) SEQ ID NO: 12,
124(Lys-Thr-Ala-Gly-Thr-Ala-Pro-Thr-Ala-Gly-Asn-Tyr-Ser) SEQ ID NO: 28, and
126(Ala-Gly-Thr-Ala-Pro-Thr-Ala-Gly-Asn-Tyr-Ser) SEQ ID NO: 55, and mixtures thereof.

We contemplate that the peptides can be used in vaccine constructed for systemic administration.

EXAMPLES

The peptides in (8), (9), and (10) above can be made by classical solution phase synthesis, solid phase synthesis or recombinant DNA technology. These peptides can be incorporated in an oral vaccine to prevent infection by CFA/I bearing enteropathogenic E. coli. The herein offered examples provide methods for illustrating, without any implied limitation, the practice of this invention in the prevention of diseases caused by enteropathogenic organisms.

The profile of the representative experiments have been chosen to illustrate the effectiveness of the immunogenic polymeric matrix-antigen composites.

All temperatures not otherwise indicated are in degrees Celcius (deg C.) and parts or percentages are given by weight.

Materials and Methods

Animals. New Zealand White male rabbits were purchased from Hazelton Research Products (Denver, Pa.), and were shown to be free of current RDEC-1 infection by culture of rectal swabs. Animals were 1–2 kg of body weight and lacked agglutinating anti-AF/RI serum antibody at the time of the study.

Antigens. AF/RI pili from E. coli RDEC-1 (015:H:X non-typable) were purified by an ammonium sulfate precipitation method. The final preparation migrated as a single band on SDS-polyacrylamide gel electrophoresis and was shown to be greater than 95% pure by scanning with laser densitometry when stained with coomassie blue. Briefly, equal molar parts of DL-lactide and glycolide were polymerized and then dissolved to incorporate AF/RI into spherical particles. The microspheres contained 0.62% protein by weight and ranged in size from 1 to 12 micrometers. Both the microencapsulated and non-encapsulated AF/R1 were sterilized by gammairradiation (0.3 megarads) before use.

Synthetic peptides (16 amino acids each) were selected by theoretical criteria from the amino acid sequence of AF/R1 as deduced from the nucleotide sequence. Three sets of software were used for the selections. Software designed to predict B cell epitopes based on hydrophilicity, flexibility, and other criteria was developed by the University of Wisconsin Genetics Computer Group. Software designed to predict T cell epitopes was based on the Rothbard method and was written by Stephen Van Albert (The Walter Reed Army Institute of Research, Washington, D.C.). Software designed to predict T cell epitopes based on the Berzofsky method is published as the AMPHI program. The selected peptides were synthesized by using conventional Merrifield solid phase technology. AF/RI 40–55 (Thr-Asn-Ala-Gly-Thr-Asp-Ile-Gly-Ala-Asn-Lys-Ser-Phe-Thr-Leu-Lys) SEQ. ID. NO: 38 was various dilutions of antigen and were incubated at 37° C. in 5% $CO_2$. In other experiments, cultures were conducted in 24-well plates. In these experiments, $5 \times 10^6$ cells were cultured with or without antigen in a 2 ml volume. After 4 days, 100 microliters aliquots of cells were transferred to 96-well plates for pulsing and harvesting. Previous experiments have demonstrated that optimal concentrations of antigen range from 150 ng/ml to 15 micrograms/ml in the 96-well plate assay and 1.5 ng/ml to 150 ng/ml in the 24-well plate assay. These were the concentrations employed in the current study. All cultures were pulsed with 1 Ci [$^3$H]thymidine (25 Ci/mmol, Amersham, Arlington Heights, Ill.) on day 4 of culture and were harvested for scintillation counting 6 hours later.

Statistics. All cultures were conducted in replicates of four, and standard deviations of the counts per minute (cpm) generally range from 5–15% of the average cpm. In experiments where comparison of individual animals and groups of animals is desirable, data is shown as a stimulation index (SI) to facilitate the comparison. SI were calculated by dividing the mean of cultures with antigen by the mean of cultures without antigen (media control). Statistical significance (p value) was determined by comparing the maximum response for each antigen to the media control using the Student's t test.

Results

Lymphocyte proliferation in response to protein and peptide antigens of AF/R1. To determine if lymphoid tissues from AF/R1 immune animals respond in vitro to the antigens of AF/R1, the immunity in a rabbit with preexisting high levels of anti-AF/RI, serum IgG was boosted twice by injection of 50 micrograms of purified AF/R1 pili i.p. seven days apart. A week after the final boost, in vitro lymphocyte proliferation of spleen and MLN cells demonstrated a remarkable response to AF/RI pili. In response to the synthetic peptides, there was a small, but significant proliferation of the spleen cells to all the AF/RI peptides tested as compared to cell cultures without antigen. Cells from the spleen and Peyer's patches of non-immune animals failed to respond to either AF/RI or the synthetic peptides.

Microencapsulation of AF/R1 potentiates the mucosal cellular immune response. To evaluate the effect that microencapsulation of AF/R1 may have on the cellular mucosal immune response to that antigen, naive rabbits were primed twice with 50 micrograms of either microencapsulated or non-encapsulated AF/R1 by endoscopic intraduodenal inoculation seven days apart. All rabbits were monitored daily and showed no evidence of clinical illness or colonization by RDEC-I. One week following the last priming, the rabbits were sacrificed and lymphoid tissues were cultured in the presence of AF/R1 pili or peptide antigens. In rabbits which had received non-encapsulated AF/R1, Peyer's Patch cells demonstrated a low level but significant proliferation in vitro in response to AF/RI pili (FIG. 13) but not to any of the AF/RI synthetic peptides (FIGS. 14a–d). However, in rabbits which had received microencapsulated AF/R1, Peyer's Patch cells demonstrated a markedly enhanced response not only to AF/RI (FIG. 13) but now responded to the AF/RI synthetic peptides 40–55 and 79–94 (FIGS. 14a and 14b). In addition, one of two rabbits primed with microencapsulated AF/RI (rabbit 135) responded to AF/RI 108–123, but not AF/RI 40–47/79–86 (FIGS. 14c and 14d). In contrast, the other rabbit in the group (rabbit 134) responded to AF/RI 40–47/79–96, but not to AF/RI 109–123 (FIGS. 14d and 14c).

Response of MLN cells to the antigens of AF/RI. Studies have shown that cells undergoing blastogenesis in the MLN also tend to home into mucosal areas, but experiments requiring in vitro lymphocyte proliferation of rabbit MLN cells are difficult to conduct and to interpret due to non-specific high background cpm in the media controls. Our studies have shown that this problem can be avoided by conducting the proliferative studies in 24-well plates, and then moving aliquots of cells into 96-well plates for pulsing with [$^3$H]thymidine as described in materials and methods. This method of culture was employed for the remainder of the studies. The MLN cells of all rabbits demonstrated a significant proliferation in vitro in response to AF/RI pili regardless of whether they had been immunized with microencapsulated or non-encapsulated AF/RI. However, only the rabbits which had received microencapsulated AF/R1 were able to respond to the AF/RI synthetic peptide 40–55 (FIG. 19). The MLN cells of rabbit 134 also responded to AF/RI 79–94 ($p<0.0001$), AF/RI 108–123 ($P<0.0001$), and AF/RI 40–47/79–96 ($P=0.0004$); however, none of the other rabbits demonstrated a MLN response to those three peptides (data not shown).

Response of spleen cells to the antigens of AF/RI. Proliferative responses of spleen cells to AF/RI were very weak in all animals tested (data not shown). However, in results which paralleled the responses in M[LN cells, there was a significant response to AF/RI 40–55 in rabbits which had been primed with microencapsulated AF/RI (FIG. 20). There was no response to the other ARRI synthetic peptides by spleen cells in either group of animals. The weak response of spleen cells to AF/RI provides further evidence that these animals were naive to AF/RI before the study began, and indicates that the observed responses were not due to non-specific stimulative factors such lipopolysaccharide.

Summary

We have shown that there is an enhanced in vitro proliferative response to both protein and its peptide antigens by rabbit Peyer's patch cells following intraduodenal inoculation of antigen which had been homogeneously dispersed into the polymeric matrix of biodegradable, biocompatible microspheres. The immunopotentiating effect of encapsulating purified AF/RI pili as a mucosal delivery system may be explained by one or more of the following mechanisms: (a) Microencapsulation may help to protect the antigen from degradation by digestive enzymes in the intestinal lumen. (b) Microencapsulation has been found to effectively enhance the delivery of a high concentration of antigen specifically into the Peyer's patch. (c) Once inside the Peyer's patch, microencapsulation appears to facilitate the rapid phagocytosis of the antigen by macrophages, and the microspheres which are 5–10 micrometers become localized within the Peyer's patch. (d) Microencapsulation of the antigen may improve the efficiency of antigen presentation by decreasing the amount of enzymatic degradation that takes place inside the macrophage before the epitopes are protected by combining with Class 11 major histocompatibility complex (MHC) molecules. (e) The slow, controlled-release of antigen may produce a depot effect that mimics the retention of antigen by the follicular dendritic cell. (f) If the antigen of interest is soluble, microencapsulation changes the antigen into a particulate form which appears to assist in producing an IgA B cell response by shifting the cellular immune response towards the $T_H$ and thereby not encouraging a response by $T_S$. There is evidence that the GALT may be able to discriminate between microbial and non-microbial (food) antigens in part by the form of the antigen when it is first encountered, and thus bacterial antigen do not necessarily have special antigenic characteristics that make them different from food antigens, but they are antigenic because of the bacterial context in which they are presented. The particulate nature of microspheres may serve to mimic that context. It may be important to note that we also observed a significant response to AF/R1 in animals inoculated with non-encapsulated pili; thus, some of this antigen which was still in its native form was able to enter the Peyer's patch. This may be explained by the fact that AF/RI is known to mediate the attachment of RDEC-I to the Peyer's patch M-cell. If the antigen employed in this type of study was not able to attach to micrometer M-cells, one would expect to see an even greater difference in the responses of animals which had received microencapsulated versus non-encapsulated antigen.

The microspheres used in these experiments included a size range from 1 to 12 micrometers. The 1 to 5 micrometer particles have been shown to disseminate to the MLN and spleen within migrating macrophages; thus, the observed proliferative responses by cells from the MLN and spleen may reflect priming of MLN or splenic lymphocytes by antigen-presenting/accessory cells which have phagocytosed 1 to 5 micrometer antigen-laden microspheres in the Peyer's patch and then disseminated onto the MLN. Alternatively, these responses may be a result of the normal migration of antigen stimulated lymphocytes that occurs from the Peyer's patch to the MLN and on into the general circulation before homing to mucosal sites. Proliferative responses by MLN cells are of interest because it has been shown that cells undergoing blastogenesis in the MLN tend to migrate onto mucosal areas. However, studies involving in vitro lymphocyte proliferation of rabbit MLN cells can be very difficult to conduct and to interpret due to non-specific high background cpm in the media controls. By simultaneously conducting experiments using different protocols, we have found that this problem can be prevented by avoiding the use of fetal calf serum in the culture and by initially plating the cells in 24-well plates. Using this method, the blasting lymphocytes are easily transferred to a 96-well plate where they receive the [$^3$H]thymidine, while fibroblasts and other adherent cells remain behind and thus do not inflate the background cpm.

The proliferative response to the peptide antigens was of particular interest in these studies. The rabbits that received non-encapsulated AF/RI failed to respond to any of the peptides tested either at the level of the Peyer's patch, the MLN, or the spleen. In contrast, Peyer's patch cells from the animals that received microencapsulated AF/R1 responded to all the peptides tested with two exceptions: Rabbit 134 did not respond to AF/RI 108–123, and rabbit 135 did not respond to AF/R1 40–47/79–86. The reason for these non-responses is not clear, but it probably is not due to MHC restrictions as evidenced by the fact that rabbit 134 was able to add to AF/R1 108–123 at the level of the MLN. The non-responses may be due to varying kinetics of sensitized T cell migration in different rabbits, or they may reflect differences in the efficiency of antigen presentation by cells from different lymphoid tissues of these animals. Of all the 5 synthetic peptides tested, only AF/RI 40–55, (the one selected as a probable B cell epitope), was recognized by serum from an AF/R1 hyperimmune rabbit. In addition, this peptide was the only one that was uniformly recognized by Peyer's patch, MLN, and spleen cells from both rabbit. In addition, this peptide was the only one that was uniformly recognized by Peyer's patch, MLN, and spleen cells from both rabbits that were immunized with microencapsulated AF/R1. The recognition by anti-AF/R1 serum antibodies indicates that the amino acid sequence of this peptide includes an immunodominant B cell epitope. Thus AF/R1 40–55 may readily bind to antigen-specific B cells thereby leading to an efficient B cell presentation of this antigen to sensitized T cells. Even though AF/RI 40–55 was not selected as a probable T cell epitope by either the Rothbard or Berzofsky methods, the current study clearly indicates that this peptide can also stimulate a proliferative immune response. Although further studies are required to definitively show that the proliferating cells are indeed T cells, the responses observed in this study are most likely due to the blast transformation of cells from the lineage. Therefore, AF/RI 40–55 appears to contain a T cell epitope in addition to the immunodominant B cell epitope, and this area of the AF/R1 protein may thereby play an important role in the overall immune response and subsequent protection against RDEC-1.

The proliferative responses of spleen cells was low in all animals tested; however, we feel that this may be simply a matter of the kinetics of cellular migration. The rabbits in this study were sacrificed only two weeks after their first exposure to antigen. This relatively short time period may not have provided sufficient time for cells that were produced by Peyer's patch and MLN blasts to have migrated as far as the spleen in sufficient numbers.

An ideal mucosal vaccine preparadon would not only assist in the uptake and presentation of the immunogen of interst, but it would also be effective without requiring carrier molecules or adjuvants which may complicate vaccine production or delay regulatory approval. The incorporation of antigen into microspheres appears to provide an ideal mucosal delivery system for oral vaccine immunogens because the observed immunopotentiating effect is achieved without the need for carriers of adjuvants. This ability may prove to be of great value, particularly to enhance the delivery of oral synthetic peptide vaccines to the GALT.

TABLE 1

Linear B-Cell Epitopes of CFA/I in Monkeys

| Sequence Position | Individuals Responding | Consensus Site | |
|---|---|---|---|
| 1. 11–21 | 3 | VDPVIDLLQ | SEQ ID NO: 39 |
| 2. 93–101 | 2 | AKEFEAAA | SEQ ID NO: 40 |
| 3. 124–136 | 2 | GPAPT | SEQ ID NO: 41 |
| 4. 66–74 | 2 | PQLTDVLN | SEQ ID NO: 42 |
| 5. 22–29 | 2 | GNALPSAV | SEQ ID NO: 43 |
| 6. 32–40 | 1 | KTF* | |
| 7. 38–45 | 1 | | |
| 8. 3–11 | 1 | | |

*Overlap between epitope 6 and 7

TABLE 11

Prediction of T cell epitopes within the CFA/I molecule

| Predicted Amphipathic Segments | | Rothbard |
|---|---|---|
| 7 aa blocks | 11 aa blocks | Criteria |
| 22–25 | 8–11 | 16 |
| 34–39 | 32–44 | 30 |
| 40–46 | 51–71 | 38 |
| 50–53 | 86–92 | 44 |
| 56–62 | 102–108 | 57 |
| 64–71 | 130–131 | 61 |
| 104–108 | 135–137 | 70 |
| 131–137 | | 116 |

*The sequence numbers of the first amino acid of the predicted T cell epitopes are shown. Software designed to predict T cell epitopes based on the Berzofsky method was published as the AMPHI program. It predicts amphipathic amino acid segments by evaluating 7 or 11 residues as a block and assigning a score to the middle residue of that block. Software designed to predict T cell epitopes based on the Rothbard method was written by Stephen van Albert (The Walter Reed Army Institute of Research, Washington, D.C.).

Amino acid sequence of immunodominant T cell epitopes

| Residue Number | Amino Acids |
|---|---|
| 8–17 | Thr Ala Ser Val Asp Pro Val Ile Asp Leu SEQ ID NO: 9 |
| 40–49 | Phe Glu Ser Tyr Arg Val Met Thr Gln Val SEQ ID NO: 44 |
| 72–81 | Leu Asn Ser Thr Val Gln Met Pro Ile Ser SEQ ID NO: 14 |
| 134–144 | Asn Tyr Ser Gly Val Val Ser Leu Val Met SEQ ID NO: 45 |

*Of the 19 decepeptides that supported a significant proliferative response and contained a serine at either position 2, 3, or 4, nine has a serine specifically at position 3. Some of the most robust responses were to the peptides that contained a serine residue at the third position. The amino acid sequence of four such decapeptides which are believed to be immunodominant T cell epitopes is shown.

Demonstrative Evidence of Protective Immunity

RDEC-I is an eteroadherent diarrhea producing *E. coli* in rabbit. Its attachment to the mucosa is by the adhesin (AF/R1 pili). The adhesin is an excellent vaccine candidate. It may initiate a mucosal response but is susceptible to digestion in the gut. The incorporation of AF/RI into biocompatible, nondigestible microspheres enhanced mucosal cellular immune responses to RDEC-I. We have demonstrated that immunization with AF/RI Pili in microspheres protect rabbits against infection with RDEC-1.

Six rabbits received intra-duodenal immunization of AF/R1 microspheres (0.62% coreloading by weight) at 200 ug AF/R1 on day 0 then boosted with 100 ug AFRI in microspheres on days 7, 14, and 21 followed by RDEC-1 challenge with $10^5$ organisms one week latter than observed for I week and then sacrificed, unimmunized rabbits were challenged with $10^5$ RDEC-1 only and observed 1 week than sacrificed. Also, 2 rabbits were immunized only then were sacrificed 10 days latter. Only one of these animals had bile IgA antibodies to AF/RI but both had specific sensitized T cells which released IL-4 upon challenge in the spleen, Peyer's patch and illeal lamina propria. All nine immunized animals developed diarrhea and weight loss which was significant at the $p<0.001$ level compared to the immunized animals which displayed no diarrhea and no weight loss. The immunized animals colonized the intestinal tract with RDEC-I the same as the unimmunized animals. However, there was a striking difference regarding the adherence of RDEC-I to the mucosa. No adherence was seen in cecum in the immunized animals compared to 4/7 in the unimmunized side animals. This difference was significant to the p<0.01 level. The RDEC-I exposure although not producing disease in the immunized animals did effect a booster immunization as relected in the increase in and-AF/R1 antibody containing cells in the muscosa similar to the immunized rabbits. This study clearly demonstrated complete protection against RDEC-I infection and strongly indicates similar results should be expected with entertoxigenicity E. coli using the Colony Forming Antigens (CFA's) in microsphere vaccines.

Summary Statement of Protective Immunity Showings

RDEC-I infection of rabbits causes an enteroadherent E. coli diarrheal disease, and provides a model for the study of adherence-factor immunity. Pilus adhesions are vaccine candidates, but purified pili are subject to intestinal degradation. Previously we showed potentiation of the mucosal cellular immune response to the AF/RI pilus of RDEC-1 by incorporation into biodegradable polylactide-coglycolide microspheres (AF/RI-MS). We now present efficacy testing of this vaccine. Six rabbits were primed with 200 ug and boosted with 100 ug of AF/R1 -MS weekly x3, then challenged at week 5 with 101 CFU of RDEC-1 expressing AF/R1. Nine unvaccinated rabbits were also challenged. Two rabbits vaccinated with AF/R1 -MS were sacrificed at week 5, without challenge, for measurement of anti-AF/RI antibodies in bile (by ELISA) and anti-AF/R1 containing cells (ACC) in the intestinal lamina propria (by immunohistochemistry). Attachment of RDEC-I to intestinal epithelial cells was estimated (0.4+) by immunoperoxidase staining of histologic sections. Colonization of intestinal fluid was measured by culture of intestinal flushes. Results: Rabbits given AF/R1 -MS remained well and 4/6 gained weight after challenge, whereas 9/9 unvaccinated rabbits lost weight after challenge (mean weight change +10 vs −270 gms p<0.001), (see FIG. 35). The mean score of RDEC-1 attachment to the cecal epithelium was 0 in vaccinated, and 2+ in unvaccinated animals (see FIG. 36). RDEC-1 colonization (log CFU/gm) in cecal fluids was similar in both groups (mean 6.3 vs 7.3; p=0.09) (see FIG. 34). ACC were not seen in the lamina propria of vaccinated but unchallenged animals, but anti-pilus IgA antibody levels in bile were increased 1 S.D. over negative controls in 1 animal. Conclusions: Vaccination with AF/R1 -MS was safe and protected rabbits against RDEC-1 disease. Protection was associated with interference with RDEC-1 adherence to the mucosal surface, but lumenal colonization was not prevented.

More recently, applicants have focused on areas of this invention related to an immunostimulating composition for the burst-free, sustained, programmable release of active material(s) over a period from 1 to 100 days, which comprises encapsulating nicrospheres, which may contain a pharmaceutically-acceptable adjuvant, wherein said microspheres are comprised of (a) a blend of uncapped and end-capped biodegradable-biocompatible poly(DL-lactide-co-glycolide) as the bulk matrix, wherein the relative ratio between the amount of lactide and glycolide components are within the range of 90:10 to 40:60 and the poly(DL-lactide-co-glycolide) is a blend of uncapped and end-capped forms in ratios ranging from 100:0 to 1 to 99, and (b) active material such as an immunogenic substance comprising Colony Factor Antigen (CFA/II, hepatitis B surface antigen (HBsAg)), and/or a physiologically similar antigen that serves to elicit the production of antibodies in a mammal (human or nonhuman).

These areas of invention are referred to herein as Phase II and Phase III, respectively, and are itemized as follows:

178. An immunostimulating composition for the burst-free, sustained, programmable release of active material (s) over a period from 1 to 100 days, which comprises encapsulating-microspheres, which may contain a pharmaceutically-acceptable adjuvant, wherein said microspheres having a diameter between 1 nanogram (ng) to 10 microns (um) are comprised of (a) a blend of uncapped and end-capped biodegradable-biocompatible poly(DL-lactide-co-glycolide) as the bulk matrix, wherein the relative ratio between the amount of lactide and glycolide components are within the range of 90:10 to 40:60, and the poly(DL-lactide-co-glycolide) is a blend of uncapped and end-capped forms in ratios ranging from 100:0 to 1 to 99, and (b) active material such as an immunogenic substance comprising Colony Factor Antigen (CFA/II), hepatitis B surface antigen (HBsAg), and/or a physiologically similar antigen that serves to elicit the production of antibodies in a mammal (human or nonhuman).

179. An immunostimulating composition according to Item 178 wherein the amount of said immunogenic substance is within the range of 0.1 to 1.5% based on the volume of said bulk matrix.

180. An immunostimulating composition according to Item 179 wherein the relative ratio between the lactide and glycolide component is within the range of 48:52 to 52:48.

181. An immunostimulating composition according to Item 179 wherein the size of more than 50% of said microspheres is between 5 to 10 um in diameter by volume.

182. A vaccine comprising an immunostimulating composition of Item 181 and a sterile, pharmaceutically-acceptable carrier therefor.

183. A vaccine comprising an immunostimulating composition of Item 182 wherein said immunogenic substance is Colony Factor Antigen (CFA/II).

184. A vaccine comprising an immunostimulating composition of Item 182 wherein said immunogenic substance is hepatitis B surface antigen (HBsAg).

185. A method for the vaccination against bacterial infection comprising administering to a human, an antibactericidally effective amount of a composition of Item 183.

186. A method according to item 184 wherein the bacterial infection is caused by a bacteria selected from the group consisting essentially of Salmonella typhi, Shigella Sonnei, Shigella Flexneri, Shigella dysenteriae, Shigella boydii, Escheria coli, Vibri cholera, versinia, staphylococus, clostridium, and campylobacter.

187. A method for the vaccination against viral infection comprising administering to a human an antivirally effective amount of a composition of Item 184.

188. A diagnostic assay for bacterial infections comprising a composition of Item 181.

189. A method of preparing an immunotherapeutic agent against infections caused by a bacteria comprising the step of immunizing a plasma donor with a vaccine according to Item 183 such that a hyperimmune globulin is produced which contains antibodies directed against the bacteria.

190. A method preparing an immunotherapeutic agent against infections caused by a virus comprising the step of immunizing a plasma donor with a vaccine according to Item 184 such that hyperimmune globulin is produced which contains antibodies directed against the hepatitis B virus.

191. An immunotherapy method comprising the step of administering to a subject an immunostimulatory amount of hyperimmune globulin prepared according to Item 189.

192. An immunotherapy method comprising the step of administering to a subject an immunostimulatory amount of hyperimmune globulin prepared according to Item 190.

193. A method for the protection against infection of a mammal (human or nonhuman animal) by enteropathogenic organisms or hepatitis B virus comprising administering to said mammal an immunogenic amount of an immunostimulating composition of Item 180.

194. A method according to Item 193 wherein the immunostimulating composition is administered orally.

195. A method according to Item wherein the immunostimulating composition is administered parenterally.

Part II

In sum, the Colony Factor Antigen (CFA/II) from enterotoxigenic *E coli* (ETEC) prepared under GMP was successfully incorporated into biodegradable polymer microspheres (CFA/II BPM) and found to be safe and immunogenic when administered intra-duodenally to rabbits. CFA/II was incorporated into poly(DL-lactide-co-glycolide) (PLGA) microspheres which were administered by direct endoscopy into the duodenum. Following vaccination, Peyer's patch cells responded by lymphocyte proliferation to in vitro challenge with CFA/II indicating the CFA/II BPM to be immunogenic when administered intra-intestinally. Also, B cells secreting specific anti CFA/II antibodies were found in spleens following vaccination. No pathological changes were found following total necropsies of 10 rabbits vaccinated with CFA/II BPM. As a potency test, high serum IgG antibody titers to CFA/II were produced following intramuscular administration of CFA/II BPM to additional rabbits. The CFA/II BPM contained 63% between 5–10 um by volume particle size distribution; 1.17% protein content; 2.15% moisture; <0.01% acetonitrile; 1.6% heptane; 22 nonpathogenic bacteria and 3 fungi per I mgm protein dose; and passed the general safety test. We conclude that the CFA/II BPM oral vaccine is immunogenic and safe to begin a Phase I clinical safety study following IND approval.

Introduction

Enterotoxigenic *Escherichia coli* (ETEC) causes diarrheal disease with an estimated 650,000,000 cases annually in developing countries resulting in 500,000 deaths predominantly in the pediatric age groups. Currently there is no vaccine against ETEC induced diarrhea. The availability of an effective oral vaccine would be of great value to the people of South America, Africa and Asia as well as the millions of people who travel to these high risk areas and account for half of the annual cases.

The first step in pathogenesis is adherence to the small intestine epithelial cells by protein fimbrial (pilus) adhesins called colonization factor antigen (CFA). Three major CFAs have been recognized, CFA/I, CFA/II and CFA/IV. (25)

Ten human volunteers who were immunized orally twice weekly for 4 weeks with CFA/II developed a poor antibody response and did not show any significant protection when challenged with pathogenic ETEC (26). This disappointing response was attributed to adverse effects of gastric acid, even at neutral pH, of fimbrial proteins (27). When the vaccine was administered by inoculation directly into the duodenum, 4 of 5 immunized volunteers developed a significant rise in secretory IgA with CFA/II antibody (26).

D and L-lactic acid and glycolic acid, as homo- and copolymers, are biodegradable and permit slow and continued release of antigen with a resultant adjuvant activity. These polymers have been shown to be safe in a variety of applications in human beings and in animals (28–32). Delivery of antigens via microspheres composed of biodegradable, biocompatible lactide/glycolide polymers (29–32) may enhance the mucosal response be protecting the antigen from digestion and targeting them to lymphoid cells in Peyer's patches (29–32). McQueen et al. (33) have shown that *E coli* AF/RI pili in PLGA microspheres, introduced intra-duodenally in rabbits, protected them against diarrhea and weight loss when challenged with the parent strain rabbit diarrheagenic strain of *E coli* (RDEC-1). Only one vaccinated rabbit of six lost weight and only one had soft pelleted stool. In contrast, all control unvaccinated animals became ill, lost weight, and shad soft pellets or unformed mucoid stool. Significant lymphocyte proliferation to AF/R1 from Peyer's patches and ordinary IgA anti AF/R1 antibody levels were seen.

In order to improve the CFA/II vaccine it was incorporated into PLGA microspheres under GMP in order to protect it from digestion and target it to the intestinal lymphoid system. The CFA/II BPM vaccine has undergone pre-clinical evaluation and has been found to be safe and immunogenic.

Materials and Methods

Preparation of CFA/II Pilus Vaccine. Under Good Laboratory and Good Manufacturing Practices, *E. coli* strain M424C1-06; 816 producing CFA/II were cultured in 75–80 CFA agar plates (24×24 cm) for 24 hrs then harvested by scraping. The harvest was homogenized at slow speed for 30 minutes with over head drive unit and cup immersed in an ice bath. The homogenate was centrifuge at 4° C. at 16,500×g for 30 minutes. The supernatant saved and the pellet rehomogenized and centrifuged with the supernatants pooled. The supernatant pool was centrifuged at 50,000×g for 45 minutes. The supernatant treated with ammonium sulfate at 20% saturation, stirred 30 minutes at 4° C. than stored at 4° C. for 16 hrs then centrifuged at 19,700×g for 30 minutes. The supernatant saved and treated with ammonium sulfate at 45% saturation, stirred 30 minutes at 4° C., stored at 4° C. for 66–72 hrs, then centrifuged at 19,700×g for 45 minutes. The pellet was resuspended in about 100 mls of PBS containing 0.5% formalin and held at 22° for 18 hrs then dialyzed for 45–50 hrs against PBS at 4° C. using a total of 12 liters in 2 liter amounts. The dialysis was terminated when the PBS contained less then 0.03% formalin using Nessler's reagent and fuchsin sulfuose acid reagent. The final product contained 1 mgm protein/ml PBS, was sterile and passed the general safety test.

Preparation of Desalted CFA/II Vaccine. Two ml of the CFA/II vaccine were placed into a Centricon 30 tube and centrifuged at 1700 rpm at 4–6° C. (Beckman model GPR centrifuge equipped with GA-24 fixed angle rotor) until all the buffer solution passed through the filter (about 90–120 minutes). Sterile water was added to each tube to disperse the CFA/II retained on the filter. The desalted antigen dispersions from all tube were pooled and then divided into five equal parts by weight so as to contain 20 mg of the CFA/II each. The desalted antigen dispersion was stored at −10 to −20° C.

Freeze Drying of the Desalted CFA/II Dispersion. 80 mg of sucrose was added to each part of the CFA/H dispersion. The resulting mixture was flash-frozen using a dry ice-acetone bath (100–150 ml od acetone and 50–100 g of dry ice). The frozen solution was freeze dried overnight using Repp Sublimator 16 freeze dryer at vacuum of 1 micrometer of mercury and a shelf temperature not exceeding 37° C.

CFA/II Biodegradable Polymer Microspheres

Particle size distribution. About 1 mgm of microspheres were dispersed in 2 ml of 1% Polysorbate 60° (Ruger Chemical Co. Inc. Irvington, N.J.) in water in a 5 ml capacity glass vial by sonication. This dispersion was observed under a calibrated optical microscope with 43× magnification. Using a precalibrated eye-piece micrometer, the diameter of 150 randomly chosen microspheres, was determined and the microsphere size distribution was determined.

Scanning Electron Microscopic Analysis. Microspheres were sprinkled or the surface of 10 mm stub covered with a non-conductive adhesive (Sticky-Tab, Ernest F. Fullem, Inc., Lutham, N.Y.) Samples were coated with gold/palladium in an automatic sputter-coating oppararus (Samsputter-2A, Tonsimis Research Corporation). The samples were examined with a Hitachi S-450 scanning electron microscope operated at 15–20 KV.

Preparation of CFA/II Microspheres. Solvent extraction technique was used to encapsulate the freeze dried CFA/II into poly(lactide-co-glycolide) (Medisorb Technologies International, visocity 0.73 dl/g) microspheres in the 1–10 um size range to achieve theoretical antigen loading of 1% by weight. The freeze dried antigen-sugar & matrix was dispersed in an acetolnitrile solution of the polymer and then emulsified to achieve desired droplet size. Microspheres were solidified and recovered by using heptane as extracting solvent. The microsphere batches were pooled and vacuum dried to remove traces of solvent.

Protein Content. The CFA/II microspheres were dissolved in 0.9% SDS in 0.1N NaOH for 18 hr with stirring then neutralized to pH 7 and assayed. The micro bicichoninic acid (BCA) method was utilized with both lactic acid and glycolic acid blanks and compared to bovine serum albumin (BSA) standard and results expressed as percent by weight.

Moisture Content. One hundred and fifty mgm of CFA/II microspheres were dissolved in 3 ml of acetonitrile by sonication for 3 hours. One ml sample was injected into a Karl Ficher titrimeter and triter reading observed was recorded and acetonitrile blank was substracted to determined percent water content.

Acetonitrile and Heptane Residuals. Ten mgm of CFA II microspheres were dissolved in 1 ml DMF then analysed using gas chromatography and comparing peak heights to external standards of either acetonrile or heptane diluted in DMF with 10 mgm of blank microspheres. The results are expressed as percent by weight. Microbial load. One hundred mgm of CFAM microsphere(single dose) are suspended in 2 ml of sterile saline than poured into 2 blood agar plates (1 ml each). All colonies are counted and identified after 48 hours in culture at 37° C. and expressed as total number. Similar amount of microspheres is in 0.25 ml aliquots poured onto 4 different fungal culture plates (Sabhiragar, casein peptone agar with chloramphenicol-, brain heart infusion agar with chloramphenol and genimycin or chloramphenicol alone) and cultured at 30° for 5 weeks and the calories counted & identified and expressed as total number.

CFA/II Release From Microsphere Study. Thirty mgm samples in triplicate were placed in 2 ml conical upright microcentrifuge tubes containing 1 ml of PBS at pH 7.4. The tubes were capped and kept immerized in a water bath maintained at 37° C. with constant agitation. The samples were withdrawn at 1, 3, 6, 8, 15 and 22 hour time intervals by centrifuging the sample tubes for 5 minutes at the maximum speed of bench top centrifuge. The release medium was collected through a 5 um nylor screen for CFA/II protein analysis using the micro BCA method and comparing results to BSA standard and expressing results as percent cumulative release of CFA/II.

General Safety Test. Two doses of one hundred mgm CFA/II microspheres were suspended by sonication for 5 minutes in 3.1 mls of sterile vaccine dilutent consisting of injectable saline containing 0.5% Polysorbate 60° N.F., 0.03 ml were injected intraperitoneally into each of 2 mice and 3 mis were administered by gastric lavage to each of 2 guinea pigs. The animals were weighed both before and at 7 days following the vaccine administration. All animals were observed daily for any signs of toxicity.

Rabbits. 1.5–2 kilogram male specific pathogen free New Zealand white rabbits, obtained from closed colony maintained at the National Institute of Health, Bethesda, Md. They were selected for study if they did not have measurable serum antibodies at 1:2 dilution to CFA/II antigens by ELISA and were not colonized by *E. coli* as determined by culture of rectal swabs.

Intra-Muscular Immunization of Rabbits and ELISA. Two Rabbits were immunized with CFA/II microsphere vaccine at 25 ug protein in two different sites intra-muscularly on day 0. Sera were obtained from all animals before immunization on day 0 and days 7 and 14. The sera were tested by ELISA for IgG antibodies to CFA/II antigen and individual *coli* surface (CS) proteins CS3 and CS1. ELISA plates were coated with 3 ug/ml of either CFA/II antigen, CS3 or CS1 protein (150 ul/well) and incubated with 150 ul/well of PBS with 0.1% BSA for four hours at room temperature. The PBS with 0.1% BSA is washed out with PBS and 100 ul/well of different dilutions of each rabbit serum in triplicate was added to the plates. The dilutions ranged from undiluted to 1:1,000,00. The plates were incubated with the sera for 3 hours at 37° C. The sera were washed out with PBS and then horse radish peroxidase-conjugated goat anti-rabbit IgG was added to the plates at a 1:1000 dilution (100 ul/well). The plates were incubated for 1 hour at room temperature with the peroxidase conjugate. The conjugates were washed out of the plates with PBS and 100 ul/well of an ABTS substrate solution (Kikegaard and Perry Laboratories) was added to each well in the plates. The plates were read using the ELISA reader (Dynatech Laboratories MR 580) at a wave length of 405 nm after 15 minutes. The results are measured and expressed as antibody titers.

Intra-duodenal Vaccination of Rabbits. Rabbits (N=5) were vaccinated with CFA/II microspheres containing either 25 or 50 ug of protein suspended in 1 ml of PBS containing 0.5% Polysorbate $60^{10}$ on day 0 and 7 by sonication. The microspheres were injected through an Olympus BF type P10 bronchoscope into the duodenum of the rabbits following sedation with an intra muscular injection of ketamine HCl (50 mgm I.M.) (Ketaset, Fort Dodge Laboratories, Fort Dodge, Iowa) and Lylazine (10 mgm I.M.) (Rompom Malay Corporation, Shnanee, Kans.). The endoscope was advanced ready under direct vission into the stomach which was insufflated with a 50 ml bolus of room air via a catheter passed through the biospy channel. The catheter was advanced through the pylorus 34 cm into the duodemum and the microsphere suspension in 1 ml of PBS was injected, followed by a 9 ml flush of PBS and removal of the air bolus. The rabbits were sacrificed by chemical euthanasia at day 14.

Anti-CFA/II Stimulated Lymphocyted Transformation. The Peyer's Patchs were removed and cell suspension obtained by teasing and irrigation with a 20 guage needle and syringe. The cells were placed in 2 ml of media at a concentration of $2.5 \times 10^6$ cells/ml for each well of a 24 well plate. These cells were challenged separately with BSA and the CFA/11 antigen at doses of 500, 50 and 5 ng/ml in triplicate wells. The plates were incubated at 37° C. with 5% $CO_2$. On day 4 the cells were mixed while still inside the wells and 100 ul were transferred into each of 4 wells in a 96 well flat bottom microculture plate. Thus, the challenge at each antigen dose represented by 3 wells in the 24 well plate is now represented by 12 wells in the 96 well plate. After the cells have been transferred, each well is pulsed with 20 ul of 50 uCi/ml tritiated thymidine. These pulsed plates were incubated for 6 hrs then harvester with 96 Mach II Cell harvested Tourtec, Inc.). The lymphocyte proliferation was determined by the tritriated thymidine incoporation measured in kilo counts per minute (Kcpm) using the 1205 Beta Plate Liquid scintillation counter (LKB, Wallac, Inc.). The results are expressed as mean Kcpm±SD and compared to media controls.

Anti-CFA/11 Antibody Secreting B Cells. Spleen Cells were obtained from immunized rabbits on day 14 following intra-duodenal immunization with CFA/II microsphere vaccine. The cells were placed in 96 well round bottom microculture plate at a final concentration of $6 \times 10^5$ cells/well and incubated for 0, 1, 2, 3, 4 and 5 days at 37° C. with $5CO_2$. 96 well flat bottom microculture plates were coated with 3 ug/ml of CFA/II antigen overnight blocked with PBS with 0.05% Polysorbate $60^6$. On the harvest days, the cells were gently flushed out of the wells of the round bottom plates and transferred to the corresponding well in the antigen coated, 96 well flat bottom microculture plates to be tested for the presence of antibody secreting cells using ELISPOT technique. The plates were incubated with the cells overnight at 4° C. The cells were then washed out of the flat bottom plates with PBS, and 100 ul/well of horserudish-peroxidase conjugated, goat anti-rabbit total antibody (IgM, IgG, and IgA) at a 1:1000 dilution were added to the plates. The Plates were incubated for 1 hour at room temperature, at which time, the conjugate was washed out of the plates with PES. 0.1 mgm of agarose was dissolved in 10 ml of PBS by boiling. After the agar solution cooled but not hardened, 6 mgm of 4-chloro-naphthol, 2 mls of methanol and 30 ul of hydrogen peroxide were added to make the substrate solution. The solution was placed into the flat bottom plates (100 ul/well) and the plates were held at 4° C. overnight so the agar could harden. The number of browish spots per 15 wells (total of $9 \times 10^6$ spleen cells) was counted and represents the number of antibody secreting cells per $9 \times 10^6$ spleen cells.

Pathological Evaluation. Rabbits were euthanized by parenteral overdose of sodium pentobarbital and were subjected to complete necropsy. Sample of tissue including small and large intestine with gut associated lymphoid tissue, spleen, mesenteric and mediastinal lymph nodes, lung, trachea, liver and kidney were fixed by immersion in 10% neutral buffered formalin. Tissues were routinely processed for light microscopy and embedded in paraffin. Five micron thick sections were stained with hematoxylin and eosin.

Statistical Analysis. The paired student t-test was used to determine p values.

Results

Particle Size Distribution. The results of size frequency analysis of 150 randomly chosen microspheres are shown in (FIG. 37). The particle size distribution is plotted in % frequency against particle size in diameter (size) expressed in um. The average number frequency diameter is 4.6 um. The average volume frequency diameter is 4.6 um. The percent volume between diameters of 5–10 um is 63% and the percent volume less than 10 um diameter is 88%.

Scanning Electron Microscopy. The microspheres are seen in (FIG. 38) which is a scanning electron photomicrograph. Nearly all the microspheres are less than 10 um as compared to the 5 um bar. Also the surfaces of the microsphere are smooth and demonstrate lack of pores.

Protein Content. The protein loads of the individual batches are the following: K62A8, 1.16%±0.10 SD; K63A8, 1.023%±0.17 SD; K64A8, 1.232%±0.13 SD; and K65A8, 0.966%±0.128 SD. The mean average protein load is 1.16%±0.15 SD. The protein load of the CFA/II microsphere vaccine in the final dose vial is the following: Lot L74F2, 1.175%±0.17 SD.

Moisture Content. The CFA/II microsphere vaccine (Lot 74F2) percent water content was found using the Karl Fischer titrimeter method to be 2.154% using triplicate samples.

Acetonitrile and Heptane Residuals. The acetonitrile residuals of the 4 individual CFA/II microsphere batches are the following: K62A8, <0.1%; K62A8, <0.1%, K64A8, <0.1%; and K65A8, <0.1%. The acetonitrile residual of the CFA/II microsphere vaccine in the final dose vial is the following: Lot L74F2, 0.07±0.05%. The heptane residual of the 4 individual CFA/II microsphere batches are the following: K62A8, 1.9%; K63A8, 1.4%; K64A8, 1.6% and K65A8, 1.6%. Following pooling in heptane and subsequent drying, the heptane residual of the CFA/II microsphere vaccine in the final dose vial is the following: Lot L74F2, 1.6±0.1%.

Microbial load. One hundred milligrams (a single dose) of CFA/II microsphere vaccine (Lot L74F2) in the final dose vial was suspended in a 2 ml of sterile saline and 1 ml poured onto a blood agar culture plate x2.

Twenty two colonies grew after 48 hours of culture and 21 were identified as coagulase negative staphlycoccus and 1 as a micrococus species. All these bacteria are considered to be nonpathogenic to humans. An additional 100 mgms of CFAM microsphere vaccine (Lot L74F2) were suspended in 2 ml of sterile saline and 0.25 ml poured onto four different fungal culture agars and cultered for 5 weeks. Three fungal colonies grew and each was identified as A. glaucus.

CFA Release From Microsphere Study. Three thirty mgm samples were incubated each in 1 ml of PBS, pH 7.4 at 37° C. for 0, 1, 3, 6, 8, 15 and 22 hours. The superanates were removed and replaced at these times. The protein content was determined for each supernate sample and the results are seen in (FIG. #39). The results are plotted as percent release of CFA/II against time in hours. An average of 8% of CFA/II is released at one hour rising to 20% at 8 hours then a slower release to 25% at 22 hours.

General Safety Test. Two one hundred milligrams (a single dose) of CFA/II microsphere vaccine in the final dose vials were suspended in 3.1 mls of the sterile dilulent consisting of, 0.85 N saline prepared for injection plus Polysorbrate $60^8$ at 0.5%. Two Swiss mice (16.5 gm) were injected intraperitoneally with 0.03 mls and two Hartley guinea pigs (350 gm) were administered by gastric lavage 3.0 mls.

None of these animals displayed any signs of toxicity for 7 days. The mice gained and average of 2.3 gms and the guinea pigs gained and average, of 43 grams. The CFA/II microsphere vaccine therefore passed the general safety test.

Serum IgG Antibody Responses. Two rabbits were immunized in two separate sites intramuscularly with 25 ug of protein of CFA/II microsphere vaccine (Lot L74F2) in the final dose vial. Sera samples were obtained before and 7 and 14 days following immunization. The IgG antibody titers to CFA/II CS1 and CS3 protein were determined using ELISA and the results seen in (FIG. 32). The results are expressed as mean antibody titers against the different antigens at 0, 7 and 14 days. High antibody titers greater than 1000 were seen at 7 days to both CS1 and CS3 protein which rose to greater than 10,000 by day 14. The individuals titers to CFA/II are seen in (FIG. 33). Rabbit 109 developed an antibody titer of 1,000 by day 7 rising to 3,000 by day 14. Rabbit 108 had a log higher rise at day 7 and 2 log higher rise at day 14 being $3\times10^6$ at day 7 going to $1\times10^5$ at day 14.

Anti-CFA/II Stimulated Lymphocyte Transformation. Five rabbits were immunized intra-duodenally with CFA/II microspheres containing either 25 ug of protein (human dose equivalent) or 50 ug of protein on days 0 and 7 and then sacrificed on day 14. The Peyer's patch lymphocytes were challenged in vitro with CFA/II, antigen, BSA media and alone. The lymphocyte transformation was determined by tritriated thymidine incorporation. The results of the high dose immunization are seen in (FIG. 34). The results are expressed as Kcpm against antigen dose. No response to BSA or media control is seen in any of the five rabbits. All rabbits responded by lymphocyte transformation in a dose dependent manner to the CFA/II.

The highest dose responses were 3–10×'s the media control are highly significant with a p value of <0.002. The results of the 5 rabbits receiving the low dose immunization are seen in (FIG.35). Rabbit #80 gave no response probably due to poor Peyer's patch cell population which did not respond were to Conconavallin A mitogenic stimulation either. The remaining 4 rabbits gave positive responses with the high CFA/II dose response being 2–8× media control and highly significant with p values of <0.009. Again no response were seen to BSA compared to the media control.

Anti-CFA/II Antibody Secreting B-Cells Five rabbits immunized intraduodenally with CFA/11 microsphere containing 50 ug of CFA/H protein at days 0, 7 than sacrificed at day 14 were studied. The spleen cells were placed into microculture then ELISPOT forming B-Cells secreting specific anti CFA/II antibody determined at days 0, 1, 2, 3, 4 and 5. The results are seen in (FIG. 36) and expressed as # of antibody secret-ng cells per $9\times10^6$ spleen cell against culture days. Positive responses were seen in all 5 rabbits on days 2–5. Days of maximum responses occurred on day 3 for rabbits 65 and 66; day 4 for rabbit 85; and day 5 for rabbits 83 and 86. The responses are highly significant being 7–115 times higher than the 1–2 cells seen on all days in 4 control rabbit (67, 69, 72, 89) (FIG. 45). Here is a composite graph expressing the mean counts±ISD for all days of culture.

Pathological Evaluation. A consistent finding in the spleens of all rabbits both the 25 and 50 ug protein dose groups was minimal to mild diffuse lymphocytic hyperplasia the periarteriolar lymphatic sheaths (T cell dependent areas). Two of five rabbits of the 50 ug dose group (#83 and #86) also had mild lymph ocytic hyperplasia of splenic follicular (B cell dependent) areas.

The three rabbits in an untreated control group had histologically normal spleens.

Reactive hyperplasia of mesenteric lymph nodes was often seen in vaccinated rabbits. Two of five rabbits in the 25 ug dose equivalent group (#83 and #86) also had minimal to mild lymphocytic hyperplasia of cortical follicular (B cell dependent) areas. The mesenteric lymph nodes of the other vaccinated rabbits and of the untreated control rabbits were within normal limits. Incidental or background lesions found in one or more rabbits of all three group were acute minimal to mild pneumonia and foreign body microgranulomas of the cecal gut associated lymphoid tissue.

Discussion

McQueen et al (33) has found that the AF/R1 adhesin of rabbit diarrheagenic *Escherichia coli* (RDEC-1) incorporated into biodegradable microspheres could function as a safe and effective oral intestinal vaccine in the rabbit diarrhea model. The AF/R1 was incorporated into poly D,L-lactide-co-glycolide) microspheres and administered intraduodenally. Jarboe et al (34) reported that Peyer's patch cells obtained from rabbits immunized intra-duodenually with AF/R1 in microspheres responded with lymphocte proliferation upon in vitro challenge with AF/R1. This early response at 14 days gave a clear indication as to the immunogenicity of *E. coli* pili contained within the polymer microspheres.

In developing an effective oral vaccine against enterotoxigenic *E. coli*, CFA/II pili given as an oral vaccine was found to be ineffective. The CFA/II pilus proteins were found to be rapidly degraded when treated with 0.1 mHCl and pepsin conditions mimicking those contained in the stomach (27). The CFA/II was found to be immunogenic when given in high doses intraintestinally producing intestinal secretary IgA antibodies (26).

The CFA/II vaccine has now been incorporated into poly(D,L lactide-co-glycolide) microspheres under Good Manufacturing Practices and tested under Good Laboratory Practices. The microspheres, are spherical, smooth surfaced and without pores. The majority (63%) are between 5–10 um in diameter by volume. This size range has been suggested to promote localization within the Peyer's patch in mice and perhaps enhance local immunization (29–32). The protein content being 1.174% is close to 1% which was the goal of the vaccine formulation. One percent was chosen because 0.62% was the core loading of the AF/R1 microspheres which were effective. Also a small percentage perhaps 1–5% (35) is anticipated to be taken up from the intestine, a higher protein content would lead to considerable loss of protein.

The organic residuals are of course a concern. Heptane exposure would be 1.7 mgm per vaccine dose. This is compared to the occupational maximum allowable exposure of 1800 mgm/15 min. Therefore, the heptane contained with the CFA/II microsphere vaccine appears to be a safe level. The acetonitrile is very low –0.1 mgm per vaccine dose. The human oral TDLO is 570 mgm/Kg (any non lethal toxicity). Therefore, the acetonitrile contained with the CFA/II microsphere vaccine appears to be at a safe level. The CFA/II vaccine was produced under sterile conditions. However, the process of incorporation of the desalted CFA/II vaccine into the polymer.

The antibody secreting B-cells demonstrated in the rabbit spleen at 14 days is a clear indication that B-cells have been immunized. They may represent resident B-cells immunized in the spleen or B-cells immunized at the level of the Peyer's patches and are migrating through the spleen to return to the intestial mucosal lamina propria (1–3). The delay of several days before secreted antibody is detected suggests either manuration is required of the B-cells or that down regulation may be present initially and lost with time in culture.

Further evidence of immunization by the CFA/II microsphere vaccine given intra-duodenally is demonstrated by the lymphatic hyperplasia in the spleen seen to a greater extend in the rabbits receiving the lower dose 5/5 compared to 2/5 of the rabbits receiving the higher 50 ug protein dose. On the other hand, greater T-cell dependent area lymphoytic hyperplasia in the mesenteric lymph nodes were seen in rabbits receiving the higher 50 ug dose, 4/5 compared to 2/5. These changes are most likely due to the vaccine since similar changes were not seen in three untreated control rabbits. Also no abnormal pathological changes attributable to the vaccine were seen.

The CFA/II BPM vaccine has undergone pre-clinical evaluation and has been found safe and immunogenic. This vaccine is ready for clinical Part I safety testing following FDA's IND approval.

Part III

In sum, alum precipitation, vaccination regimen and controlled delivery by microencapsulation were studied to determine what criteria must be satisfied to provide a protective immune response to hepatitis B surface antigen (HBsAg) after a single injection of vaccine. In mouse studies, the 50% effective dose ($ED_{50}$) for the alum precipitated Heptavax B vaccine (Merck, Sharp and Dohme) was 3.8 ng when administered in a 3 injection regimen, but was 130 ng when one immunizing dose was used. Antigen release studies revealed that HBsAg is bound tightly to the alum, indicating that the antigen remains in situ until scavenged by phagocytic cells the $ED_{50}$ with a 3 dose regimen of aqueous HBsAg was 180 ng, a opposed to over 2000 ng for daily injections of low doses for 90 days and 240 ng for a regimen that employed initially high doses that decreased geometrically at3 day intervals over 90 days. The $ED_{50}$ was 220 ng for a single dose regimen of HBsAg microencapsulated in poly (DL-lactide-co-glycolide), in a form that was too large to be phagocytized and had an antigen release profile similar to that achieved with the geometrically decreasing regimen of doses. This indicates that single injection of microencapsulated immunogens can achieve similar effects in vivo to those achieved with multiple dose regimens. For HBsAg the effect to be achieved appears to be 3 pulses of particulate immunogens that can be scavenged by phagocytes.

Introduction

A major disadvantage of inactivated vaccines lies in their inability to confer lasting immunity. Due to rapid elimination from the body, multiple doses and boosters are usually required for continued protection[37]. Alum adjuvants, achieving their effects by mechanisms of antigen presentation and sustained antigen release[38], have been used successfully to increase the potency of several inactivated vaccines including those against tetanus, anthrax, and serum hepatitis[39,40]. Though useful, alum preparations are deficient in several aspects. Control over quantity and rate of antigen release is limited, often resulting in a continued requirement for immunization schedules consisting of multiple injections given over a period of several months to years. Alum adjuvants are also non-biodegradable and thus remain within the body, serving as a nidus for scar tissue formation[38] long after they have served their function.

Protracted, multiple immunization schedules are unacceptable during massive mobilization and deployment of troops. Changing global disease patterns and deployment of new biological warfare agents by enemy forces require flexibility in the number and types of vaccine antigen administered to soldiers departing for combat. Any immunization schedule requiring completion during engagement in non-linear combat would compromise this flexibility and place an unreasonable burden on our health care delivery system.

The main objective of this study was, therefore, to develop a biodegradable, controlled-release adjuvant system capable of eliminating the need for multistep vaccination schedules. This investigation was designed to: (1) determine in an animal model hepatitis B vaccine release rate characteristics desirable for single-step immunization, (2) incorporate those release rate characteristics into a one-step biodegradable poly(DL-lactide-co-glycolide) (DL-PLG) microencapsulated hepatitis B surface antigen (HBsAg) vaccine, and (3) conduct an in vivo trial comparing the effectiveness of this single-step vaccine against the conventional three-step hepatitis vaccine currently employed[41]. The results were intended to provide the foundation for further development of single step vaccines against hepatitis and other militarily significant diseases[42].

Materials and Methods

Vaccine potency assay. Due to its availability, compatibility with cage mates, and potential application to the study of hepatitis B vaccine[43], the female Walter Reed (ICR) stain mouse was used. A hepatitis B vaccine potency assay for comparing the six-month immunization schedule currently in use[41] with that of a single-step immunization by sustained antigen release was established according to the following protocol: Specimens for baseline antibody titers were collected from twenty mice by exsanguination. Immediately prior to exsanguination, all mice employed in this and other exsanguination procedures in these studies were anesthetized with a 0.1 mi injection of V-Pento. Groups of 12 mice were then immunized according to a schedule consisting of either 0.25 ug, 0.025 ug, 2.5 ng, 0.25 ng, 2.5 pg, or 0.25 pg Heptavax B vaccine (HBV) administered in 50 microliter volumes subcutaneously (s.c.) at the beginning and end of the first, and end of the second month of the protocol. Antibody responses to the vaccine were monitored immediately before the third injection and approximately one month after the third injection. Specimens for antibody determination were collected by exsanguination of seven anesthetized mice from each group and assayed along with the baseline samples by the Abbott Ausab radioimmunoassay. Percent seroconversion verses micrograms vaccine employed with calculated by the method of Reed and Muench[43]. These data were employed to establish a mouse vaccine potency assay calibrated to detect differences between Heptavax B and other forms of hepatitis b vaccine.

In vitro antigen release rate from Heptavax B vaccine. Antigen release from aluminum hydroxide adjuvant in HBV was measured by pumping 2 cc per hour of 1:20,000 thimerosal in saline at 4° C. across a 0.2 u pore diameter Acrodisc filter apparatus containing 20 ug of vaccine. The effluent, collected by a Gilford fraction collector, was assayed periodically over several weeks for protein by UV absorption at 280 nm on a Beckman model 25 double beam spectrophotometer, and for HBsAg by the Abbot Ausria 11 radioimmunoassay made quantitative by using HBsAg standards supplied by Merk, Sharp, and Dohme. Accuracy of the HBsAg standards were verified by Biuret protein determination and by UV absorbance at 215 nm and 225 nm[44]. Nonspecific antigen retention on the Acrodisc filter was assessed by measuring percent recovery of a known quantity of HBsAg. Spontaneous degradation of vaccine antigen was monitored by comparing daily rations of antigen to total protein detected in the effluent.

Evaluation of HBsAg stability. These studies were designed to characterize the stability of the aqueous antigen to the various physical conditions employed in the microencapsulation process. Conditions tested included lyophilization with reconstitution in distilled water, cyclohexane, methylene chloride, chloroform, methyl alcohol, acetone, iso-octane, hexane, acetone, pentane, or heptane; irradiation while lyophilized; and, exposure to elevated temperatures. Samples exposed to organic solvents were first lyophilized, reconstituted with the test solvent, evaporated to dryness under nitrogen at room temperature and reconstituted with distilled water. Test samples were compared against untreated controls by assaying serial dilutions of each with the Abbot Ausria H procedure and comparing the plots of counts per minute verse dilution.

Assessment of the effect of antigen release rate on vaccine potency. Three regimens simulating patterns of free HBsAg release that could be achieved by microencapsulation were contrasted with the three monthly dose regimen of Heptavax B for immunizing mice. To do so, 24 ICR mice were divided into groups and vaccinated as indicated below. Seven mice from each subgroup were exsanguinated at the end of the second and third months of the experiment. The sera were separated and assayed for specific antibody response to HBsAg by Abbot Ausab procedure.

HV regimen a: 14 mice/treatment receiving 3 s.c. injections of 250, 25, 2.5 or 0.25 ng doses of HBV a month apart.

HBsAg regimen a: 14 mice/treatment receiving 3 s.c. injections of 250, 25, 2.5 or 0.25 ng doses of aqueous HBsAg a month apart.

HBsAg regimen b: 14 mice/treatment receiving total doses of 750, 7.5, 7.5 or 0.75 ng of aqueous HBsAg over 3 months by s.c. injections of $ZX_Y$ ng at 3 day intervals, where Z is the total dose, y is the injection number, and X is the fraction indicated on the graph in FIG. 1 minus the fraction for the previous injection.

HBsAg regimen c: 14 mice/treatment receiving daily s.c. injections of 8.33, 0.833, 0.0833 or 0.00833 ng of aqueous HBsAg for 3 months.

Microencapsulation in DL:PLG. Microencapsulated immunogens were fabricated by Southern Research Institute, Birmingham, Ala. DL-PLG polymers were synthesized from the cyclic diesters, DL lactide and glycolide, by using a ring-opening melt polymerization catalyzed by tetraphenyl tin[45]. The resulting polymer was dissolved i methylene chloride, filtered free of insoluble contaminants and precipitated in methanol. Lactide-co-glycolide mole ratio of the product was determined by nuclear magnetic resonance spectroscopy. Encapsulation of HBsAg in DL:PLG polymer was achieved by an organic phase separation process[46]. Microcapsules of the desired size (approximately 100 micron diameter in these studies) were isolated from each batch by wet sieving with hexane through standard mesh stainless steel sieves and then dried for 24 hours in a vacuum chamber maintained at room temperature.

In vitro analysis of encapsulated antigens. Integrity of encapsulated antigen was assessed by comparing the antigen to total protein ratios present in microcapsule hydrolysates with those obtained from suspensions of pure unencapsulated antigen. Centrifuge tubes containing 1 ug of either microencapsulated or pure vaccine antigen in 1 ml saline were incubated at 4° C. with shaking. Samples were collected at weekly intervals by interrupting the incubation, sedimenting the contents of the tubes by centrifugation and withdrawing the supernates. Sediments were resuspended in 200 microliters of saline and supernates were assayed for HBsAg by the Abbott Ausria H radioimmunoassay. The HBsAg standard described earlier in this report was used as the calibrator. Antigen destruction due to the encapsulation procedure was monitored by a comparison between the antigen assayed from the hydrolysate and from the untreated antigen control.

Assessment of the potency of DL:PLG microencapsulated HBsAg for immunizing ICR mice when used alone and in combination with Heptavax B vaccine. HBsAg loaded microcapsules that had been fabricated by Southern Research Institute to release the majority of their HBsAg load within 40 to 50 days were serially diluted in 10-fold steps by mixing the dry, loaded capsules with blank placebo capsules of similar size and composition. The resulting stock and diluted microcapsule preparations were placed onto lyophilizer when not in use in order to assure minimum spontaneous degradation prior to injection. On the day of injection, a predetermined weight of microcapsules or placebo-diluted microcapsules was added to each syringe. Immediately prior to injection either one or two ml of injection vehicle (2 wt % carboxymethyl cellulose and 1 wt & Tween 240 in water, Southern Research Institute) were drawn into the microcapsule-loaded syringes, mixed and injected. All mice were vaccinated s.c. as indicated below:

Group 1: 14 mice/treatment receiving 25, 25, 2.5, 0.25 or 0.925 ng, HBV.

Group 2: 14 mice/treatment receiving 1000, 250, 25 or 2.5 ng aqueous HBsAg with Bovine Serum Albumin (BSA).

Group 3: 7 mice receiving 1600 ng microencapsulated HBsAg (HBsAg) plus 0.25 ng HBV and 14 mice/treatment receiving 160, 16, 1.6 or 0.16 ng HBsAg plus 0.25 ng HBV.

Group 4: 7 mice receiving 1600 ng HBsAg plus 2.5 ng HBV and 14 mice/treatment receiving 160, 16, 1.6 or 0.16 ng HBsAg plus 2.5 ng HBV.

Group 5.: 7 mice receiving 1600 ng HBsAg plus 25 ng HBV and 14 mice/treatment receiving 160, 16, 1.6 or 0.16 ng HBsAg plus 25 ng NBV.

Group 6: 7 mice receiving 2500 ng HBsAg and 14 mice-treatment receiving 250, 25, 2.5 or 0.25 ng HBsAg. Fifty-three days after receiving the above injections, the mice were anesthetized with an 0.1 cc injection of V-Pento and exsanguinated. Blood samples were allowed clot and the sera were separated by centrifugation. The serum samples were assayed for antibody to HBsAg by the Abbott Ausab procedure.

Results

Heptavax B vaccine potency. As can be seen from Table 12, the total dose of vaccine which produced seroconversion in 50% of the mice.

TABLE 12

| | Potency of Heptavax B vaccine in ICR mice. | | | | | | | |
|---|---|---|---|---|---|---|---|---|
| No. | ng Heptavax B per Injection | | | | | | | $ED3D_{50}$ |
| Inj. | 250 | 25 | 2.5 | .25 | .025 | .0025 | .00025 | ng |
| 2 | 5/5 | 4/4 | 3/6 | 2/6 | 0/5 | 1/4 | 0/4 | 1.7 |
| 3 | 6/6 | 6/6 | 4/6 | 1/6 | 0/6 | 1/6 | 1/6 | 2.0 |

TABLE 12-continued

Potency of Heptavax B vaccine in ICR mice.

| No. | ng Heptavax B per Injection | | | | | | | ED3D$_{50}$ |
|---|---|---|---|---|---|---|---|---|
| Inj. | 250 | 25 | 2.5 | .25 | .025 | .0025 | .00025 | ng |

*Number positive seroconversions per number vaccinated. The vaccinated mice (ED50) for HBV was approximately 2 ng, whether the vaccine was given in 2 or 3 injections.

In vitro antigen release rate from HBV. HBsAg release from the 20 ug of Heptavax was not detected in any of the 21 fractions of saline collected from the Acrodisc polycarbonate filter over a 30 day period. The lower limit of detection for the Abbott Auria II assay employed was approximately 4.8 ng/ml. The Acrodisc filter used in the antigen release study was back-washed with 10 mls normal saline. Quantitation of the HBsAg present within this back-wash eluent revealed the presence of the original 40 ug of Heptavax vaccine which had been loaded into the filter at the start of the experiment. This is the concentration which one would expect to obtain if there had been no deterioration of the original 40 ug/ml HBsAg loaded onto the filter, none of the antigen eluted from the alum adjuvant, and none of the vaccine had adsorbed onto or passed through the filter.

Evaluation of antigen stability. Considerable effort was expended in assessing the effects of physical conditions on the antigenicity of HBsAg to insure that the conditions used for microencapsulation would not cause serious degradation of the immunogen. Since microencapsulation must be performed on dried materials which are suspended in organic solvents, the HBsAg, which was provided as a solution, had to be lyophilized. Initial attempts at lyophilizing HBsAg in normal saline resulted in a total loss of detectable antigen within samples. Dilution of the HBsAg sample 1:10 in distilled water prior to freezing resulted in reservation of nearly 100% of the antigen detectable in the original sample. Studies of antigen stability at elevated temperature revealed that HBsAg may be heated to 50° C. for up to one hour without appreciable loss of antigen. The studies involving exposure of lyophilized antigen to organic solvents indicated that iso-cane and hexane had minimal effects on antigenicity, but that 95% to 100% of antigenicity was lost upon exposure to either methylene chloride, chloroform, cyclohexane, or methyl alcohol. Moderate antigen loss occurred in the presence of acetone, pentane and heptane. As a result of these studies, hexane was chosen as the solvent for microencapsulation.

Assessment of the effect of antigen release rate on vaccine potency. The results (Table 13) indicated that immunogen formation (i.e., the alum adjuvant of Heptavax B) had far more

TABLE 13

Effect of immunogen formulation and vaccination regimen on potency for immunizing ICR mice.

| Immunogen Formulation | Regiment | ng Total Dose HBsAg | | | | ED$_{50}$ |
|---|---|---|---|---|---|---|
| | | 750 | 75 | 7.5 | .75 | ng |
| Heptavax B | a | 7/7* | 6/6 | 5/7 | 1/7 | 3.8 |
| Aqu. HBsAg | a | 4/6 | 3/7 | 0/7 | 0/6 | 180 |
| Aqu. HBsAg | b | 6/7 | 0/7 | 1/7 | 0/7 | 240 |
| Aqu. HBsAg | c | 1/7 | 0/7 | 0/7 | 0/7 | >2000 |

*Number positive seroconversions per number vaccinated.
a 3 injections of 1/3 total dose a month apart.
b Injections administered every three days for 90 days in decreasing dosages according to a logarithmic progression.
c Injections of 1/90 total dose daily for 90 days.

effect on potency than did the vaccination regimen, and that pulsing with large doses of immunogen was more effective than continuous administration of small doses.

HBsAg release from DL:PLG microcapsules. The microcapsules employed in this study were designed to disintegrate within three weeks after hydration. It is evident from the release curve (FIG. 10), that they performed as designed, releasing approximately 17% of their total load in an initial pulse and approximately 7% of the remaining available HBsAg over the first three weeks.

Assessment of the potency of DL:PLG microencapsulated HBsAg for immunizing ICR mice when used alone and in combination with Heptavax B vaccine. The results (Table 14) indicate that the microencapsulated HBsAg had approximately the same immunogenicity as did the Heptavax B. Neither immunogens were sufficiently potent to effect with a singly injection seroconversion rates similar to those achieved after three injections of Heptavax B (Table 12).

Only the Immunogen

TABLE 14

Potencies of Heptavax B and microencapsulated HBsAg by single injection S.C. when administered alone and in combination to immunize ICR mice.

| Immunogen | Var. Dose ng Const | | ng Variable Dose | | | | Var. Dose Tot. Dose | |
|---|---|---|---|---|---|---|---|---|
| | Dose | mHBsAg | 2500 | 250 | 25 | 2.5 | .25 ED$_{50}$ ng | ED$_{50}$ ng |
| Heptavax B | 0 | 13/14* | 8/14 | 4/14 | 0/13 | | 130 | 130 |
| Heptavax B | 0.16 | | 11/13 | 4/14 | 1/14 | | 1.7 | 1.8 |
| Heptavax B | 1.6 | | 10/13 | 1/14 | 0/13 | | 100 | 100 |
| Heptavax B | 16 | | 3/14 | 1/14 | 1/14 | | >470 | >490 |
| Heptavax B | 160 | | 3/12 | 2/11 | 1/12 | | >370 | >530 |
| Heptavax B | 1600 | | 7/7 | 7/7 | 7/7 | | <0.8 | 1600 |
| Mic. HBsAg | 0 | 3/6 | 6/15 | 1/13 | 2/10 | 2/14 | 220 | 220 |

*Number positive seroconversions per number vaccinated.

combination of Heptavax B with 0.16 ng mHGsAg provided this level of seroconversion. At the $ED_{50}$ endpoint, the 0.16 ng dose of mHGsAg is approximately 10% of the total dose. Similarly, a small amount of Heptavax B appeared to enhance the immunogenicity of the microencapsulated immunogen, although the combination was clearly less immunogenic when the two formulations were present at equivalent concentrations.

Discussion

The potential advantage of microcapsules lies in their ability to be programmed during fabrication into forms that have quite difference release profiles, including slow and steady release, multiple bursts of antigen over a period of time, or combinations of release forms. Sieving allows choice of microcapsule size, and the ability of DL-PLG to sequester antigen from the host's immune system until release occurs enhances control over exposure of the recipient's immune system to antigen over a sustained period of time. These characteristics provided the impetus for these studies as they indicate potential for achieving the effects of a multiple injection regimen by controlling release in vivo after a single injection.

The results of these studies are important for gaining an understanding of the fundamental differences between the manner in which alum and microcapsules interact with the immune system. The antigen release studies showed that alum firmly bound the antigen on its surface, whereas the microcapsules sequestered the antigen load within the interstices of an immunologically inertpolymer. Release of antigen from microcapsules was spontaneous and gradual while antigen release from alum was probably enzymatically mediated within, host macrophages. Alum thus performed at least two useful functions as an adjuvant: by bearing its entire load of antigen upon its surface, it provided a large single exposure of antigen to the host; and, by being readily phagocytized by host macrophages, it served as a means of targeting the antigen to the immune system.

In order for microcapsules to be efficacious as a vaccine delivery system, a means of incorporating the two properties common to alum adjuvant must be devised. These properties, which where discussed above, are targeting antigen to the immune system and delivering the antigen load in a single concentrated pulse at its target. A gradual, sustained release of free antigen, as was achieved with the 100 micron microcapsules used in these studies, could be expected to elicit an immune response similar to that seen with either regimen b or regimen c (Table 13), where multiple injections of small doses were employed. In fact, as shown in Table 11, the microencapsulated immunogen elicited a response similar to that achieved with regimen b. This is probably due to the fact that the microcapsules release approximately 10% of their antigenic load immediately after injection.

Microcapsules with extended release patterns tend to be large (>10 microns in diameter) and thus fail to be readily phagocytized. In order for the larger microcapsules with prolonged antigen release characteristics to be efficacious, the antigen eventually released from those microcapsules would have be in a form which targeted and concentrated it within the recipient's immune system. This might be effectively achieved by microencapsulation of antigen-coated alum or by microencapsulating cluster of smaller (<10 microns) microcapsules.

Microcapsules under 10 microns in diameter tend to be readily phagocytized and also tend to undergo rapid spontaneous degradation due to their high surface to volume ratio. These smaller microcapsules would be well suited for eliciting a primary response if their pulse of antigen release could be programmed to occur after phagocytosis.

Literature Cited

1. Mooi, F. R., and F. K. de Graaf. 1985. Molecular biology of fimbriae of enterotoxigenic *Escherichia coli*. Curr. Top. Microbiol. Immunol. 118:119–138.
2. Evans, D. G., D. J. Jr. Evans, S. Clegg, and J. A. Pauley. 1979. Purification and characterization of the CFA/I antigen of enterotoxigenic *Escherichia coli*. Infect. Immun. 25:738–748.
3. Evans, D. G., D. J. Jr. Evans, W. S. Tjoa, and H. L. Dupont. 1978. Detection and characterization of colonization factor enterotoxigenic *Escherichia coli* isolated from adults with diarrhea. Infect. Immun. 19:727–736.
4. McConnell, M. M., H. Chart, and B. Rowe. 1989. Antigenic homology within human enterotoxigenic *Escherichia coli* fimbrial colonization factor antigens—CFA/I, *coli*-surface—associated antigens (Cs)1, Cs2, Cs4, and Cs17, FEMS Micro. Lett. 61:105–108.
5. Cheney, C. P., and E. C. Boedeker. 1983. Adherence of an enterotoxigenic *Escherichia coli* strain, serotype 078:H11, to purified human intestinal brush borders. Infect Immun. 39:1280–1284.
6. Miles, M. A., G. R. Wallace, and J. L. Clarke. 1989. Multiple peptide synthesis (Pepscan method) for the systematic analysis of B- and T-cell epitopes: application to parasite proteins. Parasitology Today 5:397–400.
7. Rothbard, I. B., and W. R. Taylor. 1988. A sequence pattern common to T cell epitopes. EMBO. J. 7:93–100.
8. DeLisi, C., and I. A. Berzofsky. 1985. T-cell antigenic sites tend to be amphipathic structures. Proc. Natl. Acad. Sci, USA 82:7048–7052.
9. Margalit, H., I. L. Spounge, J. L. Cornette, K. B. Cease, C. DeLisi, and J. A. Berzofsky. 1987. Prediction of Immunodominant helper T cell antigenic sites from the primary sequence. J. Immunol. 138:2213–2229.
10. Berzofsky, J. A. 1988. Structural basis of antigen recognition by T lymphocytes. J. Clin. Invest. 82:1811–1817.
11. Stille, C. J., L. J. Thomas, V. E. Reyes, and R. E. Humphreys. 1987. Hydrophobic strip-of-helix algorithm for selection of T cell-presented peptides. Mol. Immunol. 24:1021–1027.
12. Lozzi, L., M. Rusdci, M. Cord, M. G. Cusi, P. E. Valensin, L. Bracci, A. Santucci, P. Soldani, A. Spreafico, and P. Neri. 1990. Structure of rebella El glycoprotein epitopes established by multiple peptide synthesis. Arch. Virol. 110:271–276.
13. Troalen, F., A. Razafindratsita, A. Puisieux, T. Voeltzel, C. Bohuon, D. Bellet, and J. M. Bidart. 1990. Structural probing of human lutropin using antibodies raised against synthetic peptides constructed by classical and multiple antigen peptide system approaches. Mol. Immunol. 27:363–368.
14. Tan, X. H., M. Ratnam, S. M. Huang, P. L. Smith, and J. H. Freisheim. 1990. Mapping the antigenic epitopes of human dihydrofolate reductase by systematic synthesis of peptides on solid supports. J. Biol. Chem. 265:8022–8026.
15. Van der Zee, R., W. Van Eden, R. H. Meloen, A. Noordzij, and J. Van Embden. 1989. Efficient mapping and characterization of a T cell epitope by the simultaneous synthesis of multiple peptides. Eur. 1. Immunol. 19:43–47.
16. Geysen, H. M., R. H. Meloen, and S. J. Barteling. 1984. Use of peptide synthesis to probe viral antigens for epitopes to a solution of a single amino acid. Proc. Natl. Acad. Sci. USA 81:3998–4002.

17. Isaacson, R. E. 1977. K99 surface antigen of *Escherichia coli*: Purification and partial characterization. Infect. Immun. 15:272–279.

18. Klemm, P. 1982. Primary structure of the CFAI fimbrial protein from human enterotoxigenic *Escherichia coli* strains. Eur. 124:339–348.

19. Devereux, I., P. Haeberli, and O. Smithies. 1984. A comprehensive set of sequence analysis programs for the VAX. Nucleic Acids Res. 12:387–395.

20. Hall, R. H., D. J. Maneval, J. H. Collins, J. L. Theibert and M. M. Levine. (1989). Purification and analysis of colonization factor antigen I, *coli* surface antigen 1, and *coli* surface antigen 3 fimbriae from enterotoxigenic *Escherichia coli*. J. Bacteriol. 171, 6372–4.

21. Kadalainen, T. K., D. G. Evans, M. So and C. H. Lee. (1989). Molecular cloning and nucleotide sequence of the colonization factor antigen I gene of *Escherichia coli*. Infect Immun. 57, 1126–30.

22. Kraitzen, H. D., J. Wiltfang, M. Karas, V. Neuhoff, and N. Hilschmann. (1989) Gas-phase sequencing after electroblotting on polyvinylidene difluoride membranes assigns correct molecular weights to myoglobin molecular weight markers. Anal. Biochem. 183, 1–8.

23. Matsiduria, P. 1987. Sequence from picomole quantities of proteins electroblotted onto polyvinylidene diflouride membranes. J. Biol. Chem. 262, 10035–10038.

24. Schagger, H. and G. von Jagow. 1987. Tricine-sodium dodecyl sulfate-polyacrylamide gel electrophoresis for the separation of proteins in the range of 1 to 100 kKa. Anal. Biochem. 166, 368–379.

25. Kaper, J. B. and Levine, M. M. Progress towards a vaccine against enterotoxigenic *Escherichia coli* vaccine 1988, 6, 197–199.

26. Levine M., Morris, I. G. Losnosky, G., Boedeker E., and Rowe, B. Fimbriae (pili) adhesins as vaccine. In: *Molecular Biology of Microbial Pathogenicity, Protein-Cargohydrate Interactions in Biological System.* (Ed. Lark, D., et. al.) Academic Press, London, 1986, pp. 143–145.

27. Schmidt, M., Kelly E. P., Tseng, L.-Y., and Boedeker, E. C. Towards and oral *E. coli* pilus vaccine for traveler's diarrhea: suspentibility of purified colonization factor antigen/II to proteolytic digestion. Gastroenterology 1985, 88, A1575.

28. Wise, D. L. Fellmann, T. D. Sanderson, J. E. and Wentworth, R. R. glycolic acid polymer. In: *Drug carriers in biology and medicine* (Ed. Gregoriades, G.) Academic Press, London, 1979: 237–270.

29. Eldridge, J. H. Gilley, R. M. Staas, J. K. Moldoveanu, Z., Meulbroek, J. A. and Tice, T. r. Biodegradable microspheres: vaccine delivery system for oral immunization. Curr. Top. Microbiol, Immunol. 1989, 146, 59–66.

30. Eldride, J. H. Hammond, C. I. Meubroek, J. A. Staas, J. K., Gilley, R. M., and Tice, T. R. Controlled vaccine release in the gut-associated lymphoid tissue. I. Orally administered biodegradable microsphere target the Peyer's patches. J. Controlled release 2989, 11, 205.

31. Eldridge., J. H. Staas, J. K., Meubrock J.A., McGhee, J. R., Tice, T. R. and Gilley, R. M. Biodegradable microsphere as a vaccine delivery system. Mol. Immunol, 1991, 28, 287–294.

32. Moldoveanu, Z. Staas, J. K. Gilley, R. M., Ray, R., Compans, R. W. Eldridge, J. H. Tice, T. R., and Mestecky, J. Immune Response to influenae virus in orall and systemically immunized. Curr. Top. Microbiol. Immunol. 1989, 146, 91–99.

33. McQueen, C. E., Boedeker, E. C., Reid, R. H., Jarboe, D., Wolf, M., Le, M., and Brown, W. R. Pili in microsphere protect rabbits for diarrhea induced by *E. coli* strain RDEC-1. Vaccine (in press).

34. Jarboe, D., Reid, R., McQueen, C., and Boedeker, E., In vitro lymphocyte proliferation after sensitization or rabbit lymphoid tissue with encapsulated or non-encapsulated AF/R1 pilus adhesin of *E. coli* strain RDED-1. Abstracts of the Annual Meeting of the American Society of Microbiology, May 1990, 1990, 121.

35. Ebel, J. P. A method for quantifying particle absorption from the small intestine of the mouse. Pharm. Res. 1990, 7, 848–851.

36. Levine, M. M., Ristaino, P., Morley, G., Smyth, C., Knutton, S., Boedeker, E., Black, R., Young, C., Clements, M. L. Cheney, C., and Patnaik, R. *Coli* surface antigens 1 and 3 colonization: Morphology, purification, and immune responses in humans. Infect, Immun, 1984, 44, 409–420.

37. Spector, S. A. 1981. Immunoprophylaxis and immunotherapy, pp 770–793. In: Medical Microbiology and Infectious Diseases. A. I. Braude (editor), W.B. Sauders Company, Philadelphia.

38. Jolles, P., and A. Parif. 1973. Aluminum adjuvants in human sensitization. pp 106–108: In: Chemical basis if adjuvants, molecular biology, biochemistry, and biophysics, Volume 13. A. K. Kleinzeller, G. F. Springer, and H. G. Willman (editors), Springer-Verlag, Berlin.

39. Brackman, P. S., and F. R. Fekety, 1958. Industrial anthrax. Ann. NY Acad. Sci. 70:575–584.

40. Maupas, P., A. Goudeau, P. Coursaget, J. Drucker, and P. Bagros. 1978. Hepatitis B vaccine efficacy in high risk settings, a two year study. Intervirol. 10: 196–208.

41. Merck, Sharp, and Dohme. Heptavax-B Vaccine package insert. 6. Dean, J. A., and A. J. Ognibene. 1982. Hepatitis. pp 419–441. In: Medical Department, United States Army Internal Medicine in vietnam, Vol 11: General Medicine and Infectious Disease. A. J. Ognibene, O. Brrett (editors), Office of the Surgeon General and Center of Military History, Wash. D.C.

42. Gerety, R. J. 1979. Hews from the National Institute of Allergy and Infectious Diseases: Summary of an international workshop on Hepatitis B vaccines. J. Infect. Dis. 140:642–648.

43. Reed, J. J., Muench, H. 1939. A simple method of estimating fifty percent endpoints. Amer. 1. Hyg. 27:493–497.

44. Bradford, M. 1976. A rapid an sensitive method for the quantitation of microgram quantities of protein utilizing the pracile of protein-dye binding. Anal. Biochem. 72:248–254.

45. Jackanicy, T. M, et al. 1983. Polylactc acid as a biodegradable carrier for contraceptive steroids. Contraception 8:227–234.

11. Kulkarni, R. K., E. G. Morre, A. F. Hegyeli, and F. Leonard. 1971. Biodegradable poly(lactic acid) polymers. J. Biomed. Mater. Res. 5:169–181.

46. Cutright D. E., P. Bienvenido, J. Beasley, III, W. T. Larson, and W. R. Posey. 1974. Degrdation rates of polymers and copolymers and polyglycolic acids. Oral Surg. 37:142–152.

Phase III

This phase of the invention relates to providing novel biocompatable and biodegradable microspheres for burst-free programmable sustained release of biologically active agents, inclusive of polypeptides, over a period of up to 100 days in an aqueous physiological environment. Potentially release period is capable of being further modulated beyond 100 days to about 365 days by careful selection of a ratio of uncapped and end-capped biodegradable-biocompatable copolymer and molecular weights.

Several publications and patents are available for sustained release of active agents from biodegradable polymers, particularly, poly(lactide/glycolides) (PLGA). Prior usages of PLGA for controlled release of polypeptides have involved the use of molar ratios of lactide/glycolide (L/G) of 75/25 to 100/0 for molecular weights >20,000. Further prior art preparations of PLGA utilized fillers or additives in the inner aqueous layer to improve the stability and encapsulation efficiency and/or to increase the viscosity of the aqueous layer, thereby modulating polymer hydrolysis and the biologically active agent or polypeptide release.

In addition, the prior art use of PLGA copolymers were end-capped, in that the terminal carboxyl end groups were blocked. In these end-capped co-polymers, the microcapsule preparations exhibited a low to moderate burst release of—10–40% of the entrapped polypeptide in the first 24 hours after placement in an aqueous physiological environment. In part, these characteristics are due to the use of fillers in the inner aqueous phase. Further, a 1-month release of polypeptide is known with the use of a 75/25 co-polymer of PLGA of Mw—20,000.

Investigations in controlled release research has been proceeding especially to obtain a 1 to 2 month delivery system for biologically active agents or polypeptides using poly(lactide/glycolide) polymers. However, most of these systems have one or more of the following problems: Poor encapsulation efficency and large 'burst release' followed by an intermediate 'no release' or 'lag phase' until the polymer degrades. In general, release from these polymers occur over a period from about 4 weeks to about several months. In addition, in order to achieve this release a 50/50 copolymer of MW™ 30,000 or a 75/25 copolymer of Mw™ 10,000 are employed which often results in residual polymer remaining at the site of administration long after the release of active core.

This invention provides biocompatable and biodegradable microspheres that have been designed for novel, burst free, programmable sustained release of biologically active agents, including polypeptides over a period of up to 100 days in an aqueous physiological environment.

Unlike currently available release systems, which rely on the use of fillers/additives such as gelatin, albumin, dextran, pectin, polyvinyl pyrrolidone, polyethylene glycol, sugars, etc., and are still prone to low encapsulation efficiencies and "burst effects", this invention achieves high encapsulation and "burst-free" release without the use of any additive. In this invention, burst-free, programmable sustained release is achieved through the use of a unique blend of the 'uncapped' and end-capped forms of poly(lactide/glycolide) polymer in the molecular weight range of 2,000 to 60,000 daltons.

In general, microspheres described in this invention are produced by a unique emulsification technique wherein an inner water-in-oil (w/o) emulsion is stabilized by dispersing in a solvent-saturated aqueous phase containing an emulsion stabilizer. A ternary w/o/w emulsion is then formed by emulsifying the above w/o emulsions in an external pre-cooled aqueous phase containing an o/w emulsifier. Essentially, the inner w/o emulsion is comprised of an aqueous layer containing from—2 to about 20% (w/w) of the active agent to be entrapped and an oil layer containing poly(lactide/glycolide) copolymer in concentrations ranging from—5 to about—50% (w/w oil phase). The copolymer includes molecular weight ranging from 2,000 to about 60,000 daltons, with molar composition of lactide/glycolide from 90/10 to 40/60 and a blend of its uncapped and end-capped forms in a ratio of 100/0 to 1/99. Very high encapsulation efficiencies of about 80 to 100% are achieved depending on polymer molecular weight and structural form.

Programmable release of active core over variable durations between 1–100 days is achieved by a judicious selection of process parameters such as polymer concentration, peptide concentration and the aqueous/oil phase ratio.

This invention is particularly suitable for high encapsulation efficiencies and burst-free, continuous programmable release of polypeptides of molecular weights ranging from 1,000 to about 250,000 daltons, and also other biologically active agents over a period of 1–100 days. A uniqueness of the invention is that when using a 100/0 blend of the uncapped and capped polymer, the final phase of active core release is concurrent with the complete solubilization of the polymer to innocuous components, such as lactic and glycolic acids. This is a significant advantage over the currently available 30 day—release systems wherein a major regulatory concern is about toxicity of residual polymer at the site of administration, long after release of the active core.

This invention relates to the design of biocompatable and biodegradable microspheres for novel, programmable sustained release of biologically active agents, including polypeptides over a period of up to 100 days in an aqueous physiological environment with little or no burst release.

The microcapsules described in this invention are suitable for administration via several routes such as parenteral (intramuscular, subcutaneous), oral, topical, nasal, rectal and vaginal routes.

Unlike currently available release systems which rely on the use of fillers/additives such as gelatin, albumin, dextran, pectin, polyvinyl pyrrolidone, polyethylene glycol, sugars, etc. and are still prone to low encapsulation efficiencey and "burst effects", this invention achieves high encapsulation efficiency and 'burst-free' release without the use of any additive. In this invention, burst-free, programmable sustained release is achieved through the use of a unique blend of the 'uncapped' and end-capped forms of poly(lactide/glycolide) polymer.

The 'uncapped' form refers to "poly(lactide/glycolide) with free carboxyl end groups" which renders the polymer more hydrophilic compared to the routinely used end-capped form. Currently used 'end-capped' polymer hydrates between 4–12 weeks depending on the molecular weight, resulting in an intermediate 'no release' or a 'lag phase'. The uncapped polymer hydrates typically between 5 to 60 days depending on the molecular weight, thus releasing its core continuously without a lag phase. A careful blend of the two forms and appropriate molecular weights and L/G. ratios, results in a continuous release between 1 to 100 days. In addition, release within this time is programmable by a judicious selection of process parameters such as polymer concentration, peptide concentration and the aqueous/oil phase ratio.

The copolymer in this invention includes molecular weight ranging from 2,000 to 60,000 daltons, a lactide/glycolide ratio of 90/10 to 40/60 and a ratio of the uncapped/capped forms in the ratio of 100/0 to 1/99. The molecular weight of the polypeptide may be in the range of 1000 to 250,000 daltons while that of other biologically active agents may range from 100 to 100,000 daltons.

Microcapsules described in this invention are prepared by a unique aqueous emulsification technique which has been developed for use with the uncapped polymer to provide superior sphere morphology, sphere integrity and narrow size distribution. This is accomplished by first preparing an inner water-in-oil (w/o) by mixing the solutions of polymer in an organic solvent such as methylene chloride and the biologically active agent in water. This is followed by stabilization of the w/o emulsion in a solvent-saturated aqueous solution containing an o/w emulsifier such as polyvinyl alcohol. A ternary emulsion is then formed by emulsifying the w/o emulsion in an external aqueous phase containing the same emulsifier as above at concentrations ranging from 0.25–1% w/v. Microcapsules are hardened upon solvent removal by evaporation, rinsed to remove residual emulsifier and lyophilized. Low temperature is used both at the time of primary emulsification (w/o emulsion formation) and during the formation of the final w/o/w emulsion to achieve stable emulsion and superior sphere characteristics.

In the context of the invention, a biologically active agent is any water-soluble hormone drugs, antibiotics, antitumor agents, antiinflammatory agents, antipyretics, analgesics, antitussives, expectorants, sedatives, muscle relaxants, antiepileptics, antiulcer agents, antidepressants, antiallergic drugs, cardiotonics, antiarrhythmic drugs, vasodilators, antihypertensives, diuretics, anticoagulants, antinarcotics, etc. and the agents listed in the summary of the invention section herein.

More precisely, applicants have discovered a pharmaceutical composition and process with the following itemized features:

1. A controlled release microcapsule pharmaceutical formulation which may contain a pharmaceutically-acceptable adjuvant, for burst-free, sustained, programmable release of a biologically active agent over a duration from 1–100 days, comprising an active agent encapsulated within a biodegradable poly(lactide/glycolide) having a lactide/glycolide ratio of uncapped/end-capped 90/10 to 40/60 and the uncapped/end-capped form of poly(lactide/glycolide) in the ratio of 100/0 to 1/99.
2. The pharmaceutical formulation of item 1, wherein the biodegradable poly(lactide/glycolide) has a ratio of uncapped and end-capped forms, in ratios ranging from 100/0 to 1/99.
3. The microcapsules of items 1 or 2 wherein the copolymer (lactide to glycolide L/G) ratio for uncapped and end-capped polymer is 52/48 to 48/52.
4. The microcapsules of items 1 or 2 wherein the copolymer L/G ratio for uncapped and end-capped polymer is 90/10 to 40/60.
5. The microcapsules of items 1 or 2 or 3 or 4 wherein the molecular weight of the copolymer is between 2,000–60,000 daltons.
6. The microcapsules of items 1 or 2 or 3 or 4 or 5 wherein the biologically active agent is a peptide or polypeptide.
7. The microcapsules of item 6, wherein said polypeptide is histatin consisting of 12 amino acids and having a molecular weight of 1563.
8. The microcapsules of items 1 or 2 or 3 or 4 or 5 or 6 characterized by the capacity to completely release histatin in an aqueous physiological environment from 1–35 days with a 100/0 blend of uncapped and end-capped poly(lactide/glycolide) having a L/G ratio of 48/52 to 52/48, and a molecular weight—15,000.
9. The microcapsules of items 1 or 2 or 3 or 4 or 5 or 6 characterized by the capacity to completely release histatin in an aqueous physiological environment from 18–40 days with a 100/0 blend of uncapped and end-capped poly(lactide/glycolide) having a L/G ratio of 48/52 to 52/48 and a molecular weight range of 28,000–40,000.
10. The microcapsules of items 1 or 2 or 3 or 4 or 5 or 6 characterized by the capacity to release up to 90% of the histatin in an aqueous physiological environment from 28–70 days with a 0/100 blend of uncapped and end-capped poly(lactide/glycolide) having a L/G ratio of 48/52 to 52/48 and a molecular weight range of 10,000–40,000 daltons.
11. The microcapsules of items 1 or 2 or 3 or 4 or 5 or 6 characterized by the capacity to release up to 80% of histatin in an aqueous physiological environment from 56–100 days with a 0/100 blend of uncapped and end-capped poly(lactide/glycolide) having a L/G ratio of 75/25 and a molecular weight of—15,000 daltons.
12. The microcapsules of items 7 or 8 or 9 or 10 or 11 having analogs of histatin with chain lengths of from 11–24 amino acids of molecular weights from 1,500–3,000 daltons and characterized by the following structures:
  1. DSHAKRHHGYKRKFHEKHHSHRGY, SEQ. ID. NO: 1
  2. KRHHGYKRKFHEKHHSHRGYR,SEQ. ID. NO: 2
  3. KRHHGYKRKFHEKHHSHR, SEQ. ID. NO: 3
  4. RKFHEKHHSHRGYR, SEQ. ID. NO: 4
  5. AKRHHGYKRKFH, SEQ. ID. NO: 5
  6. *AKRHHGYKRKFH, SEQ. ID. NO: 5
  7. KRHHGYKRKF, SEQ. ID. NO: 6
  * D-amino acid
13. The microcapsules of items 1 or 2 or 3 or 4 or 5 wherein the biologically active agent is a polypeptide Luteinizing hormone releasing hormone (LHRH) that is a decapeptide of molecular weight 1182 in its acetate form, and having the structure:
  p-EHWSYGLRPG SEQ. ID. NO: 7.
14. The microcapsule of items 6 or 7 or 8 or 9 or 10 or 11 or 12 or 13 having a molecular weight of from 1,000 to 250,000 daltons.
15. The microcapsules of items 6 or 7 or 8 or 9 or 10 or 11 or 12 or 13 or 14 wherein release profiles of variable rates and durations are achieved by blending uncapped and capped microspheres as a cocktail in variable amounts.
16. The microcapsules of items 6 or 7 or 8 or 9 or 10 or 11 or 12 or 13 or 14 wherein release of profiles of variable rates and duration are achieved by blending uncapped and capped polymer in different ratios within the same microspheres.
17. The microcapsules of items 6 or 7 or 8 or 9 or 10 or 11 or 12 or 13 or 14 or 15 or 16 wherein the entrapped polypeptide is any of the vaccine agents against enterotoxigenic *E. coli* (ETEC) such as CFA/I, CFA/II, CS1, CS3, CS6 and, CS17 and other ETEC-related enterotoxins.
18. The microcapsules of items 6 or 7 or 8 or 9 or 10 or 11 or 12 or 13 or 14 or 15 or 16 or 17 wherein the entrapped polypeptide consists of peptide antigens of molecular weight range of about 800–5000 daltons for immunization against enterotoxigenic *E. coli* (ETEC).
19. The microcapsules of items 1 or 2 or 3 or 4 or 5 wherein said biologically active agents are selected from the group consisting of water-soluble hormone drugs, antibiotics, antitumor agents, anti inflammatory agents, antipyretics, analgesics, antitussives, expectorants, sedatives, muscle relaxants, antiepileptics, antiulcer agents, antidepressants, antiallergic drugs, cardiotonics, antiarrhythmic drugs, vasodilators, antihypertensives, diuretics, anticoagulants, and antinarcotics, in the molecular weight range of 100–100,000 daltons.
20. The microcapsules of items 1 or 2 or 3 or 4 or 5 or 6 or 7 or 8 wherein said biodegradable poly(lactide/glycolide) is in an oil phase, and is present in about 1–50% (w/w).
21. The microcapsules of items 1 or 2 or 3 or 4 or 5 or 6 or 8 or 9 or 10 or 11 or 12 or 13 or 14 or 15 or 16 or 17 wherein concentration of the active agent is in the range of 0.1 to about 60% (w/w).
22. The microcapsules of items 1 or 2 or 3 or 4 or 5 or 6 or 8 or 9 or 10 or 11 or 12 or 13 or 14 or 15 or 16 or 17 wherein a ratio of the inner aqueous to oil phases is about 1/4 to 1/40 (v/v).
23. A process for preparing controlled release microcapsule formulations characterized by burst-free, sustained, programmable release of biologically active agents comprising: Dissolving biodegradable poly(lactide/glycolide), in uncapped form in methylene chloride, and dissolving a biologically active agent or active core in water; adding the aqueous layer to the polymer solution and emulsifying to provide an inner water-in-oil (w/o) emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring the resulting water-in-oil-in-water (w/o/w) emulsion for sufficient time to remove said solvent, and rinsing hardened microcapsules with water and lyophilizing said hardened microcapsules.
24. A process for preparing controlled release microcapsule formulations characterized by burst-free, sustained, programmable release of biologically active agents comprising:
dissolving biodegradable poly(lactide/glycolide) in end-capped form in methylene chloride, and dissolving a biologically active agent or active core in water; adding the aqueous layer to the polymer solution and emulsifying to provide an inner water-in-oil emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring a resulting water-in-oil-water (w/o/w) emulsion for sufficient time to remove said solvent; and rinsing hardened microcapsules with water; and lyophilizing said hardened microcapsules.
25. The process of items 23 or 24 wherein a solvent-saturated external aqueous phase is added to emulsify the inner w/o emulsion prior to addition of the external aqueous layer, to provide microcapsules of narrow size distribution range between 0.05–500 Fm.
26. The process of items 23 or 24, wherein a low temperature of about 0–4 EC is provided during preparation of the inner w/o emulsion, and a low temperature of about 4–20 EC is provided during preparation of the w/o/w emulsion to provide a stable emulsion and high encapsulation efficiency.
27. The process of items wherein a 100/0 blend of uncapped and end-capped polymer is used to provide release of the active core in a continuous and sustained manner without a lag phase.
28. The microcapsules of items 6, wherein, when the entrapped polypeptide is active at a low pH, such as LHRH, adrenocorticotropic hormone, epidermal growth factor, calcitonin released polypeptide is bioactive.
29. The microcapsules of items 6 or.7 or 8 or 9 or 10 or 11, wherein, when entrapped peptide such as histatin is inactive at a low pH, a pH-stabilizing agent of inorganic salts are added to the inner aqueous phase to maintain biological activity of the released peptide.
30. The microcapsules of items 6 or 7 or 8 or 9 or 10 or 11 wherein, when entrapped polypeptide such as histatin is inactive at a low pH, a non-ionic surfactant such as polyoxyethylene sorbitan fatty acid esters (Tween 80, Tween 60 and Tween 20) and polyoxyethylene—polyoxypropylene block copolymers (Pluronics) is added to the inner aqueous phase to maintain biological activity of the released polypeptide.
31. The microcapsules of items 29, wherein placebo spheres loaded with the pH-stabilizing agents are coadministered with polypeptide-loaded spheres to maintain the solution pH around the microspcsules and preserve the biological activity of the released peptide in instances where the addition of pH-stabilizing agents in the inner aqueous phase is undesirable for the successful encapsulation of the acid pH sensitive polypeptide.
32. The microcapsules of item 30 wherein placebo spheres loaded with non-ionic surfactant are coadministered with polypeptide-loaded spheres to maintain biological activity of the released peptide where the addition of non-ionic surfactants in the inner aqueous phase is undesirable for successful encapsulation of the acid pH sensitive polypeptide.
33. The microcapsules of items 1 or 2 or 3 or 4 or 5 or 6 or 8 or 9 or 10 or 11 or 12 or 13 or 14 or 15 or 16 or 17 comprising a blend of uncapped and capped polymer, wherein complete solubilization of the copolymer leaves no residual polymer at the site of administration and occurs concurrently with the complete release of the entrapped agent.
34. A process of using microcapsules of items 1 or 2 or 3 or 4 or 5 or 6 or 7 or 8 or 9 or 10 or 11or 12 or 13 or 14 or 15 or 16 or 17 or 18 or 19 or 20 for human administration via parenteral routes, such as intramuscular and subcutaneous.
35. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human administration via topical route.
36. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human administration via oral routes.
37. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human administration via nasal, transdermal, rectal, and vaginal routes.
38. A process for a meliorating or preventing a disease or disorder in a mammal comprising administering perenterally, including intramuscular and subcutaneously, to said mammal a pharmaceutically-effective amount of a microcapsule of claim 1 or 2 or 3 or 4 or 5 or 6 or 7 or 8 or 9 or 10 or 11 or 12 or 13 or 14.

Conservation of Bioactivity of Polypeptides

As the polymer degrades rapidly, there is a preciptitous drop in pH accompanied by the release of soluble oligomers in the microenvironment which may affect the biological activity of acid pH-sensitive peptides/proteins. In such instances, biological activity can be maintained by the use of inorganic salts or buffering agents in the inner aqueous phase codissolved with the peptide.

The following unique advantages are characteristics of this invention:
1. Burst-free, prolonged, sustained release of polypeptides and other biocompatible and biodegradable microcapsules up to 100 days in an aqueous physiological environment without the use of additives in the core.
2. Release of active core programmable for variable durations over 1–100 days, by using a blend of uncapped and capped polymer of different molecular weights and copolymer ratio, and by manipulating the process parameters.
3. Complete release of the active core is concurrent with complete solubilization of the carrier polymer to innocuous components, such as lactic and glycolic acids, especially when using a 100/0 blend of uncapped/capped polymer. This is of tremendous significance, as most biodegradable polymers currently used for 1–30 day delivery, do not degrade completely at the end of the intended release duration, thereby causing serious concern of regulatory authorities on the effects of residual polymer at the site of administration.
4. Ease of administration of the microcapsules in various dosage forms via several routes, such as parenteral (intramuscular and sucutaneous), oral, topical, nasal, vaginal, etc.

The hydrophilic homo-and co-polymers based on D,L-lactide and glycolide contains hydrophilic adjusted homo- and co-polymers with free carboxylic end groups, and is characterized by the formula:

Poly(D,L-lactide-co-glycolide) 50:50

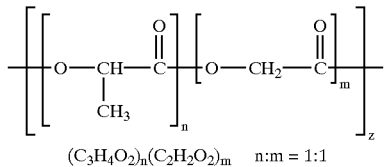

$(C_3H_4O_2)_n(C_2H_2O_2)_m$   n:m = 1:1

Wherein Z=Molecular Weight/130; for example Z=92 for Mw 12,000 and 262 for Mw 34,000.

While the molar ratio of the lactide to glycolide may vary, it is most preferred that the lactide to glycolide copolymer ratio be 50:50.

Reference is now made to FIG. 48 which depicts a blood-drug concentration versus time graph that shows conventional drug administration using a series of dosages compared to an ideal controlled release system. Unfortunately, many drugs have a blending of the two forms in a single formulation comprising different ratios of uncapped to capped polymer, would significantly influence the polymer hydration and hence release of the active core thereby providing release curves of any desirable pattern. Manipulation of polymer hydration and degradation resulting in modulation of release of active core is achieved by the addition of uncapped polymer to end-capped polymer in amounts as low as 1% up to 100%.

Therapeutic range, above which they are toxic and below which they are ineffective. Oscillating drug levels that are commonly observed following systemic administration causes alternating periods of ineffectiveness and toxicity. A sustained-release encapsulated biologically active agent or polypeptide preparation, ideally, will maintain the drug in the desired therapeutic range by means of a single dose, as depicted in the THERAPEUTIC RANGE in FIG. 1, where the ideal case for controlled release is shown.

In FIG. 2, there is shown a scanning electron micrograph of PLGA microspheres prepared using 50/50 uncapped polymer of Mw 8–12 k dalton. The uncapped polymer has solid, smooth spherical surfaces, and is suited to provide a "burst free" release system.

Table I is a summarization of the microsphere process description for preparing a peptide system (Histatin peptide) having a controlled release over the course of from 1 to 100 days.

Release profiles can be modified by a judicious blend of uncapped and capped polymers either in separate microspheres or in the same microspheres. Release from microcapsule formulations 1 through 21 listed in Table 1, occur independently of each other and hence the cumulative release from blends of these formulations are additive. By blending several formulations of uncapped and end-capped microspheres, release curves of any desired duration can be tailored. In addition, based on the release characteristics of uncapped and end-capped polymers, blending of the two forms in a single formulation comprising different ratios of uncapped to capped polymer, would significantly influence the polymer hydration and hence release of the active core thereby providing release curves of any desirable pattern. Manipulation of polymer hydration and degradation resulting in modulation of release of active core is achieved by the addition of uncapped polymer to end-capped polymer in amounts as low as 1% up to 100%.

While referring to Table 15 in conjunction with FIG. 50, it can be seen that the cumulative Histatin release from PLGA microspheres from several batches prepared using 50/50 and 75/25 uncapped and end-capped, polymer modulates release between 1 to 100 days by varying the process parameters. 1–35 days by uncapped 50/50, 18–56 days by capped 50/50 and 56–100 days by capped 75/25.

In referring to FIG. 51, a view is provided through a scanning electron micrograph of PLGA microspheres designed for a one to two month release system prepared using end-capped polymer of Mw 30–40 k daltons.

FIG. 52 depicts the cumulative Histatin release from PLGA microspheres, in which the release profiles are from several batches prepared using 50/50, uncapped and capped polymer, and varying the process parameters to modulate release between 28 to 60 days.

FIG. 53 represents cumulative Histatin release from PLGA microspheres—combined release profiles are from several batches prepared using 50/50 uncapped and capped polymer, and varying the process parameters to modulate release between 1–60 days.

In the context of this invention, a biologically active agent is any water-soluble antibiotics, antitussives, expectorants, sedatives, muscle relaxants, anti epileptics, antiulcer agents, anti-depressants, anti-allergic drugs, cardiotonics, antiarrhythmics drugs, vasodilators, antihypertensives, diuretics, anticoagulants, hormone drugs, anti-narcotics, etc.

In general, "burst free" sustained release delivery of biologically active agents from PLGA microshperes is accomplished in the context of this invention using of 90/10 to 40/60 molar ratios, and ratios of uncapped polymer to end-capped polymer of 100/0 to 1/99.

In general, the approaches for designing the biologically active agents encapsulated in the uncapped and combination uncapped/end-capped PLGA microspheres and characteristics of these encapsulants are briefly set forth below as follows:
1. Providing PLGA microspheres of surface morphologies using 50/50 uncapped and capped polymers of Mw—8–40K daltons as shown in FIGS. 2 and 4.
2. Providing in vitro release of a polypeptide, Histatin from PLGA microspheres, as shown in FIGS. 3 and 5, using uncapped and capped polymer of Mw—8–40K daltons and molar ratios such as 50/50 and 75/25.

For example, design of a 1–12 week bioactive compound release system is achieved using PLGA with the following specifications:
1. Polymer molecular weight:
   about 2–60K daltons
2. Copolymer molar ratio (L/G):
   90/10 to 40/60
3. Polymer end groups:
   uncapped and/or end-capped
and combining judiciously within the following parameters:
4. Polymer concentration
   from 5 to 50%
5. Inner aqueous to oil phase ratio:
   1:5 to 1:20 (v/v)
6. Peptide loads:
   from 2 to about 40% (w/w polymer)
and by using the unique aqueous emulsification method described in the invention.

The uniqueness and novelty of invention may generally be summarized in a brief way as follows:
1. Use of uncapped poly(lactide/glycolide) to achieve burst-free, continuous, sustained, programmable release of biologically active agents over 1–100 days.
2. Use of a unique aqueous emulsification system to achieve superior microsphere characteristics such as uniform sphere morphology and narrow size distribution.
3. Burst-free, prolonged, sustained release of polypeptides and other biologically actice agents from biocompatible and biodegradable microcapsules up to 100 days in an aqueous physiological environment without the use of additives in the inner core.
4. Release of active core programmable for variable durations over 1–100 days by using a blend of uncapped and capped polymer for different molecular weights and copolymer rations and manipulating the process parameters.
5. Complete release of the active core concurrent with complete solubilization of carrier polymer to innocuous components such as lactic and glycolic acids, especially when using a 100/0 blend of uncapped/capped polymer. This is of tremendous significance as most biodegradable polymers currently in use for 1–30 day delivery, do not degrade completely at the end of the intended release duration causing serious concern for regulatory authorities on the effects of residual polymer at the site of administration.
6. Ease of administration of the microcapsules in various dosages forms via several routes such as parenteral (intramusclar and subcutaneous), oral, topical, nasal, vaginal, etc.

The following examples are illustrative of, but not limitations upon the microcapsule compositions pertaining to this invention.

Example 12

Polylactide/glycolide (PLGA) microcapsules are prepared by a unique aqueous emulsification technique which has been developed for use with the uncapped polymer to provide superior sphere morphology, sphere integrity and narrow size distribution (See FIGS. 1a and 1b). This is accomplished by dissolving the polymer in a chlorinated hydrocarbon solvent such as methylene chloride and dissolving the biologically active agent in water. A w/o emulsion is then formed by mixing the solutions of polymer and the active agent by sonication, followed by emulsion stabilization in a solvent 7 saturated aqueous solution containing polyvinyl alcohol. A ternary emulsion is then formed by emulsifying the w/o emulsion in an external, pre-cooled aqueous phase containing polyvinyl alcohol (0.25–1% w/v). Microcapsules are hardened upon removal of solvent by evaporation, rinsed to remove any residual emulsifier, and then lyophilized.

Table 15 lists the microcapsule compositions, Nos. 1–21 thus prepared, consisting of a biologically active polypeptide, Histatin (composed of 12 amino-acids and a molecular weight of 1563) and blends of uncapped and capped polymer of ratios 100/0 to 1/99, and having a lactide/glycolide ratio of 90/10 to 40/60, and a molecular weight range between 2000 to 60,000 daltons.

Example 13

Microcapsule compositions are prepared as described in Example 2 wherein the copolymer L/G ratio is 48/52 to 52/48, and the ratio of uncapped/capped polymer is 100/0. The active core is Histatin (Mw 1563), the polymer molecular weight is—15,000 and the polymer concentrations vary from 7% to -40% w/w. Compositions 1,2,4 12–14 and 16–18 are listed in Table 15.

Release profiles of the active core from the compositions in an aqueous physiological environment, such as phosphate-buffered saline, pH 7.0 maintained at 37" 1EC are plotted as cumulative percentage release versus time, and presented in FIG. 50.

Burst-free, variable release from 1–35 days is achieved by varying the polymer concentration from 7 to -40% w/w in the oil phase.

Example 14

Microcapsule compositions are prepared as described in Example 13, wherein the aqueous/oil ratio is varied from 1/4 to 1/20 (v/v). Compositions 1,2,4 and 12 are listed in Table 15.

Release profiles of the active core from the compositions in an aqueous physiological environment described in Example 2 are plotted as cumulative percentage release versus time, and presented in FIG. 50.

Burst-free, continuous release from 1–35 days, with different onset and completion times are achieved by selecting different w/o ratios in the inner core.

TABLE 15

Microcapsule compositions Containing Histatin polypeptide

| Composition # | Polymer Description L/G Ratio & Type | Mol. Wt. (Mw × $10^3$) | Conc. in DCM (w/w) | Theoretical peptide Core Load (%) | Internal Phase Ratio (w/o) | Emulsification Technique |
|---|---|---|---|---|---|---|
| 1. | 50/50, U | 12 | 38 | 5 | 1:20 | A |
| 2. | 50/50, U | 12 | 18.5 | 2 | 1:20 | A |
| 3. | 50/50 | 34 | 10 | 5 | 1:20 | A |
| 4. | 50/50, U | 12 | 38 | 5 | 1:4 | A |
| 5. | 50/50 | 34 | 7 | 5 | 1:10 | B |
| 6. | 50/50 | 34 | 10 | 5 | 1:10 | B |
| 7. | 50/50 | 34 | 10 | 5 | 1:10 | A |
| 8. | 75/25 | 12 | 10 | 5 | 1:10 | B |
| 9. | 75/25 | 12 | 23.5 | 5 | 1:10 | B |
| 10. | 50/50 | 12 | 10 | 5 | 1:10 | B |
| 11. | 50/50 | 12 | 7 | 5 | 1:10 | B |

TABLE 15-continued

Microcapsule compositions Containing Histatin polypeptide

Polymer Description

| Composition # | L/G Ratio & Type | Mol. Wt. (Mw × 10³) | Conc. in DCM (w/w) | Theoretical peptide Core Load (%) | Internal Phase Ratio (w/o) | Emulsification Technique |
|---|---|---|---|---|---|---|
| 12. | 50/50, U | 12 | 10 | 5 | 1:10 | B |
| 13. | 50/50, U | 12 | 7 | 2.3 | 1:10 | B |
| 14. | 50/50, U | 12 | 10 | 5 | 1:10 | B |
| 15. | 50/50, U | 34 | 10 | 5 | 1:10 | B |
| 16. | 50/50, U | 12 | 10 | 5 | 1:10 | B |
| 17. | 50/50, U | 12 | 20 | 5 | 1:10 | B |
| 18. | 50/50, U | 12 | 40 | 5 | 1:10 | B |
| 19. | 50/50, U | 34 | 5 | 5 | 1:10 | B |
| 20. | 50/50, U | 34 | 10 | 5 | 1:10 | B |
| 21. | 50/50 U | 34 | 15 | 5 | 1:10 | B |

Acronyms:
L/G ratio: Copolymer composition of lactide/glycolide
DCM: Methylene Chloride
Mw: Molecular weight in daltons
A: w/o/w emulsification without an intermediate step for emulsion stabilization
B: w/o/w emulsification with an intermediate step for emulsion stabilization
U: Uncapped polymer

Example 15

Microcapsule compositions are prepared as described in Example 13, wherein the polymer molecular weight is 28,000–40,000 and polymer concentrations vary from 5% to -15% w/w. Compositions 19–21 are listed in Table 15.

Release profiles of the active core from the compositions in an aqueous physiological environment are described in Example 2 are plotted as cumulative percentage release versus time and presented in FIG. 51.

Burst-free, variable release from 18–40 days is achieved by varying the polymer concentration.

Example 16

Microcapsule compositions are prepared as described in Example 13, wherein the ratio of uncapped/capped polymer is 1/99 and polymer concentrations vary between 5% to -12% w/w. Compositions 10 and 11 are listed in Table 15.

Release profiles of the active core from the compositions in an aqueous physiological environment are described in Example 13, and plotted as cumulative percentage release versus time and presented in FIG. 50.

Burst-free, variable release from 28–70 days is achieved by varying the polymer concentrations in the oil phase.

Example 17

Microcapsule compositions are prepared as described in Example 16, wherein polymer molecular weight is 28,000–40,000 and polymer concentrations vary between 5% to -12% w/w. Compositions 5 and 6 are listed in Table 15.

Release profiles of the active core from the compositions in an aqueous physiological environment are described in Example 12 and are plotted as cumulative percentage release versus time, and presented in FIG. 52.

Burst-free, variable release from 28–70 days is achieved by varying the polymer concentration.

Example 18

Microcapsule compositions are prepared as described in Example 17, wherein the aqueous/oil ratio varies between 1/5 to 1/25 (v/v) Compositions 3 and 7 are listed in Table 15.

Release profiles of the active core from the compositions in an aqueous physiological environment are described in Example 12, and plotted as cumulative percentage release versus time, and presented in FIG. 52.

Burst-free, variable release from 28–70 days is achieved by varying the aqueous/oil ratios.

Example 19

Microcapsule compositions are prepared as described in Example 16, wherein the copolymer ratio is 75/25 and polymer concentrations vary between 5% to -25% w/w. Compositions 8 and 9 are listed in Table 15.

Release profiles of the active core from the compositions in an aqueous physiological environment are described in Example 13, and are plotted as cumulative percentage release versus time, and presented in FIG. 50.

Burst-free, variable release from 56–™90 days is achieved by varying the polymer concentration in the oil phase.

Example 20

Microcapsule compositions are described in Example 12, wherein the active core is Luteinizing hormone releasing hormone (LHRH, a decapeptide of molecular weight 1182) and the polymer concentration is -40% w/w. Release profiles of the active core from the composition in an aqueous physiological environment is described in Example 12, and is plotted as cumulative percentage release versus time, and presented in FIG. 4.

Burst-free, continuous and complete release is achieved within 35 days, similar to Histatin acetate.

Example 21

Microcapsule compositions are prepared as described in Example 12, wherein an additive such as sodium salt (carbonate or bicarbonate) is added to the inner aqueous phase at concentrations of 1–10% w/w to maintain the biological activity of the released polypeptide.

Burst-free, variable release from 1–28 days is achieved similar to Examples 13 and 14, and the released polypeptide is biologically active until 30 days, due to the presence of the sodium salt.

Example 22

Microcapsule compositions are prepared as described in Example 13, wherein an additive such as a nonionic surfactant, polyoxyethylene/polyoxypropylene block copolymer (Pluronics F68 and F127) is added to either the inner oil or the aqueous phase at concentrations from 10–100% w/w, to maintain the biological activity of the released polypeptide.

Burst-free, continuous release from 1–35 days is achieved similar to Examples 13 and 14, and the released polypeptide is bioactive due to the presence of the surfactant.

Example 23

Cumulative histatin release from the microcapsule compositions described in Examples 12 through 22 and release profiles plotted in FIGS. 49 and 50 show the burst-free, programmable peptide release for variable duration from 1–100 days. Virtually any pattern of cumulative release is achievable over a 100 day duration by a judicious blending of several compositions, as shown in these FIG. 53.

Burst-free Delivery System for Biologically-active Agents Useful as Vaccines Effective Against Infections with Gram-negative Bacteria and Lipopolysaccharide ("LPS") Mediated Pathology Induced by Gram-negative Bacterial Infections A further illustration of Phases II and III of this invention is the formulation of a vaccine effective in inducing the production of antibodies with which to immunize a second subject passively against infection by Gram-negative bacteria and LPS-mediated pathology, comprising a non-covalent polyvalent complex formed between purified, detoxified LPS derived from *E. coli* and purified outer membrane/protein derived from *N. meningitidis*, encapsulated within a matrix of poly(lactide/glycolide) copolymer having a molar composition of lactide/glycolide from 90/10 to 40/60. The poly(lactide/glycolide) copolymer which may contain a pharmaceutically-acceptable adjuvant, is comprised of a blend/mixture of uncapped free carboxy end group and end-capped forms and serves as the vaccine delivery system.

The encapsulation of biologically active agents in accordance with this invention contemplates the formulation of immunostimulating compositions and vaccines (including their method of use and serum, plasma or specific polyclonal antibodies obtained from immunized subjects with enhanced versality and effectiveness. The same vaccine will also actively immunize a host subject against Gram-negative bacterial infections and LPS-mediated pathology. Meningococcal infections and LPS-mediated pathology. Meningococcal infections are included among those Gram-negative bacterial infections protected against by the vaccine.

Moreover, included within the scope of Phases II and III of this invention is a vaccine effective against infections with Gram-negative bacteria and lipopolysaccharide ("LPS")-mediated pathology induced by Gram-negative bacterial infections. Hereafter, all references to the immunization complex is intended to include its contemplated use as the antigen within the polymeric matrix. More particularly, it relates to a non-covalent, polyvalent complex vaccine containing purified *E. coli* LPS endotoxin and purified *N. meningitides* outer membrane protein, as the antigen, encapsulated within a biodegradable-biocompatable polymeric matrix of poly(lactide/glycolide) copolymer, which vaccine, produces, in an actively immunized subject, an immune response against Gram-negative bacterial infection and the pathology caused by the LPS endotoxin. The present invention also relates to production of specific polyclonal antibodies that can be used to protect a second subject passively against Gram-negative bacterial infections and LPS-mediated pathology.

Description of the Background Art

Infections by Gram-negative bacteria and consequent septic shock are leading causes of death among hospitalized patients. It is estimated that Gram-negative sepsis has an incidence of 70,000 to 300,000 cases per year in the United States. McCabe et al., *Am. J. of Med.* 68: 344 (1980).

It is well-documented that a principal mediator of Gram-negative bacterial septic shock is a LPS endotoxin present on the outer membrane of Gram-negative bacteria. Luderitz et al., *Rev. Infect. Dis.* 61: 428 (1984); Rietsckel et al., *loc. cit.* 9(suppl.): 5527 (1987).

Attempts have been made to produce vaccines that will produce anti-endotoxin antibodies, and thereby protect against septic shock. For a review, see Cross et al., *J. Endotox. Res.* 3: 57 (1994). Ziegler et al., *N. Eng. J. Med.* 107: 1225 (1982) showed in a clinical setting that polyclonal antiserum obtained from volunteers immunized with boiled *E. coli* J5 (Rc chemotype) provided significant protection. In another study, however, the human polyclonal antibody to J5 boiled cell vaccine was not superior to normal human IgG in reducing death from Gram-negative bacteremia. Calandra et al., *J. Infect. Dis.*, 158:312 (1988). On the other hand, more recently it was shown that affinity-purified IgG derived from the serum of rabbits immunized with J5 boiled cell vaccine afforded neutropenic rats substantial protection against challenge with *P. aeruginosa*, a heterologous Gram-negative bacteria. Bhattacharjee et al., *Clin. Res.* 41(2): Abs 247. (1993). These contradictory reports point up the uncertainty and unpredictability of using boiled J5 LPS as a vaccine.

Disappointing results also have been reported in the use of anti-endotoxin monoclonal antibodies. Clinical trials of the HA-LA human monoclonal antibody (Ziegler et al., *N. Eng. J. Med.* 324: 429 (1991)), and the ES murine monoclonal IgM antibody (Greenman et al., *J. Am. Med. Assoc.* 266: 1097 (1991); Wenzel et al., 31st Intl. Conf. Antimicrob. Agts. Chemotherapy 240, Abstr. 1170 (1991)) did not generate data adequate to support product licensing. Cross et al. (1994), above.

Earlier, Kanegasaki et al. in BACTERIAL ENDOTOXIN: CHEMICAL, BIOLOGICAL AND CLINICAL ASPECTS, Homma et al., eds. (Verlag Chemie, 1984), complexed various crude LPS preparations with an outer membrane protein derived from *E. coli* and compared these complexes in two systems, namely, induction of interferon production in rabbit spleen cells and activation of preclotting enzymes of the horseshoe crab. It was reported that differing degrees of activity were exhibited by complexes derived from different LPS preparations, and that substituents not masked after complex formation are in part responsible for the variability of activity. This, in turn, may be a reflection of the great variability of the O-polysaccharide chain structure of LPS's even different strains of the same species. For example, there are over 100 serotypes of *E. coli* based on the structure of O-polysaccharide. Kenne et al. in 2 POLYSACCHARIDES 282, G. O. Asoinall, eds. (1983).

Because of these uncertainties and an unmet need of long-standing for a vaccine effective against Gram-negative bacterial infections, the present inventors have devised a novel vaccine which allows for both active and passive immunization against Gram-negative bacterial infections.

Summary of the Invention

It is therefore an object of the present invention to provide a means of both actively and passively immunizing a subject against Gram-negative bacterial infections and LPS pathology. In this regard, a subject, can be actively immunized with a non-covalent vaccine comprising a complex between purified *E. coli* LPS and purified outer membrane protein ("OMP") derived from *N. meningitidis*, encapsulated in a matrix of poly(lactide/glycolide) copolymer having a molar composition of lactide/glycolide from 90/10 to 40/60. The copolymer may contain a pharmaceutically-acceptable adjuvant, is a blend or mixture of uncapped free carboxy end group and end-capped forms. Serum or plasma from an actively immunized subject, or IgG isolated therefrom (hereafter "specific polyclonal antibody"), can be administered to, a second subject to confer on the latter a passive protection against Gram-negative bacterial infections and LPS-mediated pathology, including sepsis.

It is another object of the present invention to provide a purified, detoxified LPS endotoxin from an *E. coli* strain suitable for use in the aforementioned non-covalent complex vaccine.

It is still another object of this invention to provide a purified outer membrane protein from an *N. meningitidis* strain suitable for use in the aforementioned non-covalent complex vaccine.

It is yet an other object of the invention to provide a non-covalent complex between purified, detoxified LPS endotoxin from *H. coli* and purified outer membrane protein from *N. meningitidis*.

Another object of the present invention is to provide a method of passively immunizing a subject against Gram-negative bacterial infections using plasma or post-immune serum (antiserum), or specific polyclonal antibody purified therefrom, obtained from a host subject actively immunized with the aforementioned non-covalent complex vaccine.

Yet another object of the invention to provide a method of using the non-covalent complex vaccine of the invention for active or passive immunization of a subject against meningococcal infections.

These and other objects will become apparent by reference to the specification and examples below.

Detailed Description of the Preferred Embodiments

Figure 1:
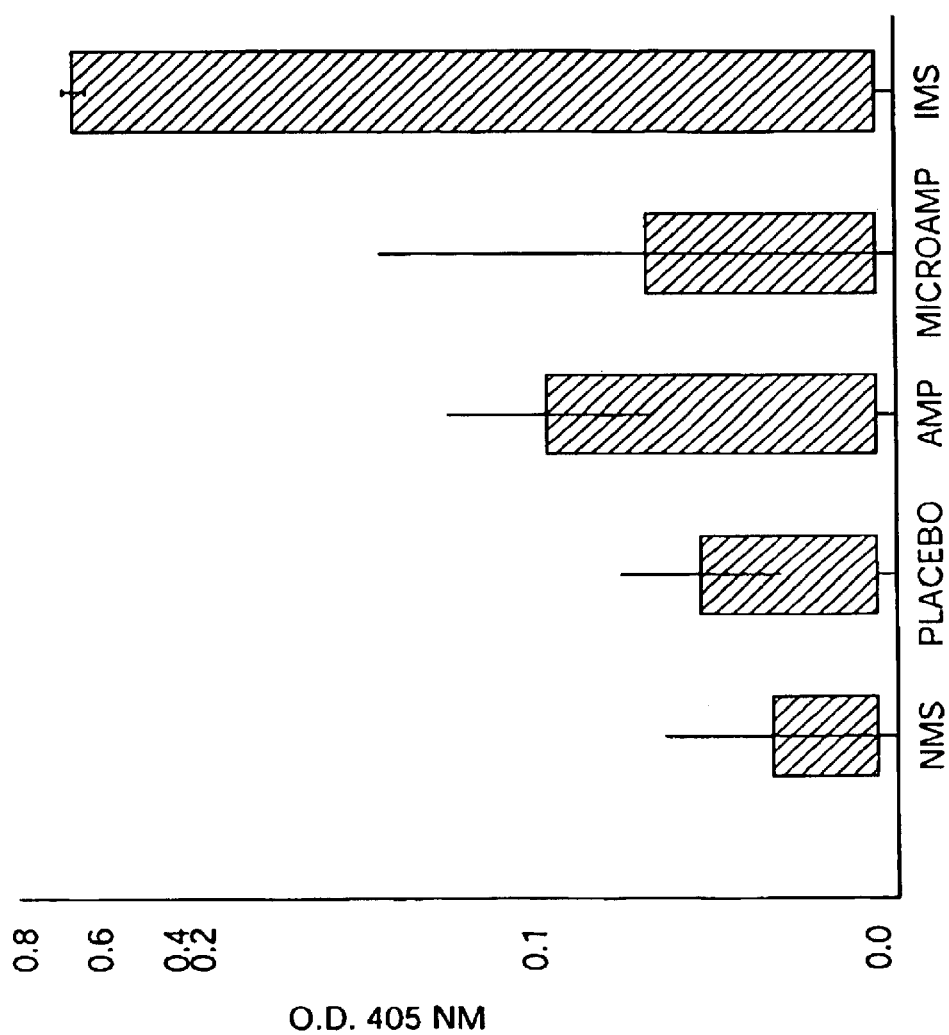
Figure 2:
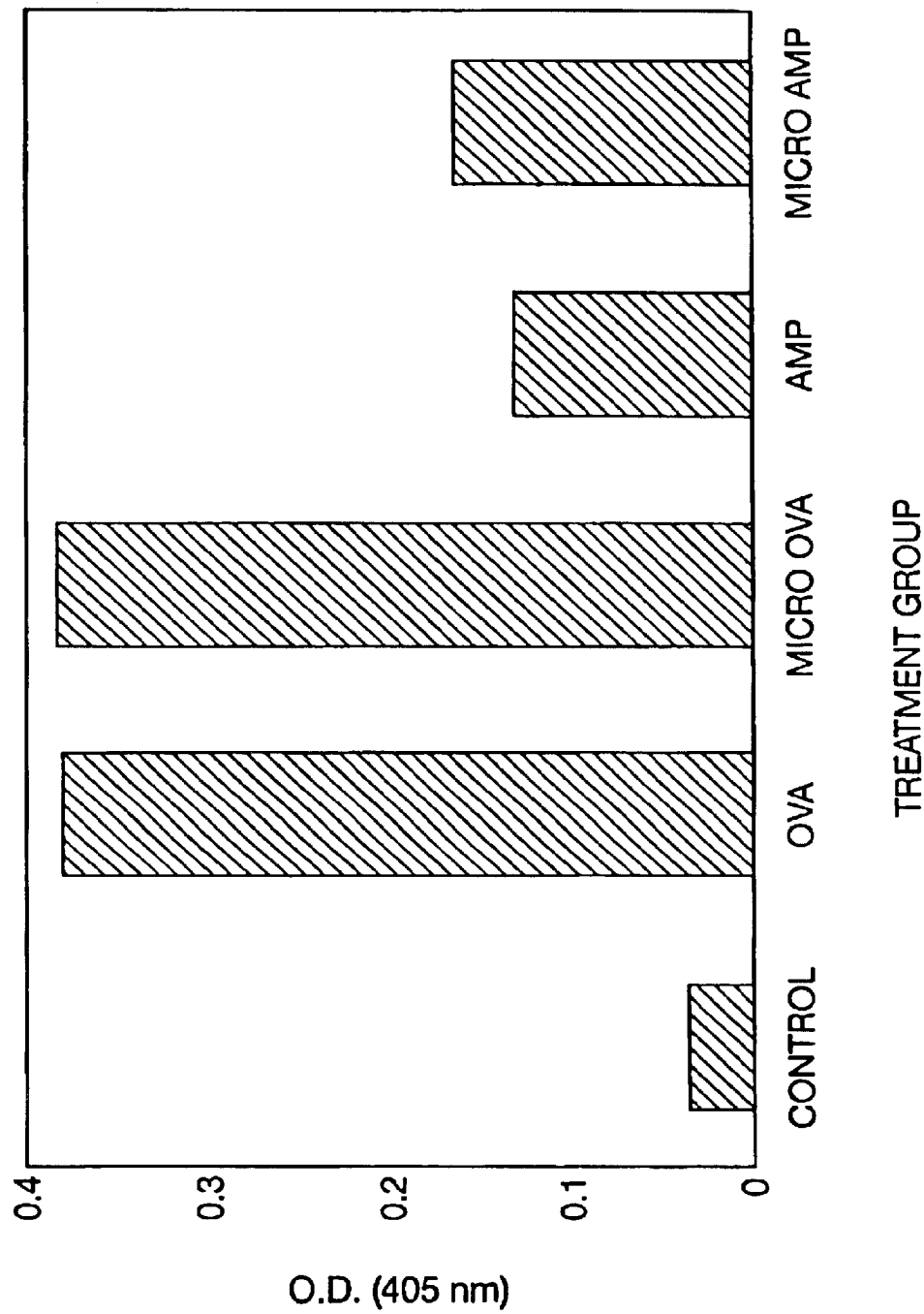
Figure 3:
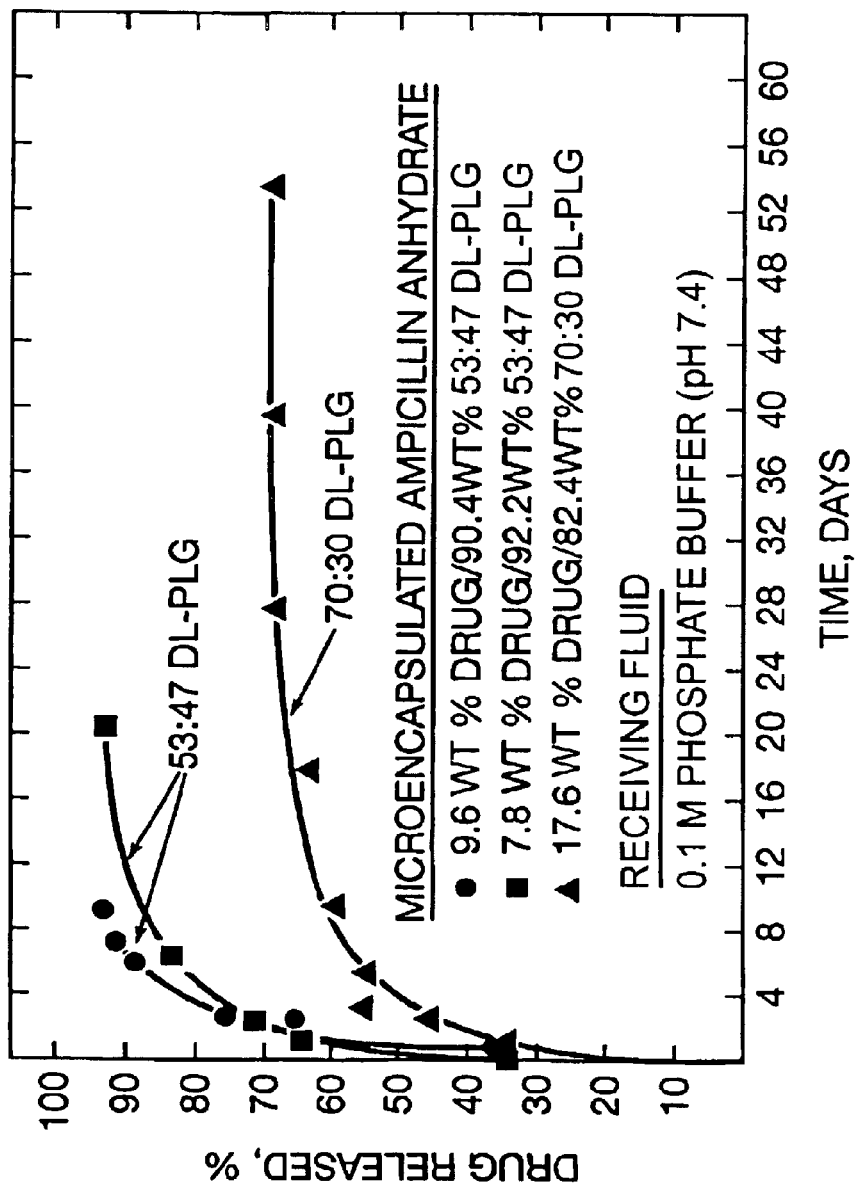
Figure 4:
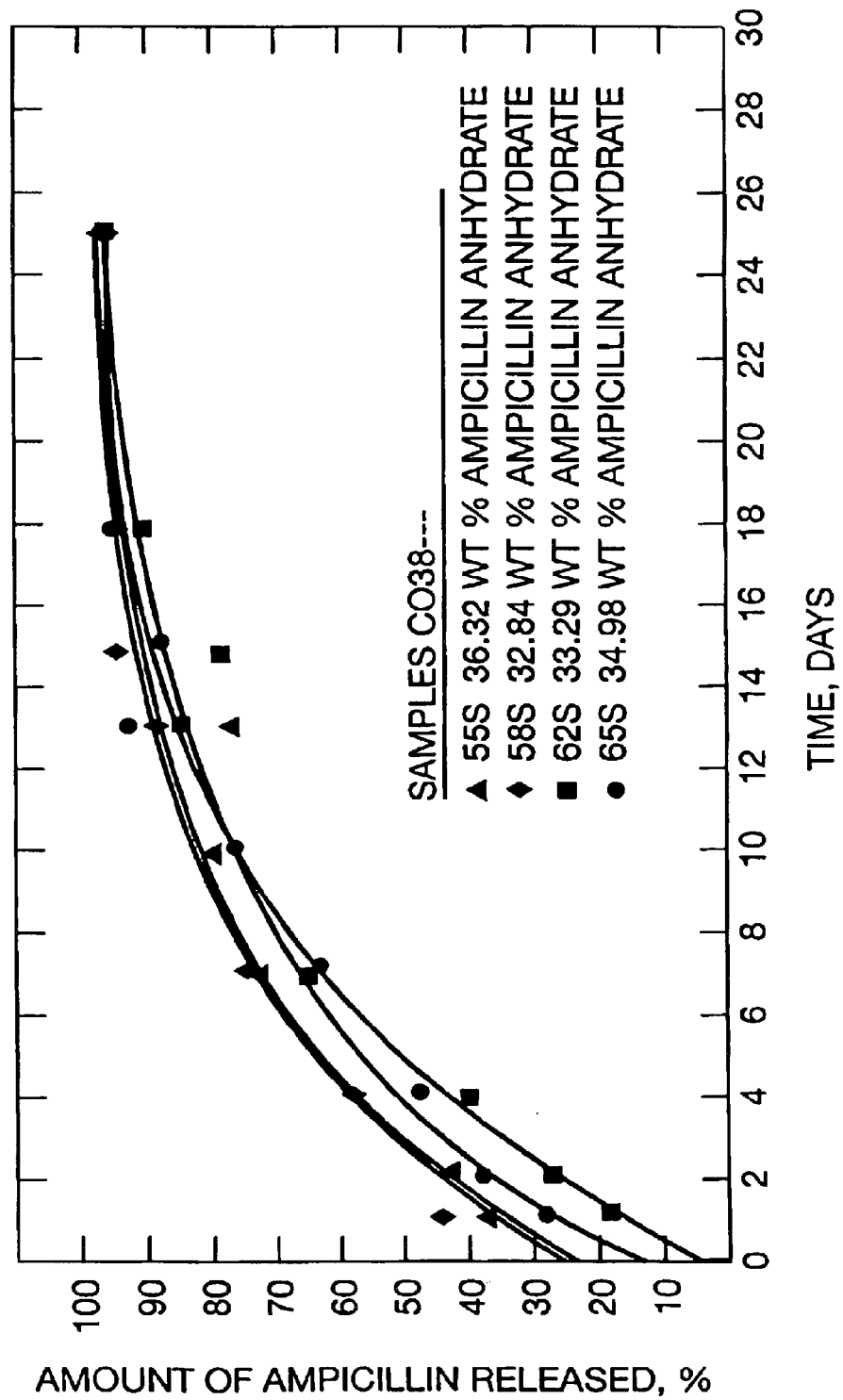
Figure 5:
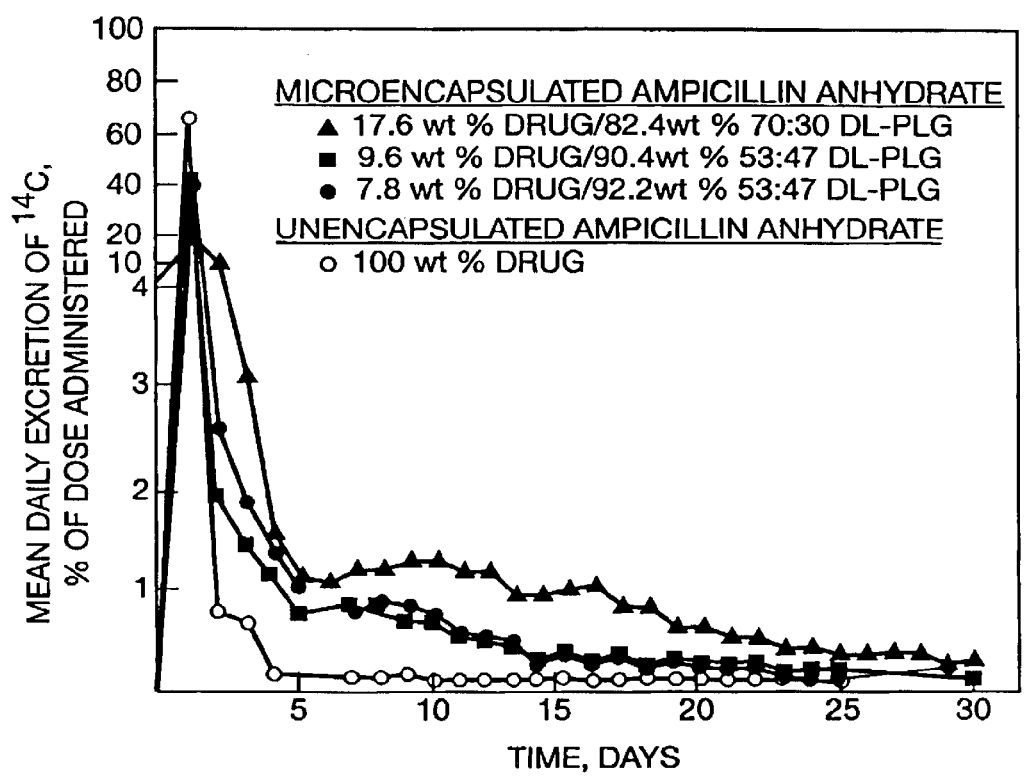
Figure 6:
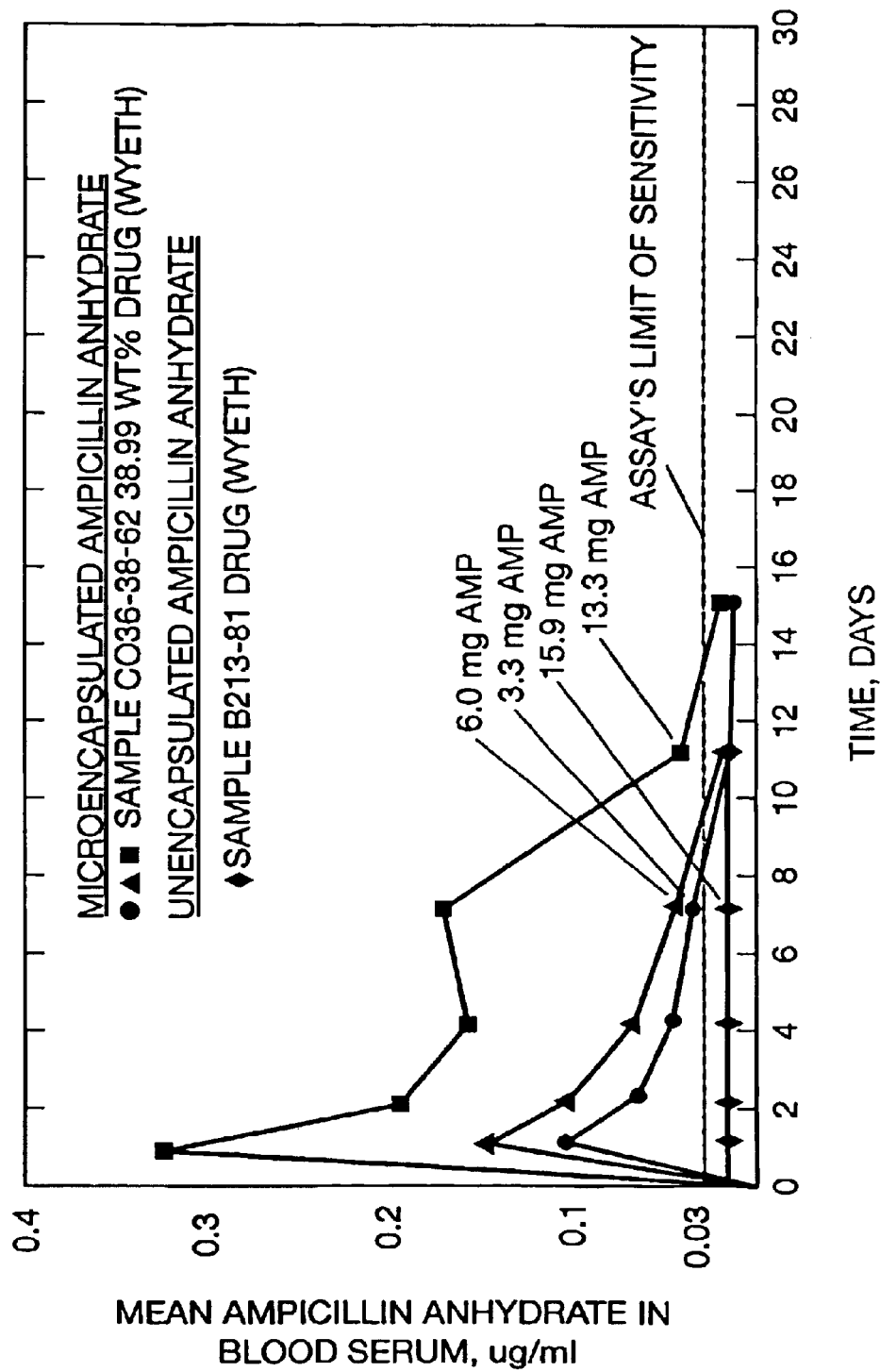
Figure 7:
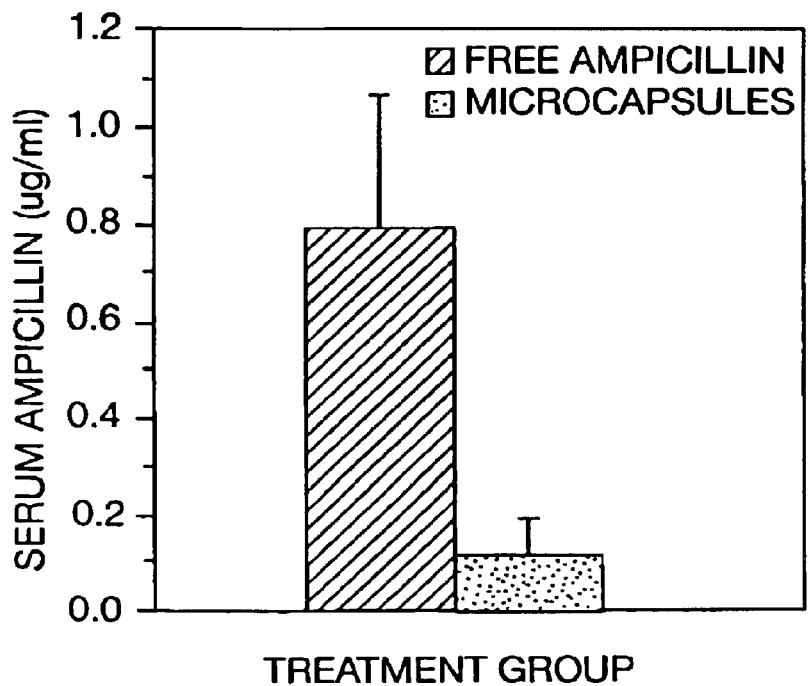
Figure 8:
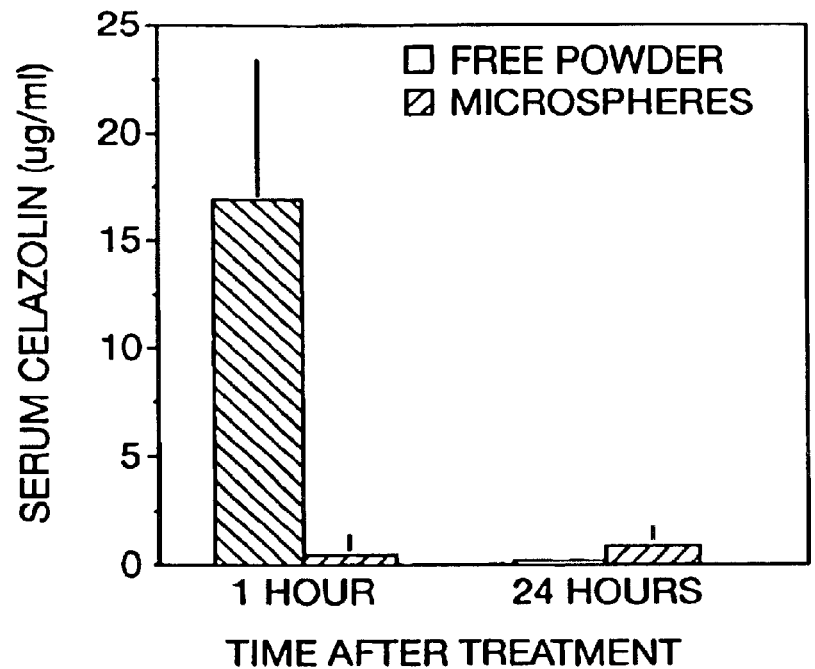
Figure 9:
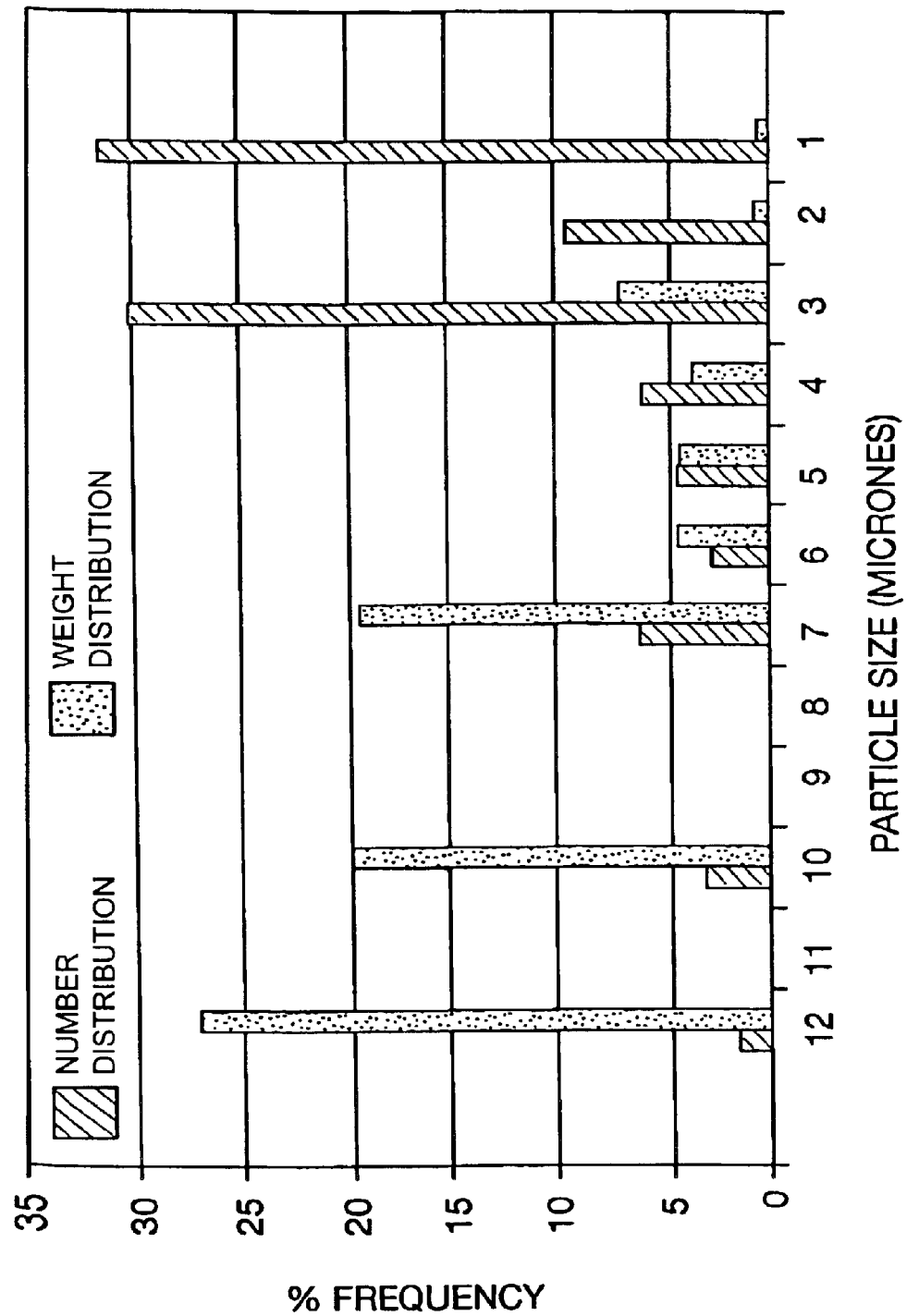
Figure 10:
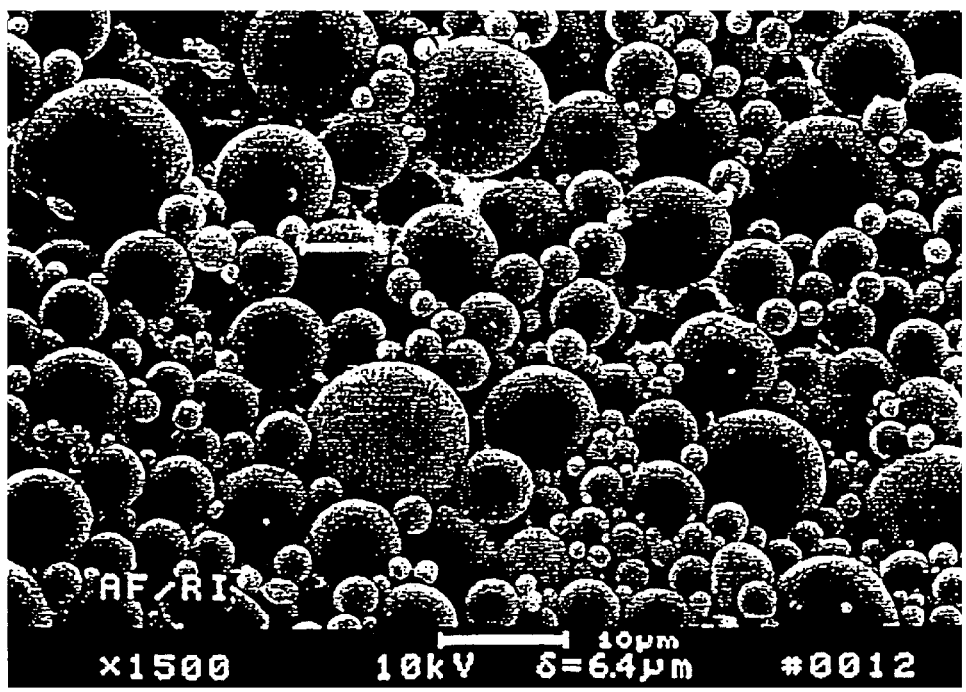
Figure 11A:
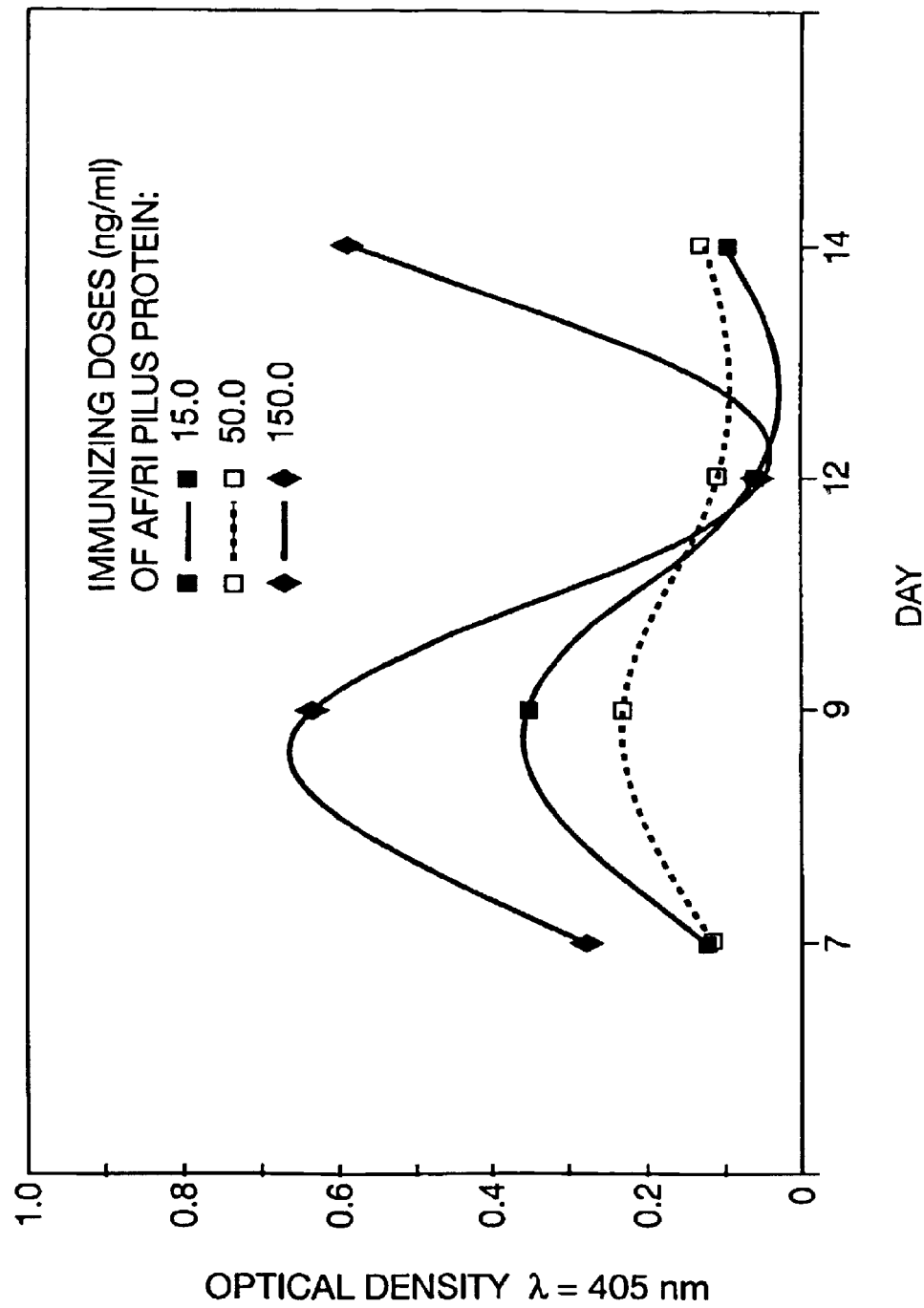
Figure 11B:
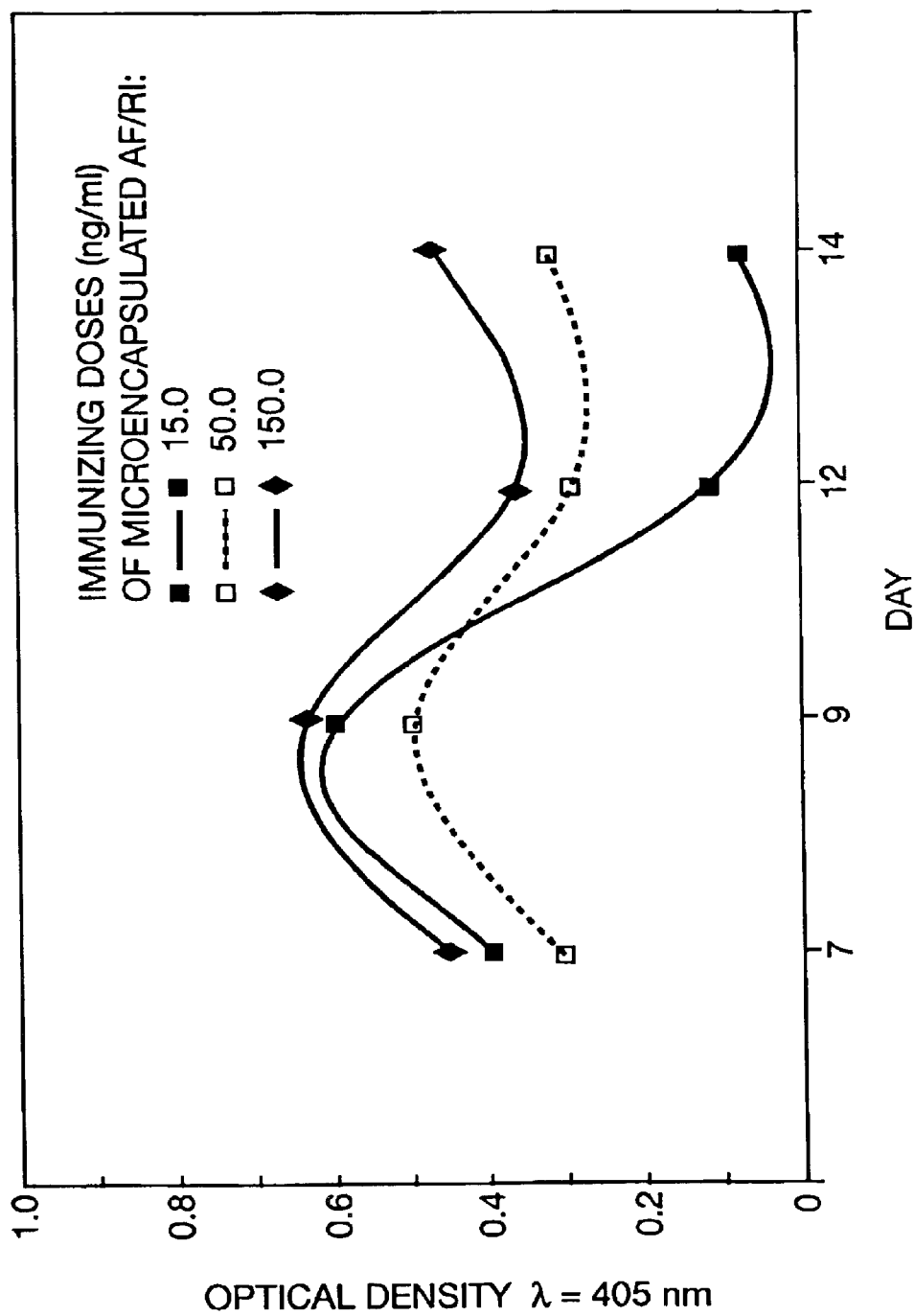
Figure 12B:
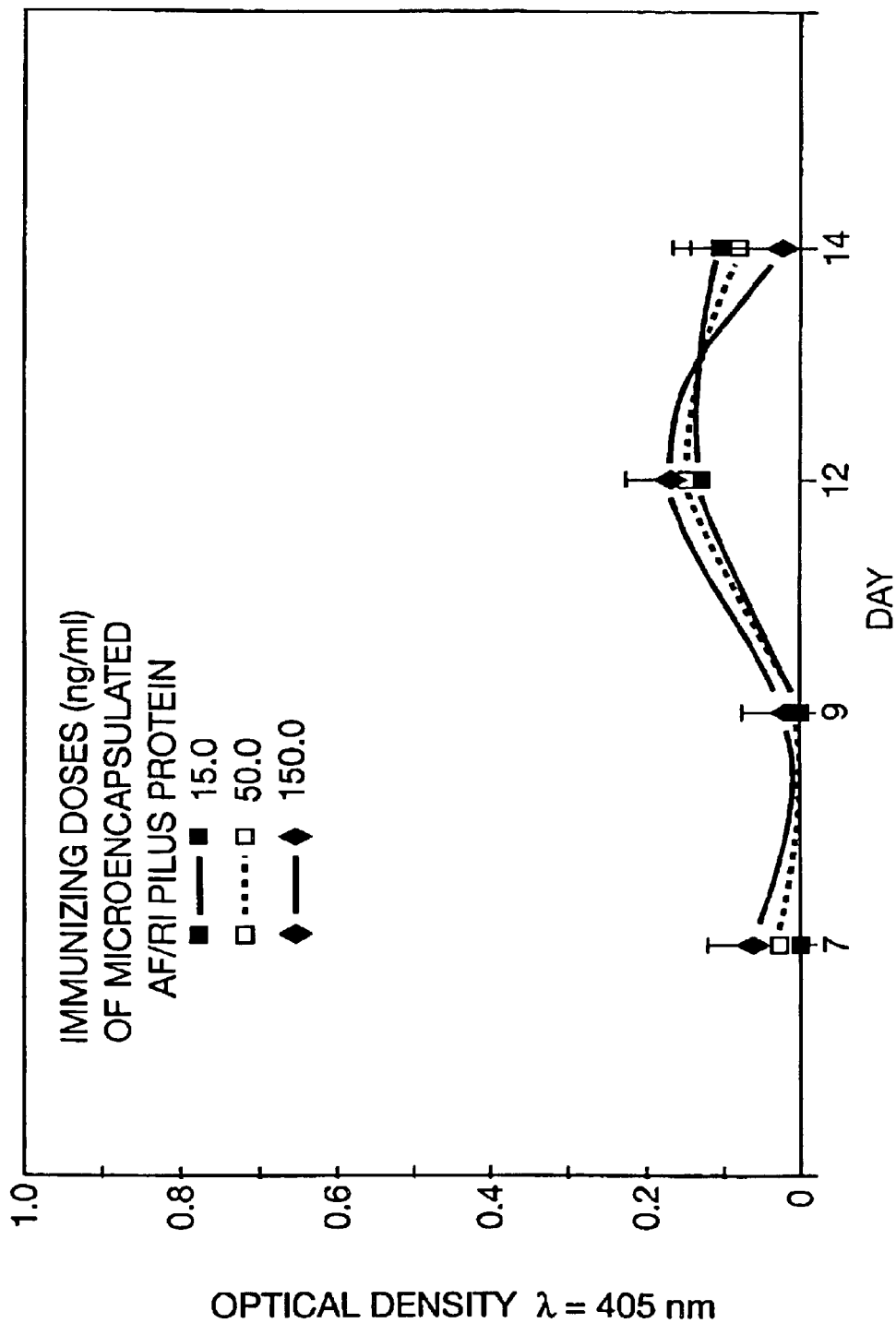
Figure 14A:
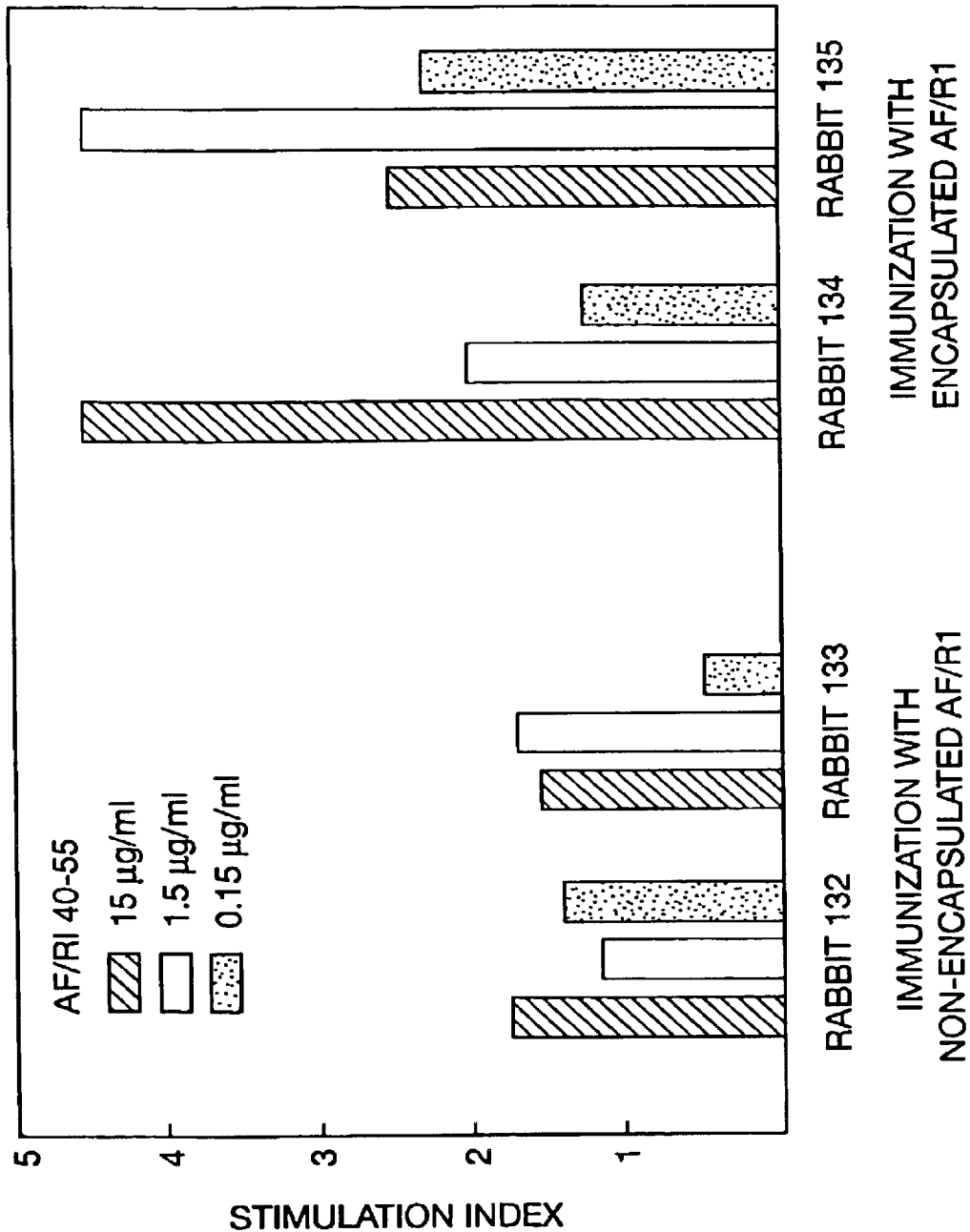
Figure 15A:
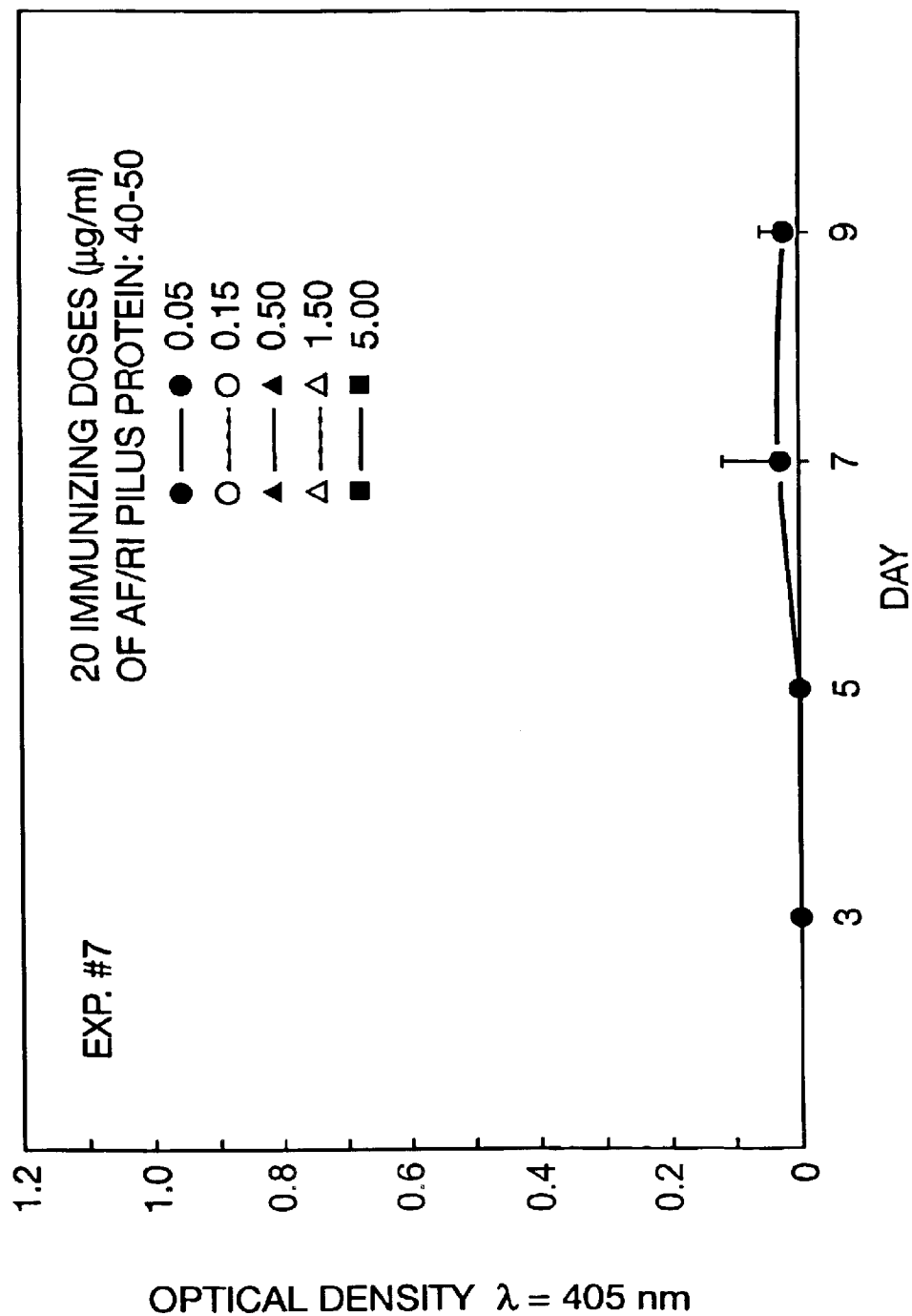
Figure 15B:
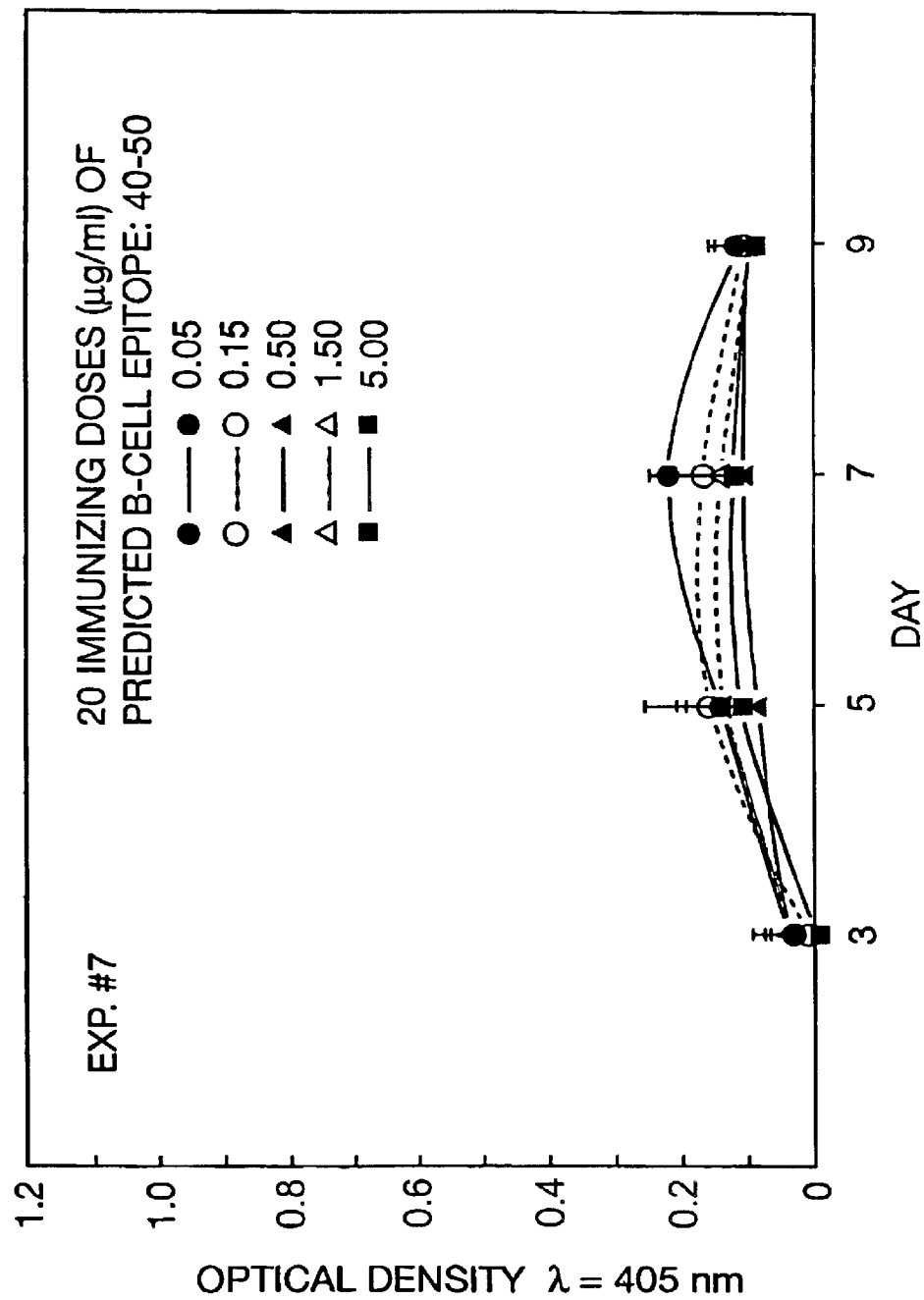
Figure 16B:
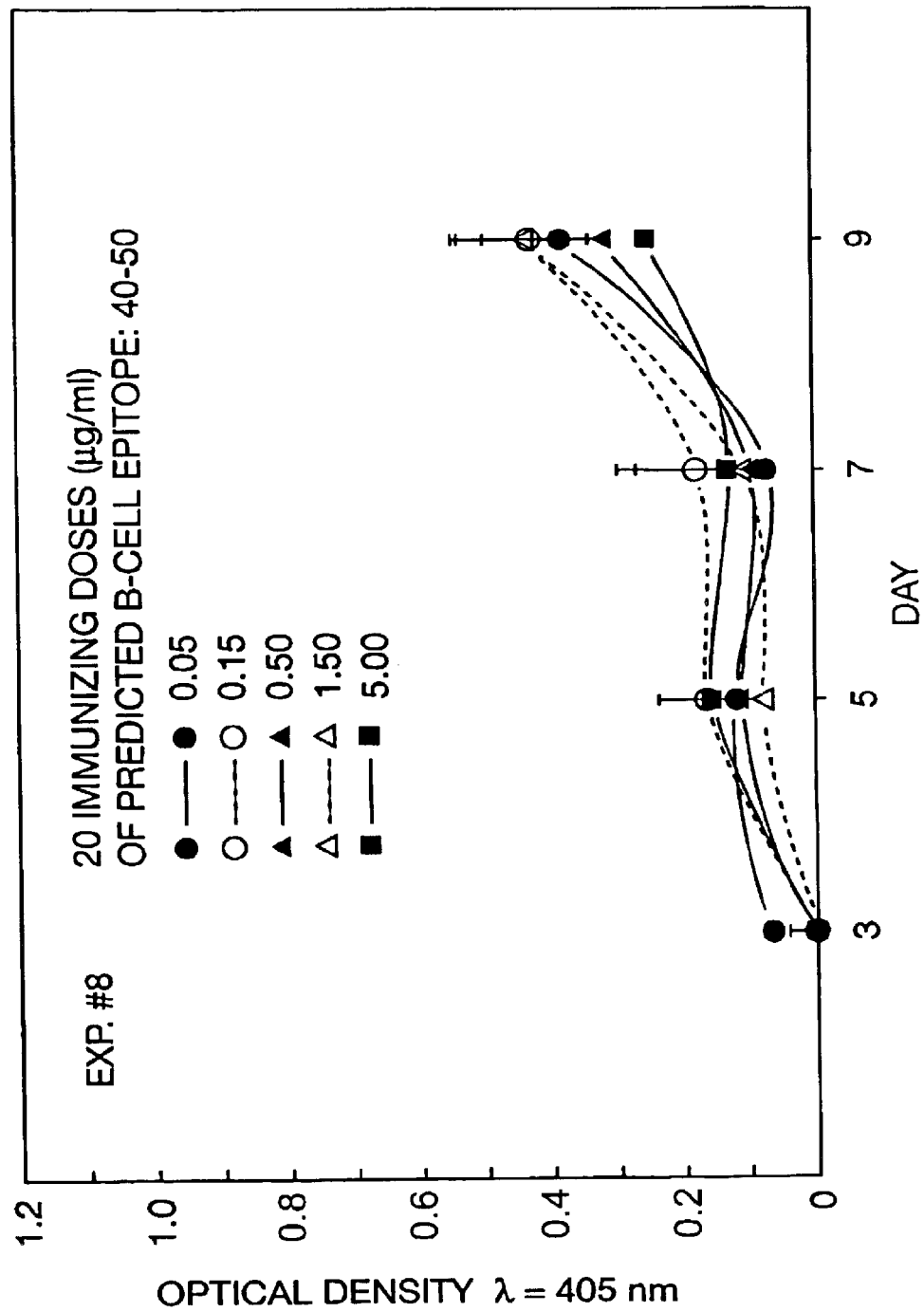
Figure 18A:
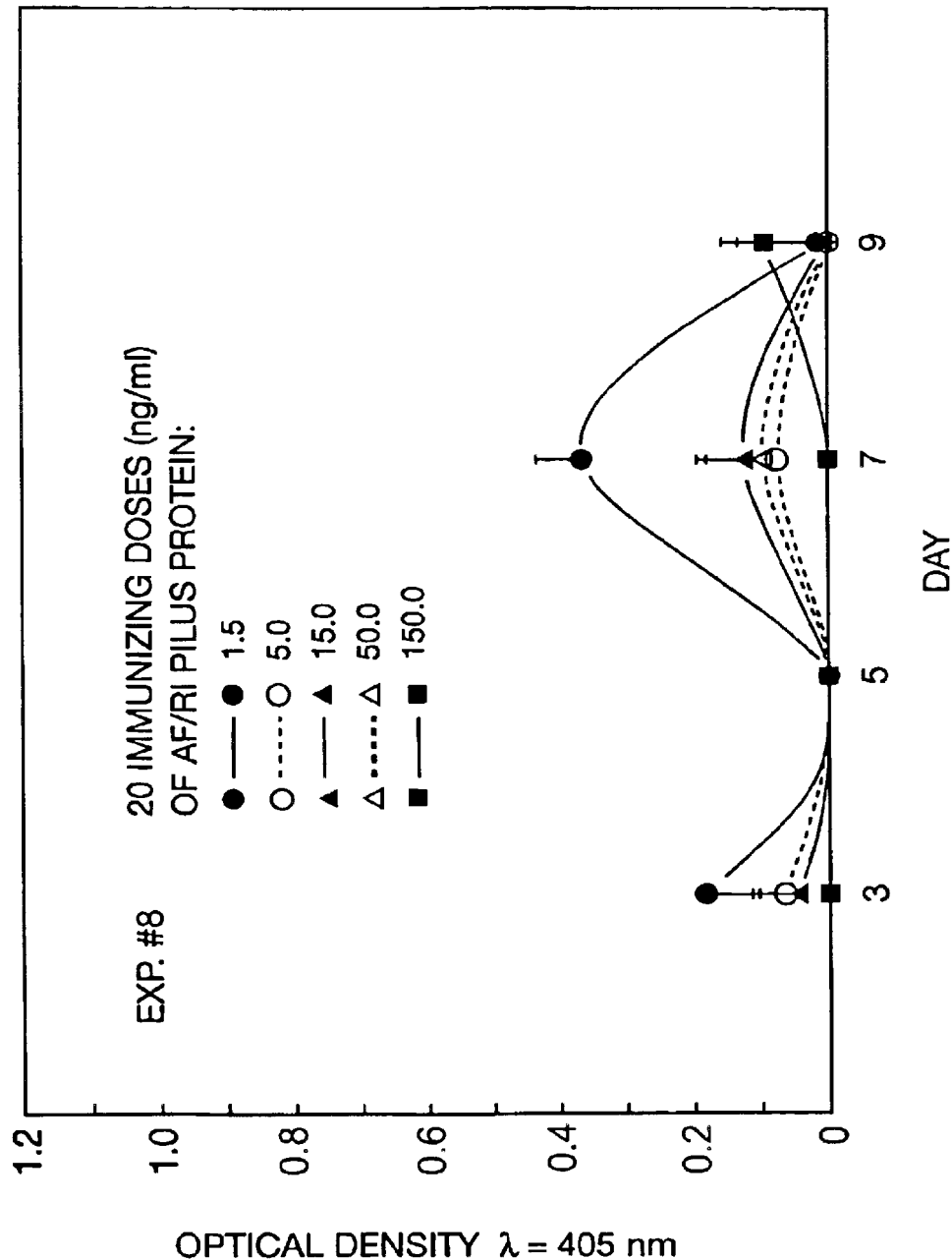
Figure 18B:
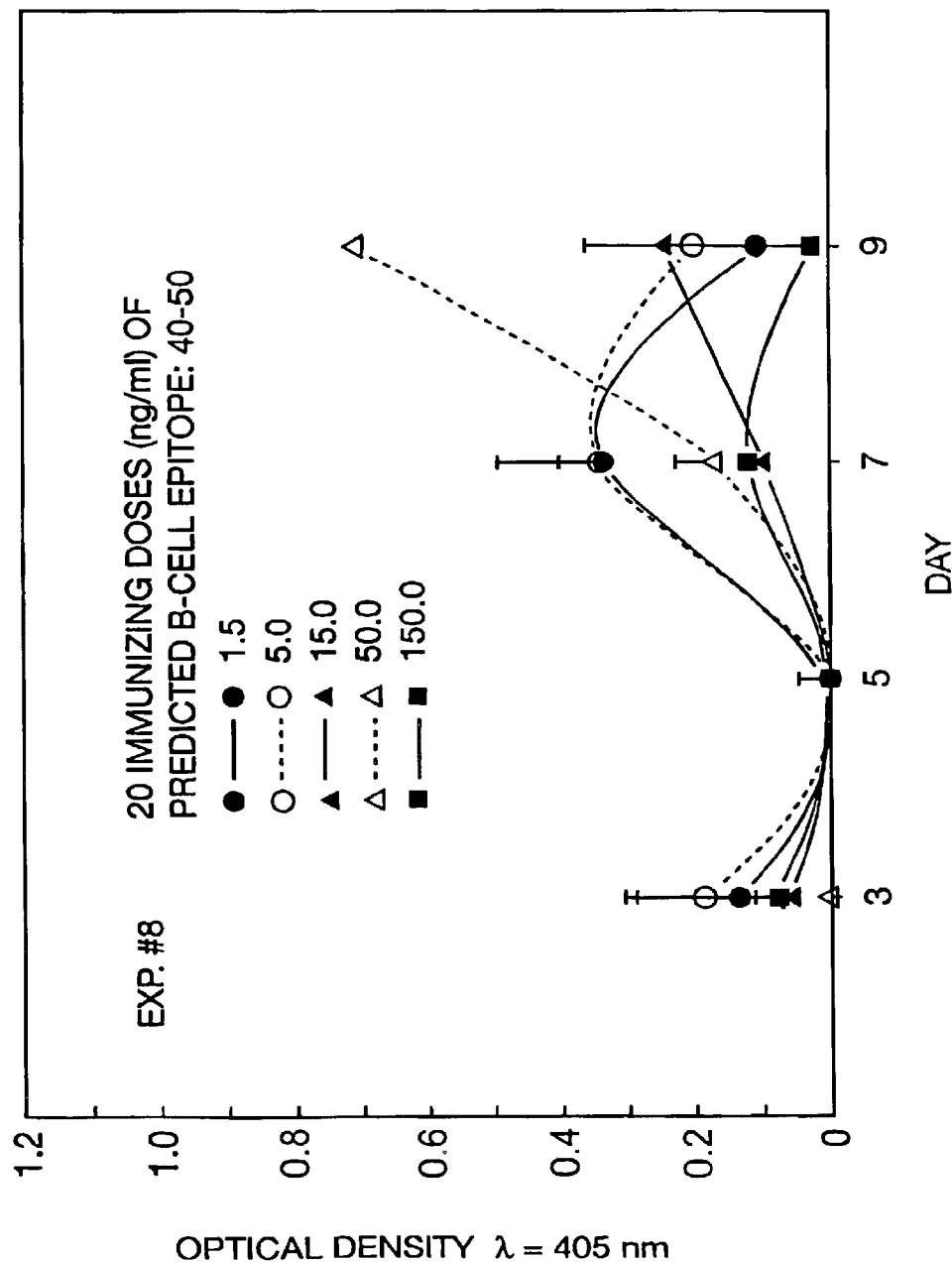
Figures 24A, 24B:
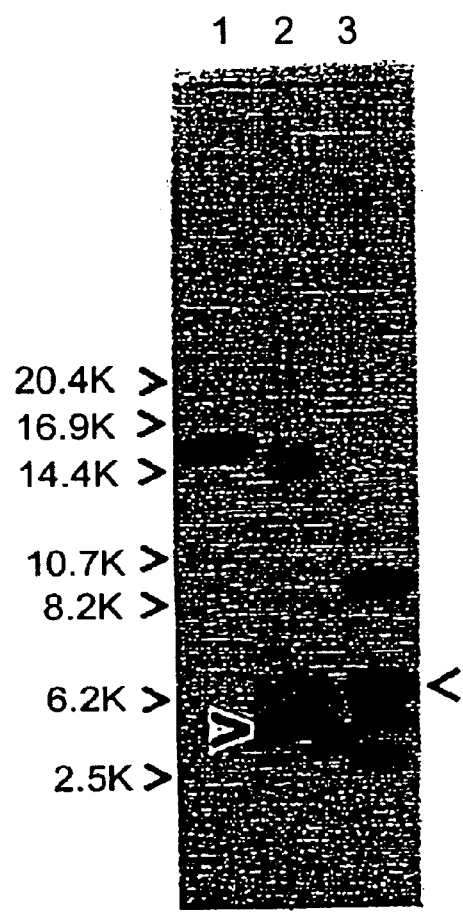
Figure 25A:
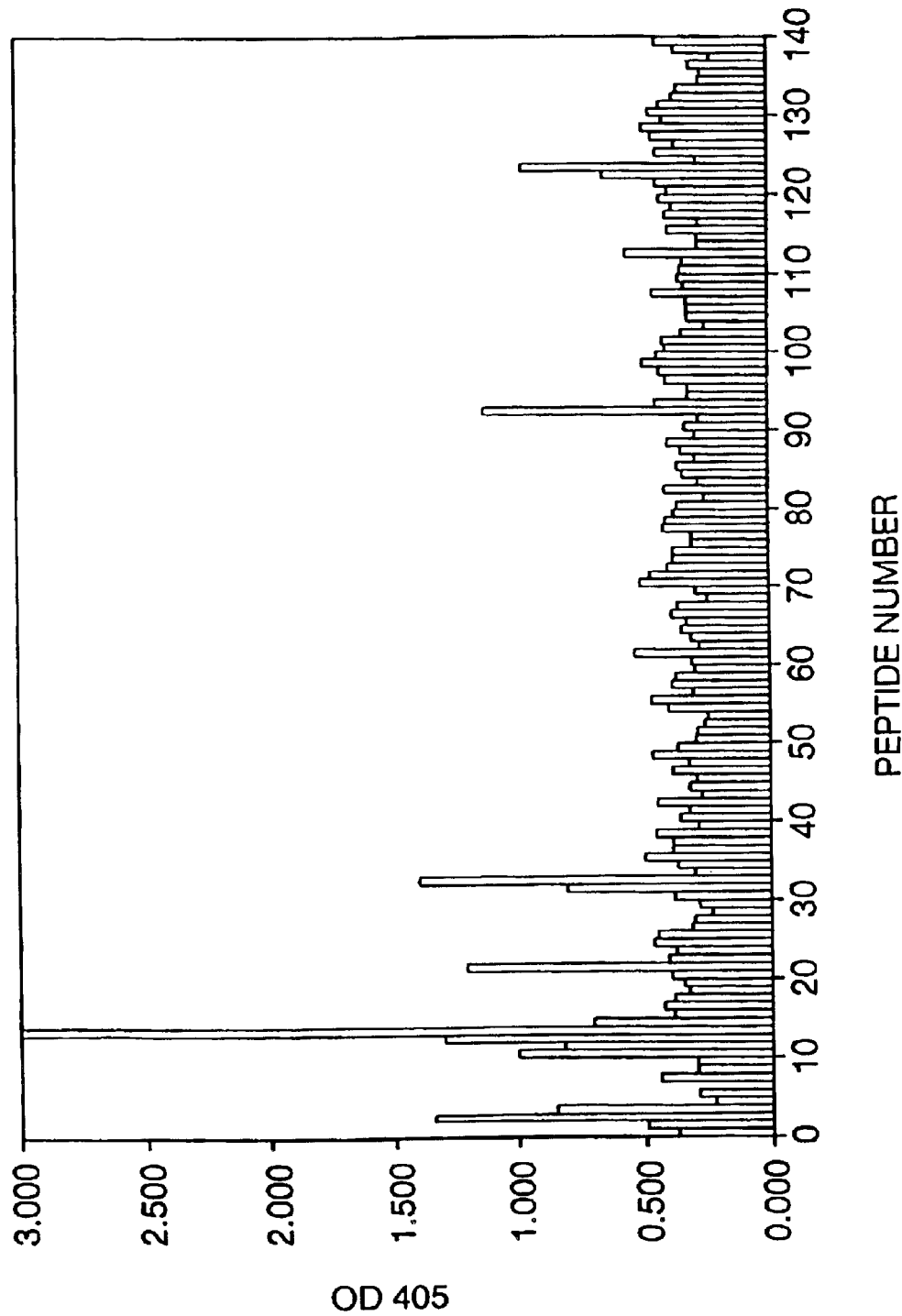
Figure 25B:
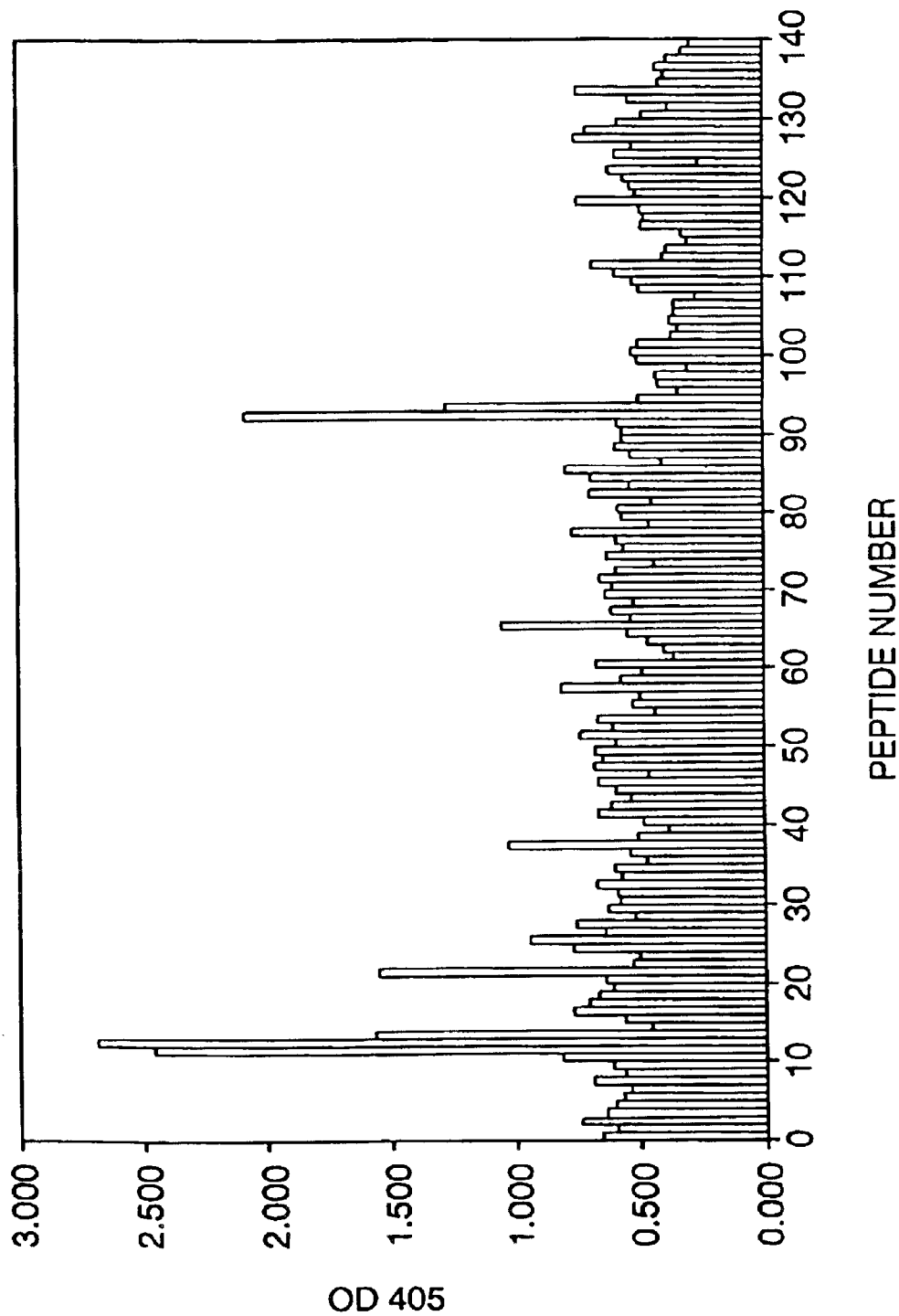
Figure 27:
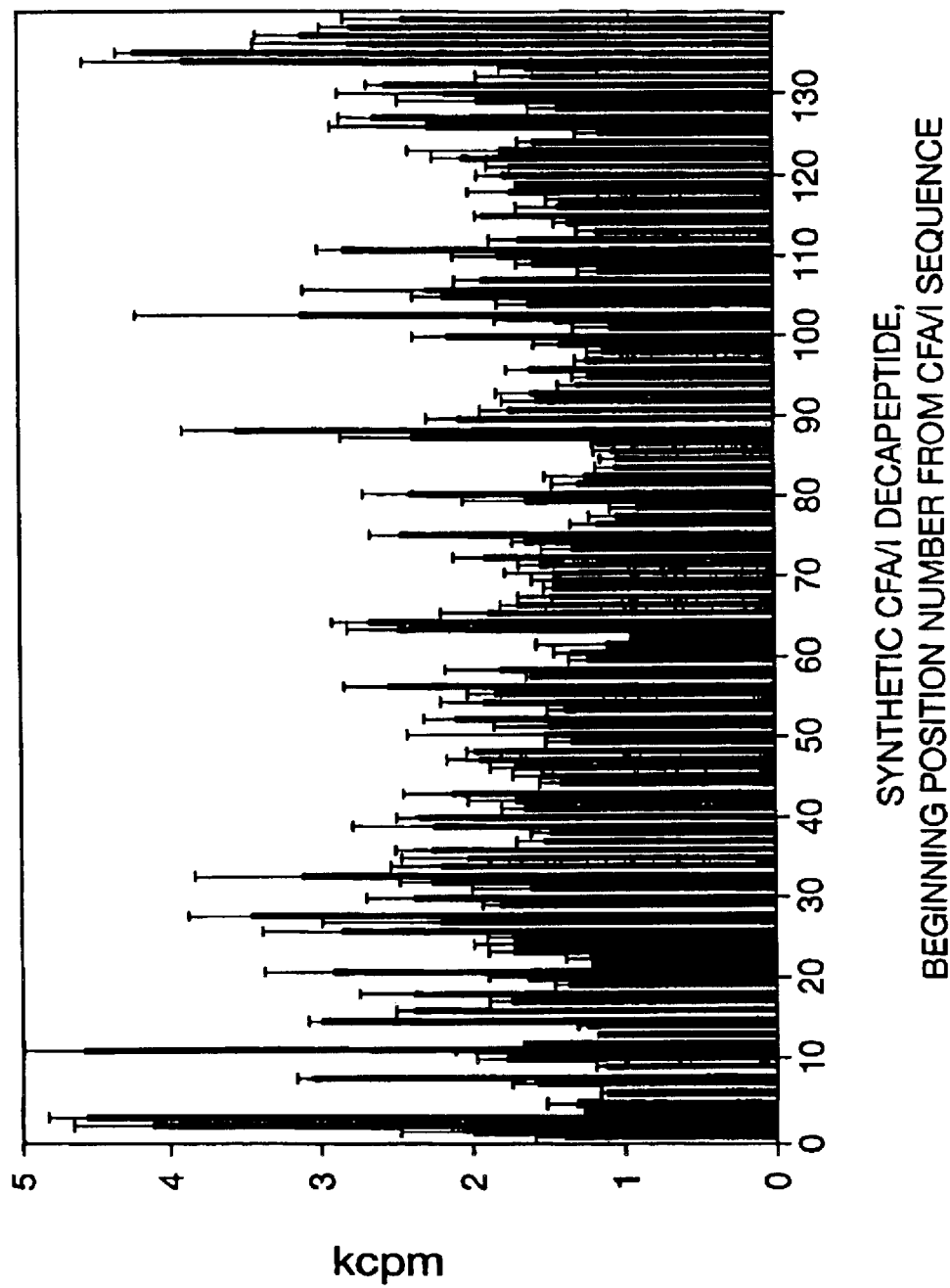
Figure 28:
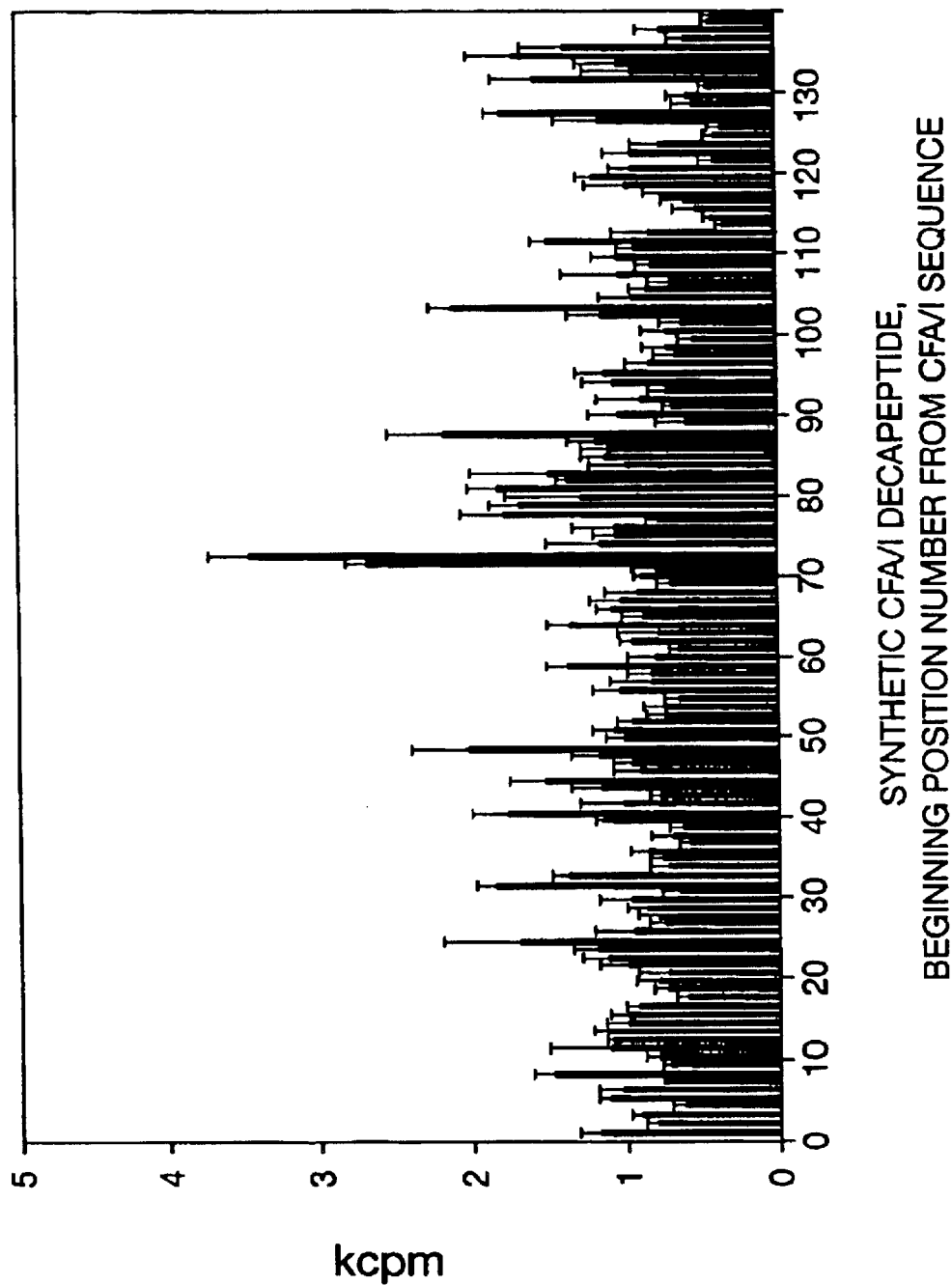
Figure 29:
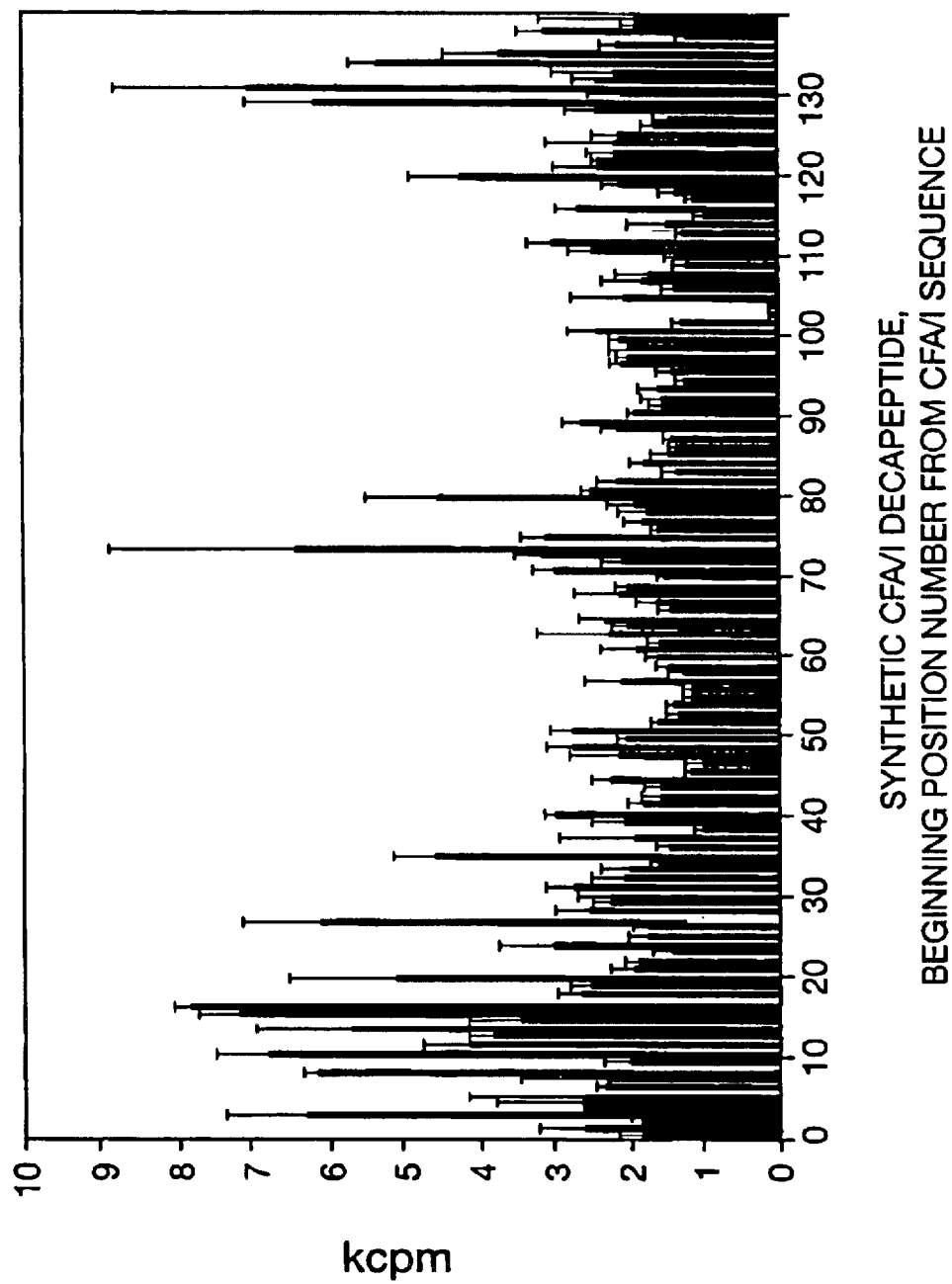
Figure 30:
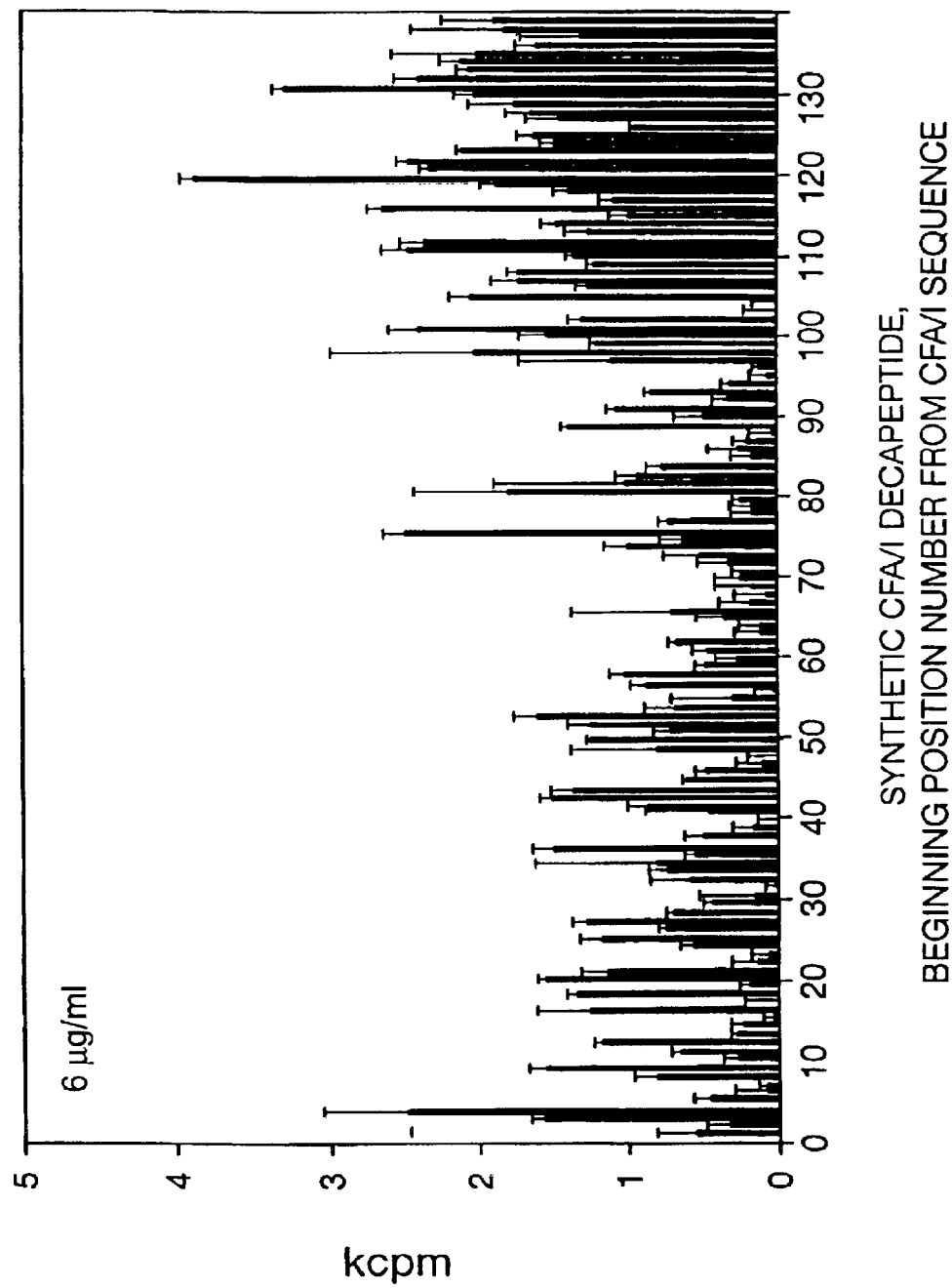
Figure 31:
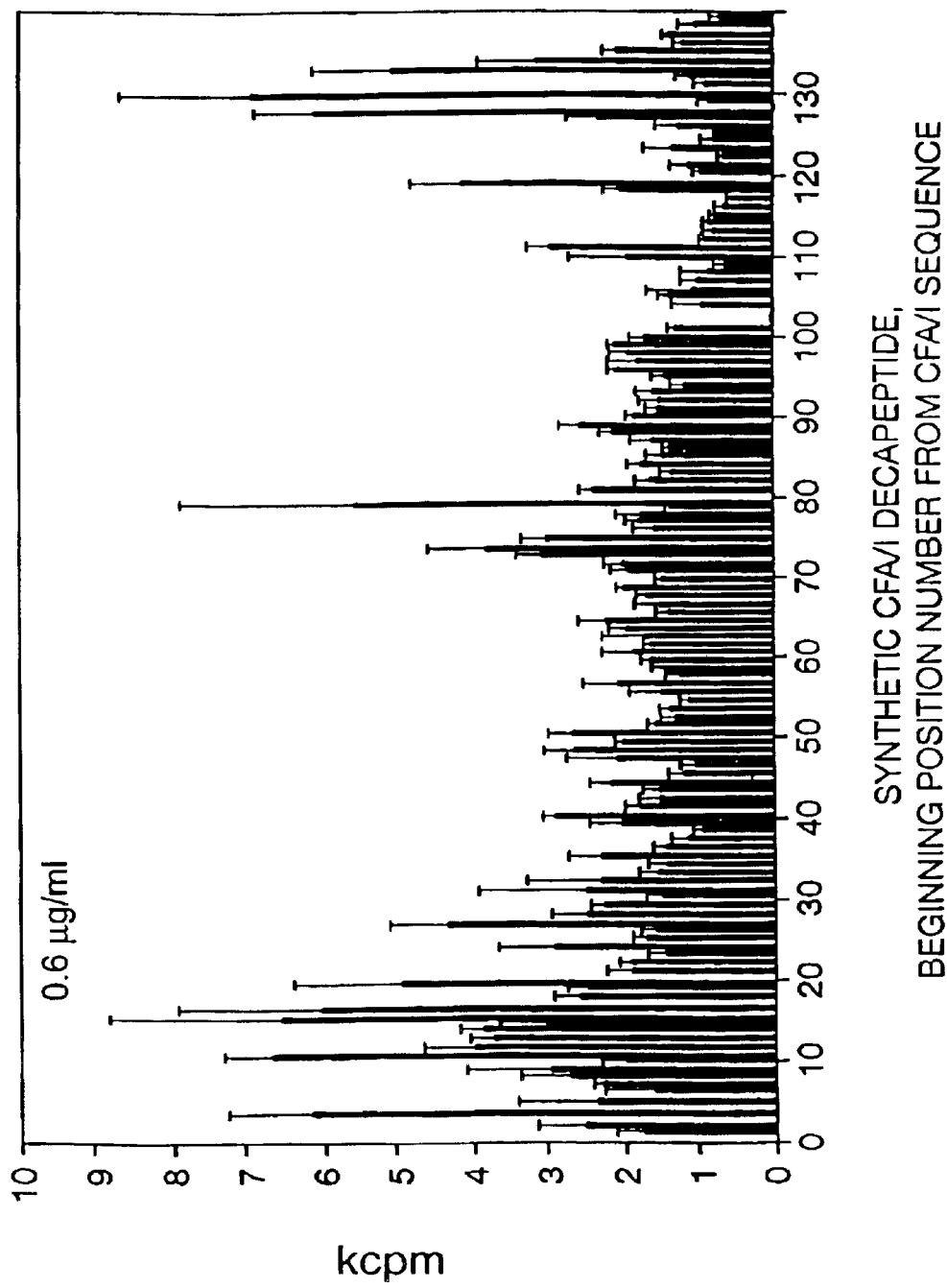
Figure 32:
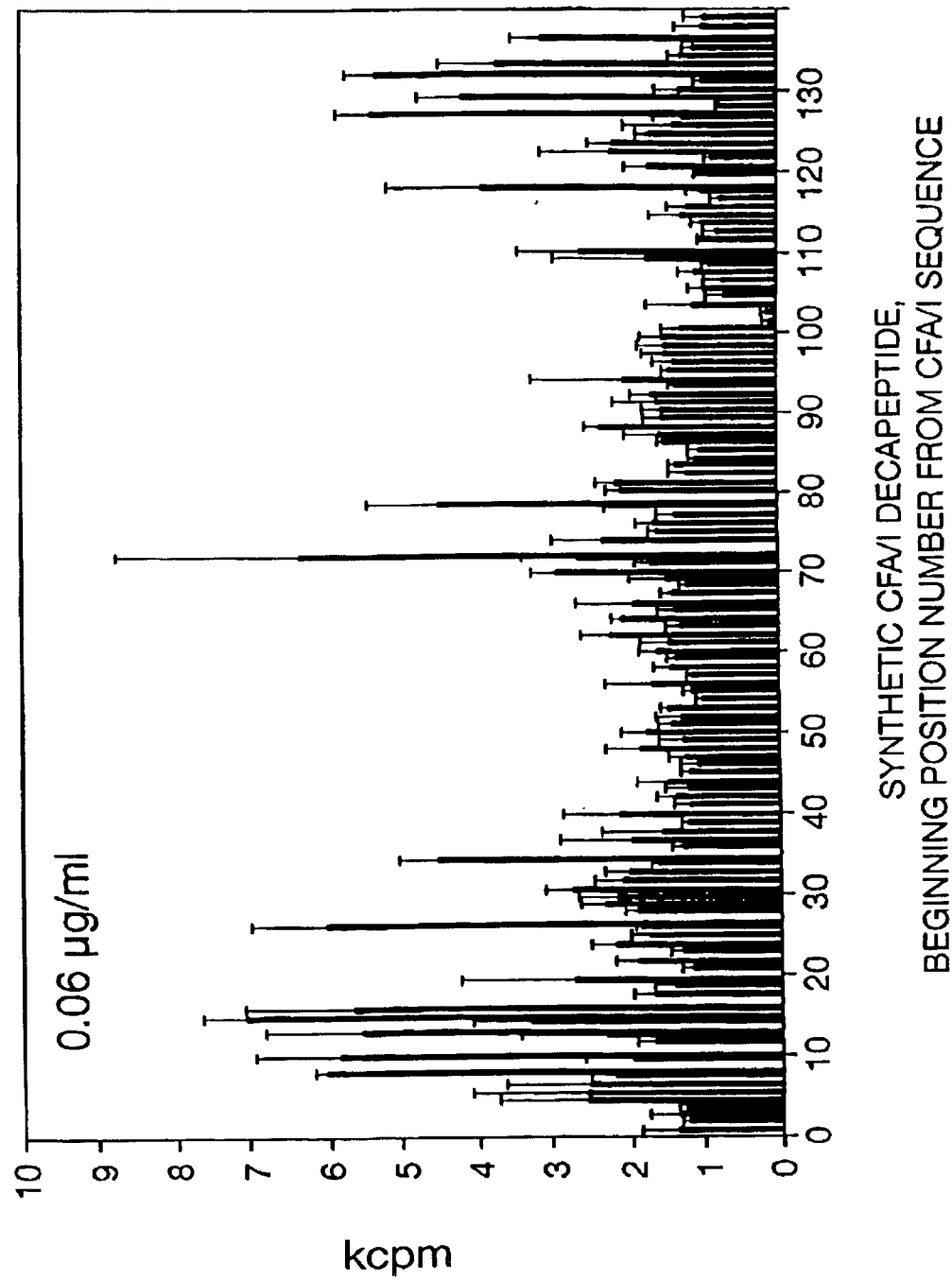
Figure 33:
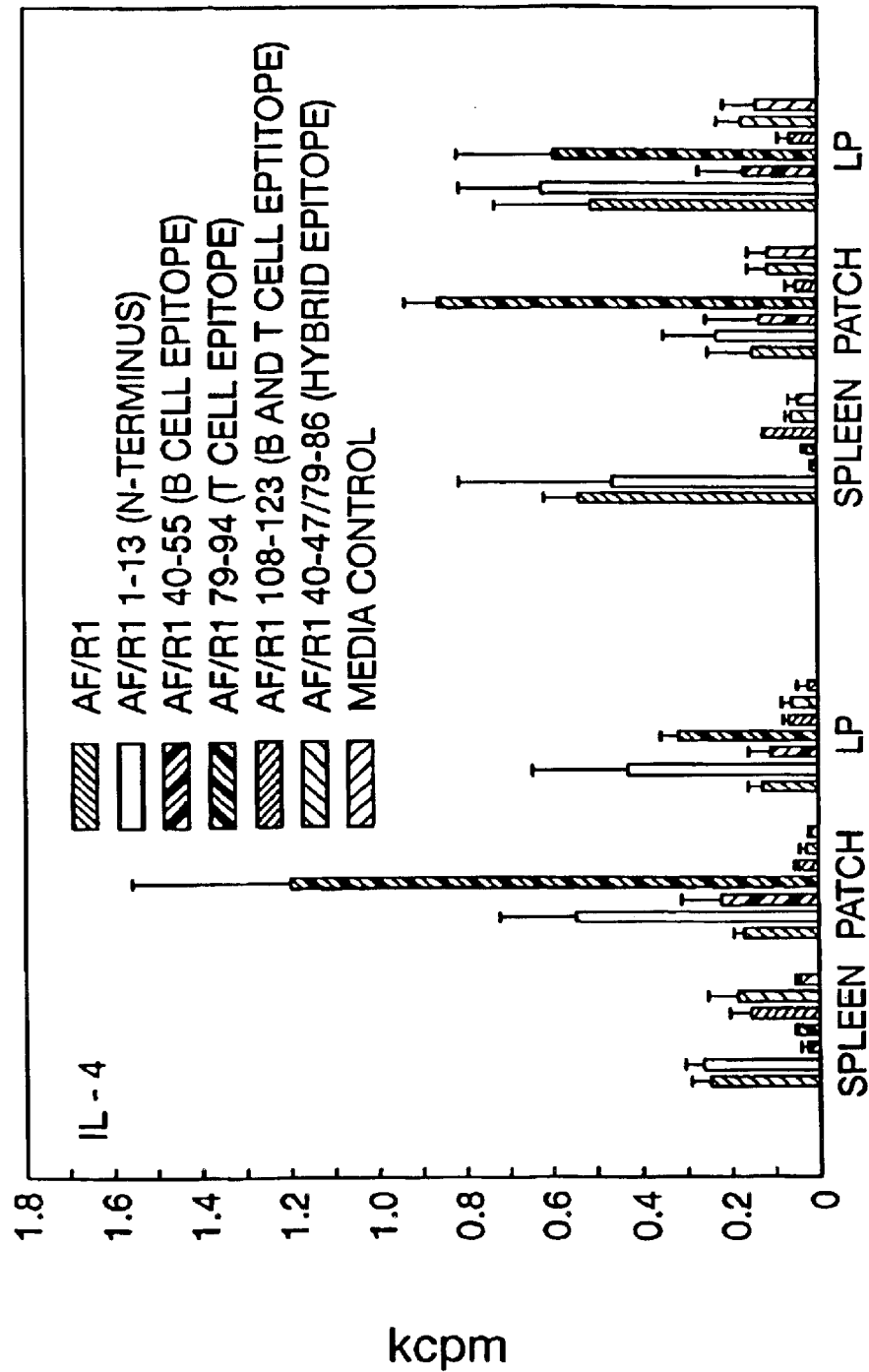
Figure 34:
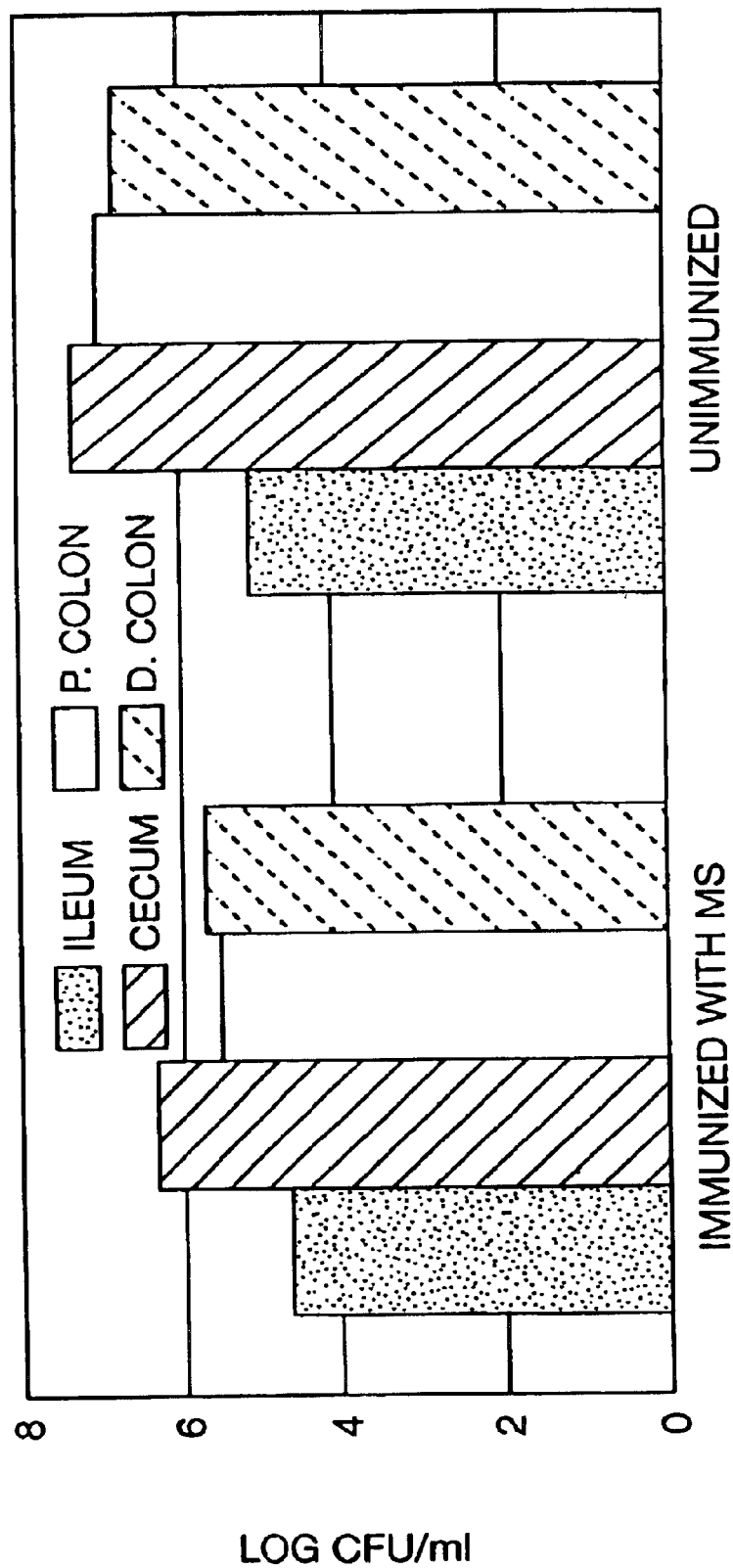
Figure 35:
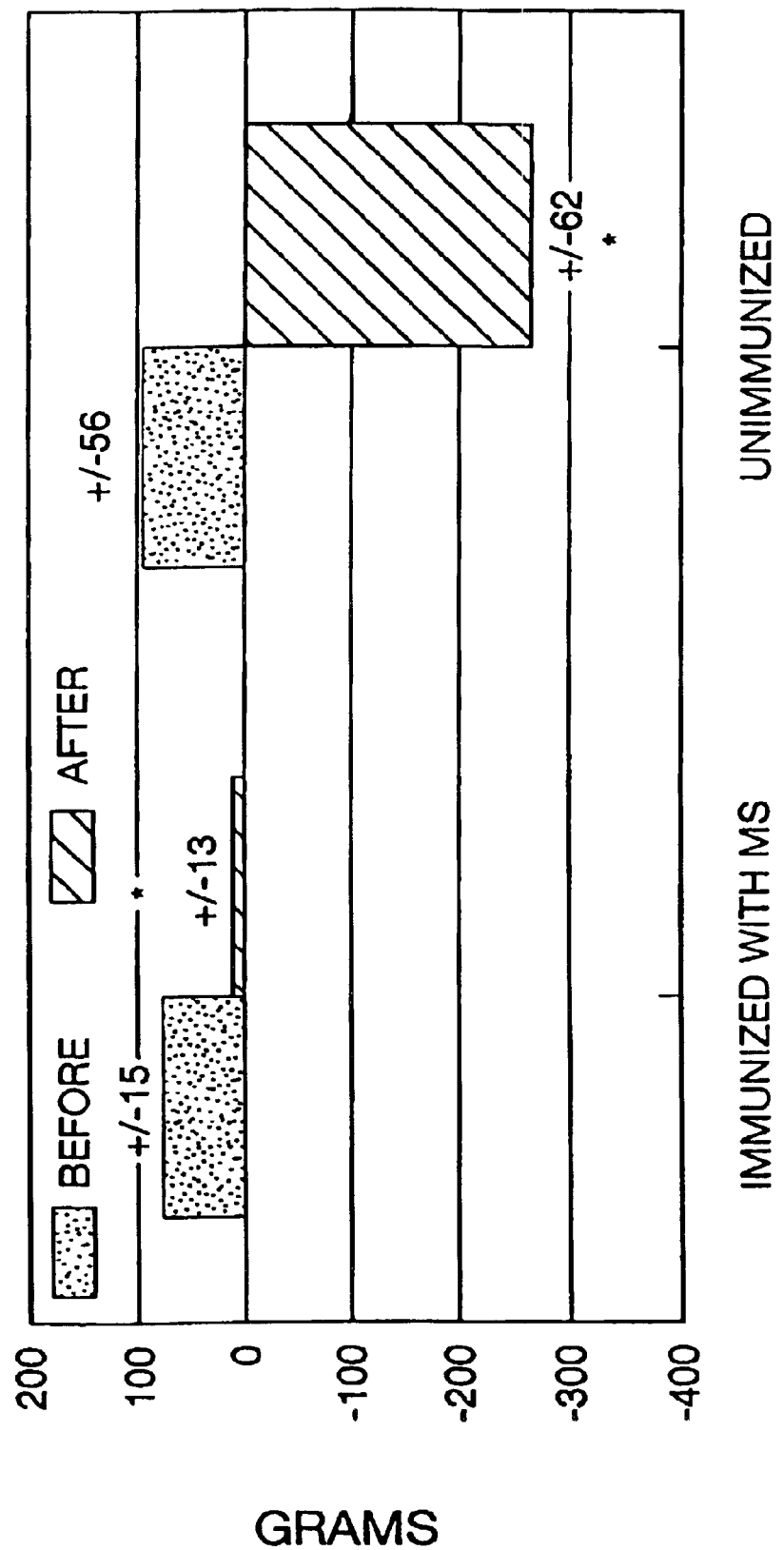
Figure 36:
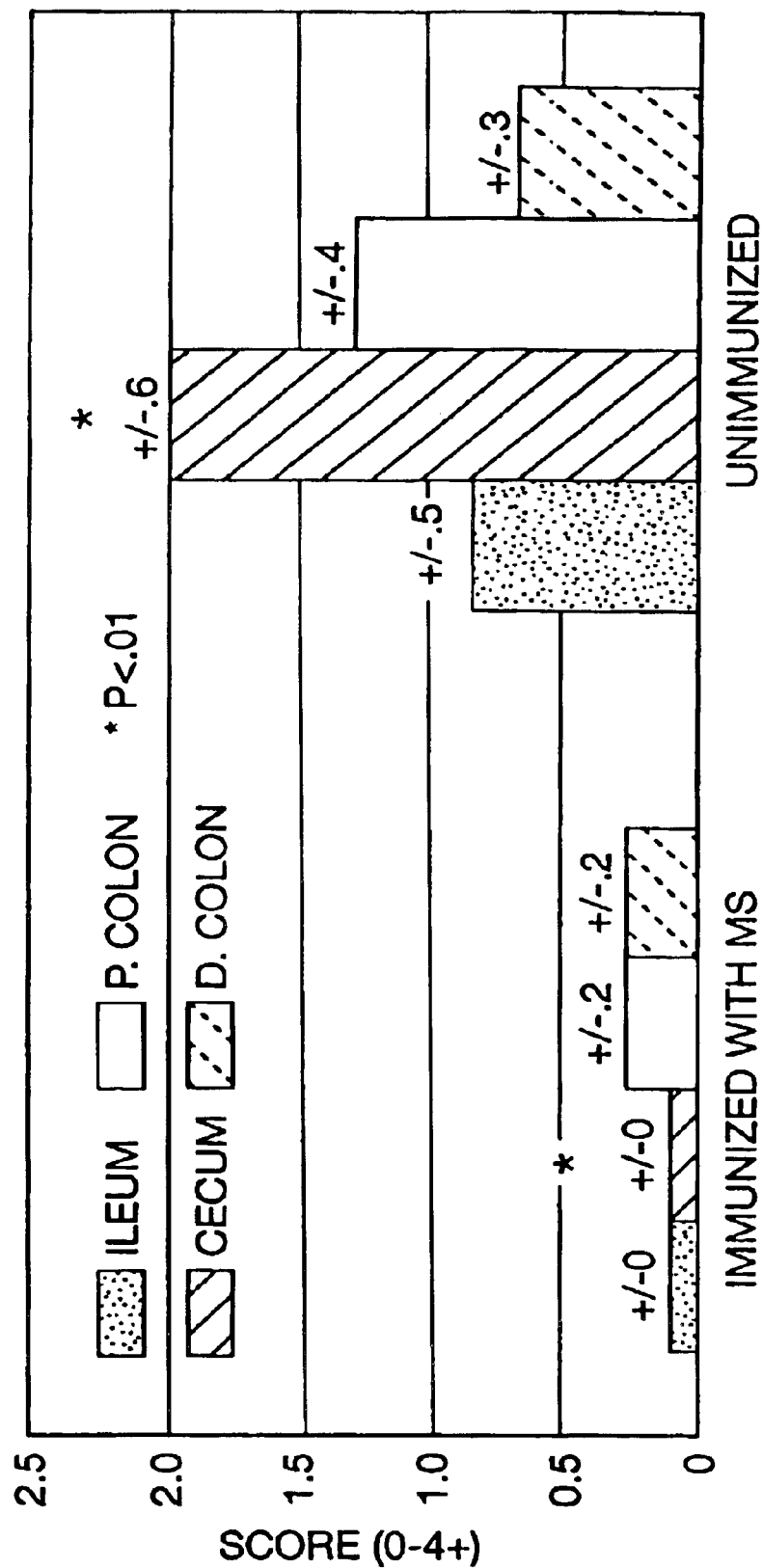
Figure 37:
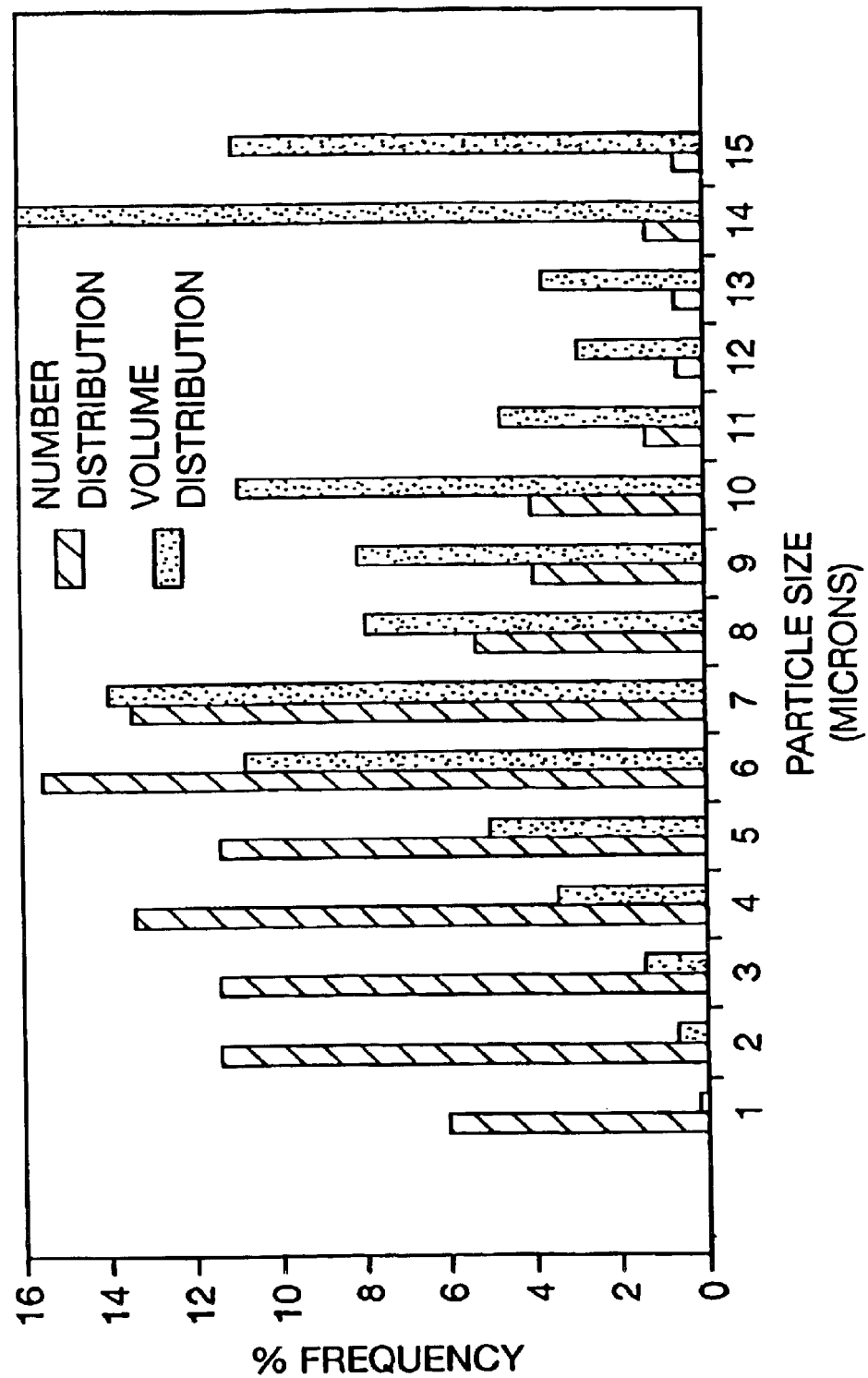
Figure 38:
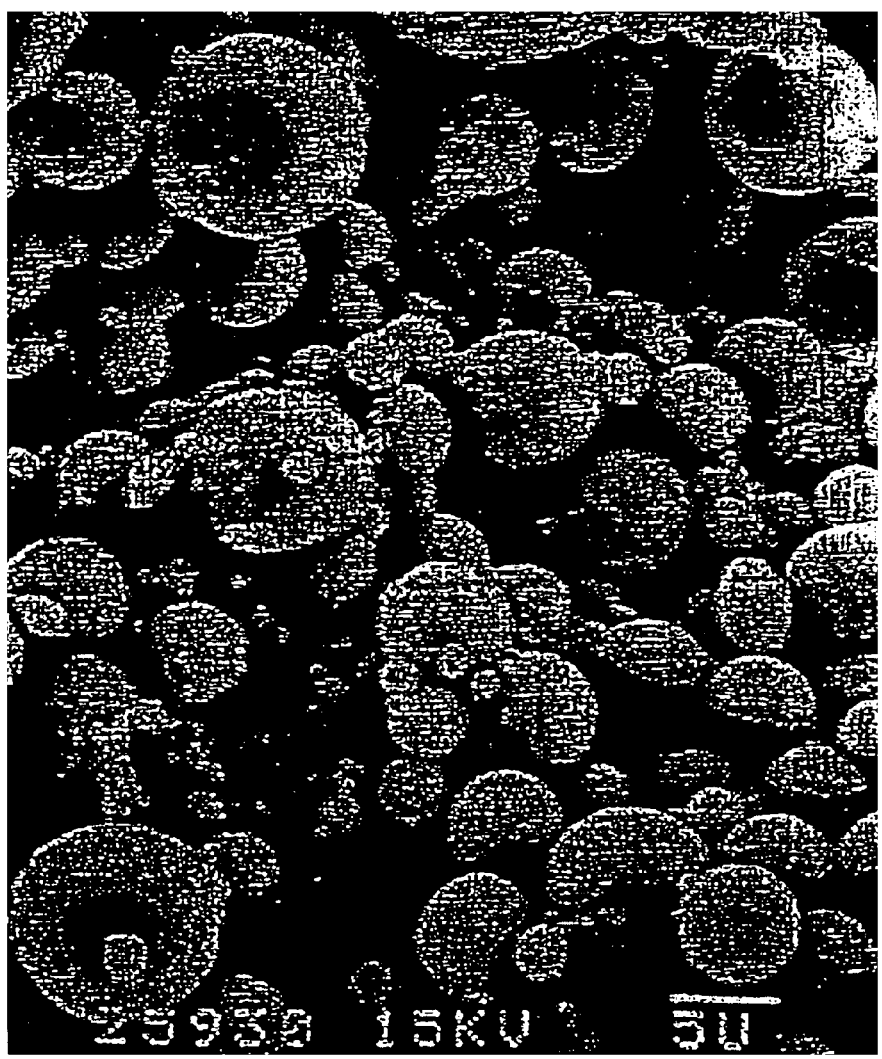
Figure 39:
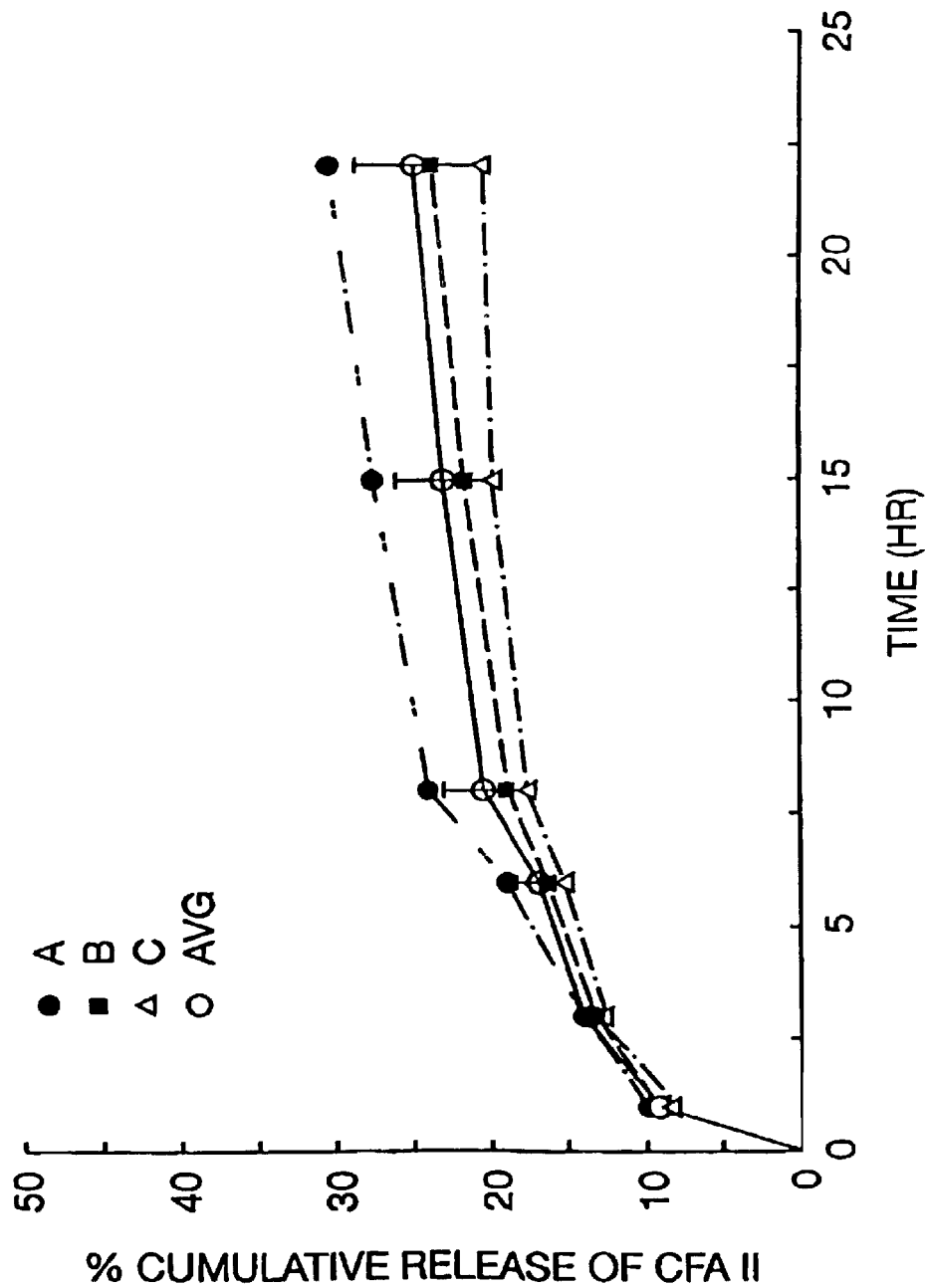
Figure 40:
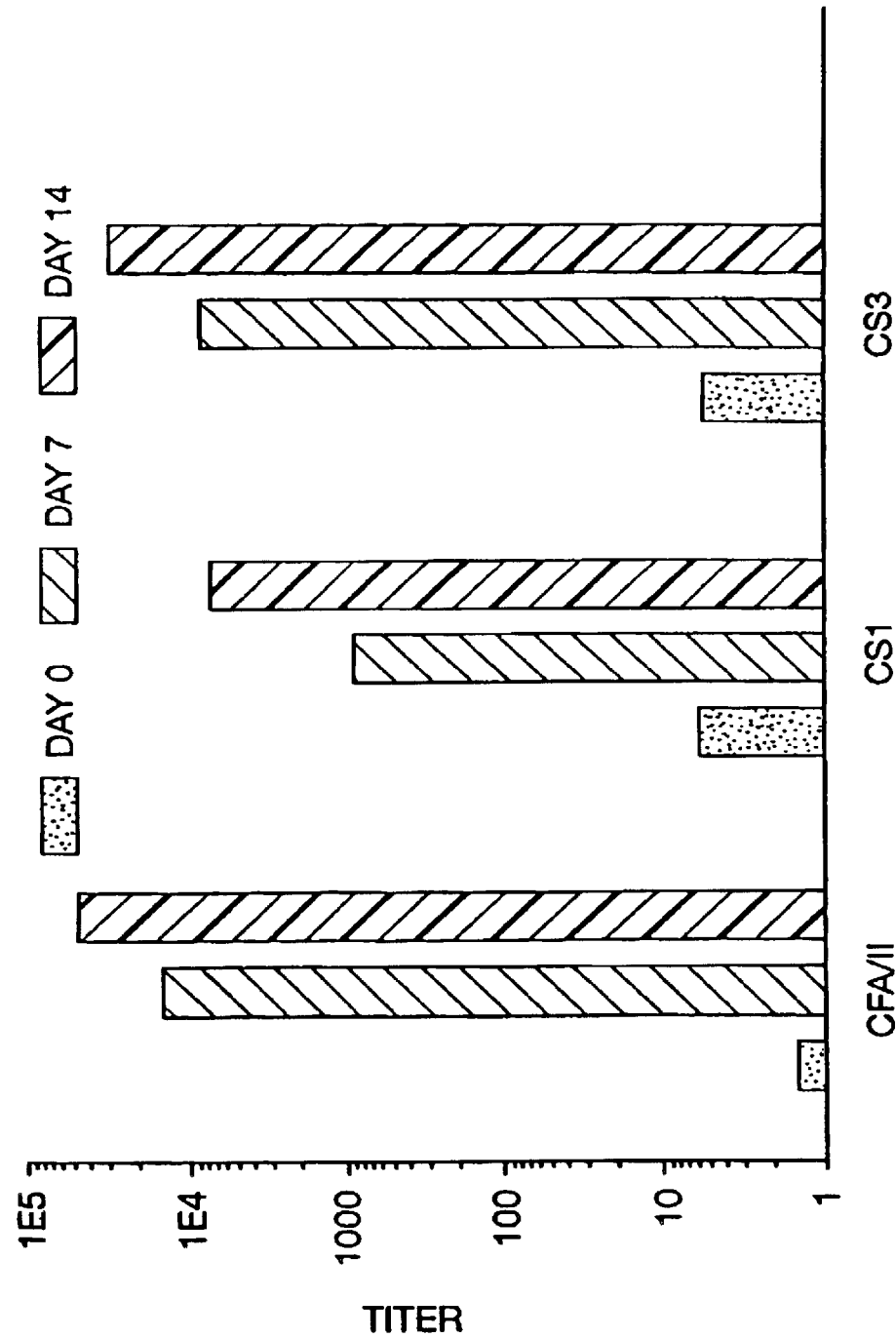
Figure 41:
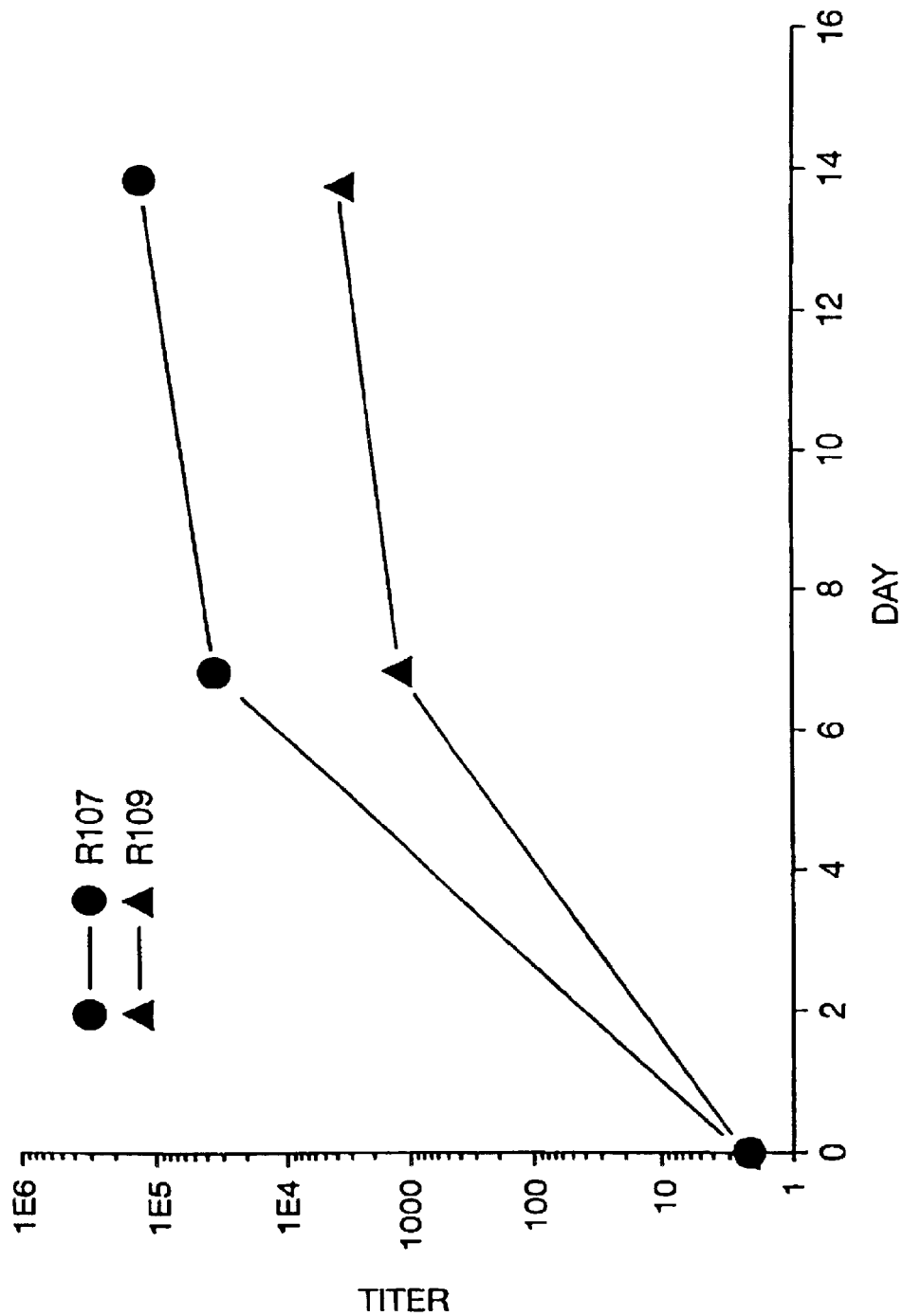
Figure 42D:
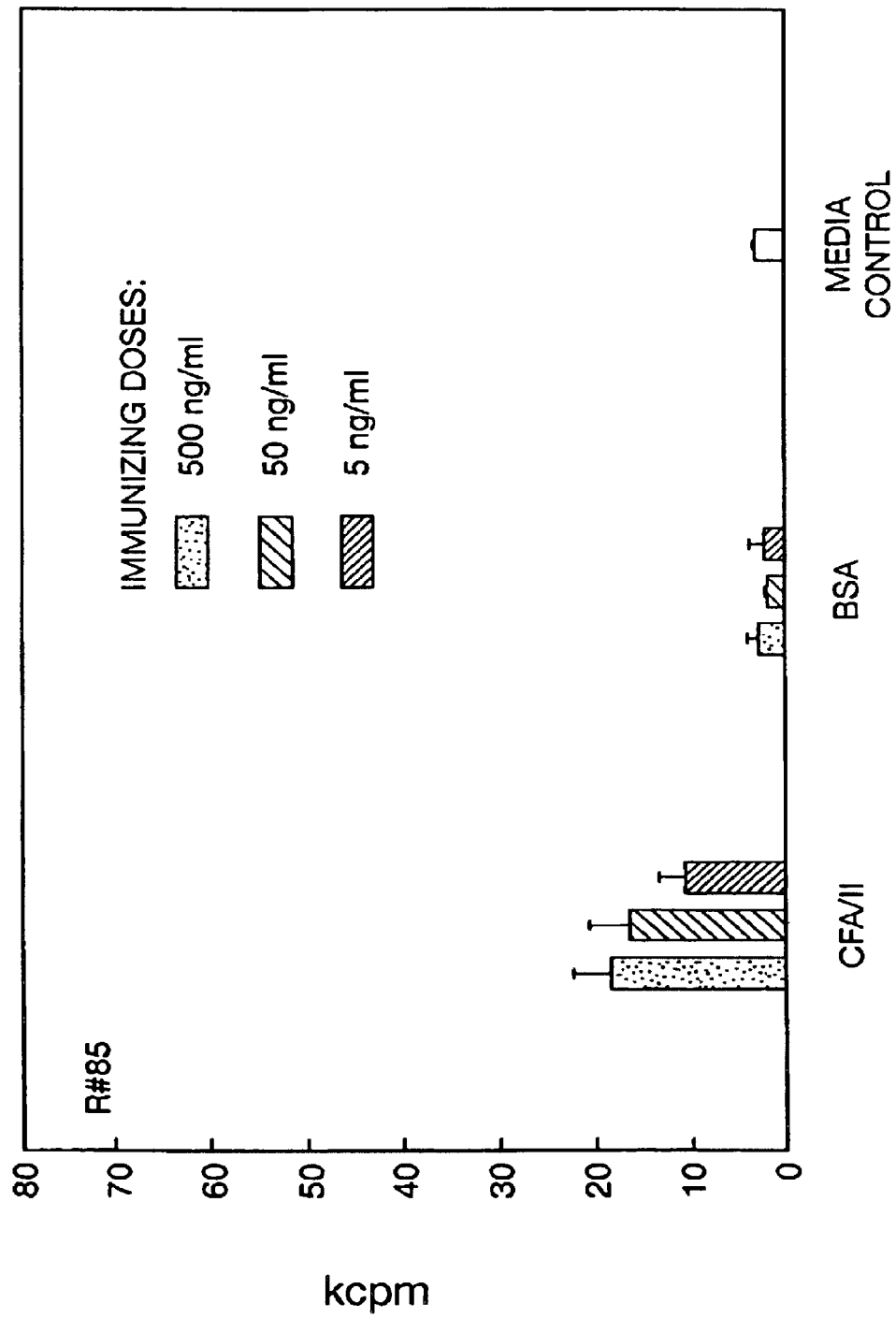
Figure 42E:
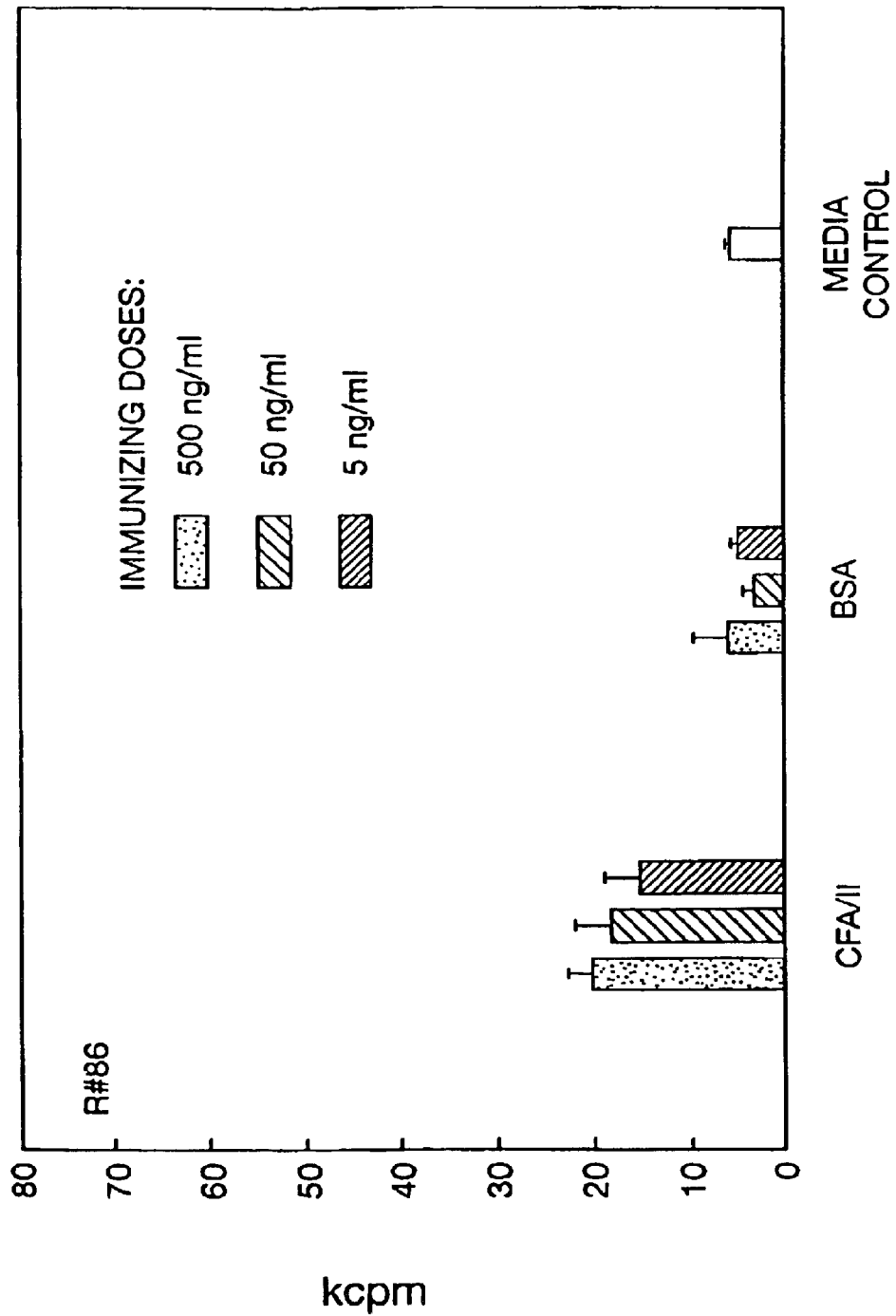
Figure 43A:
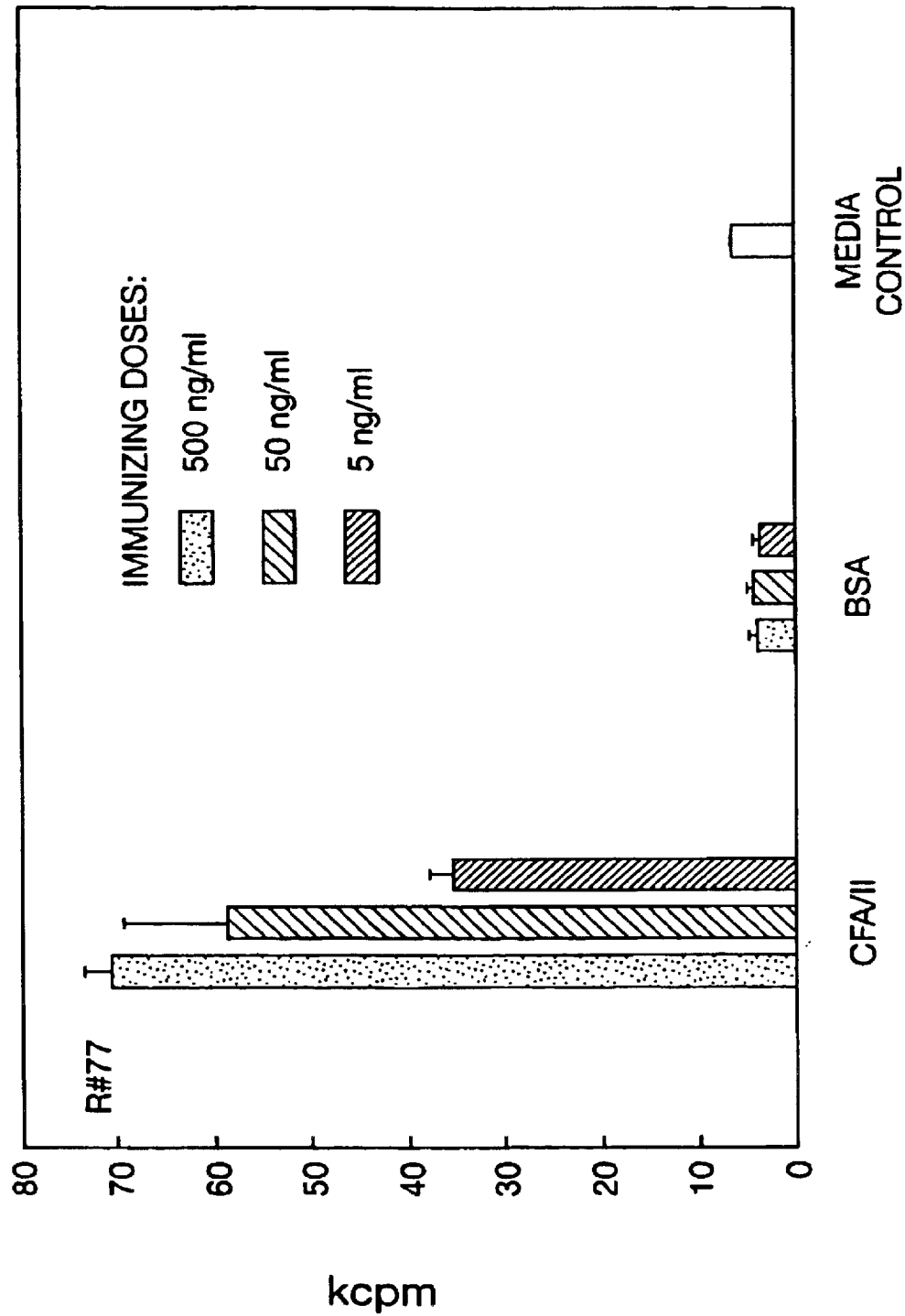
Figure 43B:
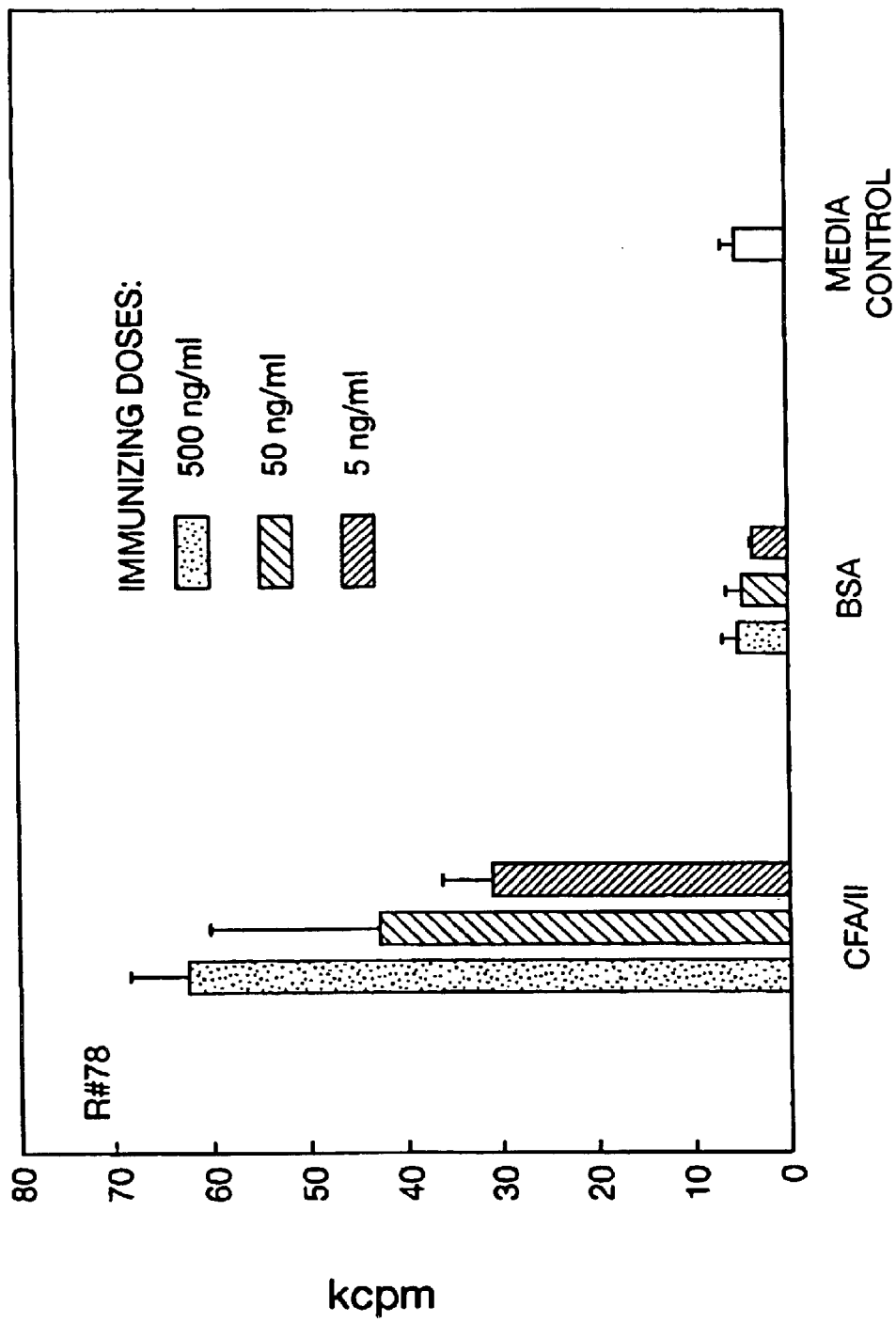
Figure 43C:
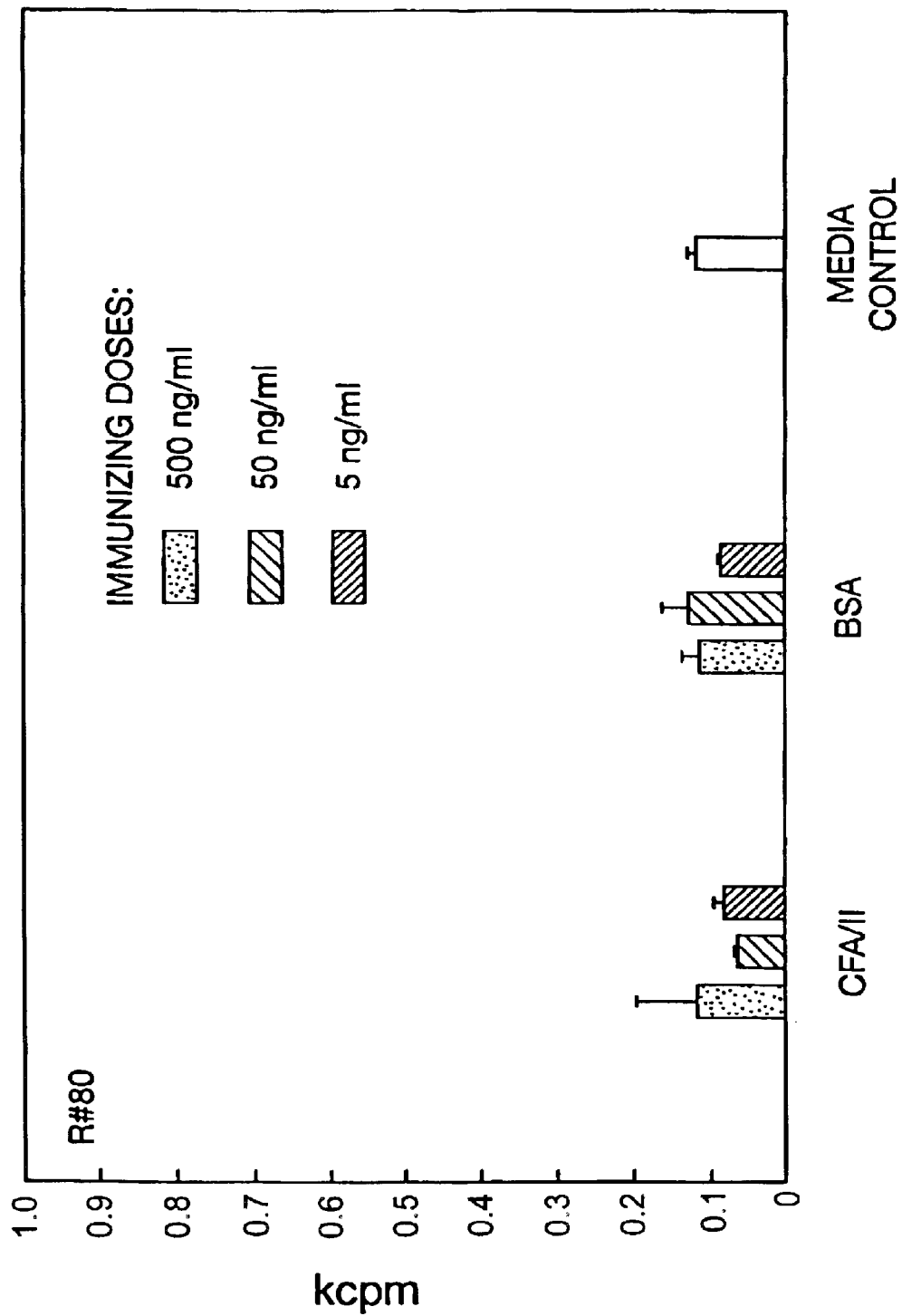
Figure 43D:
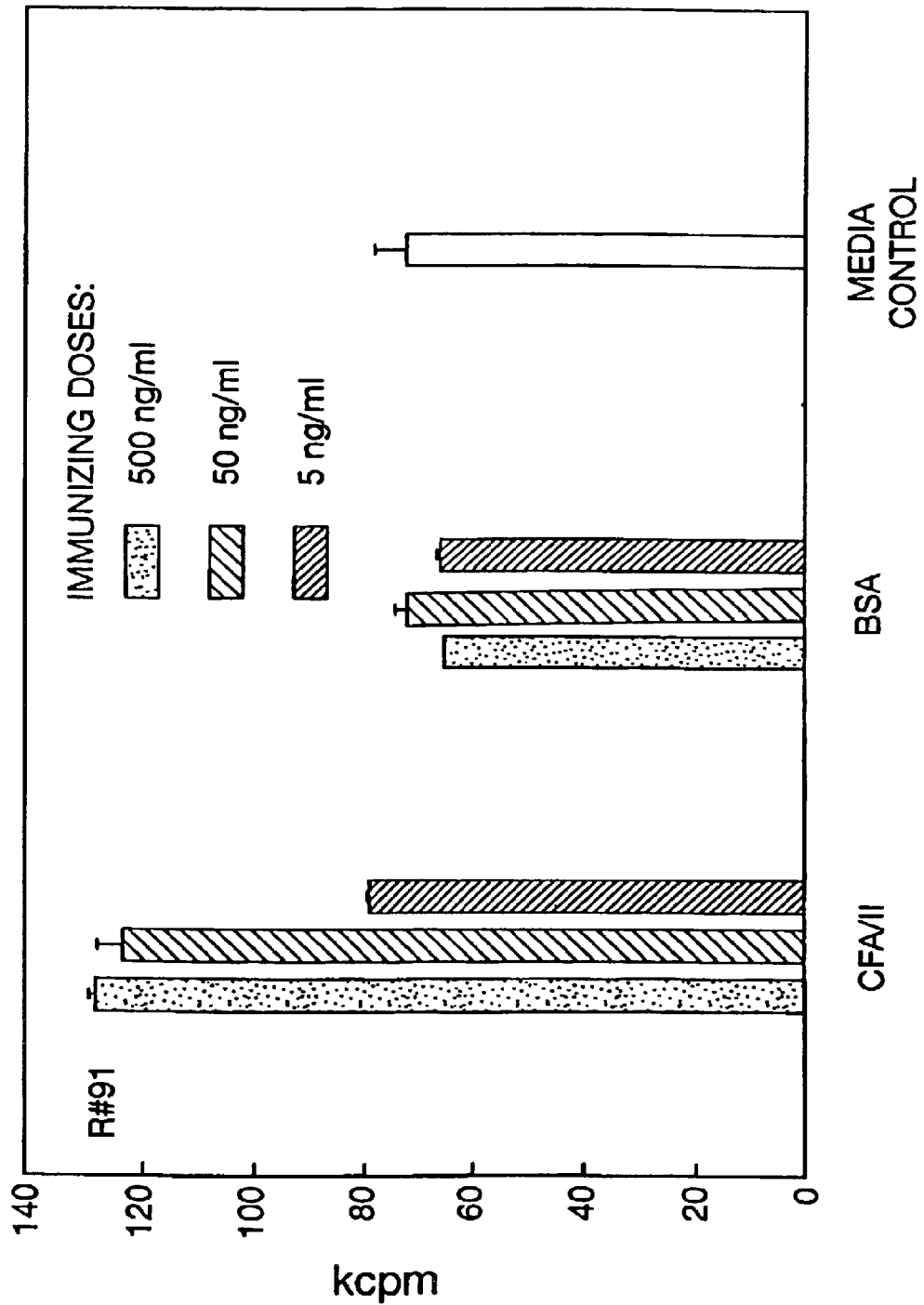
Figure 44D:
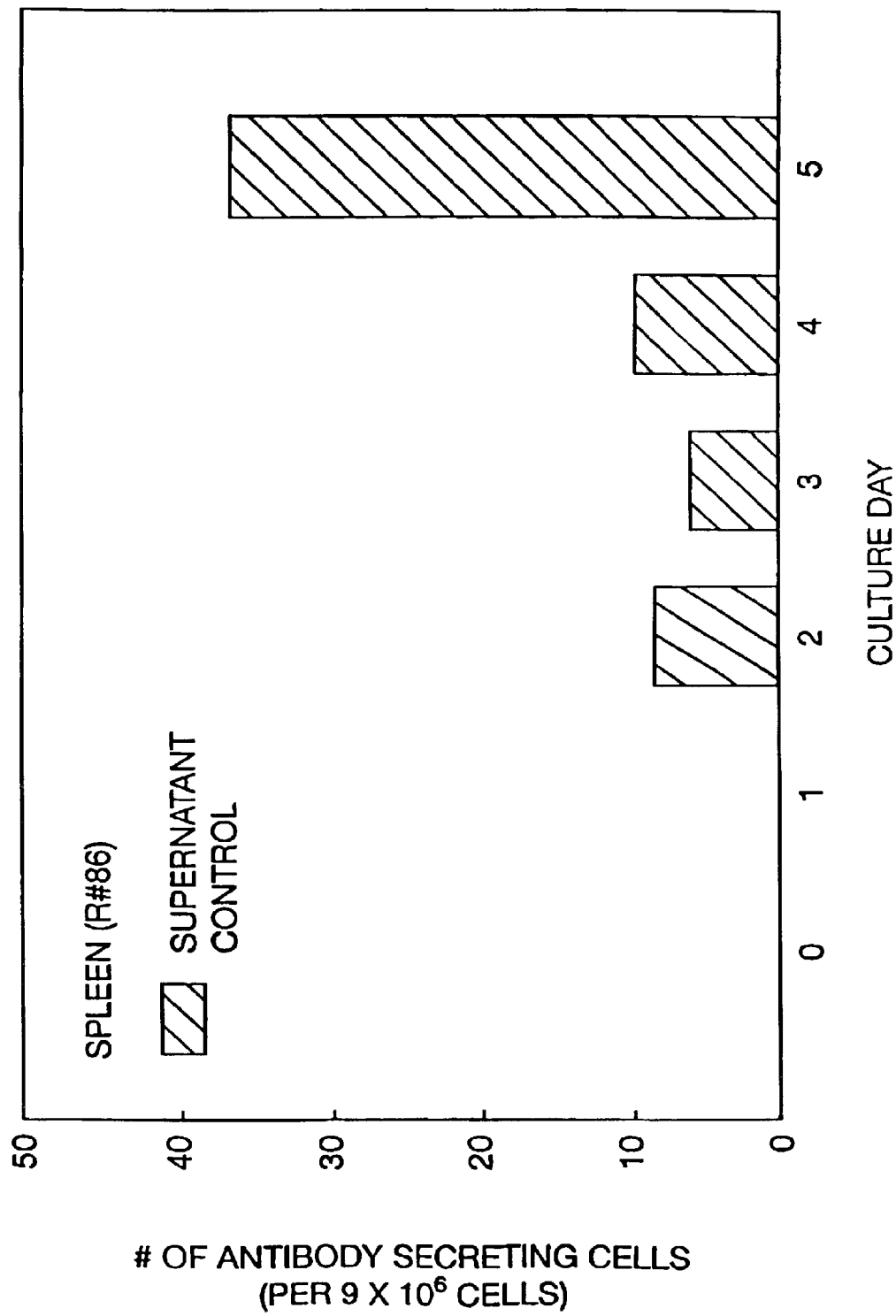
Figure 46:
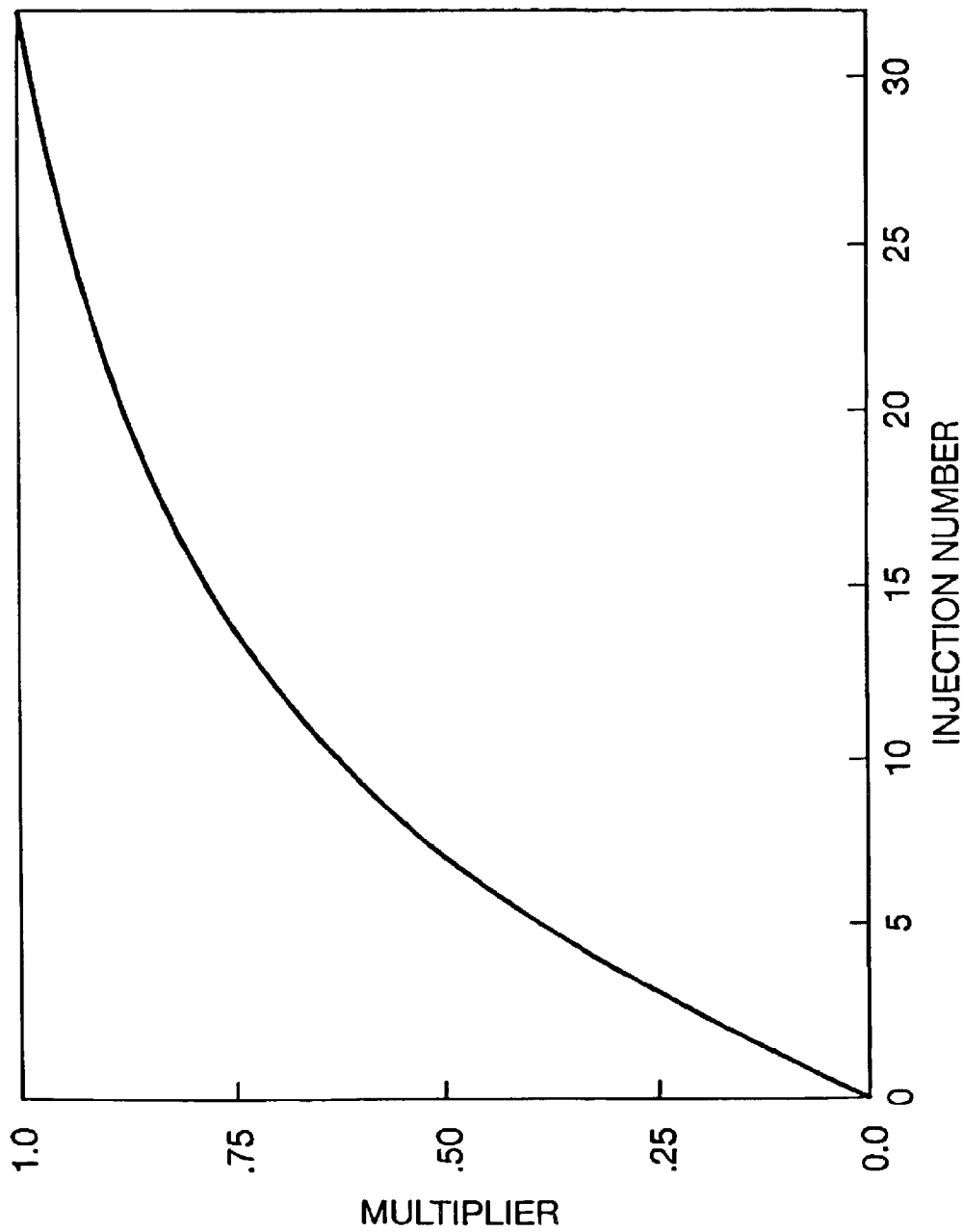
Figure 47:
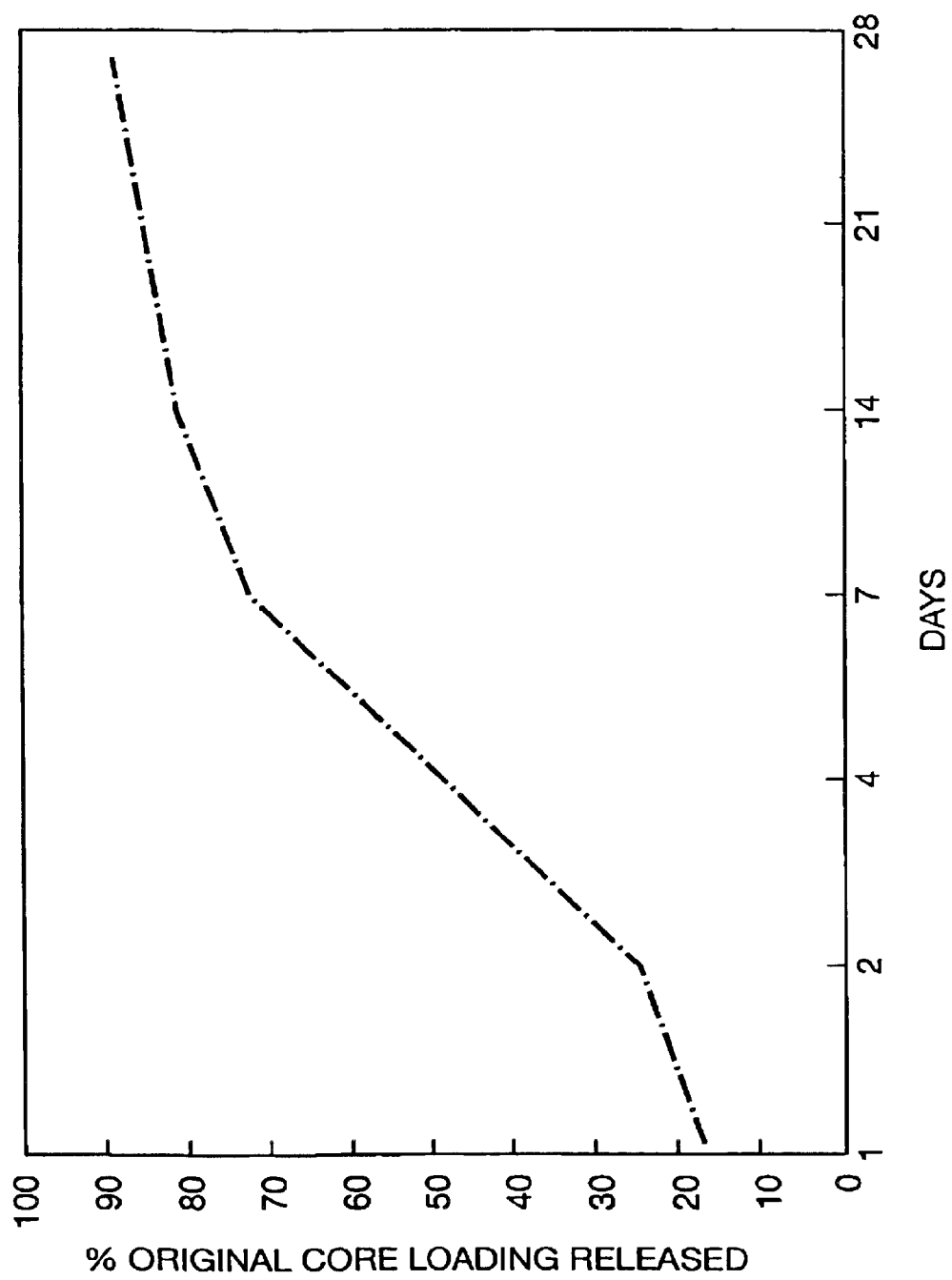
Figure 48:
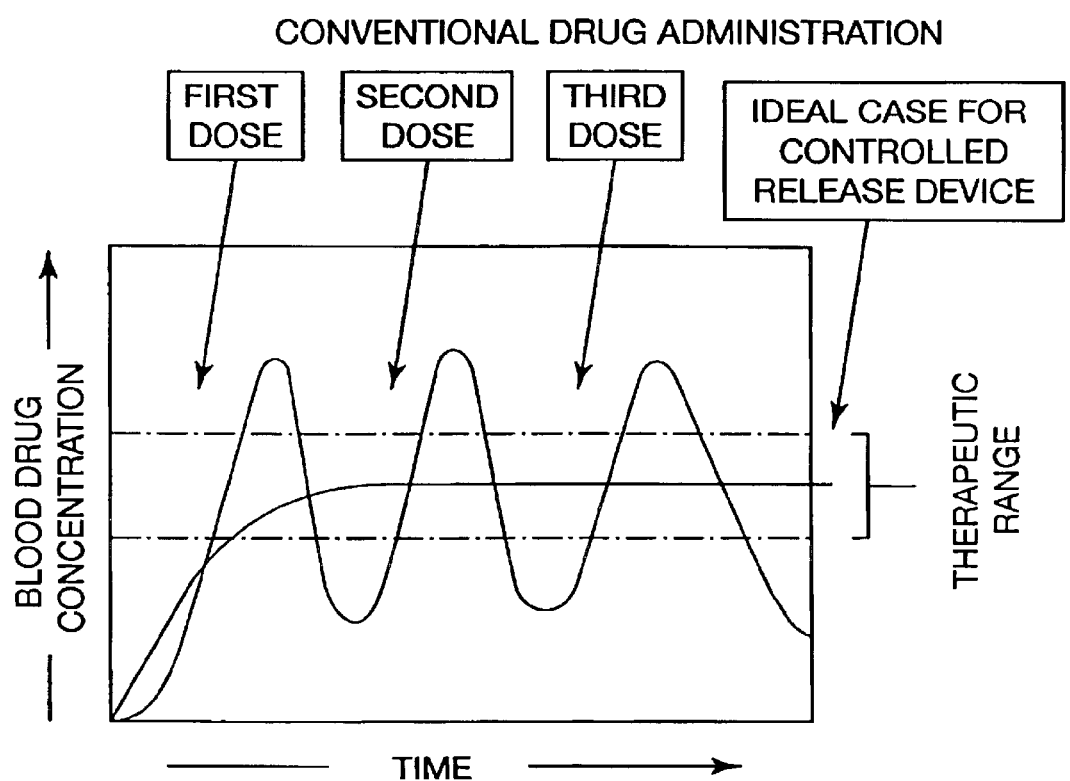
Figure 49:
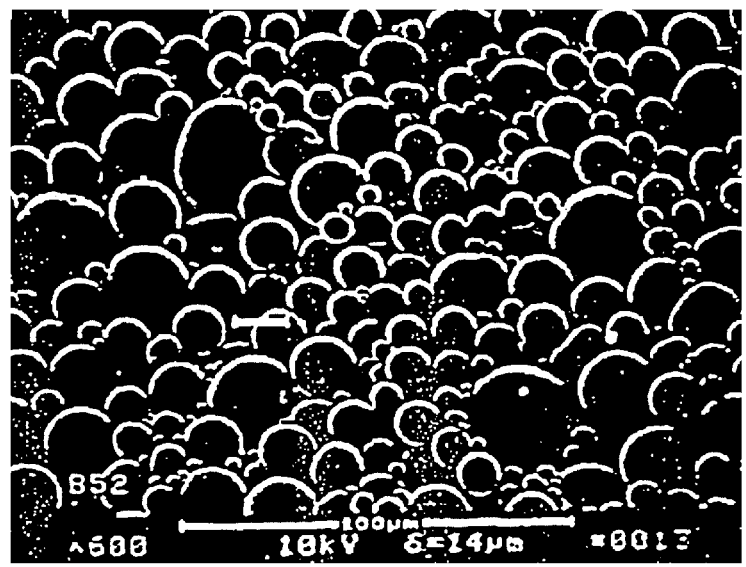
Figure 49A:
Figure 50:
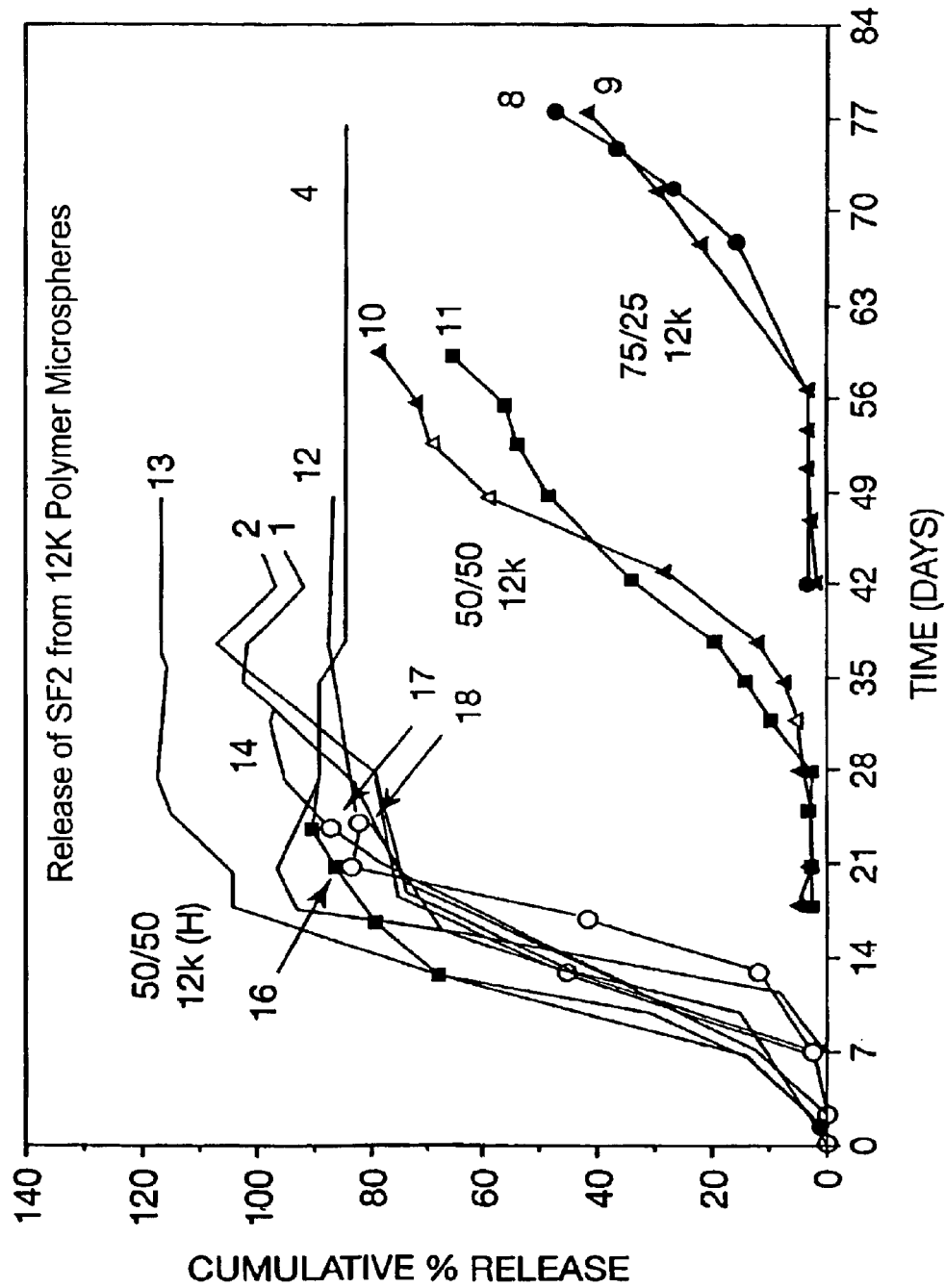
Figure 51:
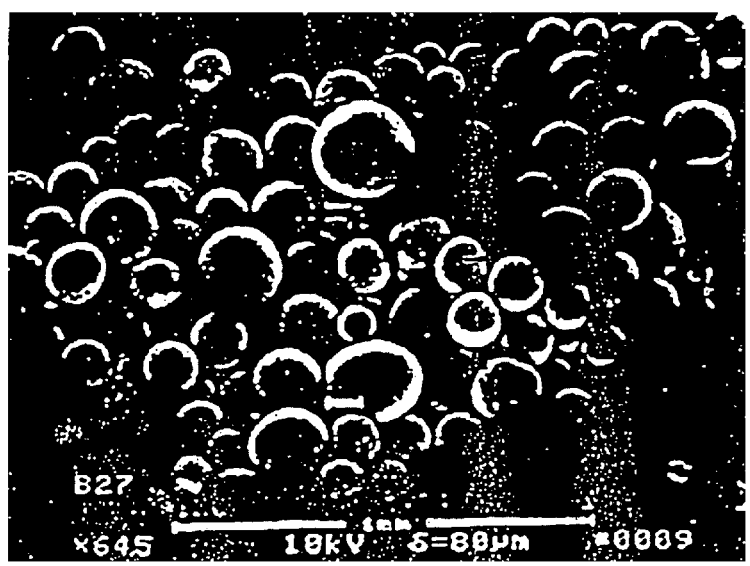
Figure 52:
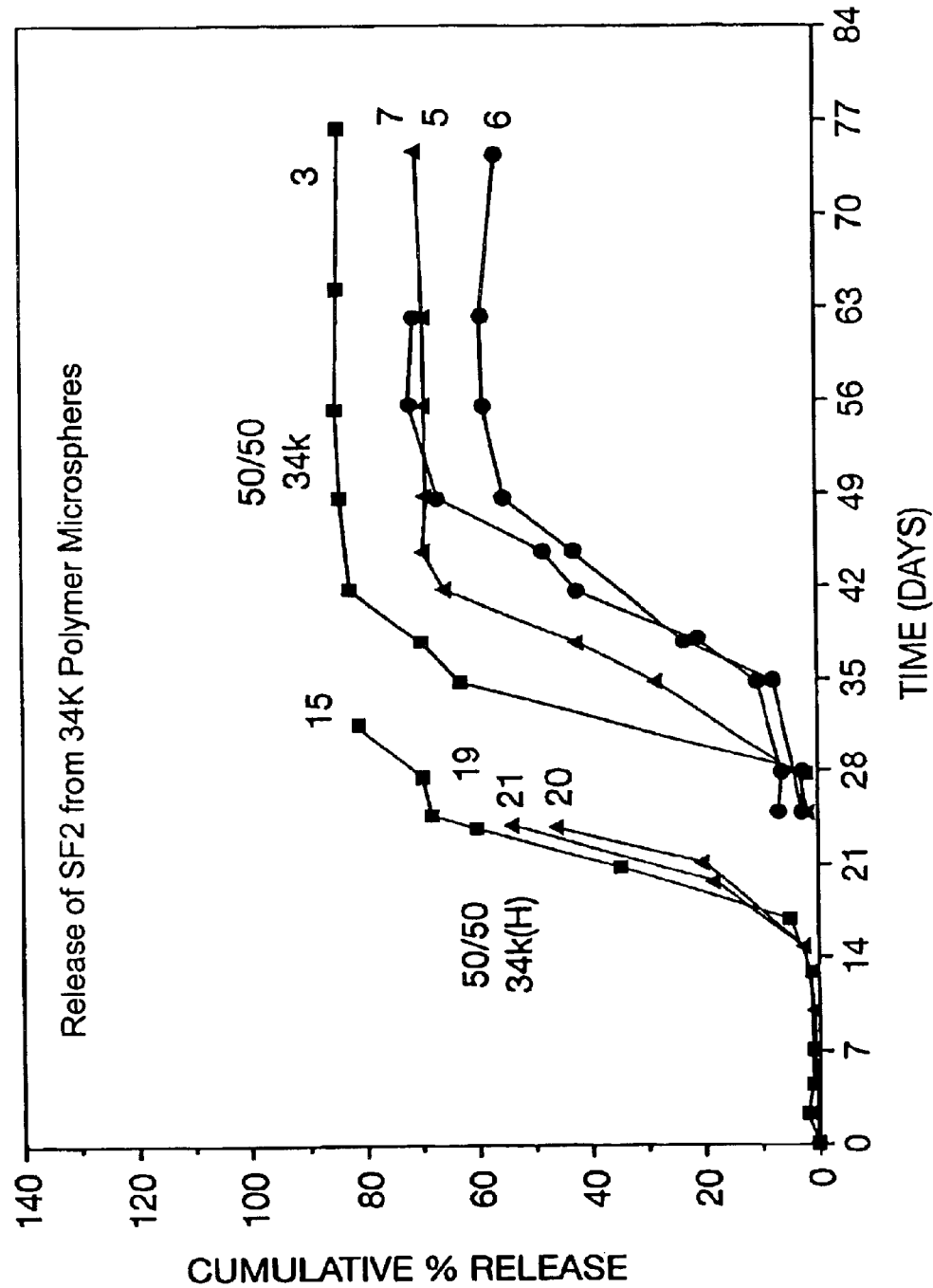
Figure 53:
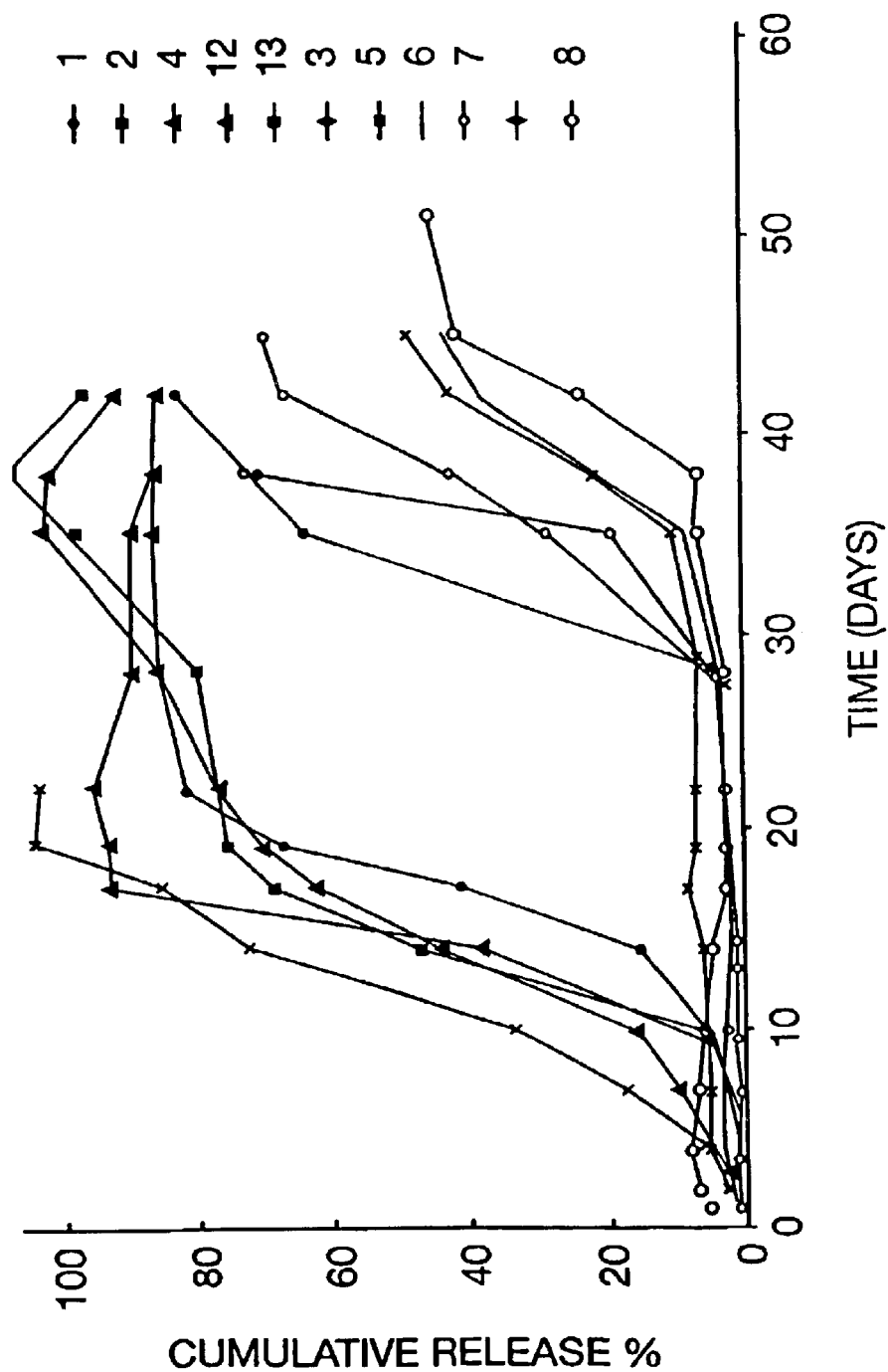
Figure 54:
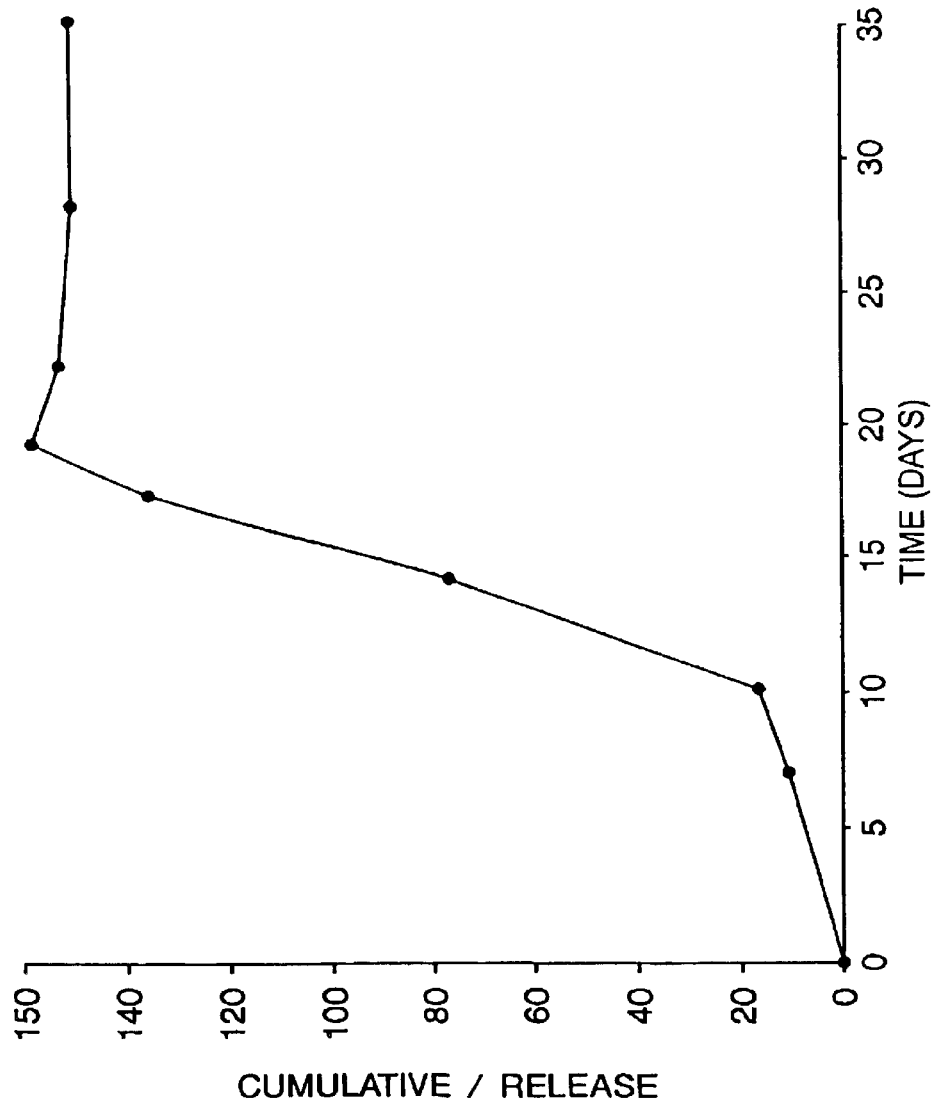

According to the present invention, a non-covalent, polyvalent complex between purified, detoxified LPS ("DLPS") derived from *E. coli* and purified outer membrane protein derived from *N. meningitidis* is provided which, when administered orally or by injection to a host subject, actively immunizes the host subject against Gram-negative bacteria and LPS-mediated pathology. Post-immune serum or plasma from the host subject, or specific polyclonal antibody purified from these fluids, can be administered to a second subject, passively immunizing the second subject against infection by Gram-negative bacteria and LPS-induced pathology.

The preferred strain of *E. coli* from which to prepare purified and detoxified LPS endotoxin is an *E. coli* J5 (Rc chemotype) strain. Native J5 LPS may be purchased from List Biological Labs, Inc., Campbell, Calif. For purification purposes it is preferred that the LPS preparation contain less than about 1% protein and less than about 1% nucleic acid. By "purified *E. coli* LPS" is meant LPS suitable for use in the invention vaccine prepared by sonicating native LPS in an alkaline solution, heating the solution at 65° C., neutralizing the cooled solution to pH 7.0, removing released fatty acids and remaining native LPS by Sephadex G-50 chromatography, and collecting the purified, detoxified DLPS. As determined in a standard rabbit pyrogenicity test, this method reduces the pyrogenicity of LPS preparations, and thus are also referred to as DLPS. An embodiment of this procedure is described in Example 1 below.

A preferred strain of meningococcus is *N. meningitidis* group B. The outer membrane protein therefrom (hereinafter "GBOMP") is prepared as described in Zollinger et al., *J. Clin. Invest.* 63:836 (1079), and U.S. Pat. No. 4,707,543 (1987), the contents of which are incorporated herein by reference. Briefly, meningococcal group B cells are warmed to about 55 to 60° C. for a brief period, and disrupted in a shearing device such as OMNIMIX, sold by DuPont Instruments (Newtown, Conn.). The shearate is centrifuged at forces up to 100,000×g to isolate in the pellet the outer membrane complex ("OMC"). The OMC is dissolved in buffered detergent, and repeatedly fractionated with ammonium sulfate so as to collect purified GBOMP precipitating at 0.5 g/ml salt. The protein is then ultrafiltered through a membrane. This preparation will be referred to herein as "purified outer membrane protein". Details of one embodiment are provided in Example 25 below.

To prepare the inventive non-covalent complex, solutions of GBOMP and J5 LPS are mixed, incubated at room temperature until complex formation has occurred (0.5 to 2 hrs.), and dialyzed repeatedly against sterile isotonic saline for 3 to 5 days in the cold. Any insoluble material is removed by centrifugation and by filtering through a membrane (e.g., 0.45 um, Amicon). The vaccine complex is preferably stored in the cold (5° C.) until use. The protein concentration of the vaccine is generally adjusted to about 1 to 3 mg/ml. In general, the ratio of GBOMP to J5 LPS in such complexes is about 1–2. Embodiments of this procedure are provided in Examples 27 and 28.

The immunogenicity of the J5 LPS-GBOMP non-covalent complex vaccine may be tested in a rabbit system. Rabbits (preferably New Zealand white rabbits, Hazelton Res. Prods., Denver Pa.) are injected intramuscularly with a sterile saline solution of the above-described complex vaccine. It is preferred that each rabbit receive a total of 3 doses of the vaccine. Control animals may be used to test variables, such as individual components of the vaccine complex and vaccine dosage. Post-immune serum is collected from the immunized rabbits, and the amount of anti-LPS antibody present in their serum determined by an ELISA test. IgG can be isolated from this post-immune serum or plasma conventionally. Two embodiments of this procedure are shown in Example 30 and Example 32, respectively.

The aforementioned ELISA test is performed in microtitre plates essentially by the method of Engvall et al., *J. Immunol.* 109: 129 (1972), with slight modifications as will be described in detail in Example 29 below. Briefly, wells are coated with poly-L-lysine (Sigma Chem. Co., St. Louis, Mo.), and coats overlaid with either J5 LPS or lipid A. Antigen (Ag)-coated plates, after blocking nonspecific binding sites with a foreign protein, for example, casein, are incubated with serial dilutions of the rabbit serum containing antibodies (Ab). A second, enzyme-tagged antibody (Ab-E) is added to form an Ag-$Ab_1$-$Ab_2$-E complex, and the presence and amount of Ag determined calorimetrically with a chromogen (p-nitrophenyl phosphate). Absorbancies may be determined automatically, for example, using the DYNAT-ECH PLATE READER produced by Dynatech (Alexandria, Va.). ELISA absorbancy units are calculated by multiplying the serum dilution by the $A_{410\ nm}$ at an absorbancy reading near the midpoint of the linear portion of the standard curve. These procedures are described in Example 30 below.

A vaccine within the present invention will be useful for active immunization of populations at risk of acquiring septic shock, such as surgery patients, the military, police and firemen. In addition, human volunteers can be safely actively immunized with this non-covalent complex, and antibodies prepared from such human hyperimmune sera can be used for passive protection of patients, including domestic and other animals, against Gram-negative bacterial infections and sepsis.

The above-described non-covalent complex is simple to prepare and is highly cost effective. Unlike the original boiled J5 LPS vaccine employed by Ziegler et al. (1982) above, the present complex is prepared from purified, detoxified J5 LPS and purified GBOMP, and is thus well defined and preferable over the prior art boiled whole bacterial cell vaccines. The J5 LPS can be prepared in large quantities suitable for clinical use.

This is the first successful use of a purified, detoxified J5 LPS in a vaccine formulation.

The following examples are intended to illustrate preferred embodiments of this invention, and are not intended to limit the scope of the invention which is defined by the specification and appended claims.

Example 24

Preparation of Purified, Detoxified J5 LPS (J5 DLPS)

The lipopolysaccharide MPS) from *E. coli* J5 (Rc chemotype, J5 LPS, lot #16A) was purchased from List Biological Laboratories Inc. (Campbell, Calif.). This preparation contained less than 1% protein and less than 1% nucleic acid as determined by absorbances at 260/280 nm.

In view of the fact that the native J5 LPS was pyrogenic in the rabbit pyrogenicity test at a dose of 0.01 ug, it was necessary to prepare a detoxified J5 LPS for use in making a J5 DLPS-GBOMP non-covalent complex vaccine.

Native *E. coli* J5 LPS (10 mg) was dissolved into 4.5 ml of 0.1 M NaOH solution, and then sonicated for 5 minutes. The slightly hazy solution was heated in a screw-capped tube at 65° C. for 2 hours. The cooled solution was neutralized with 1.0 M HCl to a pH of about 7.0. The released fatty acids and any remaining native J5 LPS were removed by chromatography on Sephadex G-50 (1.6×60 cm) using 0.01 M pyridine-acetate buffer pH 6.5 as eluant. The purified, detoxified J5 LPS (J5 DLPS) eluted shortly after the void volume. The fractions were combined and lyophilized (yield 6.5 mg)—Such preparations were pyrogen-free at the 0.5 ug level of DLPS (see Example 28).

Example 25

Purification of *N. meningitidis* Group B Outer Membrane Protein

*Neisseria meningitidis* GBOMP was prepared by methods described previously. See Zollinger et al., *J. Clin. Invest*. 63: 836–48 (1979), and U.S. Pat. No. 4,707,543, the respective contents of which are incorporated herein by reference. Briefly, meningococcal group-B cells from strain #8529 (collection of Walter Reed Army Institute of Research, Washington, D.C.) from a 15 liter culture, collected by continuous centrifugation (135 g, wet wt.), were suspended in 300 ml buffer containing 0.05 M Trischloride, 0.15 M NaCl and 0.01 M EDTA, pH 7.4 and warmed at 56° C. for 30 minutes. The suspension, cooled to room temperature, was sheared in an Omnimixer (DuPont Instruments, Newton, Conn.) at full speed for 3 minutes and centrifuged at 30,000×g for 20 minutes. The pellets were re-extracted in the same way and the supernates were combined. The combined supernate was centrifuged at 25,000×g for 15 minutes. The resulting supernate was centrifuged at 100,000×g for 1 hour, and the pelleted outer membrane complex (OMC) was suspended in about 150 ml of distilled water by magnetic stirring. The suspension was centrifuged at 10,000×g for 15 minutes and the resulting supernate was centrifuged at 100,000×g for 1 hour. The pelleted OMC was suspended in about 75 ml of distilled water and to this suspension was added 75 ml of 2×TEEN buffer (2% Empigen BB, 0.35 M NaCl, 0.021 M EDTA, 0.10 M Tris-HCl, pH 8.0). The mixture was magnetically stirred for 1 h. Solid ammonium sulfate (500 g/L) was added to the OMC suspension, and the mixture was stirred until all the -ammonium sulfate was dissolved. The suspension was allowed to stand at room temperature for 1 hour and then centrifuged at 20,000×g for 20 minutes. The precipitated protein collected at the top of the tube was recovered by drawing off liquid from the bottom. The protein was redissolved in 150 ml of TEEN buffer (1% Empigen BB, 0.15 M NaCl, 0.01 M EDTA and 0.05 M Tris-HCl, pH 8.0). The precipitation was repeated two more times using 600 g/L of ammonium sulfate. The final precipitate was dissolved in TEEN buffer at 1–2 mg/ml and dialyzed against 4 changes of 20 volumes of TEEN buffer (containing 0.1% Empigen BB) to remove the ammonium sulfate. This outer membrane preparation was combined with more OMP extracted from the pelleted cells using detergent as follows.

The pelleted cells were suspended in about an equal volume of 1 M sodium acetate buffer pH 4.9 and 3 volumes of distilled water were added. To this mixture was added 5 volumes of a solution containing 6% Empigen BB in 1.0 M calcium chloride. The mixture was stirred at room temperature for 1 h., after which ethanol was added to a concentration of 20% volume/volume. The resulting precipitate was removed by centrifugation at about 20,000×g for 10 minutes. The pellets were discarded and the supernatant was brought to 45% ethanol volume/volume. The precipitated proteins were collected by centrifugation at about 20,000×g for.10 minutes and dissolved in TEEN buffer. Any insoluble material was removed by centrifugation at about 20,000×g for 10 minutes. The protein was further purified to remove lipopolysaccharides, capsular polysaccharide and nucleic acid by ammonium sulfate precipitation three times as described above.

The GBOMP prepared by the two sequential methods were combined and concentrated by ultrafiltration on a PM-10 membrane. The final protein concentration was 3.67 mg/ml.

Example 26

Preparation of J5 DLPS-NMGBOMP Non-covalent Complex

*N. meningitidis* group B OMP (NMGBOMP) solution 1.5 ml (3.67 mg/ml, Example 25) was added to 5.0 ml of a solution (0.8 mg/ml) of J5 DLPS in .0.9% NaCl. The mixture was kept for 1 hour at room temperature and was then dialyzed against 100 volumes of sterile 0.9% NaCl at 5° C. for 48 hours. The dialysis buffer was changed and dialysis continued at 5° C. for another 72 hours. The dialyzed solution (5.5 ml) was slightly hazy. This solution was filtered through 0.45 um membrane and stored at 5° C. Analysis showed that this J5 DLPS-NMGBOMP non-covalent complex vaccine had J5 DLPS=600 ug/ml and NMGBOMP=1.0 mg/ml.

Example 27

Preparation of J5 LPS-*N. meningitidis* GBOMP Non-covalent Complex

In another preparation, 5 mg of J5 LPS was dissolved in 5 ml of sterile 0.9% NaCl for injection, USP (Kendall and McGaw, lot #JOB029A). This gave a hazy suspension. The suspension was sonicated for 10 minutes in an Ultrasonic bath (Branson, model 5200). It remained a hazy suspension. 1.4 ml of GBOMP solution (3.67 mg/ml from Example 25) was added to the J5 LPS suspension. The mixture became clear immediately. This clear solution was dialyzed in 150 volumes of sterile 0.9% NaCl (injection quality, USP) at 5° C. for 5 days. The dialyzed solution was slightly hazy. The insoluble material was removed by centrifugation at 10,000×g for 20 minutes. The clear supernate (vaccine #1) was stored at 5° C. until used. The ratio of GBMOMP:J5 LPS was found to be 1.5:1 (w/w). A portion (3.0 ml) of this preparation was filtered through a 0.45 pm membrane. The filtered sample (vaccine #2) was stored at 5° C. until used. This second vaccine addresses the possible effect of a filtration step in the preparation of a sterile vaccine. The ratios are slightly altered. The mass ratio of GBOMP to J5 LPS in representative complexes was 1.2:1.

Example 28

Test for Pyrogenicity of the J5 DLPS-NMGBOMP Complex

The J5 DLPS-NMGBOMP non-covalent complex vaccine formulation was tested for pyrogenicity by the standard rabbit pyrogenicity assay. This vaccine was not pyrogenic at a dose containing 0.5 ug J5 DLPS. At a 10-fold higher dose (5.0 ug J5 DLPS) it was pyrogenic with an average rise in temperature of 1.3° C. (see Table 1) Based on these results, a dose containing 1.0 ug of J5 DLPS is selected. Converting this to a human dose for a 70 kg volunteer, a dose of about 35 ug of J5 DLPS is selected to provide high immunogenicity in humans.

Example 29

Enzyme-linked Immunosorbent Assay (ELISA)

The ELISA was performed in 96 well flat-bottom polystyrene microtiter plates (Costar, Cambridge, Mass.) essentially by the method of Engvall et al. above) with slight modification. The wells were first coated with 50 ug/ml poly-L-lysine type VIIB in PBS (0–01 M Na-phosphate, 0.14 M NaCl, 0.02% $NaN_3$ pH 7.4) 100 ul, at 37° C. for 1 hour. The wells were emptied and then overlaid with either J5 LPS or lipid A at 10 ug/ml in PBS for 3 hours at 37° C. Excess binding sites were then blocked with 1% casein (Fisher Scientific Co., Columbia, Md.) in PBS at 37° C. for 1 hour. The wells were washed with PBS between steps to remove unbound material. The antigen-coated plates were incubated with serial 2-fold dilutions of antibodies for 16 hours at room temperature (25° C.). Incubation with the second antibody was performed for 20 hours at room temperature. Disodium p-nitrophenylphosphate (Sigma Chemical Co.) at a concentration of 1 mg/ml in (1.0 M diethanolamine buffer, with 1 mM $MgCl_2$), pH 9.8 was used as the substrate. Absorbance was read on a Dynatech plate reader (Dynatech; Alexandria, Va.) at 410 nm. The ELISA O.D. units were calculated by multiplying the dilution of the serum with the absorbance at 410 nm at an O.D. reading near 0.5. The O.D. reading of 0.5 is at about the midpoint of the linear part of the O.D. vs dilution curve in our assay.

Example 30

Immunogenicity of J5 LPS-N. meningitidis Non-covalent Complex Vaccine in Rabbits Two groups of 2 each New Zealand white rabbits (Hazelton Research Products, Denver, Pa.), were immunized with the two vaccines in saline by intramuscular injection. The immunogenicity data are shown in Table 17.

Each rabbit received a dose containing 50 ug of GBOMP. Rabbits #62 and 63 each received vaccine #1 which has 50 ug GBOMP and 33 ug J5 LPS in the complex. Rabbits #64 and 65 received the vaccine that was filtered through a 0.45 u membrane (vaccine #2); 50 ug GBOMP and 41 ug J5 LPS were present in each dose. The rabbits received a 17 total of three doses of vaccine. As shown in Table 17, the rabbits showed about a 40 to 142-fold rise in ELISA titer against J5 LPS four weeks after the first injection and another 4 to 6-fold rise one week after the second injection. The ELISA titers dropped somewhat after the second injection, but rose after the third injection. The ELISA titers against lipid A were much lower, and showed only a marginal rise of 1.2 to 2.5-fold over pre-immunization levels.

TABLE 17

Immunogenicity of J5 LPS-N. meningitidis GBOMP Non-covalent Complex Vaccine in Rabbits ELISA Titers of Pre- and Postbleed Sera From Rabbit # 62–65*

| Rabbit# | Prebleed | Feb. 18, 1992 | Feb. 25, 1992 | Mar. 18, 1992 | Apr. 07, 1992 | FOLD |
|---|---|---|---|---|---|---|
| Elisa Titer in O.D. Units vs J5 LPS | | | | | | |
| 62 | 106 | 3,955 | 25,804 | 7,014 | 20,019 | 188 |
| 63 | 99 | 4,115 | 14,873 | 7,411 | 8,332 | 84 |
| 64 | 32 | 3,558 | NA | 3,142 | 6,054 | 189 |
| 65 | 32 | 4,550 | 16,384 | 3,891 | 13,900 | 434 |
| ELISA Titers vs E. coli Lipid A | | | | | | |
| 62 | 93 | 147 | 276 | 163 | 236 | 2.5 |
| 63 | 185 | 281 | 323 | 281 | 261 | 1.4 |
| 64 | 68 | 97 | NA | 83 | 124 | 1.8 |
| 65 | 270 | 341 | 364 | 334 | 345 | 1.2 |

*Rabbit #62–63 received the vaccine #1 and rabbit #64–65 received the vaccine #2.

The first injection was given on Jan. 16, 1992; the second injection was given on Feb. 18, 1992 and the third injection was given on Mar. 18, 1992.

NA Not available because serum was lost due to breakage of tube.

Example 31

Immunogenicity of J5 DLPS-NMGBOMP Vaccine in Rabbits

Five groups of New Zealand white rabbits (2 rabbits in each group) were immunized with the J5 DLPS-NMGBOMP non-covalent complex vaccine. Group #1 received the complex containing 25 ug J5 DLPS. Group #2 received the same dose+QS21 (a saponin adjuvant). Group #3 received the complex containing 2 ug J5 DLPS. Group #4 received the same dose as group #3+QS21. Group #5 was a control group receiving 25 ug J5 DLPS (without NMGBOMP)+QS21. All rabbits were given 3 doses of vaccine at intervals of two weeks. The immunogenicity data are shown in Table 18. The post-immune sera from rabbits in groups 1–4 showed a 30 to 1600-fold rise in titer against the J5 LPS. There was no significant difference between group #1 and 2. The ELISA antibody titers against NMG-BOMP showed 100 to 300-fold rise in titer. Again there was no significant difference between groups #1 and 2, indicating that the QS21 did not enhance the immune response to the DLPS component of this vaccine.

TABLE 18

ELISA Titers of Pre- and Post-Bleed Sera from Rabbits Immunized with J5 DLPS-GBOMP Non-covalent Complex Vaccine

| Group | Rabbit # | Prebleed | Post-1 | Post-2 | Post-3 |
|---|---|---|---|---|---|
| ELISA Titers in O.D. Units vs J5 LPS | | | | | |
| 1 | 44660 | 96 | 1,980 | 3,987 | 3,430 |
|   | 42374 | 52 | 2,035 | 5,299 | 8,243 |
| 2 | 44760 | 151 | 1,139 | 3,219 | 3,961 |
|   | 44877 | 206 | 1,856 | 2,816 | 2,688 |
| 3 | 46170 | 32 | 226 | 1,891 | 1,392 |
|   | 46880 | 40 | 432 | 3,513 | 4,614 |
| 4 | 40004 | 33 | 345 | 7,052 | 3,622 |
|   | 46298 | 305 | 635 | 3,276 | 4,012 |
| 5 | 46277 | 104 | 90 | 106 | 124 |
|   | 46886 | 24 | 31 | 37 | 51 |
| ELISA Titers in O.D. Unites vs. PA 134VA LPS | | | | | |
| 1 | 44660 | 59 | 296 | 150 | 144 |
|   | 42374 | 1,092 | 1,067 | 1,238 | 3,347 |
| 2 | 44760 | 1,187 | 2,297 | 1,388 | 1,907 |
|   | 44877 | 75 | 78 | 88 | 78 |
| 3 | 46170 | 10 | 16 | 22 | 22 |
|   | 46880 | 183 | 652 | 753 | 753 |
| 4 | 40004 | 148 | 209 | 198 | 154 |
|   | 46298 | 30 | 43 | 52 | 98 |
| 5 | 46277 | 13 | 23 | 38 | 34 |
|   | 46886 | 93 | 312 | 432 | 355 |
| ELISA Titers in O.D. Unites vs. *N. meningitidis* GBOMP | | | | | |
| 1 | 44660 | 141 | 851 | 13,337 | 12,070 |
|   | 42374 | 79 | 580 | 14,684 | 26,137 |
| 2 | 44760 | 434 | 3,072 | 20,940 | 25,472 |
|   | 44877 | 109 | 1,148 | 17,792 | 17,958 |
| 3 | 46170 | 182 | 185 | 1,811 | 2,588 |
|   | 46880 | 119 | 296 | 3,859 | 4,294 |
| 4 | 40004 | 116 | 325 | 9,497 | 13,145 |
|   | 46298 | 225 | 398 | 5,516 | 7,577 |
| 5 | 46277 | 72 | 81 | 109 | 119 |
|   | 46886 | 84 | 316 | 371 | 377 |

GR #1 Received J5 DLPS-GBOMP Vaccine 25 ug
GR #2 Received J5 DLPS-GBOMP + QS21 Vaccine 25 ug
GR #3 Received J5 DLPS-GBOMP Vaccine 2.0 ug
GR #4 Received J5 DLPS-GBOMP + QS21 Vaccine 2.0 ug
GR #5 Received J5 DLPS + Q521 Vaccine 25 ug
VACCINE:Q521 RATIO = 1:2
Post-1 = 2 weeks post primary immunization
Post-2 = 2 weeks post secondary immunization
Post-3 = 2 weeks post tertiary immunization Example 32

Bactericidal Antibody Response

The post-immune sera from the rabbits of Example 31 was bacteriocidal against both homologous (#8529) and heterologous strains (#44/76, #8566 and #8047) of Group B meningococcus. As shown in Table 19, this vaccine elicited significant increases (4 to 32-fold) in bactericidal titer against both homologous and heterologous strains. Therefore, protection by this vaccine against group B meningococcal infection will be furthered by the antibodies to group B meningococcal outer membrane protein induced by the vaccine.

TABLE 19

Bactericidal Titers of Rabbit sera

| Group | Rabbit# | Prebleed | Post-1 | Post-2 | Post-3 | Fold |
|---|---|---|---|---|---|---|
| Bactericidal Titers vs *N. meningitidis* Gr. B #8529 | | | | | | |
| 1 | 44660 | 4 | 8 | 32 | 32 | 8 |
|   | 42374 | 8 | 8 | 32 | 16 | 4 |
| 2 | 44760 | 8 | 16 | 128 | 128 | 16 |
|   | 44877 | 16 | 16 | 64 | 64 | 4 |
| 3 | 46170 | 16 | 16 | 16 | 16 | — |
|   | 46880 | 16 | 16 | 16 | 16 | — |
| 4 | 40004 | 16 | 16 | 32 | 64 | 4 |
|   | 46298 | 8 | 16 | 16 | 64 | 8 |
| Bactericidal Titers vs *N. meningitidis* Gr. B #8047 | | | | | | |
| 1 | 44660 | 8 | 8 | 8 | 8 | — |
|   | 42374 | 4 | 8 | 8 | 8 | 2 |
| 2 | 44760 | 4 | 8 | 8 | 16 | 4 |
|   | 44877 | 16 | 16 | 16 | 16 | — |
| 3 | 46170 | 16 | 16 | 16 | 16 | — |
|   | 46880 | 8 | 8 | 8 | 8 | — |
| 4 | 40004 | 4 | 16 | 16 | 16 | 4 |
|   | 46298 | 16 | 16 | 16 | 16 | — |
| Bactericidal Titers vs *N. meningitidis* Gr. B #8566 | | | | | | |
| 1 | 44660 | 32 | 32 | 64 | 64 | 2 |
|   | 42374 | 32 | 32 | 64 | 32 | 2 |
| 2 | 44760 | 16 | 32 | 128 | 128 | 8 |
|   | 44877 | 32 | 32 | 128 | 64 | 4 |
| 3 | 46170 | 64 | 64 | 64 | 64 | — |
|   | 46880 | 32 | 32 | 32 | 32 | — |
| 4 | 40004 | 32 | 32 | 64 | 64 | 2 |
|   | 46298 | 32 | 64 | 64 | 128 | 4 |
| Bactericidal Titers vs *meningitidis* Gr. B #44/76 | | | | | | |
| 1 | 44660 | 4 | 4 | 32 | 32 | 8 |
|   | 42374 | 8 | 8 | 32 | 8 | 4 |
| 2 | 44760 | 4 | 16 | 128 | 128 | 32 |
|   | 44877 | 8 | 8 | 64 | 64 | 8 |
| 3 | 46170 | 8 | 16 | 16 | 16 | 2 |
|   | 46880 | 4 | 4 | 16 | 8 | 4 |
| 4 | 40004 | 8 | 8 | 32 | 64 | 8 |
|   | 46298 | 8 | 32 | 32 | 64 | 8 |

Strain #8529 = B:15:P1.3:L3,7,9
Strain #8047 = B:2b:P1.2:L2,4
Strain #8566 = B:4:P1.15:L3,7,9
Strain #44/76 = B:15:P1.16:L3,7,9

Example 33

Cross-reactivity of IgG from Post-immune Serum of Rabbit #42374

IgG was isolated from the post-immune serum of rabbit #42374 (J5 DLPS-NMGBOMP vaccine) by affinity chromatography on Protein G-Sepharose. IgG was also isolated from pre-immune rabbit serum as a control. Bacteria grown, washed, and incubated with normal or J5 vaccine IgG, followed by FITC-labeled goat anti-rabbit IgG, and then evaluated by FACS analysis showed that IgG from the post-immune serum had significantly higher binding to a broad spectrum of gram-negative bacteria (see Table 20) than the IgG prepared from the pre-immune serum. For bacteria culture conditions in these examples, see Bhattacharjee et al., *J. Infect. Dis.*, (1994), the contents of which are incorporated by reference.

In the absence of treatment with antibiotic (Imipenem) to expose the endotoxin core, the J5 specific IgG showed enhanced binding to at least 5 of the bacteria. With antibiotic treatment, there was enhanced binding of J5 specific IgG to all Gram-negative bacteria. There was no enhanced binding of the J5 specific IgG to the Gram-positive organism, *S. aureus*, which lacks endotoxin.

TABLE 20

Binding of Detoxified J5/Group B Meningococcal Outer Membrane Protein Vaccine-induced IpG to Imipenem-treated and Untreated Whole Bacteria

| Strain | Normal No Imipenem | Rabbit IgG Imipenem | J5-specific No Imipenem | Rabbit IgG Imipenem |
|---|---|---|---|---|
| E. coli J5 | 0.38 | 37.6 | 11.5 | 40.6 |
| S. aureus | 10.6 | 6.7 | 6.8 | 1.4 |
| E. coli 2961 | 22.3 | 20.1 | 35.9 | 57.8 |
| PA 2967 | 0.4 | 3.4 | 1.0 | 35.0 |
| E. cloacae | 0.4 | 2.2 | 0.9 | 55.0 |
| 2960 | 0.7 | 0.0 | 2.4 | 18.4 |
| 3037 | 0.4 | 0.0 | 1.1 | 22.9 |
| PA 2094 | 30.0 | 24.0 | 78.9 | 68.9 |
| EC2186 | 19.4 | 16.1 | 22.3 | 52.3 |
| E. aerogenes | 5.7 | 3.4 | 11.8 | 41.7 |
| E. cloacae 2203 | 52.1 | 55.0 | 49.0 | 86.7 |
| KP 2085 | 23.3 | 37.4 | 65.9 | 95.3 |

Data are expressed as percent population positive by FCAS. Positive gate defined by line drawn defining <50% non-specific binding (i.r., addition of secondary antibody, FITC-anti-rabbit IgG, to bacteria in absence of anti-rabbit IgG). Bacteria grown, washed, treated with imipenem or buffer, washed, incubated with normal or J5 vaccine-induced rabbit IgG, followed by FITC-labelled goat or anti-rabbit IgG. At least 5,000 bacterial particles evaluated.

Example 34

Protection of Rats in#the Neutropenic Rat Model of Sepsis

The neutropenic rat model has been described before. See Collins et al., *J. Infect. Dis.* 159: 1073 (1989); Opal et al., *J. Infect. Dis.* 161: 1148 (1990). Briefly, female Sprague-Dawley rats (125–175 g) were obtained from Charles River Breeding Laboratories (Wilmington, Mass.). Cefamandole was given intramuscularly at a dose of 100 mg/kg beginning 96 hours before bacterial challenge. Cyclophosphamide was given intraperitoneally at a dose of 150 mg/kg at time 0 and at a dose of 50 mg/kg at 72 hours. At times 0, 48 and 96 hours the challenge strain of *P. aeruginosa* was given orally via an orogastric tube. Animals were monitored for fever with a Horiba non-contact digital infrared thermometer (Markson Science, Phoenix) and received antiserum or IgG fractions derived from the antiserum, at 9.0 ml/kg, intravenously via tail vein at the onset of fever (temperature>38.0° C., which was usually day 5 or 6). Control animals received normal saline on the same schedule. The animals were observed for 12 days and deaths were recorded. In a preliminary experiment, purified IgG was given at 3.0 ml/kg, 6.0 ml/kg and 9.0 ml/kg respectively (Total IgG 1.6 mg/ml) to three groups of rats. Blood samples were collected from the rats at 1, 6 and 24 hours post infusion and were analyzed by ELISA for anti-J5 LPS titers. The rat sera were also analyzed for endotoxin content. In this model neutrophils typically begin to return on days 9 to 10, and this is monitored by blood smear analysis on approximately 10% of animals during each experiment.

Figure 55:
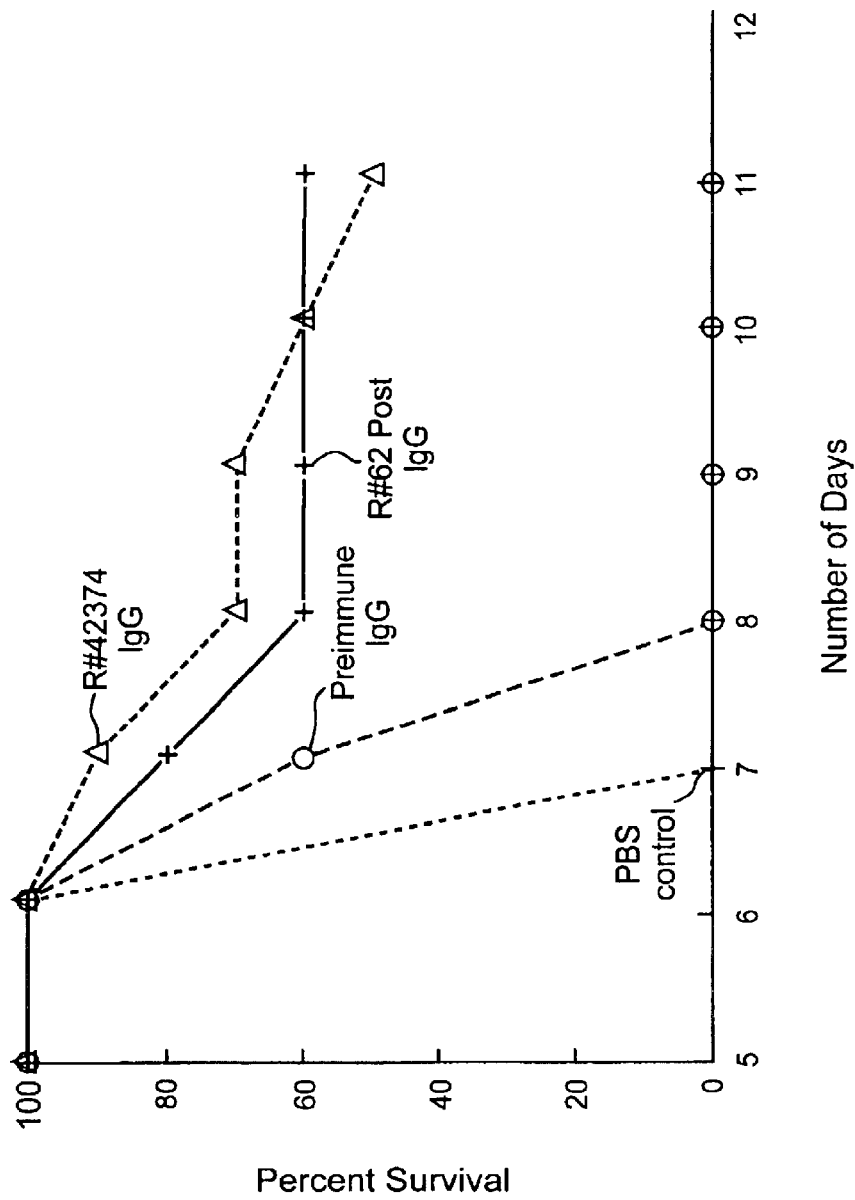
FIG. 55 shows survival data from the neutropenic rat model of sepsis, wherein the rat is treated with IgG isolated from the post-immune serum of a rabbit immunized with J5 LPS-GBOMP non-covalent complex vaccine (R #62, post-immune serum IgG, +--+); IgG isolated from the serum of rabbit #42374 that was immunized against J5 DLPS-GBOMP (A); Preimmune rabbit serum IgG (-o-); PBS control (+--+).

IgG was isolated from the post-immune serum of rabbit #62 which had been immunized with J5 LPS-NMGBOMP non-covalent complex vaccine. This IgG gave significant protection against challenge with lethal doses of a virulent strain of *P. aeruginosa* 12:4:4. Six out of 10 rats (60%) were protected compared to none of 10 rats treated with the control pre-immune serum IgG (p<0.02) see FIG. 55.

IgG was also prepared from the preimmune serum of rabbit #42374 which had been immunized with the J5 DLPS-NMGBOMP complex vaccine. Five of ten rats were protected by passive transfer of this IgG compared to none of ten rats treated with the preimmune serum IgG (P<0.02); see FIG. 55.

What we claim is:

1. A composition for the burst-free, sustained, programmable release of active material(s) over a period from 1–100 days, which comprises: (1) an active material and (2) a carrier which may contains pharmaceutically-acceptable adjuvant, comprised of a blend of uncap and end-capped biodegradable-biocompatible copolymer wherein said composition comprises a capacity to completely release histatin in an aqueous physiological environment within from 1 to 40 days with a 99/1 blend of uncapped and end-capped poly(lactide/glycolide) having a L/G ratio of 48/52 to 52/48, and a molecular weight less than 15,000.

2. The composition of claim 1 wherein the histatin can be completely released within 18 to 40 days and the molecular weight of the poly(lactide/glycolide) is within the range of 28,000 to 40,000.

3. A composition for the burst-free, sustained, programmable release of active material(s) over a period from 1–100 days, which comprises: (1) an active material and (2) a carrier which may contain pharmaceutically-acceptable adjuvant, comprised of a blend of uncapped and end-capped biodegradable-biocompatible poly(lactide/glycolide) copolymer, wherein said active material is histatin and wherein said composition is characterized by a capacity to release up to 90% of the histatin in an aqueous physiological environment from 28–70 days with a 1/99 blend of uncapped and end-capped poly(lactide/glycolide) having a L/G ratio of 48/52 to 52/48 and a molecular weight range of 10,000–40,000 daltons.

4. A composition for the burst-free, sustained, programmable release of active material(s) over a period from 1–100 days, which comprises: (1) an active material and (2) a carrier which contains pharmaceutically-acceptable adjuvant, comprised of a blend of uncapped and end-capped biodegradable-biocompatible poly(lactide/glycolide) copolymer, wherein said active material is histatin and wherein said composition is characterized by the capacity to release up to 80% of histatin in an aqueous physiological environment from 56–100 days with a 1/99 blend of uncapped and end-capped poly(lactide/glycolide) having a L/G ratio or 75/25 and a molecular weight of less than 15,000 daltons.

5. A composition for the burst-free, sustained, programmable release of active material(s) over a period from 1–100 days, which comprises: (1) a biologically active agent and (2) a cattier which contains pharmaceutically-acceptable adjuvant, comprised of a blend of uncapped and end-capped biodegradable-biocompatible poly(lactide/glycolide) copolymer wherein the biologically active agent comprises a polypeptide leutinizing hormone releasing hormone (LHRH) that is a decapeptide of molecular weight 1182 in its acetate form, and having the structure:

p-EHWSYGLRPG.

6. A composition for the burst-free, sustained, programmable release of active material(s) over a period from 1–100 days, which comprises: (1) an active material comprising a polypeptide and (2) a carrier which contains pharmaceutically-acceptable adjuvant, comprised of a blend of uncupped and end-capped biodegradable-biocompatible poly(lactide/glycolide) copolymer, wherein the entrapped polypeptide is any of the vaccine agents against enterotoxigenic *E. coli* (ETEC) selected from the group consisting of CFA/I, CFA/II, CS1, CS3,CS6 and CS17, ETEC-related enterotoxins, and combinations thereof.

7. The composition of claim 6 wherein the entrapped polypeptide consists of peptide antigens of molecular weight range of about 800–5000 daltons for immunization against enterotoxigenic *E. coli* (ETEC).

8. The composition of claim 7 wherein the entrapped polypeptide is selected from the group consisting of an antigenic synthetic peptide containing CFA/I pilus protein T-cell epitopes; B-cell spitopest or mixtures thereof.

9. A composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer, wherein said agent is selected from the group consisting of water-soluble hormone drugs, antibiotics, antitumor agents, and inflammatory agents, antipyretics, analgesics antitussivess expectorants, sedatives, muscle relaxants, antiepileptics, antiulcer agents, antidepressants, antiallergic drugs, cardiotonics, antiarrhythmic drugs, vasodilators, antihypertensives, diuretics, anticoagulants, antinarcotics, in the molecular weight range of 100–100,000 daltons.

10. A composition for the burst-free, sustained, programmable release of active material(s) over a period from 1–100 days, which comprises: (1) an entrapped polypeptide as an active agent and (2) a carrier which contains pharmaceutically-acceptable adjuvant, comprised of a blend of uncapped and end-capped biogradable-biocompatible poly(lactide/glycolide) copolymer, wherein the entrapped polypeptide is active at a low pH, and comprises LHRH, adrenocorticotropic hormone, epidermal growth factor, or calcitonin released polypeptide.

11. A composition for the burst-free, sustained, progammable release of active material(s) over a period from 1–100 days, which comprises: (1) an entrapped polypeptide as an active agent and (2) a carrier which contains pharmaceutically-acceptable adjuvant, comprised of a blend of uncapped and end-capped biodegradable-biocompatible poly(lactide/glycolide) copolymer, wherein when the entrapped polypeptide is inactive at a low pH, a non-ionic surfactant such an polyoxyethylene sorbitan fatty acid esters (Tween 80, Tween 60 and Tween 20) and polyoxyethylene— polyoxypropylene block copolymers (Fluronics) is added to the inner aqueous phase to maintain biological activity of the released polypeptide.

12. A composition for the burst-free, sustained, programmable release of active material(s) over a period from 1–100 days, which comprises: (1) an entrapped polypeptide as an active agent and (2) a carrier which contains pharmaceutically-acceptable adjuvant, comprised of a blend of uncapped and end-capped biodegradable-biocompatible poly(lactide/glycolide) copolymer, wherein when the entrapped polypeptide such as histatin is inactive at a low pH, a pH-stabilizing agent of inorganic salts is added to the inner aqueous phase to maintain biological activity of the released peptide, and further wherein placebo spheres loaded with the pH-stabilizing agents are coadministered with polypeptide-loaded spheres to maintain the solution pH around the microcapsules and preserve the biological activity of the released peptide in instances where the addition of pH-stabilizing agents in the inner aqueous phase is undesirable for the successful encapsulation of the acid pH sensitive polypeptide.

13. A composition for the burst-free, sustained, programmable release of active material(s) over a period from 1–100 days, which comprises: (1) an entrapped polypeptide as an active agent and (2) a carrier which contains pharmaceutically-acceptable adjuvant, comprised of a blend of uncapped and end-capped biodegradable-biocompatible poly(lactide/glycolide) copolymer, wherein when the entrapped polypeptide is inactive at a low pH, a non-ionic surfactant such an polyoxyethylene sorbitian fatty acid esters (Tween 80, Tween 60 and Tween 20) and polyoxyethylene-polyoxypropylene block copolymers (Flutonics) is added to the inner aqueous phase to maintain biological activity of the released polypeptide, and further wherein placebo spheres loaded with non-ionic surfactant are coadministered with polypeptide-loaded spheres to maintain biological activity of the released peptide where the addition of non-ionic surfactants in the inner aqueous phase is undesirable for successful encapsulation of the acid pH sensitive polypeptide.

14. A composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide copolymer), wherein complete solubilization of the copolymer leaves no residual polymer at the site of administration and occurs concurrently with the complete release of the entrapped agent.

15. A process of treating humans with a composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer, said process comprising administering said composition via parenteral route selected from intramuscular and subcutaneous.

16. A process of treating humans with a composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer, said process comprising administering said composition via topical route.

17. A process of treating humans with a composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer, said process comprising administering said composition via oral routes.

18. A process of treating humans with a composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer, said process comprising administering said composition via nasal, transdermal, rectal, and vaginal routes.

19. A process of treating humans with a composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer, said process comprising administering said composition in the form of an oral or nasal inhalant for the respiratory tract.

20. A process for preparing controlled release compositions characterized by burst-free, sustained, programmable release of biologically active agents, comprising: dissolving biodegradable poly(lactide/glycolide), in uncapped form in methylene chloride, and dissolving a biologically active agent or active core in water; adding the aqueous layer to the polymer solution and emulsifying to provide an inner water-in-oil (w/o) emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring the resulting water-in-oil-in-water (w/o/w) emulsion for sufficient time to remove said solvent, and rinsing hardened microcapsules with water and lyophilizing said hardened microcapsules.

21. The process of claim 20 wherein a solvent-saturated external aqueous phase is added to emulsify the inner w/o emulsion prior to addition of the external aqueous layer, to provide microcapsules of size distribution range between 0.05–500 um.

22. The process of claim 20 wherein a low temperature of about 0–4 degree C. is provided during preparation of the inner w/o emulsion, and a low temperature of about 4–20 degree C. is provided during preparation of the w/o/w emulsion to provide a stable emulsion and high encapsulation efficiency.

23. A process for preparing controlled release compositions characterized by burst-free, sustained, programmable release of biologically active agents, comprising:
dissolving biodegradable poly(lactide/glycolide) uncapped and end-capped form in methylene chloride, and dissolving a biologically active agent or active core in water; adding the aqueous layer the polymer solution and emulsifying to provide an inner water-in-oil emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring a resulting water-in-oil-water (w/o/w) emulsion for sufficient time to remove said solvent; and rinsing heardened microcapsules with water; and lyophilizing said hardened microcapsules.

24. The process of claim 20 wherein a 100/0 blend of uncapped and end-capped polymer in used to provide release of the active core in a continuous and sustained manner without a lag phase.

25. The process of claim 23 wherein a solvent-saturated external aqueous phase is added to emulsify the inner w/o emulsion prior to addition of the external aqueous layer, to provide microcapsules of narrow size distribution range between 0.05–500 um.

26. The process of claim 23 wherein a low temperature or about 0–4 degree C. is provided during preparation or the inner w/o emulsion, and a low temperature of about 4–20 degree C. is provided during preparation of the w/o/w emulsion to provide a stable emulsion and high encapsulation efficiency.

27. A method for the protection against infection of a mammal in need thereof by pathogenic organisms comprising administering orally to said mammal an immunogenic amount of an immunostimulating composition comprising an antigenic synthetic peptide encapsulated within a poly (lactide/glycolide) matrix, wherein said poly(lactide/glycolide) matrix comprises a blend of uncapped and end-capped forms, in a ratio of 100/0 to 1/99.

28. The method of claim 27 wherein the poly(lactide/glycolide) is a blend of uncapped and end-capped forms in ratios ranging from 90/10 to 40/60.

29. The method of claim 27 wherein the infection is a bacterial infection.

30. The method of claim 27 where the synthetic peptide contains an epitope selected from the group consisting of CFA/I pilus protein T-cell epitopes, B-cell epitopes or mixtures thereof.

31. The method of claim 27 wherein the infection is a viral infection.

32. The method of claim 27 wherein the infection is parasitic infection.

33. The method of claim 27 wherein the infection in a fungal infection.

34. The method of claim 29 wherein the bacterial infection is caused by a bacteria selected from the group consisting of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Legionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

35. The method in accordance with claim 27 wherein said antigenic synthetic peptide is present in the amount of 0.1 to 1%.

36. A vaccine for the immunization of a mammal in need thereof against infection caused by pathogenic organisms prepared from a composition for the burst-free, sustained, programmable release of active material(s) over a period from 1–100 days, which comprises: (1) an active agent and (2) a carrier which contains pharmaceutically-acceptable adjuvant, comprised of a blend of uncapped and end-capped biodegradable-biocompatible poly(lactide/glycolide) copolymer.

37. The vaccine according to claim 36 wherein the polymeric substance is poly(DL-lactide-co-glycolide).

38. The vaccine according to claim 37 wherein the relative ratio between the lactide and glycolide (L/G) component is within the range of 40/60 to 0/100.

39. The vaccine according to claim 38 wherein the relative ratio between the amount of lactide and glycolide component is within the range of 90/10 to 40/60.

40. A vaccine according to claim 36 wherein the pathogenic organisms are bacterial.

41. A vaccine according to claim 36 wherein the pathogenic organisms are viral.

42. A vaccine according to claim 36 wherein the pathogenic organisms are fungal.

43. A vaccine according to claim 36 wherein the pathogenic organisms are parasitic.

44. The vaccine according to claim 36 wherein the material is an antigenic synthetic peptide is selected from the group consisting essentially of Synthetic Peptides Containing CFA/I Pilus Protein T-cell Epitopes (Starting sequence I given)

4(Asn-Ile-Thr-Val-Thr-Ala-Ser-Val-Asp-Pro),
8(Thr-Ala-Ser-Val-Asp-Pro-Val-Ile-Asp-Leu),
12(Asp-Pro-Val-Ile-Asp-Leu-Leu-Gln-Ala-Asp),
15(Ile-Asp-Leu-Lou-Gln-Ala-Asp-Gly-Asn-Ala),
20(Ala-Asp-Gly-Asn-Ala-Leu-Pro-Ser-Ala-Val),
26(Pro-Ser-Ala-Val-Lys-Leu-Ala-Tyr-Ser-Pro),
72(Leu-Asn-Ser-Thr-Val-Gln-Met-Pro-Ile-Ser),
78(Met-Pro-Ile-Ser-Val-Ser-Trp-Gly-Gly-Gln),
87(Gln-Val-Leu-Ser-Thr-Thr-Ala-Lys-Glu-Phe),
126(Ala-Gly-Thr-Ala-Pro-Thr-Ala-Gly-Asn-Tyr), and
133(Gly-Asn-Tyr-Ser-Gly-Val-Val-Ser-Leu-Val), and mixtures thereof; Synthetic Peptides, Containing CFA/I Pilus Protein B-cell (antibody) Eptiopes (Starting Sequence # given)
3(Lys-Ana-Ile-Thr-Val-Thr-Ala-Ser-Val),
11(Val-Asp-Pro-Val-Ile-Asp-Leu-Leu-Gln-Ala-Asp),
22(Gly-Asn-Ala-Leu-Pro-Ser-Ala-Val),
32(Ala-Tyr-Ser-Pro-Ala-Ser-Lys-Thr-Phe-Lys-Thr-Phe-Glu-Ser-Tyr-Arg-Val),
32(Ala-Tyr-Ser-Pro-Ala-Ser-Lys-Thr-Phe)
38(Lys-Thr-Phe-Glu-Ser-Tyr-Arg-Val),
66(Pro-Gln-Leu-Thr-Asp-Val-Leu-Asn-Ser)
93(Ala-Lys-Glu-Phe-Glu-Ala-Ala-Ala),
124(Lys-Thr-Ala-Gly-Thr-Ala-Pro-Thr)
127(Gly-Thr-Ala-Pro-Thr-Ala-Gly-Asn-Tyr-Ser), and
124(Lys-Thr-Ala-Gly-Thr-Ala-Pro-Thr-Ala-Gly-Asn-Tyr-Ser), and mixtures thereof; and Synthetic Peptides Containing CFA/I Pilus Protein T-cell and B-cell (antibody) Epitopes (Starting Sequence # given)
3(Lys-Asn-Ile-Thr-Val-Thr-Ala-Ser-Bal-Asp-Pro),
8(Thr-Ala-Ser-Val-Asp-Pro-Val-Ile-Asp-Leu-Leu-Gln-Ala-Asp),
11(Bal-Asp-Pro-Bal-Ile-Asp-Leu-Leu-Gln-Ala-Asp),
20(Ala-Asp-Gly-Asn-Ala-Leu-Pro-Ser-Ala-Val),
124(Lys-Thr-Ala-Gly-Thr-Ala-Pro-Thr-Ala-Gly-Asn-Tyr-Ser), and
126(Ala-Gly-Thr-Ala-Pro-Thr-Ala-Gly-Asn-Tyr-Ser), and mixtures thereof.

45. The vaccine according to claim 40 wherein the bacteria is selected from the group consisting essentially of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Lepionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

46. The vaccine according to claim 40 wherein the antigenic synthetic peptide is selected from the group consisting of 4(Asn-Ile-Thr-Val-Thr-Ala-Ser-Val-Asp-Pro),
8(Thr-Ala-Ser-Val-Asp-Pro-Val-Ile-Asp-Leu),
12(Asp-Pro-Val-Ile-Asp-Leu-Leu-Gln-Ala-Asp),
15(Ile-Asp-Leu-Leu-Gln-Ala-Asp-Gly-Asn-Ala),
20(Ala-Asp-Gly-Asn-Ala-Leu-Pro-Ser-Ala-Val),
26(Pro-Ser-Ala-Val-Lys-Leu-Ala-Tyr-Ser-Pro),
72(Leu-Asn-Ser-Thr-Val-Gln-Met-Pro-Ile-Ser),
78(Met-Pro-Ile-Ser-Val-Ser-Trp-Gly-Gly-Gln),
87(Gln-Val-Leu-Ser-Thr-Thr-Ala-Lys-Glu-Phe),
126(Ala-Gly-Thr-Ala-Pro-Thr-Ala-Gly-Asn-Tyr), and
133(Gly-Asn-Tyr-Ser-Gly-Val-Val-Ser-Leu-Val), and mixtures thereof.

47. The vaccine according to claim 46 wherein the antigenic synthetic peptide is 4(Asn-Ile-Thr-Val-Thr-Ala-ser-Val-Asp-Pro).

48. The vaccine according to claim 46 wherein the antigenic synthetic peptide is 8(Thr-ala-ser-val-Asp-Pro-Val-I,la-asp-Leu).

49. The vaccine according to claim 40 wherein the antigenic synthetic peptide is 12(Asp-Pro-Val-Ile-Asp-Lau-Lau-Gln-Ala-Asp).

50. The vaccine according to claim 40 wherein the antigenic synthetic peptide is 15(Ile-Asp-Leu-Lou-Gln-Ala-Asp-Gly-Asn-Ala).

51. The vaccine according to claim 40 wherein the antigenic synthetic peptide is 20(Ala-Asp-Gly-Asn-Ala-Leu-Pro-Ser-Ala-Val).

52. The vaccine according to claim 40 wherein the antigenic synthetic peptide is 26(Pro-Ser-Ala-Val-Lys-Leu-Ala-tyr-Ser-Pro).

53. The vaccine according to claim 40 wherein the antigenic synthetic peptide is 72(Leu-Asn-Ser-Thr-Val-Gln-Met-Pro-Ile-Ser).

54. The vaccine according to claim 40 wherein the antigenic synthetic peptide is 78(Met-Pro-Ile-Ser-Val-Ser-Trp-Gly-Gly-Gln).

55. The vaccine according to claim 40 wherein the antigenic synthetic peptide in 87(Gln-Val-Leu-Ser-Thr-thr-Ala-Lys-Glu-Phe).

56. The vaccine according to claim 40 wherein the antigenic synthetic peptide is 126(Ala-Gly-Thr-Ala-pro-Thr-Ala-Gly-Asn-Tyr).

57. The vaccine according to claim 46 wherein the antigenic synthetic peptide is 133 (Gly-Asn-Tyr-Ser-Gly-Val-Val-Ser-Leu-Val).

58. The vaccine according to claim 44 wherein the antigenic synthetic peptide is selected from the group consisting essentially of 3(Lys-Ana-Ile-Thr-Val-Thr-Ala-Ser-Val), 11(Val-Asp-Pro-Val-Ile-Asp-Leu-Leu-Gln-Ala-Asp), 22(Gly-Asn-Ala-Leu-Pro-Ser-Ala-Val), 32(Ala-Tyr-Ser-Pro-Ala-Ser-Lys-Thr-Phe-Lys-Thr-Phe-Glu-Ser-Tyr-Arg-Val), 32(Ala-Tyr-Ser-Pro-Ala-Ser-Lys-Thr-Phe), 38(Lys-Thr-Phe-Glu-Ser-Tyr-Arg-Val), 66(Pro-Gln-Leu-Thr-Asp-Val-Leu-Asn-Ser), 93(Ala-Lys-Glu-Phe-Glu-Ala-Ala-Ala), 124(Lys-Thr-Ala-Gly-Thr-Ala-Pro-Thr), 127(Gly-Thr-Ala-Pro-Thr-Ala-Gly-Asn-Tyr-Ser), and 124(Lys-Thr-Ala-Gly-Thr-Ala-Pro-Thr-Ala-Gly-Asn-Tyr-Ser), and mixtures thereof.

59. The vaccine according to claim 58 wherein the antigenic synthetic peptide is 3(Lys-Ana-Ile-Thr-Val-Thr-Ala-Ser-Val).

60. The vaccine according to claim 58 wherein the antigenic synthetic peptide is 11(Val-Asp-Pro-Val-Ile-Asp-Lau-Leu-Gln-Ala-Asp).

61. The vaccine according to claim 58 wherein the antigenic synthetic peptide is 22(Gly-Asn-Ala-Lou-Pro-Ser-Ala-Val).

62. The vaccine according to claim 58 wherein the antigenic synthetic peptide is 32(Ala-Tyr-Ser-Pro-Ala-Ser-Lys-Thr-Phe-Lys-Thr-Phe-Glu-Ser-Tyr-Arg-Val).

63. The vaccine according to claim 58 wherein the antigenic synthetic peptide is 32(Ala-Tyr-Ser-Pro-Ala-Ser-Lys-Thr-Phe).

64. The vaccine according to claim 58 wherein the antigenic synthetic peptide is 38(Lys-Thr-Phe-Glu-Ser-Tyr-Arg-Val).

65. The vaccine according to claim 58 wherein the antigenic synthetic peptide is 66(Pro-Gln-Leu-Thr-Asp-Val-Leu-Asn-Ser).

66. The vaccine according to claim 58 wherein the antigenic synthetic peptide is 93(Ala-Lys-Glu-Phe-Glu-Ala-Ala-Ala).

67. The vaccine according to claim 58 wherein the antigenic synthetic peptide is 124(Lys-Thr-Ala-Gly-Thr-Ala-Pro-Thr).

68. The vaccine according to claim 58 wherein the antigenic synthetic peptide is 127(Gly-Thr-Ala-Pro-Thr-Ala-Gly-Asn-Tyr-Ser).

69. The vaccine according to claim 58 wherein the antigenic synthetic peptide is 124(Lys-Thr-Ala-Gly-Thr-Ala-Pro-Thr-Ala-Gly-Asn-Tyr-Ser).

70. The vaccine according to claim 44 wherein the antigenic synthetic peptide in selected from the group consisting essentially of 3(Lys-Asn-Ile-Thr-Val-Thr-Ala-Ser-Bal-Asp-Pro), 8(Thr-Ala-Ser-Bal-Asp-Pro-Bal-Ile-Asp-Leu-Leu-Gln-Ala-Asp), 11(Bal-Asp-Pro-Bal-Ile-Asp-Leu-Leu-Gln-Ala-Asp), 20(Ala-Asp-Gly-Asn-Ala-Lau-Pro-Ser-Ala-Val), 124(Lys-Thr-Ala-Gly-Thr-Ala-Pro-Thr-Ala-Gly-Asn-Tyr-Ser), and 126(Ala-Gly-Thr-Ala-Pro-Thr-Ala-Gly-Asn-Tyr-Ser), and mixtures thereof.

71. The vaccine according to claim 70 wherein the antigenic synthetic peptide is 3(Lys-Asn-Ile-Thr-Val-Thr-Ala-Ser-Bal-Asp-Pro).

72. The vaccine according to claim 70 wherein the antigenic synthetic peptide is 8(Thr-Ala-Ser-Bal-Asp-Pro-Bal-Ile-Asp-Leu-Leu-Gln-Ala-Asp).

73. The vaccine according to claim 70 wherein the antigenic synthetic peptide is 11(Bal-Asp-Pro-Bal-Ile-Asp-Leu-Leu-Gln-ala-Asp).

74. The vaccine according to claim 70 wherein the antigenic synthetic peptide is 20(Ala-Asp-Gly-Asn-Ala-Leu-Pro-Ser-Ala-Val).

75. The vaccine according to claim 70 wherein the antigenic synthetic peptide is 124(Lys-Thr-Ala-Gly-Thr-Ala-Pro-Thr-Ala-Gly-Asn-Tyr-Ser).

76. The vaccine according to claim 70 wherein the antigenic synthetic peptide is 126(Ala-Gly-Thr-Ala-Pro-Thr-Ala-Gly-Asn-Tyr-Ser).

77. The method of claim 31, wherein the viral infection is caused by a virus selected from the group consisting of hepatitis A, hepatitis B, hepatitis C, Varicella-Zoster virus, Epstein-Barr virus, Rotaviruses, polio virus, human immunodeficiency virus (HIV), herpes simplex virus type 1, human retroviruses, herpes simplex virus type 2, Ebola virus, cytomegalo viruses, Herpes Simplex viruses, Human cytomegalovirus, Varicella-Zoster Virus, Epstein-Barr Virus, Poxvirus, Influenza viruses, Parainfluenza viruses, Respiratory Syncytial virus, Rhinoviruses, coronaviruses, Adenoviruses, Measles virus, Mumps virus, Robella Virus, Human Parvoviruses, Arboviruses, Rabies virus, Enteroviruses, reoviruses, viruses Causing gastroenteritis Hepatitis Viruses, Filoviruses, Arenaaviruses, Papillomaviruses, Polyomaviruses, Human Immunodeficiency viruses, Human Retroviruses, and Spongirorm Encephalopathies.

78. The method in accordance with claim 27 wherein said peptides is an antigen in the amount or 0.1 to 1%.

79. A vaccine for the immunization of a mammal in need thereof, against infection by pathogenic organisms comprising an antigen in the amount of 0.1 to 1% encapsulated within a biodegradable-biocompatible polymeric poly(DL-lactide-coglycolide) matrix wherein the polymer is uncapped or a blend of uncapped and end-capped polymers.

80. The vaccine according to claim 79 wherein the polymer is a blend of end-capped and uncapped polymers.

81. The vaccine according to claim 80 wherein the relative ratio between the lactide and glycolide component is within the range of 90/10 to 40/60.

82. The vaccine according to claim 80 wherein the relative ratio between the amount of lactide and glycolide component is within the range of 48/52 to 52/48.

83. The vaccine according to claim 79 wherein the antigen is a bacteria or derivatives thereof.

84. The vaccine according to claim 80 wherein the antigen is a virus or derivatives thereof.

85. The vaccine according to claim 80 wherein the antigens is a parasite or derivative thereof.

86. The vaccine according to claim 80 wherein the antigen is fungus or derivative thereof.

87. The vaccine according to claim 83 wherein the bacteria is selected from the group consisting of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Lepionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

88. The vaccine of claim 84 wherein the virus is selected from the group consisting of hepatitis A, hepatitis B, hepatitis C, Varicella-Zoster virus, Epstein-Barr virus, Rotaviruses, polio virus, human immunodeficiency virus (HIV), herpes simplex virus type 1, human retroviruses, herpes simplex virus type 2, Ebola virus, cytomegalo viruses, Herpes Simplex viruses, Human cytomegalovirus, Varicella-Zoster Virus, Epstein-Barr Virus, Poxvirus, Influenza viruses, Parainfluenza viruses, Respiratory Syncytial virus, Rhinoviruses, coronaviruses, Adenoviruses, Measles virus, Mumps virus, Robella Virus, Human Parvoviruses, Arboviruses, Rabies virus, Enteroviruses, reoviruses, viruses Causing gastroenteritis Hepatitis Viruses, Filoviruses, Arenaaviruses, Papillomaviruses, Polyomaviruses, Human Immunodeficiency viruses, Human Retroviruses, and Spongirorm Encephalopathies.

89. An immunostimulating composition comprising encapsulating-microspheres, which may contain a pharmaceutically-acceptable adjuvant, wherein said microspheres having a diameter between 1 nanogram (ng) to 10 microns (um) are comprised of (a) a biodegradable-biocompatible poly(DL-lactide-co-glycolide) as the bulk matrix, wherein the copolymer (lactide to glycolide L/G) ratio for uncapped and end-capped polymer is 100/0 to 1/99 and (b) an immunogenic substance comprising a bacteria, virus, fungus, parasite, or derivative thereof, that serves to elicit the production of antibodies in animal subjects.

90. An immunostimulating composition according to claim 89 wherein the amount of said immunogenic substance is within the range of 0.1 to 1.5% based on the volume of said bulk matrix.

91. An immunostimulating composition according to claim 89 wherein the immunogenic substance comprises Colony Factor Antigen (CFA/II), hepatitis B surface antigen (HBsAg), and a mixture thereof physiologically similar antigen.

92. An immunostimulating composition according to claim 89 wherein the relative ratio between the lactide and glycolide component is within the range of 48/52 to 52/48.

93. An immunostimulating composition according to claim 89 wherein the size of more than 50% of said microspheres is between 5 to 10 um in diameter by volume.

94. An immunostimulating composition according to claim 89 wherein the immunogenic substance is the synthetic peptide representing the peptide fragment beginning with the amino acid residue 63 through 78 of Pilus Protein CS3, said residue having the amino acid sequence, 63(Ser-Lys-Asn-Gly-Thr-Val-Thr-Try-Ala-His-Glu-Thr-Asn-Asn-Ser-Ala).

95. A vaccine comprising an immunostimulating composition of claim 89 and a sterile, pharmaceutically-acceptable carrier therefor.

96. A vaccine comprising an immunostimulating composition of claim 95 wherein said immunogenic substance is Colony Factor Antigen (CFA/II).

97. A vaccine comprising an immunostimulating composition of claim 96 wherein said immunogenic substance is hepatitis B surface antigen (HBsAg).

98. A method for the vaccination against bacterial infection comprising administering to a human in need thereof, an antibactericidally effective amount of a composition of claim 95.

99. A method according to claim 98 wherein the bacterial infection is caused by a bacteria selected from the group consisting of *Salmonella typhi, Shigella Sonnei, Shigella Flexneri, Shigella dysenteriae, Shigella boydii, Escheria coli, Vibrio cholera*, Group D-2, Group E, Group G, Group I, Group 1, Listseria, Erysipelothrix, Mycobacterium, Aerobic pathogenic Actinomycetales, Enterobacteriaceae, Vibrio, aeromonas, Plesiomonas, Helicobacter, *W. succinogenes*, Acineto bacter spp., Foavobacterium, Pseudomonas, Lepionella, Brucella, Haemophilus, Bordetalla, Mycoplasmas, Gardnerella, Streptobacillus, Spirillum, Calymmatobacterium, Clostridium, Treponema, Borrelia, Leptospira, Anaerobic Gram-negative Bacteria including bacilli and Cocci, Anaerobic gram-Postive Nonsporeforming Bacilli and Cocci, versinia, staphylococcus, clostridium, Enteroccus, Streptoccus, Aerococcus, Planococcus, Stomatococcus, Micrococcus, Lactoccus, Germella, Pediococcus, Leuconostoc, Bacillus, Neisseria, Branhamella, Coryne bacterium, campylobacter, *Arcanobacterium haemolyticum*, Rhodococcus spp., Rhodococcus, Group A-4.

100. A method for the vaccination against viral infection comprising administering to a human in need thereof, an antivirally effective amount of a composition of claim 89.

101. A diagnostic assay for bacterial infections comprising a composition for the burst-free, sustained, programmable release of active material(s) over a period from 1–100 days, which comprises: (1) a biologically active agent and (2) a carrier which contains pharmaceutically-acceptable adjuvant, comprised of a blend of uncapped and end-capped biodegradable-biocompatible poly(lactide/glycolide) copolymer.

102. A method of preparing an immunotherapeutic agent against infections caused by a bacteria comprising the steps of (1) immunizing a plasma donor with a vaccine according to claim 40 such that a hyperimmune globulin is produced which contains antibodies directed against the bacteria; (2) separating the hyperimmune globulin and (3) purifying the hyperimmune globulin.

103. A method preparing an immunotherapeutic agent against infections caused by a virus comprising the step of immunizing a plasma donor with a vaccine according to claim 41 such that hyperimmune globulin is produced which contains antibodies directed against the hepatitis B virus.

104. An immunotherapy method comprising the step of administering to a subject an immunostimulatory amount of hyperimmune globulin prepared according to claim 102.

105. An immunotherapy method comprising the step of administering to a subject an immunostimulatory amount of hyperimmune globulin prepared according to claim 103.

106. A method for the protection against infection of a subject by enteropathogenic organisms or hepatitis B virus comprising administering to said subject an immunogenic amount of an immunostimulating composition of claim 89.

107. A method according to claim 104 wherein the immunostimulating composition is administered orally.

108. A method according to claim 104 wherein the immunostimulating composition is administered parenterally.

109. A method according to claim 104 wherein the immunostimulating composition is administered in four separate doses on day 0, day 7, day 14, and day 28.

110. A method for the protection against or therapeutic treatment of bacterial infection in the soft tissue or bone of a mammal in need thereof comprising administering locally to said mammal a bactericidally-effective amount of a composition for the burst-free, sustained, programmable release of active material(s) over a period from 1–100 days, which comprises: (1) an active material and (2) a carrier which contains pharmaceutically-acceptable adjuvant, comprised of a blend of uncapped and end-capped biodegradable-biocompatible poly(lactide/glycolide) copolymer, wherein the active material is an antibiotic which is controlled release within a period of about 1 to 100 days.

111. The method according to claim 110 wherein the biodegradable (lactide/glycolide) is a blend of uncapped and end-capped forms having a relative ratio between the amount of lactide and glycolide component within the range of 100/0 to 1/99.

112. A method according to claim 111 wherein the bacterial infection is (1) a subcutaneous infection secondary to contaminated abdominal surgery, (2) an infection surrounding prosthetic devices and vascular grafts, (3) ocular infections, (4) topical skin infections, (5) orthopedic infections, including osteomyelitis, or (6) oral infections.

113. The method according to claim 112 wherein the oral infections are pericoronitis or periodontal disease.

114. The method according to claim 111 wherein the administration is effected prior to infection.

115. The method according to claim 111 wherein the administration is effected subsequent to infection.

116. The method according to claim 111 wherein said animal is a human.

117. The method according to claim 111 wherein said animal is a nonhuman.

118. The method in accordance with claim 111 comprising applying to the soft tissue or bone tissue of said animal a bactericidally-effective amount of said antibiotic, selected from the group consisting of a beta-lactam, aminoglycolide, polymyxin-b, Amphotericin B, Aztreonam, cephalosporins, chloramphenicol, fusidans, lincosamides, macrolides, methronidazole, nitro-furation, Imipenem/cilastin, quinolones, refampin, polyenes, tetracycline, sulfonamides, trimethoprim, vancomycin, teicoplanin, imidazoles, and erythromycin, encapsulated within a ,biodegradable polymeric matrix of said copolymer wherein the amount of the lactide and glycolide (L/G) component is within the range of 48/52 to 52/48 based on the weight of said polymeric matrix which is present in the amount of from 40 to 95 percent, resulting in the controlled release of a bacteriacidal amount of the said antibiotic over a period of from 1 to 100 days.

119. The method of claim 118 wherein the polymeric matrix consists essentially of a poly(DL-lactide-co-glycolide) wherein the relative ratio between the amount of lactide and glycolide (L/G) component is within the range of 48/52 to 52/48.

120. The method of claim 118 wherein the bacterial infection is caused by a resistant or non-resistant bacteria selected from the group consisting of Enterobacteriaceae; Klebsiella spp.; Bacteroides sp. Enterococci; Proteus sp.; Streptococcus sp.; Staphylococcus sp.; Pseudomonas sp.; Neisseria sp.; Pedptostreptococcus sp.; fusobacterium sp.; Actinomyces sp.; Mycobacterium sp.; Listeria sp.; Corynebacterium sp.; Proprionibacterium sp.; Actinobacillus sp.; Aerobacter sp.; Borrelia sp.; Campylobacter sp.; cytophaga sp.; Pasteurella sp.; Clostridium sp., *Enterobacter aerogenes*, Peptococcus sp.; *Proteus vulgaris, Proteus morganii, Staphylococcus aureus, Streptococcus pyogenes,* Actinomyces sp., *Campylobacter fetus*, and *Legionella pneumophila*, ampilllin-resistant strain of *S. aureus*, and methicillin-resistant strain of *S. aureus*.

121. The method of claim 118 wherein the antibiotic is selected from the group consisting essentially of a beta-lactam, aminoglycolide, polymyxin-B, amphotericin B, aztreonam, cephalosporine, chloramphenicol, fusidans, lincosamides, macrolides, methronidazole, nitro-furantoin, Imipenem/cilastin, quinolones, rifampin, polyenes, tetracycline, sulfonamides, trimethoprim, vancomycin, teicoplanin, imidazoles, and erythromycin.

122. The method of claim 121 wherein the beta-lactam is cephalosporin.

123. The method of claim 121 wherein the beta-lactam is penicillin.

124. The method of claim 121 wherein the aminoglycolide is gentamicin.

125. The method of claim 121 wherein the aminoglycolide is amikacin.

126. The method of claim 121 wherein the aminoglycolide is tobramycin.

127. The method of claim 121 wherein the aminoglycolide is kanamycin.

128. The method of claim 121 wherein the beta-lactam is an ampicillin.

129. The method of claim 121 wherein the polymeric matrix consists essentially of a poly(DL-lactide-co-glycolide), wherein the relative ratio between the amount of lactide and glycolide (L/G) component is within the range of 48/52 to 58/42.

130. The method of claim 128 wherein the ampicillin is present in an amount of from 5 to 60 percent and the amount of polymeric matrix is from 40 to 95 percent.

131. The process comprising treating humans in need, thereof, suffering from diseases and/or ailments selected from the group consisting of: viral infections; bacterial infections; fungal infections; parasitic infections and more specific diseases and/or ailments; such as, aids; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; breast cancer; cutaneous & metastatic; cachexia in AIDS; campylobacter infection; cancer; pnemonia; sexually transmitted diseases (STDs); cancer; viral dieases; *candida albicians* in AIDS and cancer; candidiasis in HIV infection; pain in cancer; pancreatic cancer; parkinson's disease; peritumoral brain edema; postoperative adhesions (prevent); proliferative diseases; prostate cancer; ragweed allergy; renal disease; restenosis; rheumatoid arthritis; rheumatoid arthritis; allergies;/rotavirus infection; scalp psoriasis; septic shock; small-call lung cancer; solid tumors; stroke; thrombosis; type I diabetes; type I diabetes w/kidney transplants; type II diabetes; viseral leishmaniasis; malaria; periodontal or gum disease; cardiac rthythm; disorders; central nervous system diseases; central nervous system disorders; cervical dystonia (spasmodic torticollis); choridal neovascularization; chronic hepatitis c, b and a; colitis associated with antibiotics; colorectal cancer; coronary artery thrombosis; cryptosporidiosis in AIDS; cryptosporidiun, *paryum* diarrhea in AIDS; cystic fibrosis; cytomegalovirus disease; depression; social phobias; panic disorder; diabetic complications; disabetic eye disease; diarrhea associated with antibiotics; erectile dysfunction; genital herpes; graft-vs host disease in transplant patients; growth hormone deficiency; head and neck cancer; head trauma; stroke; heparin neutralization after cardiac bypass; hepatocallular carcinoma; HIV; HrV infection; huntington's disease; CNS diseases; hypercholesterolemia; hypertension; inflammation; inflammation and angiogensis; inflammation in cardiopulmonary bypass; influenza; migrain head ache; interstitial cystitis; kaposion sarcoma; kaposils coma in AIDS; lung cancer; melanoma; molluscum contagiosum in AIDS; multiple sclerosis; neoplastic meningitis from solid tumors; non-small call lung cancer; organ transplant rejection; osteoarthritis; rheumatoid arthritis; osteoporosis; drug addiction; shock; ovarian cancer; Amebiasis; Babesiasis; Chagas' disease (*Trypanosoma cruzi*); Cryptosporidiosis; Cysticetcosis; Fascioliasis; Filariasis; Echinococcosis; Giardiasis; Leishmaniasis; Malaria; Paragonimiasis; Toxoplasmosis; Trichinellosis; Trichomoniasis; yeast infection; and pain, with a composition for the burst-free, sustained, programmable release of active material(s) over a period from 1–100 days, which comprises: (1) an active material and (2) a carrier which contains pharmaceutically-acceptable adjuvant, comprised of a blend of uncapped and end-capped biodegradable-biocompatible poly(lactide/glycolide) copolymer.

132. A vaccine prepared from a composition for the burst-free, sustained, programmable release of active martials(s) over a period from 1–100 days, which comprises: (1) an active material and (2) a carrier which contains pharmaceutically-acceptable adjuvant, comprised of a blend of uncapped and end-capped biodegradable-biocompatible poly(lactide/glycolide) copolymer to prevent the occurrence in humans in need thereof of diseases and/or ailments selected from the group consisting of viral infections; bacterial infections; fungal infections; parasitic infections and more specific diseases and/or ailments; such as, aids; alitimer's dementia; angiogenesis diseases; aphthour ulcers in AIDS patients; asthma; atopic dermatitis; psoriasis; basal call carcinoma; benign prostatic hypertrophy; blood substitute; blood substitute in surgery patients; blood substitute in trauma patients; breast cancer; breast cancer; cutaneous & metastatic; cachexia in AIDS; campylobacter infection; cancer; pneumonia; sexually transmitted diseases (STDs); cancer; viral diseases; *candida albicans* in AIDS and cancer; candidiasis in HIV infection; pain in cancer; pancreatic cancer; parkinson's disease; periturmoral brain edema; post-operative adhesions (prevent); proliferative diseases; prostate cancer; ragweed allergy; renal disease; restenosis; rheumatoid arthritis; rheumatoid arthritis; allergies; rotavirus infection; scalp psoriasis; septic shock; small-cell lung cancer; solid tumors; stroke; thrombosis; type I diabetes; type I diabetes w/kidney transplant; type II diabetes; viseral leishmaniasis; malaria; periodontal or gun disease; cardiac rthythm disorders; central nervous system diseases; central nervous system disorders; cervical dystonia (spasmodic torticoillis); choridal neovascularization; chronic hepatitis c, b and a; colitis associated with antibiotics; colorectal cancer, coronary artery thrombosis; cryptosporidiosis in AIDS; ryptosporidium paryum diarrhea in AIDS; cystic fibrosis; cytomegalovirus disease; depression; social phobias; panic disorder; diabetic complications; disabetic eye disease, diarrhea associated with antibiotics; erectile dysfunction; genital herpes; graft-vs host disease in transplant patients; growth hormone deficiency; head and neck cancer; head trauma; stroke; heparin neutralization after cardiac bypass; hepatocellular carcinoma; HIV; HIV infection; huntington's disease; CNS diseases; hypercholesterolemia; hypertension; inflammation; inflammation and angiogensis; inflammation in cardiopulmonary bypass; influenza; migrain head ache; interstitial cystitis; kaposils sarcoma; kaposils sarcoma in AIDS; lung cancer; melanoma; molluscum contagiosum in AIDS; multiple sclerosis; neoplastic meningitis from solid tumors; non-small call lung cancer; organ transplant rejection; ostsoarthritis; rheumatoid arthritis; osteoporosis; drug addiction; shock; ovarian cancer; Amebiasis; Babesiasis; Chagas' disease (*Trypanosoma cruzi*); Cryptosporidiosis; Cysticercosis; rascioliasis; Filariasis; Echinococcosis; Giardiasis; Leishmaniasis; Xalaria; Paragonimiasis; Pneunocystosis; Schistosomiasis; Strongylodiasis; Toxocariasis; Toxoplasmosis; Trichinellosis; Trichomoniasis; yeast infection; and pain.

133. An immunostimulating composition of claim 89 wherein the immunogenic substance is derived from bacteria.

134. A composition of claim 133 wherein the immunogenic substance is comprised of (i) a non-covalent complex between purified, detoxified LPS endotoxin derived from *E. coli* and (ii) purified outer membrane protein derived from *N. meningitis*.

135. A composition of claim 134, wherein said *E. coli* is strain J5 (Rc chemotype).

136. A composition of claim 134, wherein said *N. meningitis* is group B strain.

137. A composition of claim 134, wherein said purified LPS endotoxin of said non-covalent complex is also detoxified.

138. A composition of claim 134, wherein said purified outer membrane protein to said purified LPS endotoxin in said non-covalent complex is between 1 and 2.

139. An immunostimulating composition according to claim 133 wherein the amount of said immunogenic substance is within the range of 0.1 to 1.5% based on the volume of said bulk matrix.

140. A vaccine according to claim 83, effective in actively immunizing a subject against infection by Gram-negative bacteria or against lipopolysaccharide (LPS) endotoxin-mediated pathology, comprising a non-covalent complex between purified LPS endotoxin derived from *E. coli* and purified outer membrane protein derived from *N. meningitis*.

141. A vaccine of claim 140, wherein said *E. coli* is strain J5 (Rc chemotype).

142. A vaccine of claim 140, wherein said *N. meningitis* is group B strain.

143. A vaccine of claim 140, wherein said purified LPS endotoxin of said no-covalent complex is also detoxified.

144. A vaccine of claim 140, wherein the weight ratio of said purified outer membrane protein to said purified LPS endotoxin in said non-covalent complex is between 1 and 2.

145. A method of actively immunizing a subject against infection by Gram-negative bacteria and LPS-induced pathology, comprising administering to said subject an effective amount of a vaccine of claim 140.

146. A method of claim 145, wherein said *E. coli* is strain J5 (Rc chemotype).

147. A method of claim 144, wherein said *N. meningitis* is group B strain.

148. A method of claim 144, wherein said purified LPS endotoxin is detoxified.

149. A method of claim 144, wherein said Gram-negative bacterial infection is a meningococcal infection.

150. A method of passively conferring upon a second subject protection against infection by Gram-negative bacteria or LPS-mediated pathology, comprising the steps of:
 a) actively immunizing a first subject with a vaccine of claim 140 comprising a non-covalent complex between purified LPS endotoxin derived from *E. coli* and purified outer membrane protein derived from *N. meningitis*;

b) collecting from said first subject a postimmune serum or plasma, or IgG isolated therefrom; and, c) administering to said second subject an amount of said serum or plasma or IgG isolated therefrom that is effective in conferring passive protection against a infection by Gram-negative bacteria and LPS-mediated pathology.

151. A method of claim 150, wherein said *E. coli* is strain J5 (Rc chemotype).

152. A method of claim 150, herein said *N. meningitis* is group B strain.

153. A method of claim 150, wherein said purified LPS endotoxin is detoxified.

154. Serum, plasma or specific polyclonal antibody obtained from a subject immunized with a vaccine according to claim 140.

* * * * *